United States Patent
Harkins Kincaid et al.

(10) Patent No.: US 11,584,929 B2
(45) Date of Patent: Feb. 21, 2023

(54) METHODS AND COMPOSITIONS FOR ANALYZING NUCLEIC ACID

(71) Applicant: CLARET BIOSCIENCE, LLC, Santa Cruz, CA (US)

(72) Inventors: Kelly M. Harkins Kincaid, Santa Cruz, CA (US); Joshua D. Kapp, Santa Cruz, CA (US); Christopher J. Troll, Santa Cruz, CA (US)

(73) Assignee: CLARET BIOSCIENCE, LLC, Santa Cruz, CA (US)

( * ) Notice: Subject to any disclaimer, the term of this patent is extended or adjusted under 35 U.S.C. 154(b) by 0 days.

(21) Appl. No.: 16/961,113

(22) PCT Filed: Jan. 11, 2019

(86) PCT No.: PCT/US2019/013210
§ 371 (c)(1),
(2) Date: Jul. 9, 2020

(87) PCT Pub. No.: WO2019/140201
PCT Pub. Date: Jul. 18, 2019

(65) Prior Publication Data
US 2021/0054366 A1    Feb. 25, 2021

Related U.S. Application Data

(60) Provisional application No. 62/769,787, filed on Nov. 20, 2018, provisional application No. 62/618,382, (Continued)

(51) Int. Cl.
*C12N 15/10*     (2006.01)
*C12Q 1/6855*    (2018.01)
*C12Q 1/6869*    (2018.01)

(52) U.S. Cl.
CPC ..... *C12N 15/1065* (2013.01); *C12N 15/1093* (2013.01); *C12Q 1/6855* (2013.01); *C12Q 1/6869* (2013.01)

(58) Field of Classification Search
CPC ............ C12N 15/1065; C12N 15/1093; C12Q 1/6855; C12Q 1/6869
See application file for complete search history.

(56) References Cited

U.S. PATENT DOCUMENTS

| | | |
|---|---|---|
| 5,744,306 A | 4/1998 | Murtagh, Jr. et al. |
| 6,013,438 A | 1/2000 | Didenko et al. |
| (Continued) | | |

FOREIGN PATENT DOCUMENTS

| | | |
|---|---|---|
| WO | 89/01526 A1 | 2/1989 |
| WO | 97/27330 A1 | 7/1997 |
| (Continued) | | |

OTHER PUBLICATIONS

Hashimoto, et al., "Analysis of Telomeric Single-Strand Overhang Length in Human Endometrial Cancers", FEBS Letters, 2005, 579:2959-2964.
(Continued)

*Primary Examiner* — Jeremy C Flinders
*Assistant Examiner* — Taryn Kimberly Wood
(74) *Attorney, Agent, or Firm* — Loza & Loza, LLP

(57) ABSTRACT

The technology relates in part to methods and compositions for analyzing nucleic acid. In some aspects, the technology relates to methods and compositions for preparing a nucleic acid library. In some aspects, the technology relates to methods and compositions for analyzing ends of nucleic acid fragments.

38 Claims, 32 Drawing Sheets
Specification includes a Sequence Listing.

Related U.S. Application Data filed on Jan. 17, 2018, provisional application No. 62/617,055, filed on Jan. 12, 2018.

(56) References Cited

U.S. PATENT DOCUMENTS

| | | | |
|---|---|---|---|
| 6,057,101 | A | 5/2000 | Nandabalan et al. |
| 6,261,774 | B1 | 7/2001 | Pagratis et al. |
| 6,261,782 | B1 | 7/2001 | Lizardi et al. |
| 6,607,878 | B2 | 8/2003 | Sorge |
| 6,670,120 | B1 | 12/2003 | Schmidt et al. |
| 6,677,121 | B2 | 1/2004 | Lizardi et al. |
| 6,773,886 | B2 | 8/2004 | Kaufman et al. |
| 6,927,028 | B2 | 8/2005 | Dennis et al. |
| 7,166,429 | B2 | 1/2007 | Van Eijk et al. |
| 7,282,335 | B2 | 10/2007 | Gocke et al. |
| 7,723,077 | B2 | 5/2010 | Young et al. |
| 7,741,463 | B2 | 6/2010 | Gormley et al. |
| 7,838,647 | B2 | 11/2010 | Hahn et al. |
| 8,168,388 | B2 | 5/2012 | Gormley et al. |
| 8,192,941 | B2 | 6/2012 | Kuersten |
| 8,420,319 | B2 | 4/2013 | Mikawa |
| 8,563,478 | B2 | 10/2013 | Gormley et al. |
| 8,932,816 | B2 | 1/2015 | Kuersten |
| 9,416,406 | B2 | 8/2016 | Kuersten |
| 9,506,113 | B2 | 11/2016 | Eshoo et al. |
| 9,546,399 | B2 | 1/2017 | Amorese et al. |
| 9,580,751 | B2 | 2/2017 | Hahn et al. |
| 9,605,313 | B2 | 3/2017 | Cantor et al. |
| 9,624,534 | B2 | 4/2017 | Kuersten |
| 9,783,799 | B2 | 10/2017 | Kim et al. |
| 9,834,816 | B2 | 12/2017 | Kuersten |
| 9,834,822 | B2 | 12/2017 | Talasaz |
| 9,890,375 | B2 | 2/2018 | Geng et al. |
| 9,982,255 | B2 | 5/2018 | Varley et al. |
| 10,011,866 | B2 | 7/2018 | Eshoo et al. |
| 10,017,807 | B2 | 7/2018 | Srinivasan et al. |
| 10,227,587 | B2 | 3/2019 | Zhang et al. |
| 10,240,191 | B2 | 3/2019 | Kuersten |
| 10,316,357 | B2 | 6/2019 | Makarov et al. |
| 11,299,780 | B2 | 4/2022 | Green |
| 2002/0058256 | A1 | 5/2002 | Rothberg et al. |
| 2002/0106649 | A1 | 8/2002 | Lizardi et al. |
| 2002/0142309 | A1 | 10/2002 | Dattagupta |
| 2003/0082556 | A1 | 5/2003 | Kaufman et al. |
| 2003/0104363 | A1 | 6/2003 | Arguello et al. |
| 2003/0165923 | A1 | 9/2003 | Li et al. |
| 2003/0165963 | A1 | 9/2003 | Dattagupta |
| 2003/0219878 | A1 | 11/2003 | Lindbo et al. |
| 2004/0006033 | A1 | 1/2004 | Zhu |
| 2004/0265888 | A1 | 12/2004 | Kaufman et al. |
| 2009/0317818 | A1 | 12/2009 | Ehrich et al. |
| 2010/0105049 | A1 | 4/2010 | Ehrich et al. |
| 2010/0311602 | A1 | 12/2010 | Levy et al. |
| 2011/0319290 | A1 | 12/2011 | Raymond et al. |
| 2013/0005585 | A1 | 1/2013 | Anderson et al. |
| 2013/0012399 | A1 | 1/2013 | Myers et al. |
| 2015/0004604 | A1 | 1/2015 | Eshoo et al. |
| 2015/0051088 | A1 | 2/2015 | Kim |
| 2015/0118077 | A1 | 4/2015 | Humburg |
| 2015/0132763 | A1 | 5/2015 | Amorese et al. |
| 2016/0032396 | A1 | 2/2016 | Diehn et al. |
| 2018/0002731 | A1 | 1/2018 | Wu et al. |
| 2018/0016631 | A1 | 1/2018 | Van Eijk |
| 2018/0142235 | A1 | 5/2018 | Zhang et al. |
| 2019/0194649 | A1 | 6/2019 | Raine et al. |
| 2020/0149098 | A1 | 5/2020 | Green |
| 2021/0010081 | A1 | 1/2021 | Shendure et al. |

FOREIGN PATENT DOCUMENTS

| | | |
|---|---|---|
| WO | 97/46704 A1 | 12/1997 |
| WO | 00/39333 A1 | 7/2000 |
| WO | 2006/056480 A2 | 6/2006 |
| WO | 2007/140417 A2 | 12/2007 |
| WO | 2007/147063 A2 | 12/2007 |
| WO | 2009/032779 A2 | 3/2009 |
| WO | 2009/032781 A2 | 3/2009 |
| WO | 2010/033639 A2 | 3/2010 |
| WO | 2010/115016 A2 | 10/2010 |
| WO | 2011/034631 A1 | 3/2011 |
| WO | 2011/143659 A2 | 11/2011 |
| WO | 2011/156529 A2 | 12/2011 |
| WO | 2012/103154 A1 | 8/2012 |
| WO | 2014/210353 A2 | 12/2014 |
| WO | 2015/118077 A1 | 8/2015 |
| WO | 2015/134552 A1 | 9/2015 |
| WO | 2016/081798 A1 | 5/2016 |
| WO | 2018/013837 A1 | 1/2018 |
| WO | 2019/140201 A1 | 7/2019 |

OTHER PUBLICATIONS

International Preliminary Report on Patentability dated Jan. 2019 in International Patent Application No. PCT/US2017/041974, filed on Jul. 13, 2017, 8 pages.

International Preliminary Report on Patentability Received dated Jul. 23, 2020 in PCT. Patent Application No. PCT/US2019/013210, filed on Jan. 11, 2019 and published as WO 2019/140201 on Jul. 18, 2019, 8 pages.

International Search Report and Written Opinion dated May 13, 2019 in International Patent Application No. PCT/US2019/013210, filed on Jan. 11, 2019, 11 pages.

International Search Report and Written Opinion dated Oct. 12, 2017 in International Patent Application No. PCT/US2017/041974, filed on Jul. 13, 2017, 11 pages.

Adey et al., "Rapid, Low-Input, Low-Bias Construction of Shotgun Fragment Libraries by High-Density in Vitro Transposition", Genome Biology, 2010, 11: R119:17 pages.

Altschul et al., "Gapped BLAST and PSI-BLAST: A New Generation of Protein Database Search Programs", Nucleic Acids Research, Sep. 1997, 25(17):3389-3402.

Ansari et al., "In Situ End-Labelling Detects DNA Strand Breaks in Apoptosis and Other Physiological and Pathological States", The Journal of Pathology, 1993, 170:1-8.

Aravanis et al., "Next-Generation Sequencing of Circulating Tumor DNA for Early Cancer Detection", Cell, Feb. 9, 2017, 168:571-574.

Aymard et al., "Transcriptionally Active Chromatin Recruits Homologous Recombination at DNA Double-Strand Breaks", Nature Structural & Molecular Biology, 2014, 21:366-374.

Barra et al., "EDTA-Mediated Inhibition of DNases Protects Circulating Cell-Free DNA from Ex Vivo Degradation in Blood Samples", Clinical Biochemistry, 2015, 48:976-981.

Budowle et al., "Forensically Relevant SNP Classes", BioTechniques, 2008, 44(5):603-610.

Butler et al., "The Development of Reduced Size STR Amplicons as Tools for Analysis of Degraded DNA", Journal of Forensic Sciences, Sep. 2003, 42(5):1054-1064.

Butler John, "Fundamentals of Forensic DNA Typing", Academic Press,1st Edition, Aug. 20, 2019, 519 pages.

Cahill et al., "Genomic Evidence for Island Population Conversion Resolves Conflicting Theories of Polar Bear Evolution", PLOS Genetics, e1003345, Mar. 2013, 9(3):8 pages.

Canela et al., "DNA Breaks and End Resection Measured Genome-wide by End Sequencing", Molecular Cell, Sep. 1, 2016, 63(5):898-911.

Chan et al., "Second Generation Noninvasive Fetal Genome Analysis Reveals De Novo Mutations, Single-Base Parental Inheritance, and Preferred DNA Ends", Proceedings of the National Academy of Sciences, Oct. 31, 2016, 113: E8159-E8168.

Chitrabamrung et al., "Serum Deoxyribonuclease I and Clinical Activity in Systemic Lupus Erythematosus", Rheumatology International, 1981, 1:55-60.

Collins Andrew R., "The Comet Assay for DNA Damage and Repair: Principles, Applications, and Limitation", Molecular Biotechnology, 2004, 26:249-261.

(56) References Cited

OTHER PUBLICATIONS

Crawford et al., "DNase-Chip: A High-Resolution Method to Identify DNase I Hypersensitive Sites Using Tiled Microarrays", Nature Methods, Jul. 2006, 3(7):503-509.
Cristiano et al., "Genome-Wide Cell-Free DNA Fragmentation in Patients with Cancer", Nature, Jun. 20, 2019, 570:385-389.
Crosetto et al., "Nucleotide-Resolution DNA Double-Strand Breaks Mapping by Next-Generation Sequencing", Nature Methods, Apr. 2013, 10(4):361-365.
Crowley et al., "Liquid Biopsy: Monitoring Cancer-Genetics in the Blood", Nature Reviews Clinical Oncology, Jul. 9, 2013, 13 pages.
Dabney et al., "Complete Mitochondrial Genome Sequence of a Middle Pleistocene Cave Bear Reconstructed from Ultrashort DNA Fragments", Proceedings of the National Academy of Sciences, Sep. 24, 2013, 110(39):15758-15763.
Daley et al., "Rejoining of DNA Double-Strand Breaks as a Function of Overhang Length", Molecular and cellular Biology, Feb. 2005, 25(3):896-906.
Dekker et al., "Nucleic Acids Selected Topics Related to their Enzymology and Chemistry", Review of Biochemistry, 1960, 29:453-474.
Didenko et al., "Biotin-Labeled Hairpin Oligonucleotides; Probes to Detect Double-Strand Breaks in DNA in Apoptotic Cells", American Journal of Pathology, Apr. 1998, 152(4):897-902.
Didenko et al., "Early Necrotic DNA Degradation-Presence of Blunt-Ended DNA Breaks, 3' and 5' Overhangs in Apoptosis, but only 5' Overhangs in Early Necrosis", American Journal of Pathology, May 2003, 162(5):1571-1578.
Didenko et al., "In Situ Labeling of DNA Breaks and Apoptosis by T7 DNA Polymerase", Methods in Molecular Biology, 2011, 682:37-48.
Didenko et al., "Presence of Double-strand Breaks with Single-base 3' Overhangs in Cells Undergoing Apoptosis but Not Necrosis", The Journal of Cell Biology, Dec. 1996, 135(5):1369-1376.
Diehl et al., "Circulating Mutant DNA to Assess Tumor Dynamics", Nature Medicine, Sep. 2008, 14(9):985-990.
Dorsett et al., "HCoDES Reveals Chromosomal DNA End Structures with Single Nucleotide Resolution", Molecular Cell, Dec. 18, 2014, 56(6):808-818.
Enari, "A Caspase-Activated DNase That Degrades DNA During Apoptosis, and Its Inhibitor ICAD", Nature, 1998, 391(6662):43-50.
Ershova et al., "Circulating Cell-Free DNA Concentration and DNase I Activity of Peripheral Blood Plasma Change in Case of Pregnancy with Intrauterine Growth Restriction Compared to Normal Pregnancy", Biomedical Reports, 2017, 7:319-324.
Fan et al., "Noninvasive Diagnosis of Fetal Aneuploidy by Shotgun Sequencing DNA from Maternal Blood", Proceedings of the National Academy of Sciences, Oct. 21, 2008, 105(42):16266-16271.
Fischer et al., "DNase1L2 Degrades Nuclear DNA during Corneocyte Formation", Journal of Investigative Dermatology, 2007, 127:24-30.
Fischer et al., "Essential Role of the Keratinocyte-Specific Endonuclease DNase1L2 in the Removal of Nuclear DNA from Hair and Nails", Journal of Investigative Dermatology, Jun. 2011, 131(6):1208-1215.
Frock et al., "Genome-Wide Detection of DNA Double-Stranded Breaks Induced by Engineered Nucleases", Nature Biotechnology, 2015, 33:179-186.
Genomes Project, "A Global Reference for Human Genetic Variation", The 1000 Genomes Project Consortium, Nature, Oct. 1, 2015, 526:68-74.
Gill et al., "Genotyping and Interpretation of STR-DNA: Low-Template, Mixtures and Database Matches-Twenty Years of Research and Development", Forensic Science International: Genetics, Mar. 18, 2015, 18:100-117.
Goodwin et al., "Coming of Age: Ten Years of Next-Generation Sequencing Technologies", Nature Reviews Genetics, Jun. 2016, 17:333-351.

Green et al., "A Complete Neandertal Mitochondrial Genome Sequence Determined by High-Throughput Sequencing", Cell, Aug. 8, 2008, 134(3):416-426.
Green et al., "A Draft Sequence of the Neandertal Genome", Science, May 7, 2010, 328(5979):710-722.
Green et al., "Forensic Identification from Mixed and Minute Samples", Funding Opportunity No. CFDA No. 16.560, University of California, Santa Cruz, 2017, 22 pages.
Green et al., "The Neandertal Genome and Ancient DNA Authenticity", The EMBO Journal, 2009, 28:2494-2502.
Halazonetis et al., "An Oncogene-Induced DNA Damage Model for Cancer Development", Science, Mar. 7, 2008, 319:1352-1355.
Harkins et al., "A New Method for Assessing Postmortem DNA Damage from Ancient Remains", The 86th Annual Meeting of the American Association of Physical Anthropologists, Abstract, 2017, 1 page.
Harkins et al. "A Novel NGS Library Preparation Method to Characterize Native Termini of Fragmented DNA", Nucleic Acids Research, 2020, 48(8):13 pages.
Homer et al., "BFAST: An Alignment Tool for Large Scale Genome Resequencing", PLoS ONE, Nov. 2009, 4(11): e7767:12 pages.
Jobling et al., "Encoded Evidence: DNA in Forensic Analysis", Nature Reviews Genetics, 2004, 5(10):739-751.
Kang et al., "Comparative Analysis of Circulating Tumor DNA Stability in K3EDTA, Streck and CellSave Blood Collection Tubes", Clinical Biochemistry, 2016, 30 pages.
Karlin et al., "Applications and Statistics for Multiple High-Scoring Segments in Molecular Sequences", Proceedings of the National Academy of Sciences, Jun. 1993, 90:5873-5877.
Kayser et al., "Improving Human Forensics Through Advances in Genetics, Genomics and Molecular Biology", Nature Reviews Genetics, Mar. 2011, 12(3):179-192.
Kent et al., "The Human Genome Browser at UCSC", Genome Research, 2002, 12:996-1006.
Kircher Martin, "Analysis of High-Throughput Ancient DNA Sequencing Data", Methods in Molecular Biology, Chapter 23, 2012, 840:197-228.
Kivisild Toomas, "Maternal Ancestry and Population History from Whole Mitochondrial Genomes", Investigative Genetics, 2015, 6(3):10 pages.
Knierim et al., "Systematic Comparison of Three Methods for Fragmentation of Long-Range PCR Products for Next Generation Sequencing", PLoS ONE, e28240, Nov. 2011, 6(11):6 pages.
Koohy et al., "Chromatin Accessibility Data Sets Show Bias Due to Sequence Specificity of the DNase I Enzyme", PLoS ONE, Jul. 2013, 8(7):9 pages.
Krings et al., "Neandertal DNA Sequences and the Origin of Modern Humans", Cell, Jul. 11, 1997, 90:19-30.
Lahiri et al., "DNA Isolation by a Rapid Method from Human Blood Samples: Effects of MgCl2, EDTA, Storage Time, and Temperature on DNA Yield and Quality", Biochemical Genetics, 1993, 31(718):321-328.
Langmead et al., "Ultrafast and Memory-Efficient Alignment of Short DNA Sequences to the Human Genome", Genome Biology, Article R25, Mar. 4, 2009, 10(3):10 pages.
Li et al., "Aligning sequence reads, clone sequences and assembly contigs with BWA-MEM", arXiv:1303, 2013, 3 pages.
Li et al., "Fast and Accurate Short Read Alignment with Burrows-Wheeler Transform", Bioinformatics, 2009, 25(14):1754-1760.
Li et al., "SOAP2: An Improved Ultrafast Tool for Short Read Alignment", Bioinformatics, 2009, 25(15):1966-1967.
Li et al., "The Sequence Alignment/Map format and SAMtools", Bioinformatics, 2009, 25(16):2078-2079.
Lieber et al., "Mechanism and Regulation of Human Non-Homologous DNA End-Joining", Nature Reviews Molecular Cell Biology vol. Sep. 2003, 4:712-720.
Metzker Michael I., "Sequencing Technologies—The Next Generation", Nature Review Genetics, Jan. 1, 2010, 11(1):31-46.
Meyer et al., "Illumina Sequencing Library Preparation for Highly Multiplexed Target Capture and Sequencing", Cold Spring Harbor Protocols, Jun. 2010, 2010(6):20 pages.
Miller et al., "Sequencing the Nuclear Genome of the Extinct Woolly Mammoth", Nature, Nov. 20, 2008, 456(7220):387-390.

(56) References Cited

OTHER PUBLICATIONS

Morey et al., "A Glimpse into Past, Present, and Future DNA Sequencing", Molecular Genetics and Metabolism, 2013, 110(1-2)3-24.

Mukae et al., "Molecular Cloning and Characterization of Human Caspase-Activated DNase", Proceedings of the National Academy of Sciences, Aug. 1998, 95:9123-9128.

Mulero et al., "Development and Validation of the AmpFISTR MiniFiler PCR Amplification Kit: A MiniSTR Multiplex for the Analysis of Degraded and/or PCR Inhibited DNA", Journal of Forensic Sciences, Jul. 2008, 53(4):838-852.

Oefner et al., "Efficient Random Subcloning of DNA Sheared in a Recirculating Point-Sink Flow System", Nucleic Acids Research, 1996, 24(20):3879-3886.

Parkinson et al., "Preparation of High-Quality Next-Generation Sequencing Libraries from Picogram Quantities of Target DNA", Genome Research, 2012, 22:125-133.

Patel et al., "Evaluation of Serum Alkaline DNase Activity in Treatment Monitoring of Head and Neck Cancer Patients", Tumor Biology, 2000, 21:82-89.

Poinar et al., "Metagenomics to Paleogenomics: Large-Scale Sequencing of Mammoth DNA", Science, Jan. 20, 2006, 311:392-394.

Poptsova et al., "Non-Random DNA Fragmentation in Next-Generation Sequencing", Scientific Reports, Mar. 31, 2014, 4:4532:6 pages.

Prufer et al., "Computational Challenges in the Analysis of Ancient DNA", Genome Biology, 2010, 11: R47:15 pages.

Rasmussen et al., "Ancient Human Genome Sequence of an Extinct Palaeo-Eskimo", Nature, Feb. 11, 2010, 463(7282):757-762.

Reuter et al., "High-Throughput Sequencing Technologies", Molecular Cell, May 21, 2015, 58:586-597.

Rivals et al., "MPSCAN: Fast Localisation of Multiple Reads in Genomes", WABI 2009 Algorithms in Bioinformatics, LNBI 5724, 2009, 246-260.

Rizk et al., "GASSST: Global Alignment Short Sequence Search Tool", Bioinformatics, 2010, 26(20):2534-2540.

Rushizky et al., "A Map of the Products Resulting from the Action of Micrococcal Nuclease on Thymus Deoxyribonucleic Acid and Its Use as a Guide to Specificity", Biochemical and Biophysical Research Communications, Mar. 1960, 2(3):153-158.

Sabo et al., "Genome-Scale Mapping of DNase I Sensitivity in Vivo Using Tiling DNA Microarrays", Nature Methods, Jul. 2006, 3(7):511-518.

Schweizer et al., "Targeted Capture and Resequencing of 1040 Genes Reveal Environmentally Driven Functional Variation in Grey Wolves", Molecular Ecology, 2016, 25:357-379.

Shapiro et al., "A Paleogenomic Perspective on Evolution and Gene Function: New Insights from Ancient DNA", Science, Jan. 24, 2014, 343:8 pages.

Shinozuka et al., "A Simple Method for Semi-Random DNA Amplicon Fragmentation Using the Methylation-Dependent Restriction Enzyme MspJI", BMC Biotechnology, 2015, 15:25:13 pages.

Singh et al., "A Simple Technique for Quantitation of Low-Levels of DNA Damage in Individual Cells", Experimental Cell Research, 1988, 175:184-191.

Snyder et al., "Cell-free DNA Comprises an In Vivo Nucleosome Footprint that Informs Its Tissues-of-Origin", Cell, Jan. 2016, 164(1-2):57-68.

Sosic et al., "Edlib: A C/C++ Library for Fast, Exact Sequence Alignment Using Edit Distance", Bioinformatics, Jan. 31, 2017, 33(9):1394-1395.

Stiller et al., "Patterns of Nucleotide Misincorporations During Enzymatic Amplification and Direct Large-Scale Sequencing of Ancient DNA", Proceedings of the National Academy of Sciences, Sep. 12, 2006, 103(37):13578-13584.

Sulkowski et al., "Mechanism of Action of Micrococcal Nuclease on Deoxyribonucleic Acid", Journal of Biological Chemistry, Aug. 1962, 237(8):2620-2625.

Szabo et al., "In Situ Labeling of DNA Reveals Interindividual Variation in Nuclear DNA Breakdown in Hair and May Be Useful to Predict Success of Forensic Genotyping of Hair", International Journal of Legal Medicine, 2012, 126:63-70.

Tamkovich et al., "Circulating DNA and DNase Activity in Human Blood", Annals of the New York Academy of Sciences, 2006, 1075:191-196.

Tamkovich et al., "Features of Circulating DNA Fragmentation in Blood of Healthy Females and Breast Cancer Patients", Advances in Experimental Medicine and Biology, 2016, 924:47-51.

Thalmann et al., "Complete Mitochondrial Genomes of Ancient Canids Suggest a European Origin of Domestic Dogs", Science, Nov. 15, 2013, 342:871-874.

Tsai et al., "GUIDE-Seq Enables Genome-Wide Profiling of Off-Target Cleavage by CRISPR-Cas Nucleases", Nature Biotechnology, Feb. 2015, 33(2):187-197.

Van Oorschot et al., "Forensic Trace DNA: A Review", Investigative Genetics, 2010, 1:14:17 pages.

Van Oven et al., "Updated Comprehensive Phylogenetic Tree of Global Human Mitochondrial DNA Variation", Human Mutation, 2008, 30(2): E386-394.

Vohr et al., "A Method for Positive Forensic Identification of Samples from Extremely Low-Coverage Sequence Data", BMC Genomics, 2015, 16(1034):11 pages.

Vohr et al., "A Phylogenetic Approach for Haplotype Analysis of Sequence Data from Complex Mitochondrial Mixtures", Forensic Science International: Genetics, 2017, 30:93-105.

Wan et al., "Liquid Biopsies Come of Age: Towards Implementation of Circulating Tumour DNA", Nature Reviews Cancer, Feb. 24, 2017, 17:16 pages.

Widlak et al., "Cleavage Preferences of the Apoptotic Endonuclease DFF40 (Caspase-activated Dnase or Nuclease) on Naked DNA and Chromatin Substrates", The Journal of Biological Chemistry, Mar. 17, 2000, 275(11):8226-8232.

Wong et al., "Optimizing Blood Collection, Transport and Storage Conditions for cell free DNA Increases Access to Prenatal Diagnostic Testing", Clinical Biochemistry, 2013, 46:1099-1104.

Wylie A.H, "Glucocorticoid-Induced Thymocyte Apoptosis Is Associated with Endogenous Endonuclease Activation", Nature, 1980, 284:555-556.

Yan et al., "BLISS Is a Versatile and Quantitative Method for Genome-Wide Profiling of DNA Double-Strand Breaks", Nature Communications, May 12, 2017, 8:15058:9 pages.

Zhao et al., "Quantitative Telomeric Overhang Determination Using a Double-Strand Specific Nuclease", Nucleic Acids Research, 2008, 36(3):5 pages.

Office Action dated Jun. 28, 2021 in U.S. Appl. No. 16/316,268, filed Jan. 8, 2019, 15 pages.

Monson-Miller et al., "Reference Genome-Independent Assessment of Mutation Density Using Restriction Enzyme-Phased Sequencing", BMC Genomics, 2012, 13(72):15 pages.

Shiroguchi et al., "Digital RNA Sequencing Minimizes Sequence-Dependent Bias and Amplification Noise with Optimized Single-Molecule Barcodes", Proceedings of the National Academy of Sciences, Jan. 24, 2012, 109(4):1347-1352.

Office Action dated Dec. 9, 2021 in U.S. Appl. No. 16/316,268, filed Jan. 8, 2019, 8 pages.

short insert:
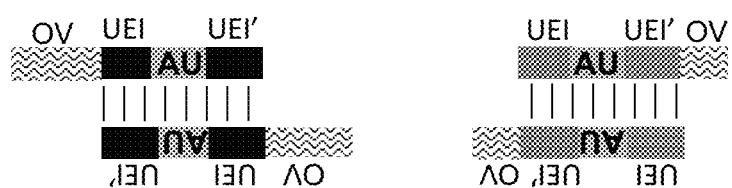
long insert:
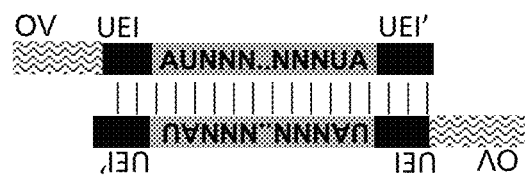
Fig. 2A

......... adapter dimer peak

– – – – DNA (mono,di-,tri) nucleosome peaks

········· adapter dimer peak

— — — — DNA (mono,di-,tri) nucleosome peaks adapter dimer peak

DNA (mono,di-,tri) nucleosome peaks

```
overhang_length: length of particular overhang
cg_count: counts of CG in overhang sequence
at_count: counts of AT in overhang sequence
ta_count: counts of TA in overhang sequence
gc_count: counts of GC in overhang sequence
cc_count: counts of CC in overhang sequence
aa_count: counts of AA in overhang sequence
tt_count: counts of TT in overhang sequence
gg_count: counts of GG in overhang sequence
otype: 5', 3', BL
len_cat: sub-nucleosome fragment (<120), multi-nucleosome fragment (120<=)
cg_perc: percent of CG in overhang sequence
at_perc: percent of AT in overhang sequence
ta_perc: percent of TA in overhang sequence
gc_perc: percent of GC in overhang sequence
cc_perc: percent of CC in overhang sequence
aa_perc: percent of AA in overhang sequence
tt_perc: percent of TT in overhang sequence
gg_perc: percent of GG in overhang sequence
overhang_perc: log 2 percent of overhang sequence/total overhangs
full_len: full length of molecule
overhang_perc: log 2 percent of overhang sequence/total overhangs
overhang_count: counts of particular overhang sequence
perc_len: len of overhang/full len of molecule
```

Fig. 21

|              | precision | recall | f1-score | support |
|--------------|-----------|--------|----------|---------|
| 0.0          | 0.77      | 0.72   | 0.75     | 1098    |
| 1.0          | 0.73      | 0.78   | 0.75     | 1053    |
|              |           |        |          |         |
| micro avg    | 0.75      | 0.75   | 0.75     | 2151    |
| macro avg    | 0.75      | 0.75   | 0.75     | 2151    |
| weighted avg | 0.75      | 0.75   | 0.75     | 2151    |

```
Optimization terminated successfully.
        Current function value: 0.646510
        Iterations 6
                    Results: Logit
==================================================================
Model:              Logit              Pseudo R-squared: 0.067
Dependent Variable: y                  AIC:              5977.6477
Date:               2018-12-13 11:30   BIC:              6048.4340
No. Observations:   4606               Log-Likelihood:   -2977.8
Df Model:           10                 LL-Null:          -3192.6
Df Residuals:       4595               LLR p-value:      4.6181e-86
Converged:          1.0000             Scale:            1.0000
No. Iterations:     6.0000
------------------------------------------------------------------
                  Coef.   Std.Err.    z     P>|z|   [0.025  0.975]
------------------------------------------------------------------
cg_count         0.7953   0.0856   9.2873  0.0000   0.6275  0.9631
gc_count         0.4197   0.0700   6.0001  0.0000   0.2826  0.5569
cc_count        -2.0761   0.5383  -3.8570  0.0001  -3.1311 -1.0211
aa_count        -1.1467   0.4797  -2.3904  0.0168  -2.0870 -0.2065
tt_count        -0.3305   0.0679  -4.8664  0.0000  -0.4636 -0.1974
gg_count         0.7290   0.0789   9.2395  0.0000   0.5744  0.8837
overhang_count  -0.0000   0.0000  -5.3226  0.0000  -0.0000 -0.0000
otype           -2.0061   0.1664 -12.0582  0.0000  -2.3322 -1.6801
cc_perc          0.0939   0.0307   3.0567  0.0022   0.0337  0.1541
aa_perc          0.0612   0.0273   2.2389  0.0252   0.0076  0.1148
overhang_perc    0.1899   0.0157  12.0826  0.0000   0.1591  0.2207
==================================================================
```

Fig. 24

```
Optimization terminated successfully.
        Current function value: 0.611193
        Iterations 6
                    Results: Logit
=================================================================
Model:              Logit            Pseudo R-squared: 0.118
Dependent Variable: y                AIC:              7917.2840
Date:               2018-12-13 11:22 BIC:              8012.0983
No. Observations:   6454             Log-Likelihood:   -3944.6
Df Model:           13               LL-Null:          -4473.6
Df Residuals:       6440             LLR p-value:      6.4961e-218
Converged:          1.0000           Scale:            1.0000
No. Iterations:     6.0000
-----------------------------------------------------------------
                   Coef.   Std.Err.    z     P>|z|   [0.025  0.975]
-----------------------------------------------------------------
overhang_length   -0.0684   0.0214  -3.2000 0.0014 -0.1102 -0.0265
cg_count           4.5480   0.4717   9.6423 0.0000  3.6236  5.4725
cc_count          -3.2054   0.4642  -6.9048 0.0000 -4.1153 -2.2956
aa_count          -3.0193   0.5009  -6.0281 0.0000 -4.0010 -2.0376
tt_count          -2.2212   0.4431  -5.0133 0.0000 -3.0895 -1.3528
overhang_count    -0.0000   0.0000  -4.8665 0.0000 -0.0000 -0.0000
otype             -1.6391   0.2238  -7.3243 0.0000 -2.0777 -1.2005
cg_perc           -0.1672   0.0255  -6.5518 0.0000 -0.2172 -0.1172
gc_perc            0.0265   0.0033   7.9831 0.0000  0.0200  0.0330
cc_perc            0.1499   0.0258   5.8199 0.0000  0.0994  0.2003
aa_perc            0.1448   0.0278   5.2067 0.0000  0.0903  0.1994
tt_perc            0.0957   0.0245   3.8994 0.0001  0.0476  0.1438
gg_perc            0.0227   0.0038   5.9898 0.0000  0.0152  0.0301
overhang_perc      0.1784   0.0168  10.6004 0.0000  0.1454  0.2114
=================================================================
```

Fig. 25

SEQUENCE LISTING

<160> NUMBER OF SEQ ID NOS: 56

<210> SEQ ID NO 1
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 1
gggtagcaag atcggaa                                                    17

<210> SEQ ID NO 2
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 2
acactctttc cctacacgac gctcttccga tcttgctacc ct                        42

<210> SEQ ID NO 3
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: modified_base
<222> LOCATION: (51)..(51)
<223> OTHER INFORMATION: a, c, t, g, unknown or other

<400> SEQUENCE: 3
ccatactgtg gtcgtcacct attacccgc gtaaaggtag gctatgtcat n 51

<210> SEQ ID NO 4
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (51)..(52)
<223> OTHER INFORMATION: a, c, t, g, unknown or other

<400> SEQUENCE: 4
gtgaattgtt gatgtcctgg gtgcctcgtc ccaaaagctg tcctcacgac nn    52

<210> SEQ ID NO 5
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (51)..(53)
<223> OTHER INFORMATION: a, c, t, g, unknown or other

<400> SEQUENCE: 5
gcttctcgaa cccgcgatcc ggccgatccg gcataatggg ttgatttaga nnn   53

<210> SEQ ID NO 6
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (51)..(54)
<223> OTHER INFORMATION: a, c, t, g, unknown or other

<400> SEQUENCE: 6
cgacacggat attccatcaa gagacgggcc tatggtccct gtgatgatgt nnnn  54

<210> SEQ ID NO 7
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (51)..(55)
<223> OTHER INFORMATION: a, c, t, g, unknown or other

<400> SEQUENCE: 7
accttgtgtg ttgctgaagc aaagccgcgt gaccgtttta accagcgaac nnnnn 55

<210> SEQ ID NO 8
<211> LENGTH: 56
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (51)..(56)
<223> OTHER INFORMATION: a, c, t, g, unknown or other

<400> SEQUENCE: 8
attttaccac gagttcctta cgacggctgt gatgccacgg taggcaggta nnnnnn        56

<210> SEQ ID NO 9
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other

<400> SEQUENCE: 9
ncgctttacg ggtcctgggc cggggtgcga taccttgcag aaatcgaggc c             51

<210> SEQ ID NO 10
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other

<400> SEQUENCE: 10
nnaggactct gccgtcgacg agttcgttaa ttcacggcat cacgtgcgta gt            52

<210> SEQ ID NO 11
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(3)
<223> OTHER INFORMATION: a, c, t, g, unknown or other

<400> SEQUENCE: 11
nnnacctccg tcgcgctatg ttctgttgca ttcgaccttc tccgttctgt ggg           53

<210> SEQ ID NO 12
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(4)
```

<223> OTHER INFORMATION: a, c, t, g, unknown or other

<400> SEQUENCE: 12
nnnnacaaga ggagcatccg tattaccgcc tatatcgcct acgtttagag catt    54

<210> SEQ ID NO 13
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(5)
<223> OTHER INFORMATION: a, c, t, g, unknown or other

<400> SEQUENCE: 13
nnnnngtaaa tcccacacag ctgtcggctt atatggtcat tggacggcgt aatag    55

<210> SEQ ID NO 14
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(6)
<223> OTHER INFORMATION: a, c, t, g, unknown or other

<400> SEQUENCE: 14
nnnnnnccag acagccatag aggttacaag catagcaatt tgcatcagtt cgcaga    56

<210> SEQ ID NO 15
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
atgacatagc ctacctttac gcggggtaat aggtgacgac cacagtatgg    50

<210> SEQ ID NO 16
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gtcgtgagga cagcttttgg gacgaggcac ccaggacatc aacaattcac    50

<210> SEQ ID NO 17
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
tctaaatcaa cccattatgc cggatcggcc ggatcgcggg ttcgagaagc            50

<210> SEQ ID NO 18
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
acatcatcac agggaccata ggcccgtctc ttgatggaat atccgtgtcg            50

<210> SEQ ID NO 19
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gttcgctggt taaaacggtc acgcggcttt gcttcagcaa cacacaaggt            50

<210> SEQ ID NO 20
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
tacctgccta ccgtggcatc acagccgtcg taaggaactc gtggtaaaat            50

<210> SEQ ID NO 21
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ggcctcgatt tctgcaaggt atcgcacccc ggcccaggac ccgtaaagcg            50

<210> SEQ ID NO 22
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
actacgcacg tgatgccgtg aattaacgaa ctcgtcgacg gcagagtcct            50

<210> SEQ ID NO 23
<211> LENGTH: 50
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
cccacagaac ggagaaggtc gaatgcaaca aacatagcg cgacggaggt            50

<210> SEQ ID NO 24
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
aatgctctaa acgtaggcga tataggcggt aatacggatg ctcctcttgt            50

<210> SEQ ID NO 25
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
ctattacgcc gtccaatgac catataagcc gacagctgtg tgggatttac            50

<210> SEQ ID NO 26
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
tctgcgaact gatgcaaatt gctatgcttg taacctctat ggctgtctgg            50

<210> SEQ ID NO 27
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
acactctttc cctacacgac gctcttccga tctataccgc                      40

<210> SEQ ID NO 28
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (41)..(41)
<223> OTHER INFORMATION: a, c, t, g, unknown or other
```

```
<400> SEQUENCE: 28
acactctttc cctacacgac gctcttccga tctgatatcg n                    41

<210> SEQ ID NO 29
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (41)..(42)
<223> OTHER INFORMATION: a, c, t, g, unknown or other

<400> SEQUENCE: 29
acactctttc cctacacgac gctcttccga tctgtctgac nn                   42

<210> SEQ ID NO 30
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (41)..(43)
<223> OTHER INFORMATION: a, c, t, g, unknown or other

<400> SEQUENCE: 30
acactctttc cctacacgac gctcttccga tctgagccaa nnn                  43

<210> SEQ ID NO 31
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (41)..(44)
<223> OTHER INFORMATION: a, c, t, g, unknown or other

<400> SEQUENCE: 31
acactctttc cctacacgac gctcttccga tctcgccata nnnn                 44

<210> SEQ ID NO 32
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (41)..(45)
<223> OTHER INFORMATION: a, c, t, g, unknown or other

<400> SEQUENCE: 32
acactctttc cctacacgac gctcttccga tctcgtatat nnnnn                45

<210> SEQ ID NO 33
```

```
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (41)..(46)
<223> OTHER INFORMATION: a, c, t, g, unknown or other

<400> SEQUENCE: 33
acactctttc cctacacgac gctcttccga tctgactaag nnnnnn            46

<210> SEQ ID NO 34
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
acactctttc cctacacgac gctcttccga tctagtacgg                   40

<210> SEQ ID NO 35
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
acactctttc cctacacgac gctcttccga tctagcagcg                   40

<210> SEQ ID NO 36
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
acactctttc cctacacgac gctcttccga tctccatatg                   40

<210> SEQ ID NO 37
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
acactctttc cctacacgac gctcttccga tctagcctgg                   40

<210> SEQ ID NO 38
<211> LENGTH: 40
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 38
acactctttc cctacacgac gctcttccga tctatacgcg                             40

<210> SEQ ID NO 39
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
acactctttc cctacacgac gctcttccga tctgctaggc                             40

<210> SEQ ID NO 40
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gcggtataga tcggaagagc acacgtctga actccagtca c                           41

<210> SEQ ID NO 41
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
cgatatcaga tcggaagagc acacgtctga actccagtca c                           41

<210> SEQ ID NO 42
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
gtcagacaga tcggaagagc acacgtctga actccagtca c                           41

<210> SEQ ID NO 43
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
ttggctcaga tcggaagagc acacgtctga actccagtca c                           41

<210> SEQ ID NO 44
```

```
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
tatggcgaga tcggaagagc acacgtctga actccagtca c                            41

<210> SEQ ID NO 45
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
atatacgaga tcggaagagc acacgtctga actccagtca c                            41

<210> SEQ ID NO 46
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
cttagtcaga tcggaagagc acacgtctga actccagtca c                            41

<210> SEQ ID NO 47
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other

<400> SEQUENCE: 47
nccgtactag atcggaagag cacacgtctg aactccagtc ac                           42

<210> SEQ ID NO 48
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other

<400> SEQUENCE: 48
nncgctgcta gatcggaaga gcacacgtct gaactccagt cac                          43

<210> SEQ ID NO 49
<211> LENGTH: 44
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(3)
<223> OTHER INFORMATION: a, c, t, g, unknown or other

<400> SEQUENCE: 49
nnncatatgg agatcggaag agcacacgtc tgaactccag tcac            44

<210> SEQ ID NO 50
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(4)
<223> OTHER INFORMATION: a, c, t, g, unknown or other

<400> SEQUENCE: 50
nnnnccaggc tagatcggaa gagcacacgt ctgaactcca gtcac           45

<210> SEQ ID NO 51
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(5)
<223> OTHER INFORMATION: a, c, t, g, unknown or other

<400> SEQUENCE: 51
nnnnncgcgt atagatcgga agagcacacg tctgaactcc agtcac          46

<210> SEQ ID NO 52
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(6)
<223> OTHER INFORMATION: a, c, t, g, unknown or other

<400> SEQUENCE: 52
nnnnnngcct agcagatcgg aagagcacac gtctgaactc cagtcac         47

<210> SEQ ID NO 53
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 53
gtgactggag ttcagacgtg tgctcttccg atct                                  34

<210> SEQ ID NO 54
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
agatcggaag agc                                                         13

<210> SEQ ID NO 55
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
agatcggaag agcacacgtc tgaactccag tcac                                  34

<210> SEQ ID NO 56
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
acactctttc cctacacgac gctcttccga tct                                   33
```

METHODS AND COMPOSITIONS FOR ANALYZING NUCLEIC ACID

RELATED PATENT APPLICATIONS

This patent application is a 35 U.S.C. 371 national phase application of International Patent Cooperation Treaty (PCT) Application No. PCT/US2019/013210, filed on Jan. 11, 2019, entitled METHODS AND COMPOSITIONS FOR ANALYZING NUCLEIC ACID, naming Kelly M. HARKINS KINCAID et al. as inventors. International PCT Application No. PCT/US2019/013210 claims the benefit of U.S. provisional patent application No. 62/617,055 filed on Jan. 12, 2018, entitled METHODS AND COMPOSITIONS FOR ANALYZING NUCLEIC ACID, naming Kelly M. HARKINS KINCAID et al. as inventors. International PCT Application No. PCT/US2019/013210 also claims the benefit of U.S. provisional patent application No. 62/618,382 filed on Jan. 17, 2018, entitled METHODS AND COMPOSITIONS FOR ANALYZING NUCLEIC ACID, naming Kelly M. HARKINS KINCAID et al. as inventors. International PCT Application No. PCT/US2019/013210 also claims the benefit of U.S. provisional patent application No. 62/769,787 filed on Nov. 20, 2018, entitled METHODS AND COMPOSITIONS FOR ANALYZING NUCLEIC ACID, naming Kelly M. HARKINS KINCAID et al. as inventors. The entire content of the foregoing applications is incorporated herein by reference, including all text, tables and drawings.

STATEMENT OF GOVERNMENTAL SUPPORT

This invention was made with government support under contract 1 R43 CA232935-01 awarded by the National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Apr. 15, 2019, is named CBS-2001-PC_SL.txt and is 16,785 bytes in size.

FIELD

The technology relates in part to methods and compositions for analyzing nucleic acid. In some aspects, the technology relates to methods and compositions for preparing a nucleic acid library. In some aspects, the technology relates to methods and compositions for analyzing ends of nucleic acid fragments.

BACKGROUND

Genetic information of living organisms (e.g., animals, plants and microorganisms) and other forms of replicating genetic information (e.g., viruses) is encoded in nucleic acid (i.e., deoxyribonucleic acid (DNA) or ribonucleic acid (RNA)). Genetic information is a succession of nucleotides or modified nucleotides representing the primary structure of chemical or hypothetical nucleic acids.

A variety of high-throughput sequencing platforms are used for analyzing nucleic acid. The Illumina platform, for example, involves clonal amplification of adaptor-ligated DNA fragments. Another platform is nanopore-based sequencing, which relies on the transition of nucleic acid molecules or individual nucleotides through a small channel. Library preparation for certain sequencing platforms often includes fragmentation of DNA, modification of fragment ends, and ligation of adapters, and may include amplification of nucleic acid fragments (e.g., PCR amplification).

The selection of an appropriate sequencing platform for particular types of nucleic acid analysis requires a detailed understanding of the technologies available, including sources of error, error rate, as well as the speed and cost of sequencing. While sequencing costs have decreased, the throughput and costs of library preparation can be a limiting factor. One aspect of library preparation includes modification of the ends of nucleic acid fragments such that they are suitable for a particular sequencing platform. Nucleic acid ends may contain useful information. Accordingly, methods that modify nucleic acid ends (e.g., for library preparation) while preserving the information contained in the nucleic acid ends would be useful for processing and analyzing nucleic acid.

SUMMARY

Provided in some aspects are methods for producing a nucleic acid library, comprising combining a nucleic acid composition comprising target nucleic acids and a plurality of oligonucleotide species, where a) some or all of the target nucleic acids comprise an overhang; b) some or all of the oligonucleotides in the plurality of oligonucleotide species comprise two strands, and an overhang at a first end and two non-complementary strands at a second end; where the overhang is capable of hybridizing to a target nucleic acid overhang, where each oligonucleotide species has a unique overhang sequence and length; c) each oligonucleotide in the plurality of oligonucleotide species comprises an oligonucleotide overhang identification sequence specific to one or more features of the oligonucleotide overhang; and d) the nucleic acid composition and the plurality of oligonucleotide species is combined under conditions in which oligonucleotide overhangs hybridize to target nucleic acid overhangs having a corresponding length, thereby forming hybridization products.

Provided in some aspects are methods for producing a nucleic acid library, comprising a) combining a nucleic acid composition comprising target nucleic acids and a plurality of oligonucleotide species, where i) each oligonucleotide in the plurality of oligonucleotide species comprises one strand capable of forming a hairpin structure having a single-stranded loop, where the loop comprises one or more ribonucleic acid (RNA) nucleotides, ii) some or all of the target nucleic acids comprise an overhang, iii) some or all of the oligonucleotides in the plurality of oligonucleotide species comprise an overhang capable of hybridizing to a target nucleic acid overhang, where each oligonucleotide species has a unique overhang sequence and length, iv) each oligonucleotide in the plurality of oligonucleotide species comprises an oligonucleotide overhang identification sequence specific to one or more features of the oligonucleotide overhang, and v) the nucleic acid composition and the plurality of oligonucleotide species is combined under conditions in which oligonucleotide overhangs hybridize to target nucleic acid overhangs having a corresponding length, thereby forming hybridization products; and b) contacting the hybridization products under cleavage conditions with one or more cleavage agents capable of cleaving the hybridization products within the hairpin loop at the RNA nucleotide(s), thereby forming cleaved hybridization products.

Also provided in some aspects are compositions comprising a plurality of oligonucleotide species, where a) each oligonucleotide in the plurality of oligonucleotide species comprises one strand capable of forming a hairpin structure having a single-stranded loop, where the loop comprises one or more ribonucleic acid (RNA) nucleotides; b) some or all of the oligonucleotides in the plurality of oligonucleotide species comprise an overhang capable of hybridizing to an overhang in a target nucleic acid, where each oligonucleotide species has a unique overhang sequence and length; and c) each oligonucleotide in the plurality of oligonucleotide species comprises an oligonucleotide overhang identification sequence specific to one or more features of the oligonucleotide overhang.

Provided in some aspects are methods for modifying nucleic acid ends, comprising a) combining a nucleic acid composition comprising target nucleic acids and a plurality of oligonucleotide species, where i) each oligonucleotide in the plurality of oligonucleotide species comprises one or more cleavage sites capable of being cleaved under cleavage conditions, ii) some or all of the target nucleic acids comprise an overhang, iii) some or all of the oligonucleotides in the plurality of oligonucleotide species comprise two strands and a first overhang and a second overhang, where each overhang is capable of hybridizing to a target nucleic acid overhang, where each oligonucleotide species has a unique overhang sequence and length, iv) each oligonucleotide in the plurality of oligonucleotide species comprises at least two oligonucleotide overhang identification sequences specific to one or more features of the first and second oligonucleotide overhangs, and v) the nucleic acid composition and the plurality of oligonucleotide species is combined under conditions in which oligonucleotide overhangs hybridize to target nucleic acid overhangs having a corresponding length, thereby forming hybridization products; b) contacting the hybridization products under cleavage conditions with one or more cleavage agents capable of cleaving the hybridization products at the one or more cleavage sites, thereby forming cleaved hybridization products; and c) contacting the cleaved hybridization products with a strand-displacing polymerase, thereby forming blunt-ended nucleic acid fragments.

Also provided in some aspects are compositions comprising a plurality of oligonucleotide species, where a) each oligonucleotide in the plurality of oligonucleotide species comprises one or more cleavage sites capable of being cleaved under cleavage conditions; b) some or all of the oligonucleotides in the plurality of oligonucleotide species comprise two strands and a first overhang and a second overhang, where each overhang is capable of hybridizing to a target nucleic acid overhang, where each oligonucleotide species has a unique overhang sequence and length; and c) each oligonucleotide in the plurality of oligonucleotide species comprises at least two oligonucleotide overhang identification sequences specific to one or more features of the first and second oligonucleotide overhangs.

Provided in some aspects are methods for modifying nucleic acid ends, comprising a) combining a nucleic acid composition comprising target nucleic acids and a plurality of oligonucleotide species, where i) some or all of the oligonucleotides in the plurality of oligonucleotide species comprise two strands and an overhang at a first end and one or more modified nucleotides at a second end, where the overhang is capable of hybridizing to a target nucleic acid overhang, where each oligonucleotide species has a unique overhang sequence and length, ii) some or all of the target nucleic acids comprise an overhang, iii) each oligonucleotide in the plurality of oligonucleotide species comprises an oligonucleotide overhang identification sequence specific to one or more features of the oligonucleotide overhang, and iv) the nucleic acid composition and the plurality of oligonucleotide species is combined under conditions in which oligonucleotide overhangs hybridize to target nucleic acid overhangs having a corresponding length, thereby forming hybridization products; and b) contacting the hybridization products with a strand-displacing polymerase, thereby forming blunt-ended nucleic acid fragments.

Also provided in some aspects are compositions comprising a plurality of oligonucleotide species, where a) some or all of the oligonucleotides in the plurality of oligonucleotide species comprise two strands and an overhang at a first end and one or more modified nucleotides at a second end, where the overhang is capable of hybridizing to a target nucleic acid overhang, where each oligonucleotide species has a unique overhang sequence and length; and b) each oligonucleotide in the plurality of oligonucleotide species comprises an oligonucleotide overhang identification sequence specific to one or more features of the oligonucleotide overhang.

Provided in some aspects are methods for modifying nucleic acid ends, comprising a) combining a nucleic acid composition comprising target nucleic acids and a plurality of oligonucleotide species, where i) the oligonucleotides in the plurality of oligonucleotide species comprise two strands and an overhang at a first end, where the first end overhang comprises a palindromic sequence; ii) some or all of the oligonucleotides in the plurality of oligonucleotide species comprise an overhang at a second end, where the second end overhang is capable of hybridizing to a target nucleic acid overhang, where each oligonucleotide species has a unique second end overhang sequence and length, iii) some or all of the target nucleic acids comprise an overhang, iv) each oligonucleotide in the plurality of oligonucleotide species comprises an oligonucleotide overhang identification sequence specific to one or more features of the second end overhang, v) each oligonucleotide in the plurality of oligonucleotide species comprises one or more modified nucleotides, and vi) the nucleic acid composition and the plurality of oligonucleotide species is combined under conditions in which first end overhangs hybridize to other first end overhangs and second end overhangs hybridize to target nucleic acid overhangs having a corresponding length, thereby forming circular hybridization products; b) contacting the hybridization products with an exonuclease, thereby generating exonuclease-treated hybridization products; c) shearing the exonuclease-treated hybridization products, thereby generating sheared exonuclease-treated hybridization products; and d) separating fragments comprising a sequence in the oligonucleotide species from fragments not comprising a sequence in the oligonucleotide species, thereby generating separated, sheared, exonuclease-treated hybridization products.

Also provided in some aspects are compositions comprising a plurality of oligonucleotide species, where a) the oligonucleotides in the plurality of oligonucleotide species comprise two strands and an overhang at a first end, where the first end overhang comprises a palindromic sequence; b) some or all of the oligonucleotides in the plurality of oligonucleotide species comprise an overhang at a second end, where the second end overhang is capable of hybridizing to a target nucleic acid overhang, where each oligonucleotide species has a unique second end overhang sequence and length; c) each oligonucleotide in the plurality of oligonucleotide species comprises an oligonucleotide overhang identification sequence specific to one or more features of the second end overhang; and d) each oligonucleotide in the plurality of oligonucleotide species comprises one or more modified nucleotides.

Provided in some aspects are methods for modifying nucleic acid ends, comprising a) combining a nucleic acid composition comprising target nucleic acids and a plurality of oligonucleotide species, where i) some or all of the oligonucleotides in the plurality of oligonucleotide species comprise (1) two strands and an overhang at a first end and two non-complementary strands at a second end, or (2) one strand capable of forming a hairpin structure having a single-stranded loop and an overhang; where the overhang is capable of hybridizing to a target nucleic acid overhang, where each oligonucleotide species has a unique overhang sequence and length, ii) some or all of the target nucleic acids comprise an overhang, iii) each oligonucleotide in the plurality of oligonucleotide species comprises an oligonucleotide overhang identification sequence specific to one or more features of the oligonucleotide overhang, and iv) the nucleic acid composition and the plurality of oligonucleotide species is combined under conditions in which oligonucleotide overhangs hybridize to target nucleic acid overhangs having a corresponding length, thereby forming hybridization products; and b) contacting the hybridization products with a strand-displacing polymerase, thereby forming blunt-ended nucleic acid fragments.

Also provided in some aspects are compositions comprising a plurality of oligonucleotide species, where a) some or all of the oligonucleotides in the plurality of oligonucleotide species comprise i) two strands and an overhang at a first end and two non-complementary strands at a second end, or ii) one strand capable of forming a hairpin structure having a single-stranded loop and an overhang; where the overhang is capable of hybridizing to a target nucleic acid overhang, where each oligonucleotide species has a unique overhang sequence and length; and b) each oligonucleotide in the plurality of oligonucleotide species comprises an oligonucleotide overhang identification sequence specific to one or more features of the oligonucleotide overhang.

Provided in some aspects are methods for modifying nucleic acid ends, comprising combining a nucleic acid composition comprising target nucleic acids and a plurality of oligonucleotide species, where a) some or all of the oligonucleotides in the plurality of oligonucleotide species comprise at least one overhang comprising RNA nucleotides, where the overhang is capable of hybridizing to a target nucleic acid overhang, where each oligonucleotide species has a unique overhang sequence and length, b) some or all of the target nucleic acids comprise an overhang, c) each oligonucleotide in the plurality of oligonucleotide species comprises an oligonucleotide overhang identification sequence specific to one or more features of the oligonucleotide overhang, and d) the nucleic acid composition and the plurality of oligonucleotide species is combined under conditions in which oligonucleotide overhangs hybridize to target nucleic acid overhangs having a corresponding length, thereby forming hybridization products.

Also provided in some aspects are compositions comprising a plurality of oligonucleotide species, where a) some or all of the oligonucleotides in the plurality of oligonucleotide species comprise at least one overhang comprising RNA nucleotides, where the overhang is capable of hybridizing to a target nucleic acid overhang, where each oligonucleotide species has a unique overhang sequence and length; and b) each oligonucleotide in the plurality of oligonucleotide species comprises an oligonucleotide overhang identification sequence specific to one or more features of the oligonucleotide overhang.

Provided in some aspects are methods for producing a nucleic acid library, comprising a) combining a nucleic acid composition comprising target nucleic acids and a first pool of oligonucleotide species, where i) some or all of the target nucleic acids comprise an overhang, ii) some or all of the oligonucleotides in the first pool of oligonucleotide species comprise an overhang capable of hybridizing to a target nucleic acid overhang, where each oligonucleotide species has a unique overhang sequence and length, iii) each oligonucleotide in the first pool of oligonucleotide species comprises an oligonucleotide overhang identification sequence specific to one or more features of the oligonucleotide overhang, iv) each oligonucleotide in the first pool of oligonucleotide species comprises a first primer binding domain, and v) the nucleic acid composition and the first pool of oligonucleotide species are combined under conditions in which oligonucleotide overhangs hybridize to target nucleic acid overhangs having a corresponding length, thereby forming a first set of combined products; b) cleaving the first set of combined products, thereby forming cleaved products; and c) combining the cleaved products and a second pool of oligonucleotide species, where i) each oligonucleotide in the second pool of oligonucleotide species comprises a first end and a second end, ii) each oligonucleotide in the second pool of oligonucleotide species comprises a second primer binding domain, where the first primer binding domain and the second primer binding domain are different, and iii) the cleaved products and the second pool of oligonucleotide species are combined under conditions in which the oligonucleotides in the second pool of oligonucleotide species attach at the first end to at least one end of the cleaved products, thereby forming a second set of combined products.

Also provided in some aspects are compositions comprising a) a first pool of oligonucleotide species, where i) some or all of the oligonucleotides in the first pool of oligonucleotide species comprise an overhang capable of hybridizing to a target nucleic acid overhang, where each oligonucleotide species has a unique overhang sequence and length, ii) each oligonucleotide in the first pool of oligonucleotide species comprises an oligonucleotide overhang identification sequence specific to one or more features of the oligonucleotide overhang, and iii) each oligonucleotide in the first pool of oligonucleotide species comprises a first primer binding domain; and b) a second pool of oligonucleotide species, where i) each oligonucleotide in the second pool of oligonucleotide species comprises a first end and a second end, and ii) each oligonucleotide in the second pool of oligonucleotide species comprises a second primer binding domain, where the first primer binding domain and the second primer binding domain are different.

Provided in some aspects are methods for producing a nucleic acid library, comprising a) combining a nucleic acid composition comprising target nucleic acids and a first pool of oligonucleotide species, where i) some or all of the target nucleic acids comprise an overhang, ii) some or all of the oligonucleotides in the first pool of oligonucleotide species comprise an overhang at a first end capable of hybridizing to a target nucleic acid overhang, where each oligonucleotide species has a unique overhang sequence and length, iii) each oligonucleotide in the first pool of oligonucleotide species comprises an oligonucleotide overhang identification sequence specific to one or more features of the oligonucleotide overhang, iv) each oligonucleotide in the first pool of oligonucleotide species comprises a first primer binding domain, and v) the nucleic acid composition and the first pool of oligonucleotide species are combined under conditions in which oligonucleotide overhangs hybridize to target nucleic acid overhangs having a corresponding length, thereby forming a first set of combined products; b) cleaving the first set of combined products, thereby forming cleaved products; and c) combining the cleaved products and a second pool of oligonucleotide species, where i) each oligonucleotide in the second pool of oligonucleotide species comprises a first strand and a second strand, where the first strand is shorter than the second strand, and where the first strand and the second strand are complementary at a first end of the oligonucleotide and the second strand comprises a single strand at a second end of the oligonucleotide, ii) each oligonucleotide in the second pool of oligonucleotide species comprises an oligonucleotide identification sequence specific to the second pool of oligonucleotide species, iii) each oligonucleotide in the second pool of oligonucleotide species comprises a second primer binding domain on the second strand, where the first primer binding domain and the second primer binding domain are different, and iv) the cleaved products and the second pool of oligonucleotide species are combined under conditions in which oligonucleotides in the second pool of oligonucleotide species attach to at least one end of the cleaved products, thereby forming a second set of combined products.

Also provided in some aspects are compositions comprising a) a first pool of oligonucleotide species, where i) some or all of the oligonucleotides in the first pool of oligonucleotide species comprise an overhang capable of hybridizing to a target nucleic acid overhang, where each oligonucleotide species has a unique overhang sequence and length, ii) each oligonucleotide in the first pool of oligonucleotide species comprises an oligonucleotide overhang identification sequence specific to one or more features of the oligonucleotide overhang, and iii) each oligonucleotide in the first pool of oligonucleotide species comprises a first primer binding domain; and b) a second pool of oligonucleotide species, where i) each oligonucleotide in the second pool of oligonucleotide species comprises a first strand and a second strand, where the first strand is shorter than the second strand, and where the first strand and the second strand are complementary at a first end of the oligonucleotide and the second strand comprises a single strand at a second end of the oligonucleotide, ii) each oligonucleotide in the first pool of oligonucleotide species comprises an oligonucleotide identification sequence specific to the second pool of oligonucleotide species, and iii) each oligonucleotide in the second pool of oligonucleotide species comprises a second primer binding domain on the second strand, where the first primer binding domain and the second primer binding domain are different.

Provided in some aspects are methods for producing a nucleic acid library, comprising a) contacting a nucleic acid composition comprising target nucleic acids with an agent comprising a phosphatase activity under conditions in which target nucleic acids are dephosphorylated, thereby generating dephosphorylated target nucleic acids, where some or all of the target nucleic acids comprise an overhang; and b) combining the dephosphorylated target nucleic acids and a plurality of oligonucleotide species, where i) some or all of the oligonucleotides in the plurality of oligonucleotide species comprise an overhang capable of hybridizing to a target nucleic acid overhang, where each oligonucleotide species has a unique overhang sequence and length; ii) each oligonucleotide in the plurality of oligonucleotide species comprises an oligonucleotide overhang identification sequence specific to one or more features of the oligonucleotide overhang; and iii) the nucleic acid composition and the plurality of oligonucleotide species is combined under conditions in which oligonucleotide overhangs hybridize to target nucleic acid overhangs having a corresponding length, thereby forming hybridization products.

Provided in some aspects are methods for analyzing nucleic acid comprising a) combining a nucleic acid composition comprising target nucleic acids and a plurality of oligonucleotide species, where i) some or all of the target nucleic acids comprise an overhang; ii) some or all of the oligonucleotides in the plurality of oligonucleotide species comprise an overhang capable of hybridizing to a target nucleic acid overhang, where each oligonucleotide species has a unique overhang sequence and length; iii) each oligonucleotide in the plurality of oligonucleotide species comprises an oligonucleotide overhang identification sequence specific to one or more features of the oligonucleotide overhang; and iv) the nucleic acid composition and the plurality of oligonucleotide species is combined under conditions in which oligonucleotide overhangs hybridize to target nucleic acid overhangs having a corresponding length, thereby forming hybridization products; b) sequencing the hybridization products, or amplification products thereof, by a sequencing process, thereby generating sequence reads, where the sequence reads comprise forward sequence reads and reverse sequence reads; and c) analyzing overhang information associated with overhang identification sequences that indicate presence of an overhang for the reverse sequence reads, thereby generating an analysis, and omitting from the analysis overhang information associated with overhang identification sequences that indicate presence of an overhang for the forward sequence reads.

Provided in some aspects are methods for assaying a population of nucleic acids, comprising assaying nucleic acid overhangs of a population of nucleic acids in a sample, thereby generating an overhang profile of the population; and based on the overhang profile, determining a characteristic of the sample.

Also provided are systems, machines and computer program products that, in some embodiments, carry out certain methods or parts of certain methods described herein.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 1A shows the stem-loop structure of a sequencing adapter with Illumina priming sites (P5 and P7) incorporated, with a single 3' overhanging thymine (T) for thymine-adenine (TA) ligation and a phosphorylated 5' end. FIG. 1B shows an adapter that is not phosphorylated, but includes unique end identifiers (UEIs) indicating the type and length of overhang (OV) present. FIG. 1C shows an adapter that further includes unique molecular identifiers (UMIs). A phosphorothioate bond is present between the last two bases on both ends of the oligo/adapter to prevent chew back from nuclease activity. *, phosphorothioate bond. G, guanine (RNA base). T, thymine. UEI, unique end identifier.

UMI, unique molecular identifier. OV, overhang. P, phosphate. P5, Illumina P5 adapter sequence. P7, Illumina P7 adapter sequence.

Figure 2B:
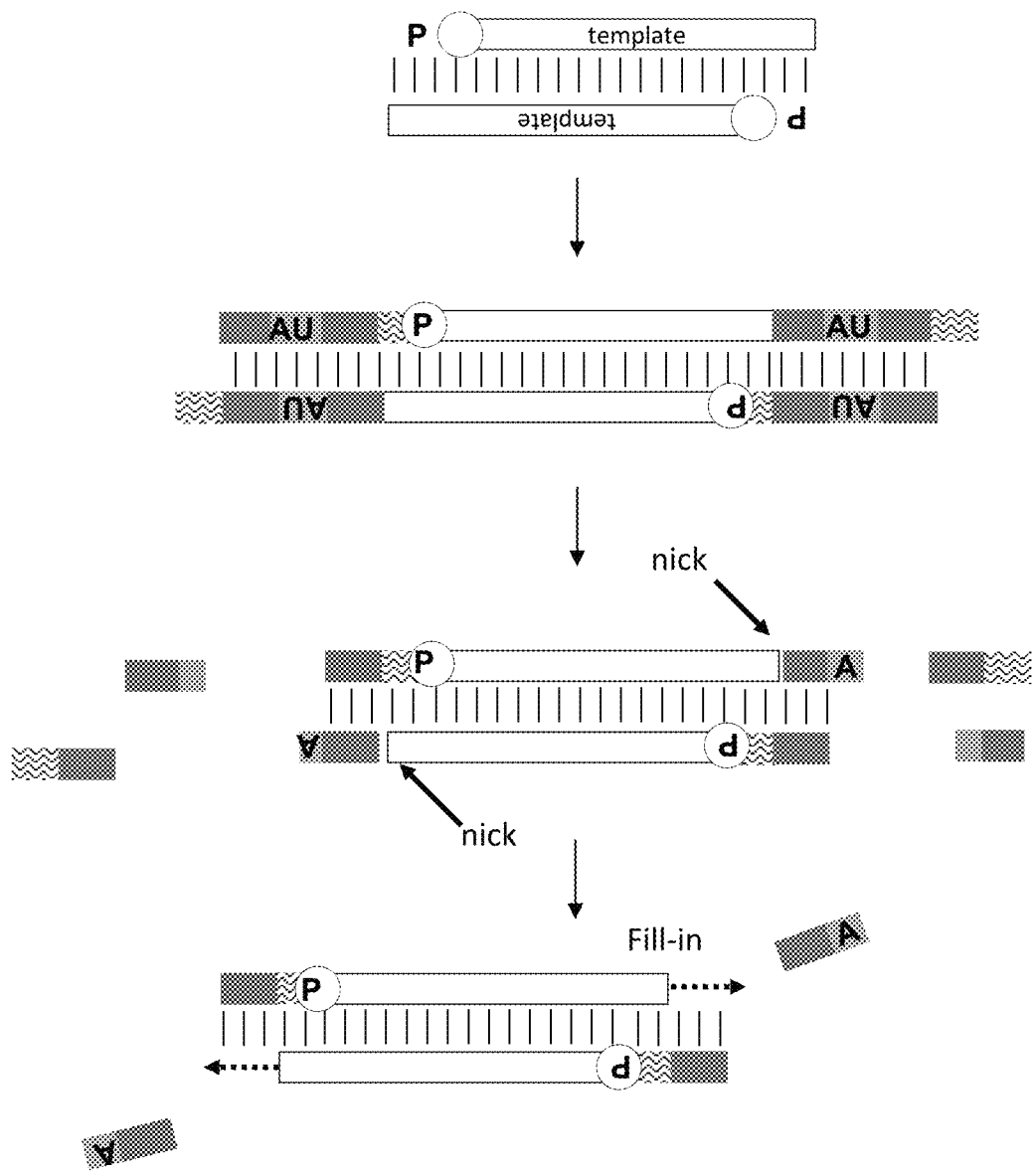

FIG. 2A shows examples of adapters with a short insert (top) or a long insert (bottom). An example of a short insert adapter with 5' overhangs is shown on the top left and an example of a short insert adapter with 3' overhangs is shown on the top right. OV, overhang. UEI, unique end identifier. A, adenine. U, uracil or deoxyuridine. FIG. 2B shows an example workflow using a short insert adapter with 3' overhangs. A first step includes phosphorylating the DNA template. As illustrated here, an example template has 3' overhangs on top and bottom strands. A next step includes ligating the 3' overhanging UEI adapters to the phosphorylated template. Nicks are present in the ligation product as shown. A further step includes enzymatically cutting UEI adapter DNA strand at deoxyuridine. A further step includes filling-in at nicks using a strand-displacing polymerase to form a complete double-stranded molecule. Unligated or residual UEI adapters remaining intact or filled-in can be eliminated. A, adenine. U, uracil or deoxyuridine. P, phosphate.

Figure 3:
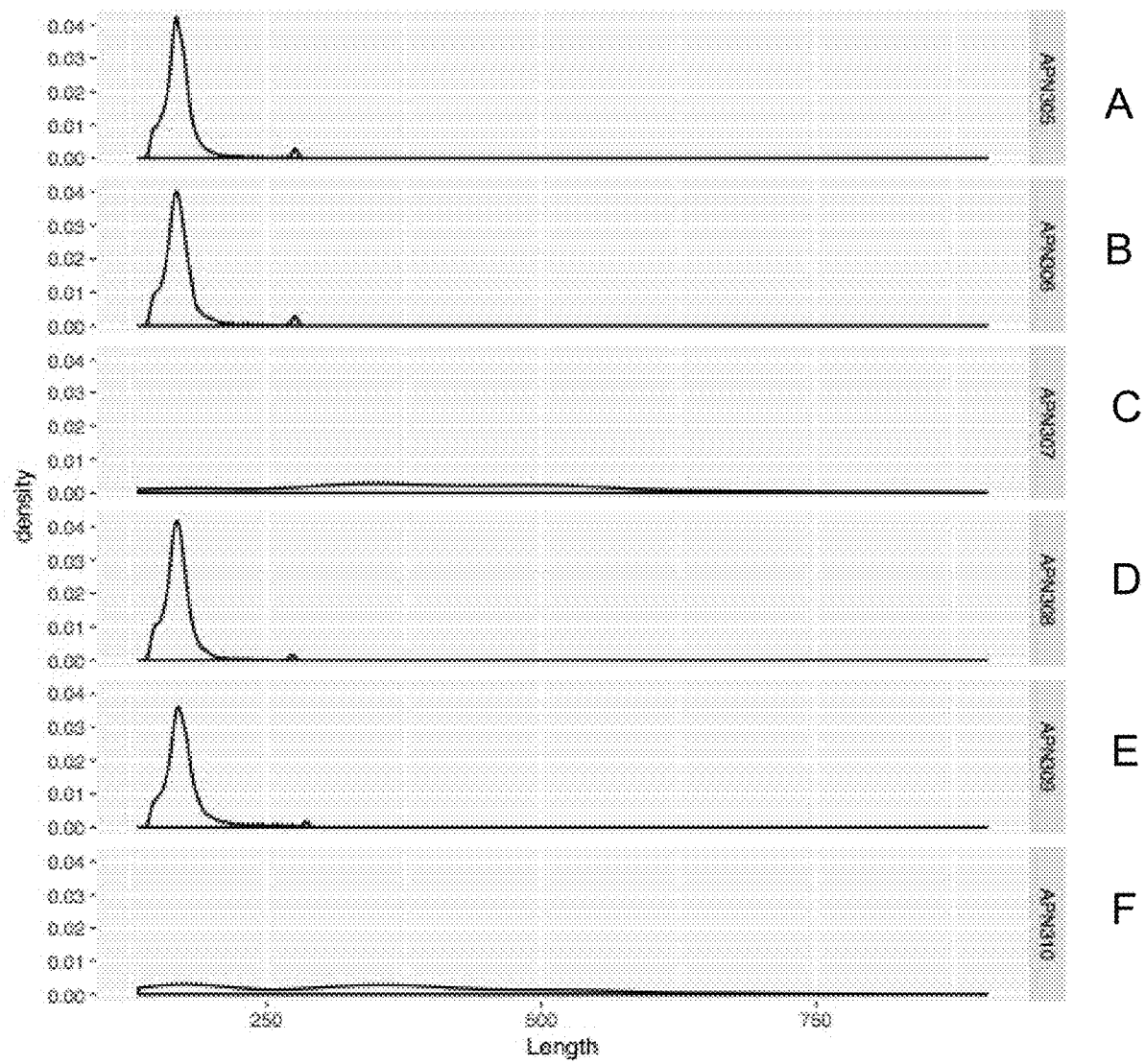

FIG. 3 shows mapped library molecule lengths from original DNA extract (not size-selected) and size selected via dual SPRI selection into high molecular weight (HMW) and low molecular weight (LMW) fragments. Panel A shows results for indiv1 all DNA, purification style 1. Panel B shows results for indiv1 all DNA, purification style 2. Panel C shows results for indiv1 HMW fraction. Panel D shows results for indiv1 LMW fraction. Panel E shows results for indiv2 LMW fraction. Panel F shows results for indiv2 HMW fraction.

Figure 4:
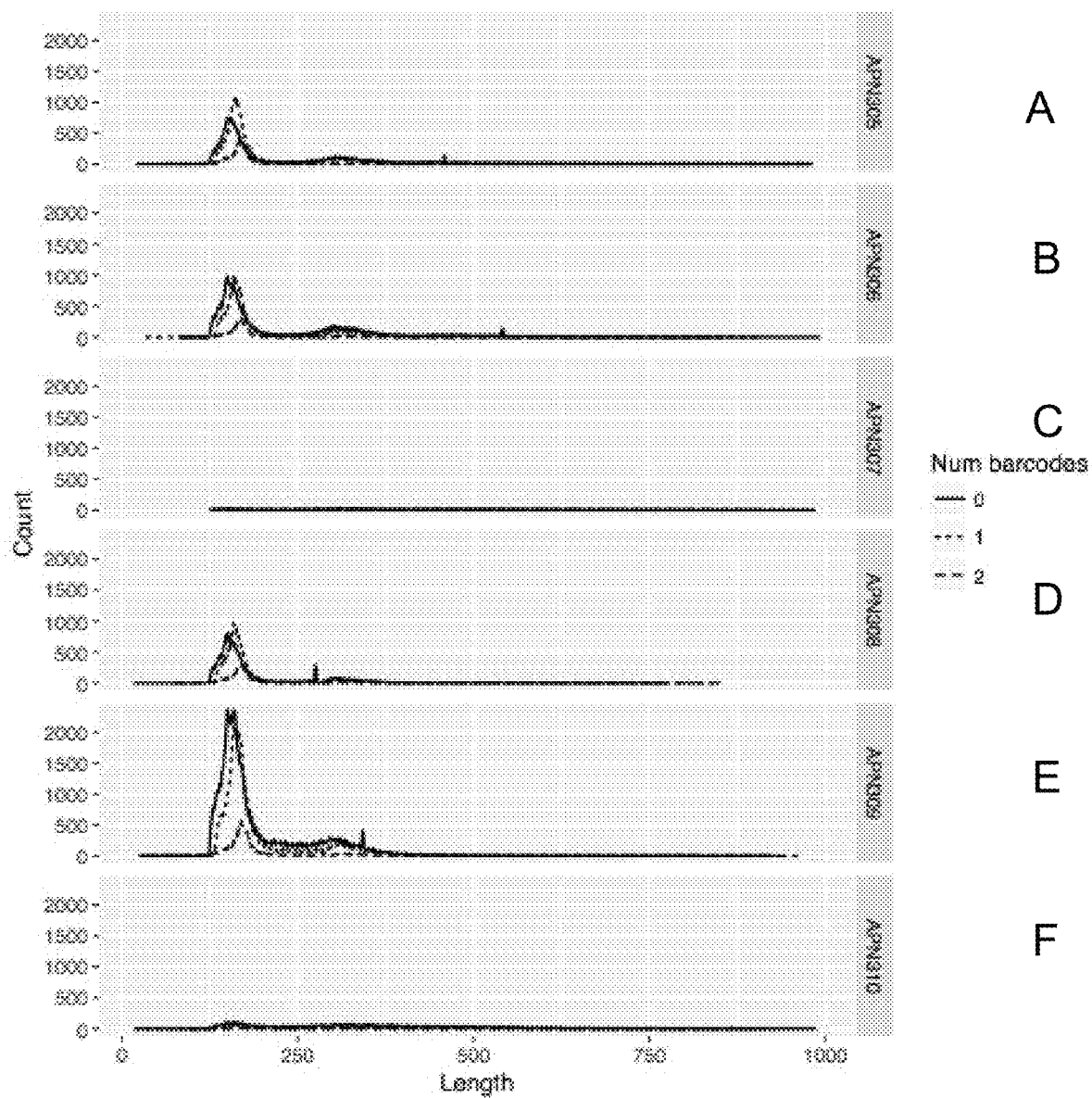

FIG. 4 shows paired-end and mapped reads with unique end identifiers (UEIs, "barcodes") present on no end (0), one end (1), or correctly on both ends (2). Panel A shows results for indiv1 all DNA, purification style 1. Panel B shows results for indiv1 all DNA, purification style 2. Panel C shows results for indiv1 HMW fraction. Panel D shows results for indiv1 LMW fraction. Panel E shows results for indiv2 LMW fraction. Panel F shows results for indiv2 HMW fraction.

Figure 5:
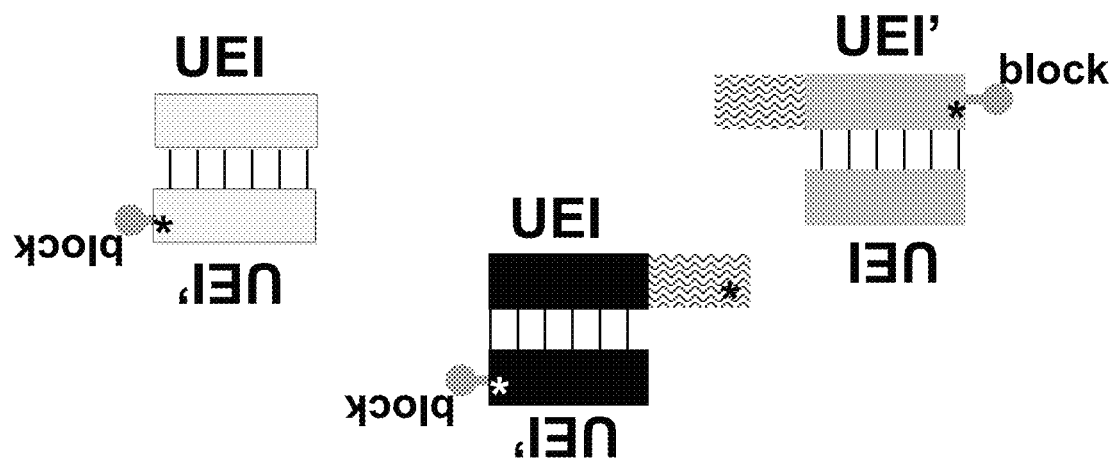

FIG. 5 shows examples of unique end identifier (UEI) adapters with a blocker at various locations.

Figure 6:
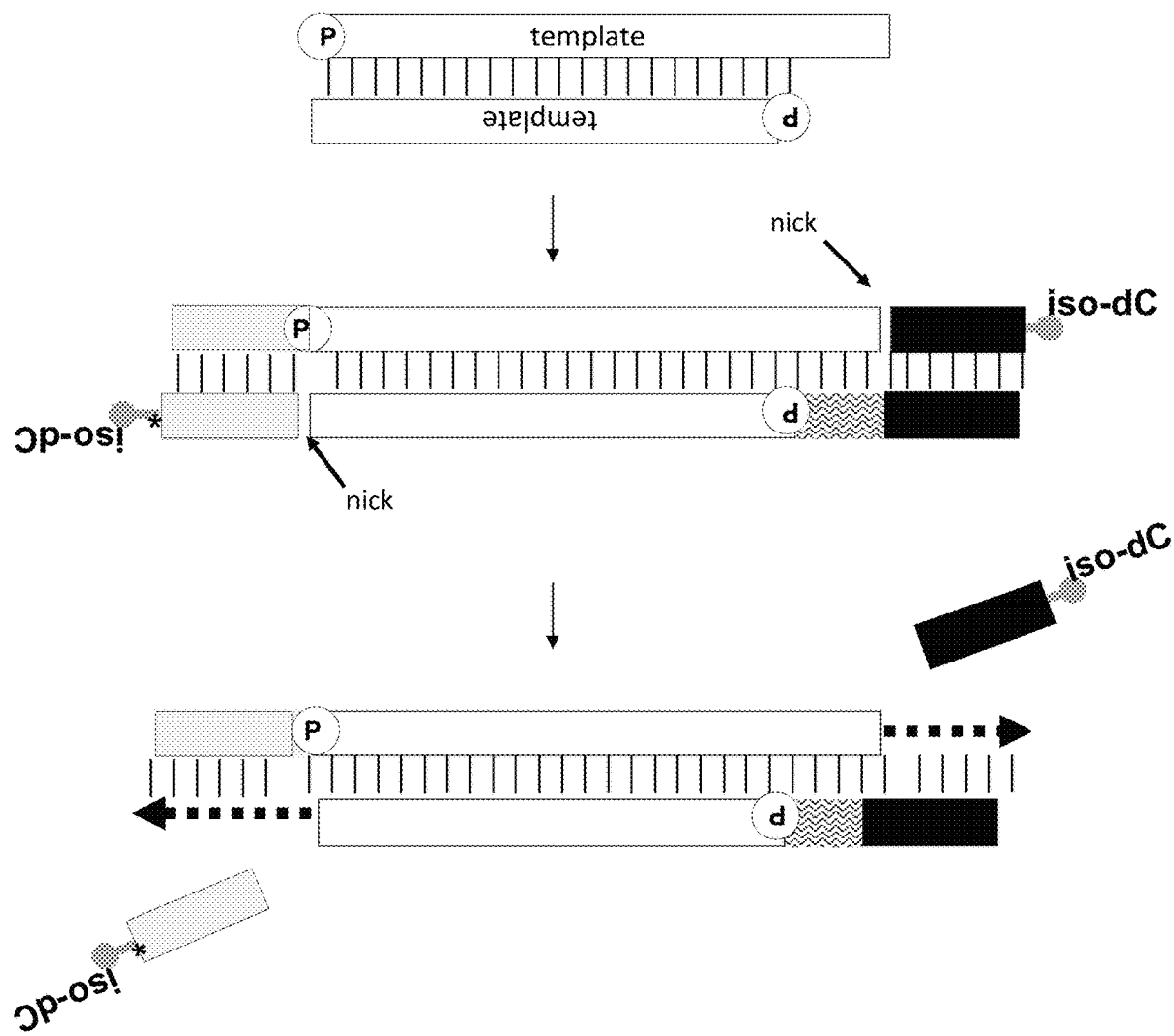

FIG. 6 shows an example workflow that includes ligating blocked unique end identifier (UEI) adapters to a phosphorylated template, filling in at nicks, and creating a blunt-ended and double-stranded molecule. P, phosphate. UEI, unique end identifier. Iso-dC, isodeoxy-cytosine.

Figure 7A:
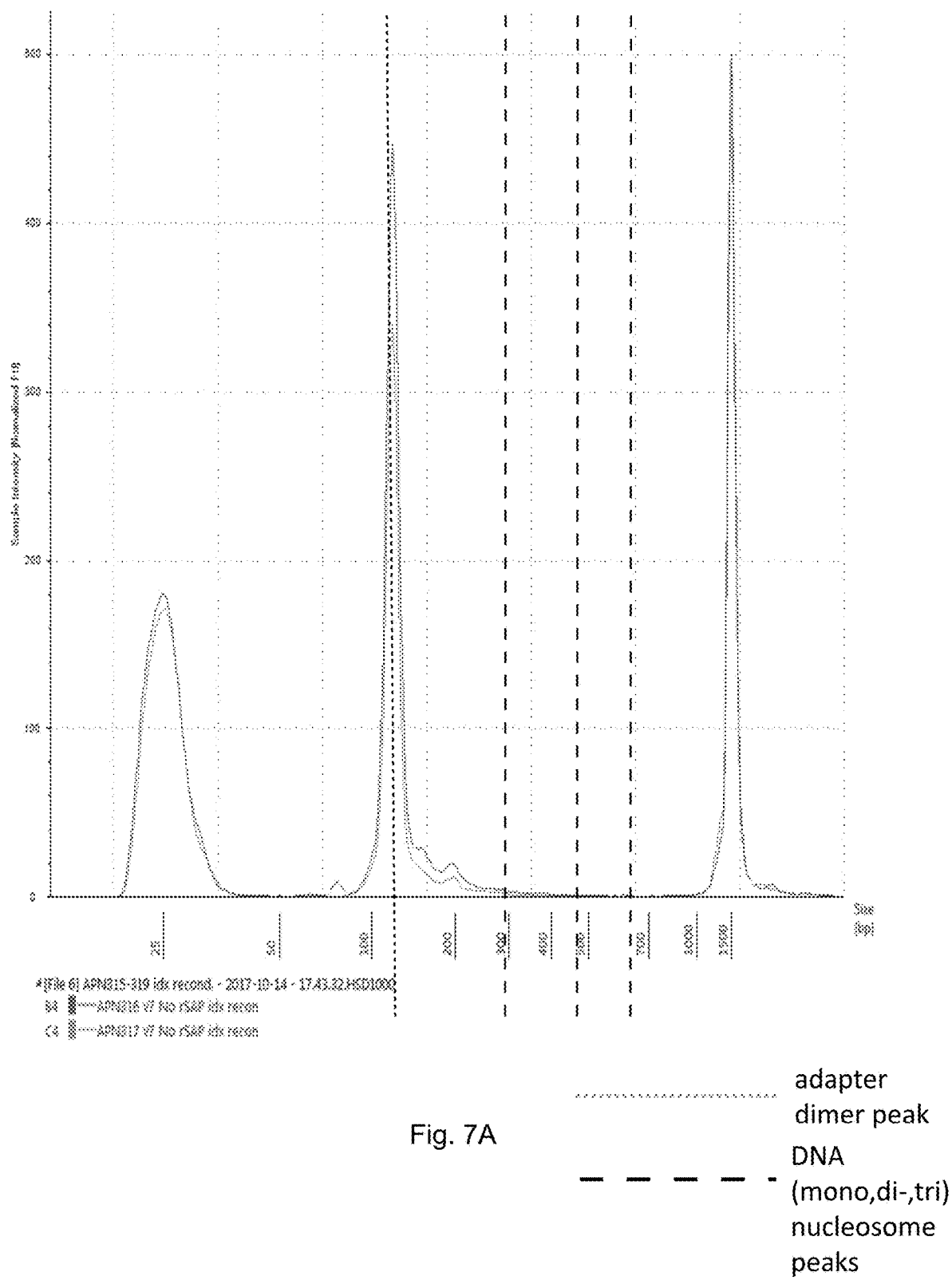
Figure 7B:
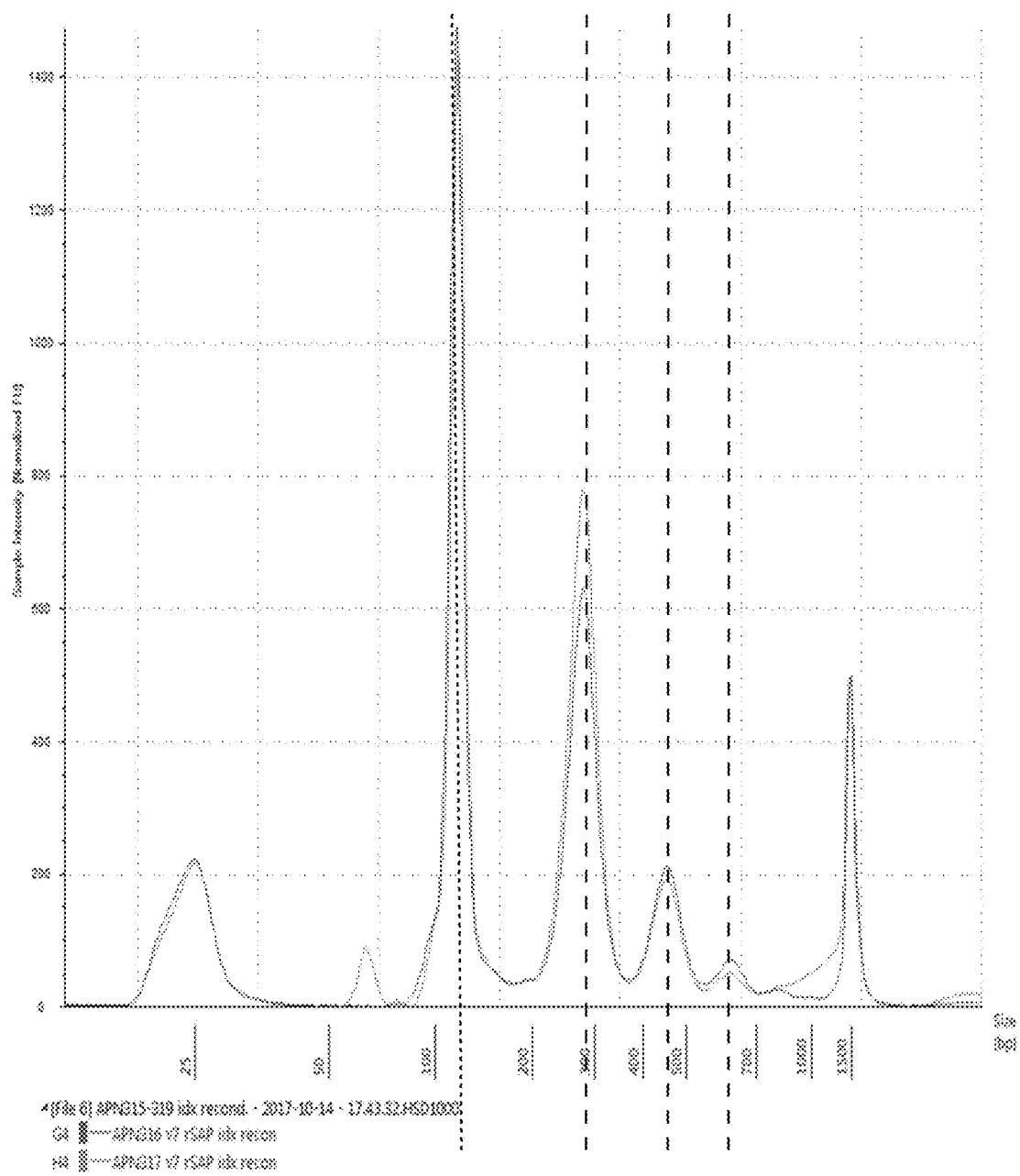
Figure 7C:
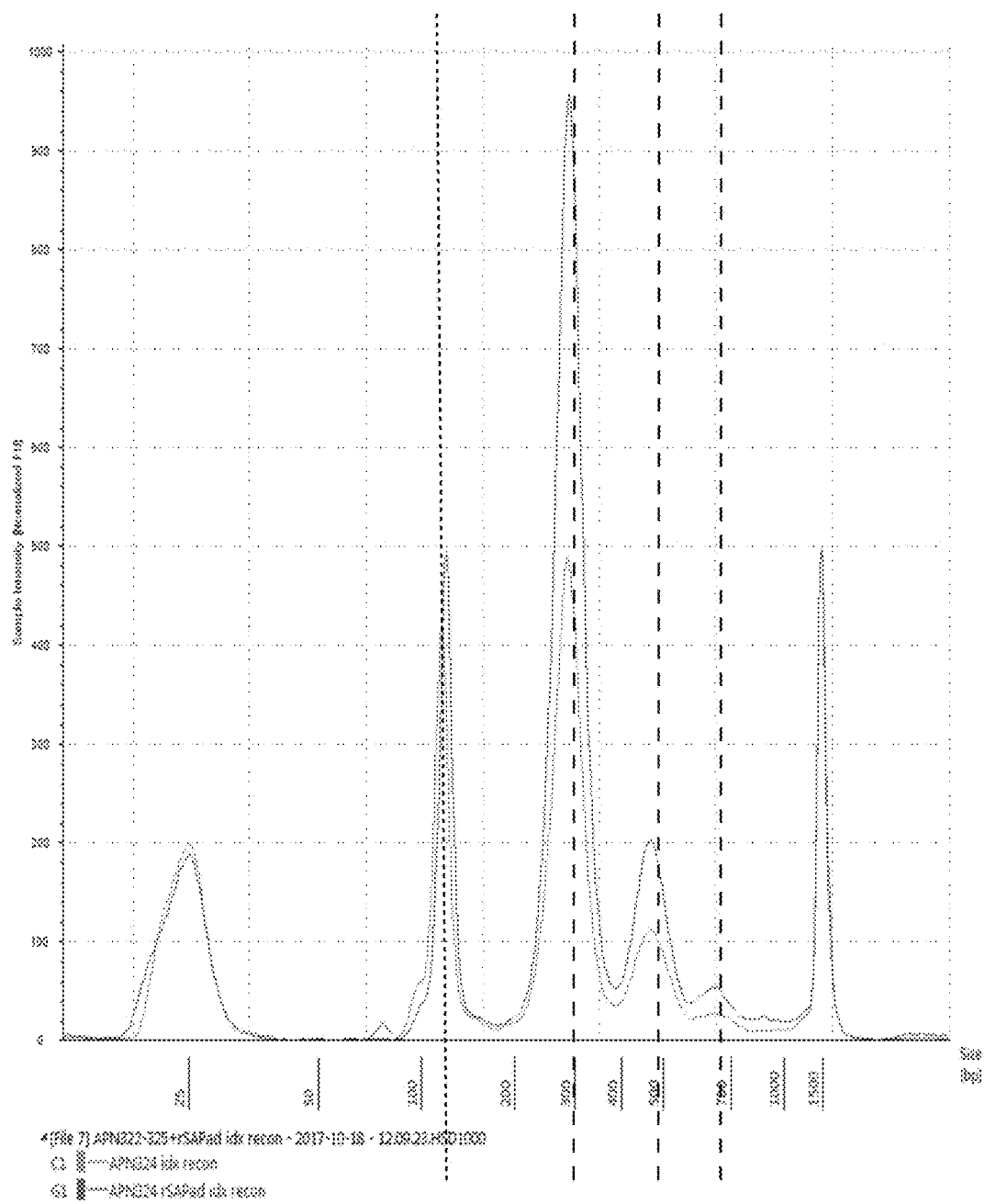

FIG. 7A to FIG. 7C show tapestation results (i.e., Agilent Tapestation 4200) depicting size distribution of cell-free DNA fragments in sequencing libraries under three conditions: no phosphatase treatment (FIG. 7A), phosphatase treatment of cell-free DNA template (FIG. 7B), and phosphatase treatment of template and library adapters (FIG. 7C). Adapter-dimer artifacts are expected at ~120 bp. One nucleosome is expected to peak at 280-290 bp with increments of ~170 bp for additional nucleosomes. FIG. 7A to FIG. 7C demonstrate improvement following phosphatase treatment illustrated by a reduction in adapter dimers and relative increase in cell-free DNA-associated peaks.

Figure 8A:
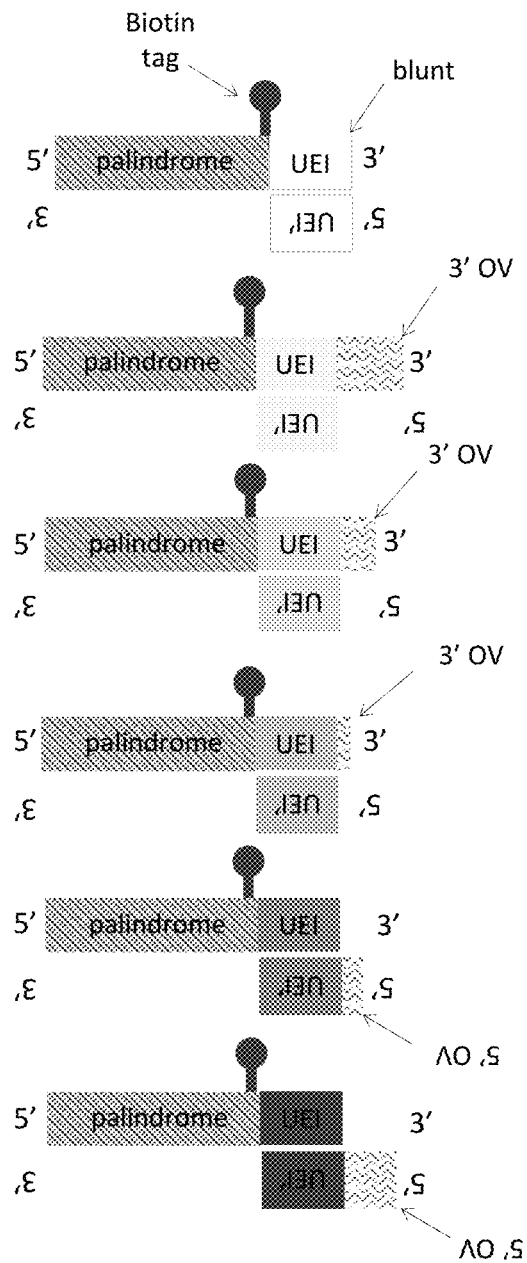
Figure 8B:
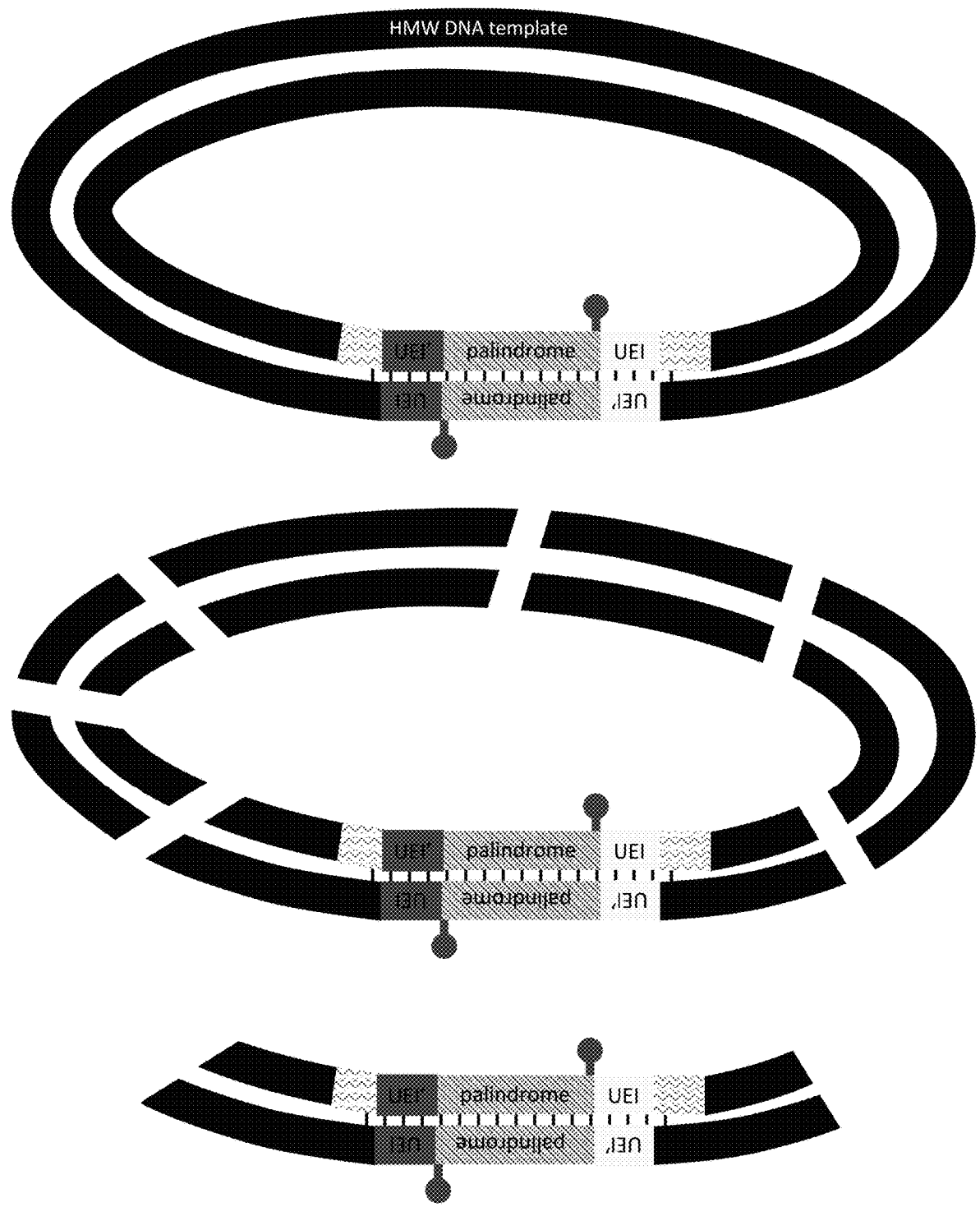

FIG. 8A shows an example adapter set, with one 5' palindromic overhang and with 5' and 3' random overhangs of varying lengths. FIG. 8B shows an overhanging adapter set ligated to a long dsDNA fragment (high molecular weight (HMW) DNA template) with native 5' and 3' overhangs. The illustration in FIG. 8B depicts, from top to bottom, examples after step 3 (ligation), step 5 (shearing), and step 6 (isolate biotinylated fragments) of a "mate pair" DNA preparation. UEI, unique end identifier. OV, overhang.

Figure 9A:
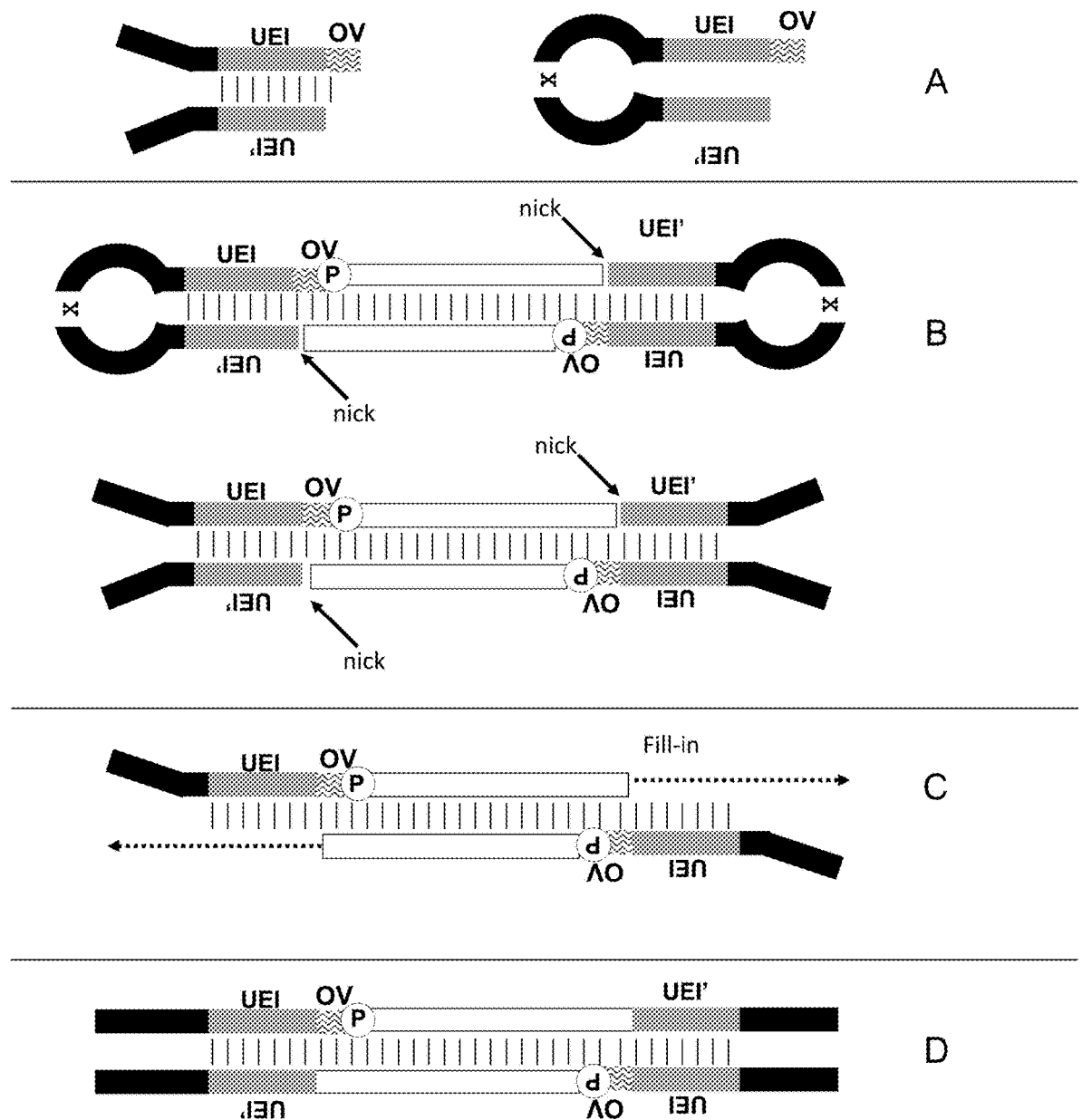

FIG. 9A shows an example method for attaching a unique end identifier (UEI) sequence in a first phase using strand-displacing polymerase, and sequencer-specific sequence (e.g., sequencing adapter) in a second phase. Panel A shows a Y adapter (left) and a hairpin adapter (right) composed of a unique end identifier (UEI) sequence (shown in gray) and random sequence (shown in black). In some instances, the Y adapter is a cleaved version of the hairpin adapter. Panel B shows ligation of the hairpin adapter to a target nucleic acid, which ligation product can be cleaved. After cleavage, the ligation product is the same as the Y-adapter ligation product. Panel C shows a fill-in step at nicks with a strand-displacing polymerase to create a fully complementary double-stranded, blunt-ended fragment. Panel D shows a nucleic acid fragment that is ready for any sequencing library preparation of choice (second phase). X, cleavable site(s). UEI, unique end identifier. OV, overhang. P, phosphate.

Figure 9B:
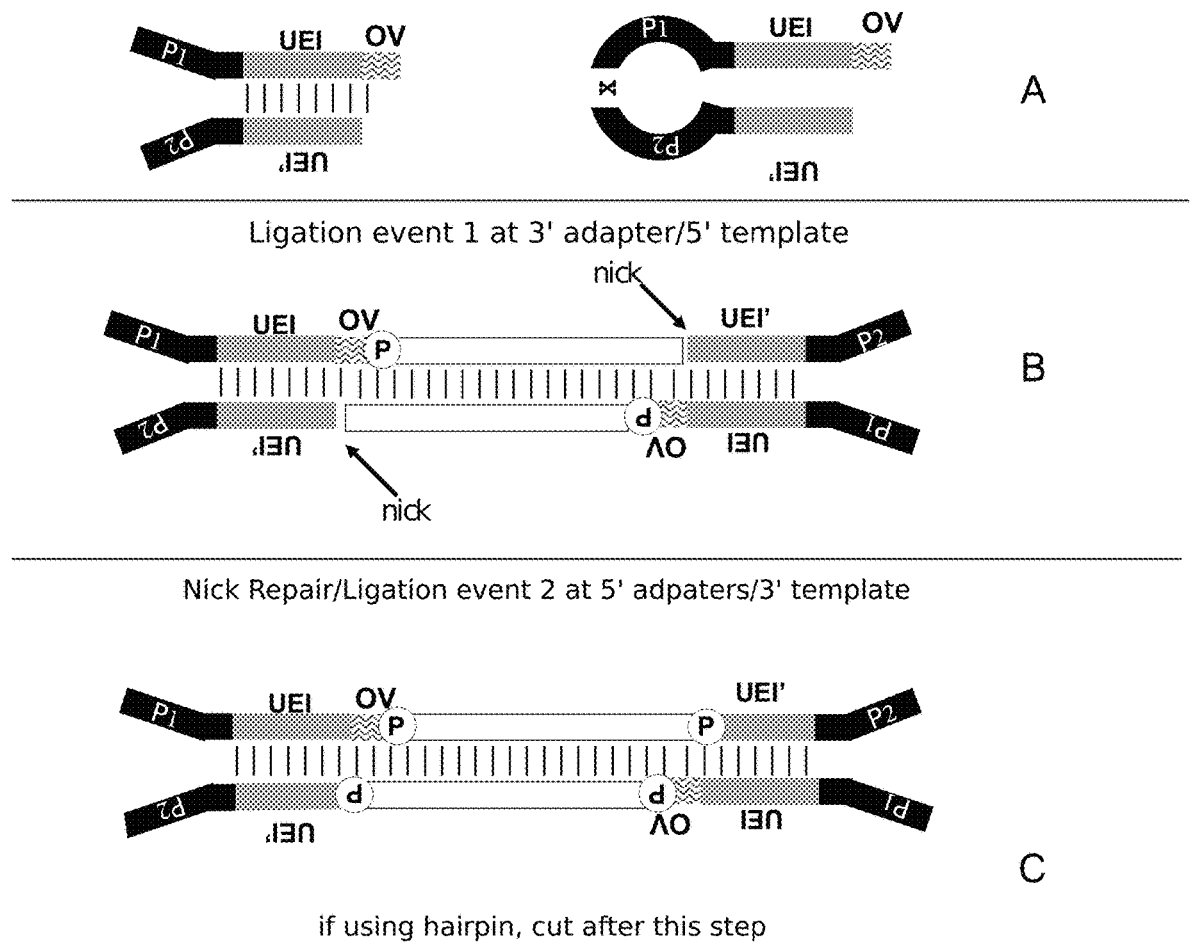

FIG. 9B shows an example method for attaching a Y adapter or a hairpin adapter to the ends of a native nucleic acid fragment. Panel A shows a Y adapter (left) and a hairpin adapter (right) composed of an overhang, a unique end identifier (UEI) sequence (shown in gray), and priming sequences (priming sequence 1 (e.g., Illumina P5 priming sequence) and priming sequence 2 (e.g., Illumina P7 priming sequence); priming region shown in black). Panel B shows ligation of the adapters to a target nucleic acid. Because the adapters are not phosphorylated, the ligation only occurs at the 5' end of the template, leaving nicks. Panel C shows that the nicks are repaired once the 5' adapter strand is phosphorylated and ligates the 3' end of the adapter. After nick repair, the hairpin adapter ligation product can be cleaved (top) at the cleavage site. After cleavage, the ligation product is the same as the Y-adapter ligation product (bottom). This method generates a double-stranded nucleic acid fragment that is ready for any sequencing library preparation of choice (second phase) and/or sequencer of choice, which may depend on the priming sequences used. OV, overhang. P, phosphate. P1, priming sequence 1. P2, priming sequence 2.

Figure 10A:
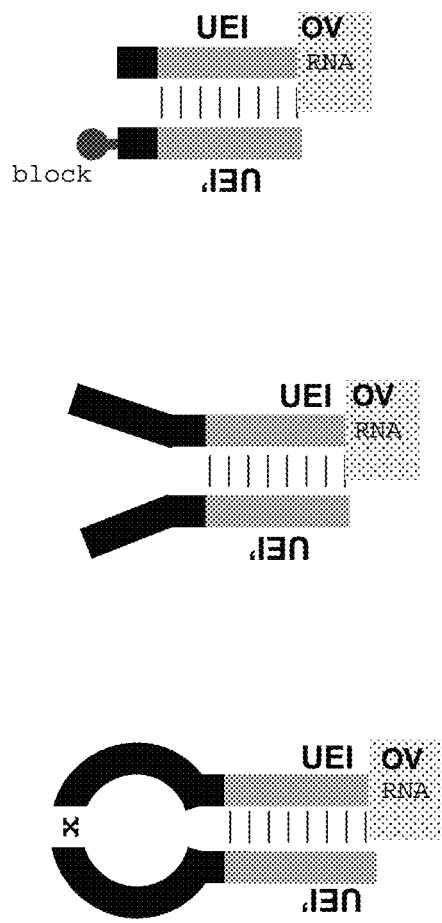
Figure 10B:
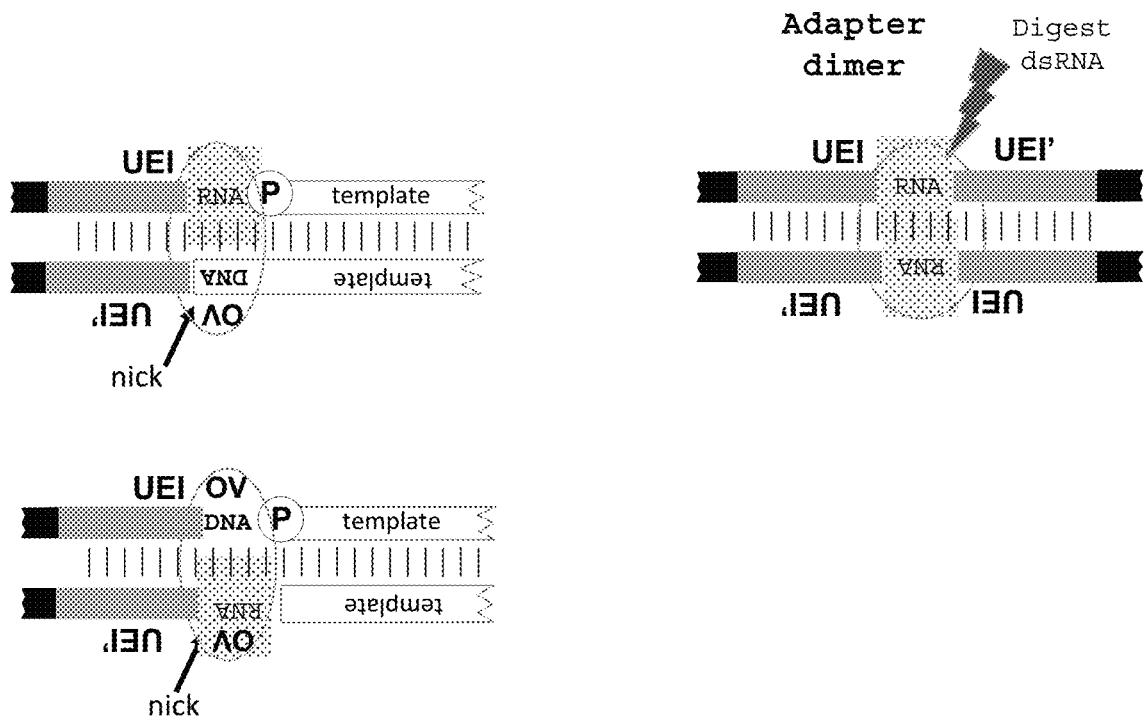
Figure 10C:
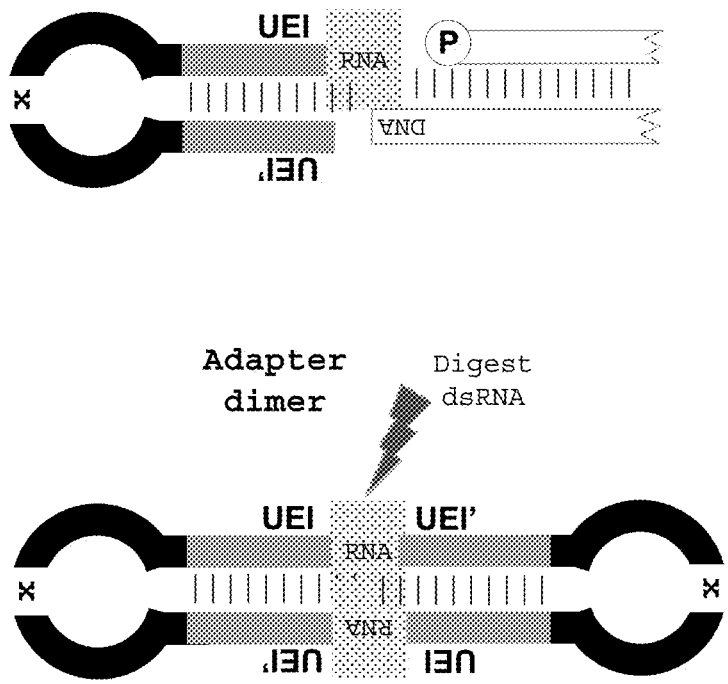

FIGS. 10A-10C show example methods for attaching a unique end identifier (UEI) sequence to native DNA template using an oligonucleotide adapter having RNA bases in the overhang ("RNA overhangs"). FIG. 10A shows example configurations of oligonucleotide adapters having RNA overhangs. Black regions represent non-complementary bases or blocking bases, with or without sequencer specific adapter sequences (e.g., P5, P7). FIGS. 10B and 10C show example methods where RNA overhang ends are ligated to phosphorylated DNA templates, creating DNA-RNA duplexes. Nicks may be repaired by ligase or strand displacing fill-in, depending on oligonucleotide adapter configuration. Adapter dimers having double stranded RNA (dsRNA) can be digested. X, cleavable site(s). UEI, unique end identifier. OV, overhang. P, phosphate.

Figure 11:
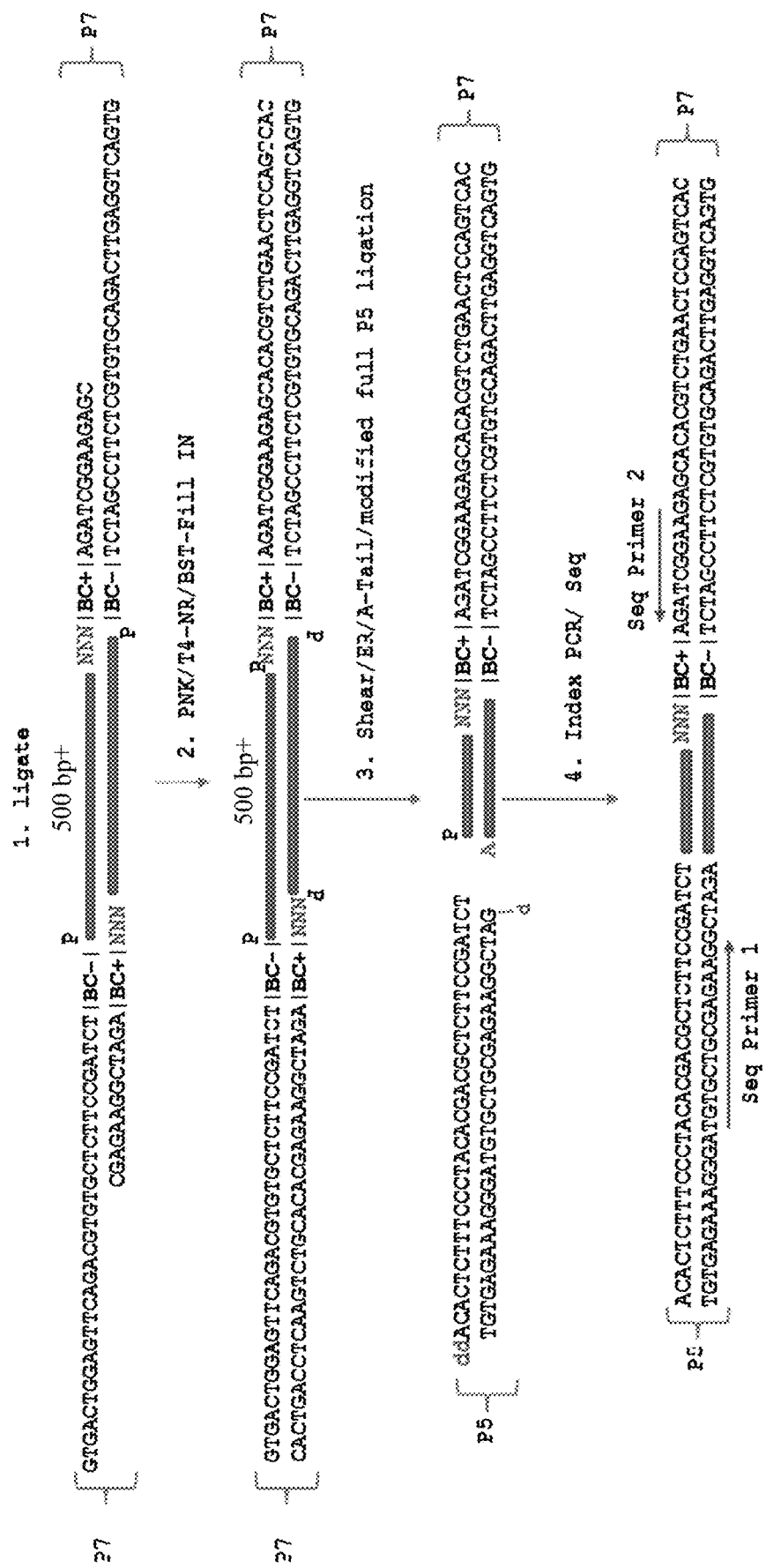

FIG. 11 shows a method for attaching oligonucleotide adapters to high molecular weight (HMW) DNA. FIG. 11 discloses SEQ ID NOS 53-54, 54, 53, 53, 55-56, 55-56 and 55, respectively, in order of appearance.

Figure 12:
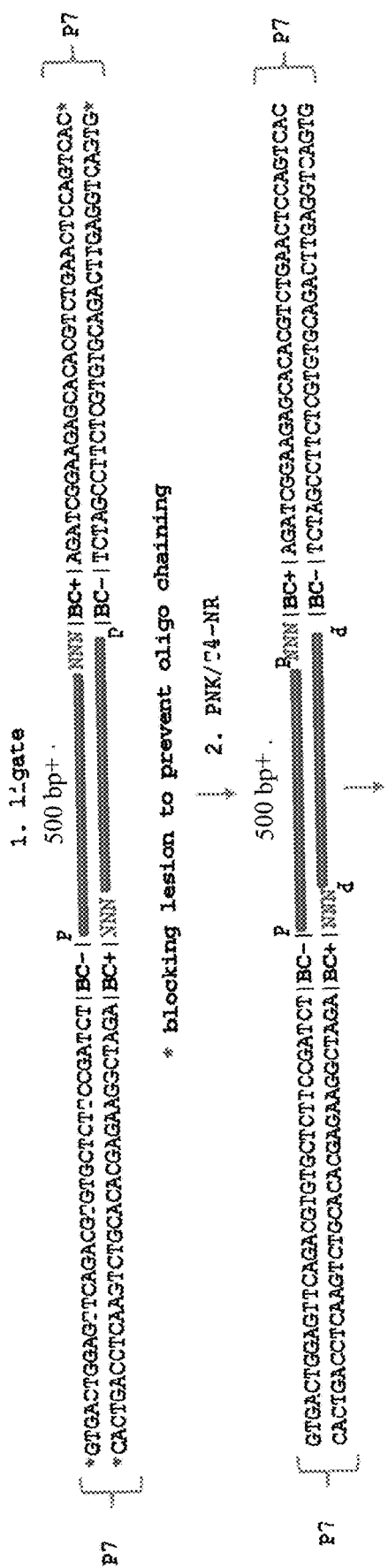

FIG. 12 shows a method for attaching oligonucleotide adapters to high molecular weight (HMW) DNA. FIG. 12 discloses SEQ ID NOS 53, 55, 53 and 55, respectively, in order of appearance.

Figure 13:
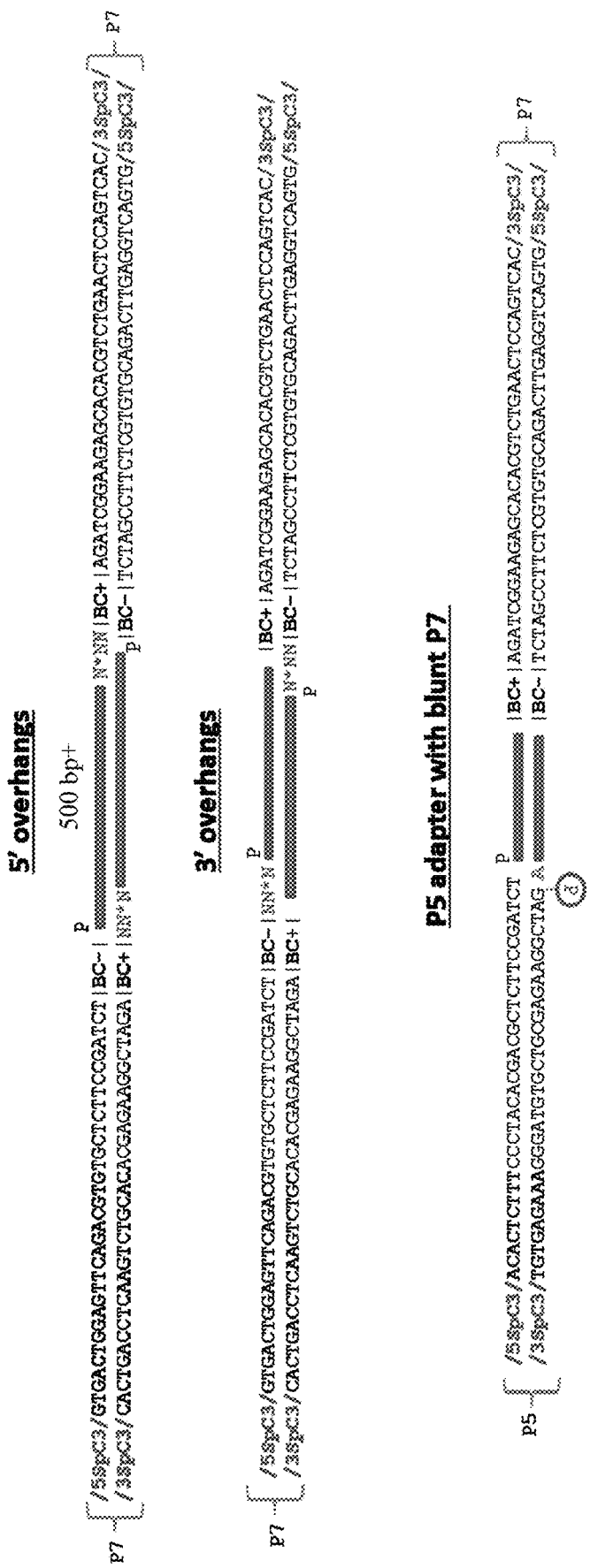

FIG. 13 shows oligonucleotide adapter designs. FIG. 13 discloses SEQ ID NOS 53, 55, 53, 55-56 and 55, respectively, in order of appearance.

Figure 14:
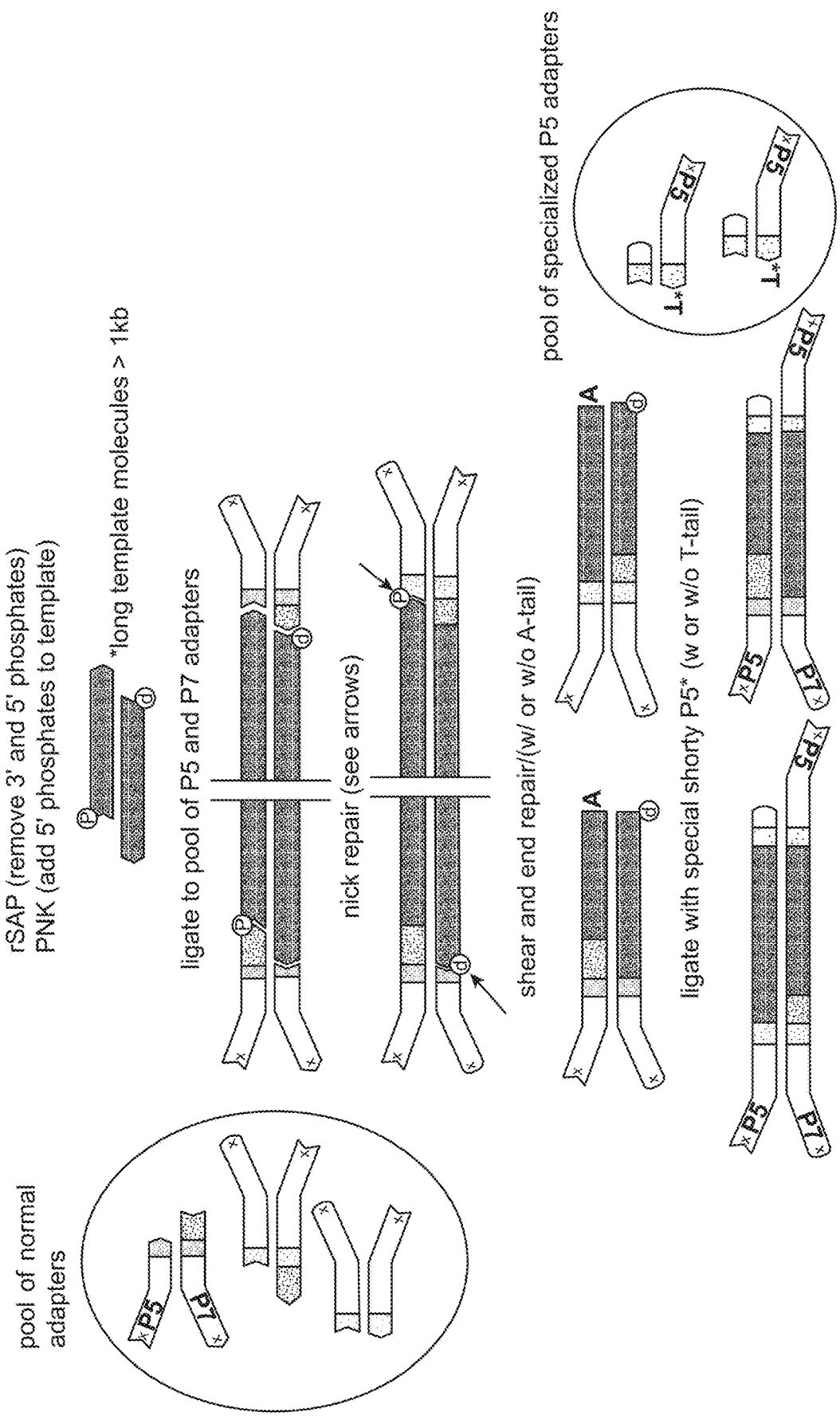

FIG. 14 shows a method for attaching oligonucleotide adapters to high molecular weight (HMW) DNA.

Figure 15:
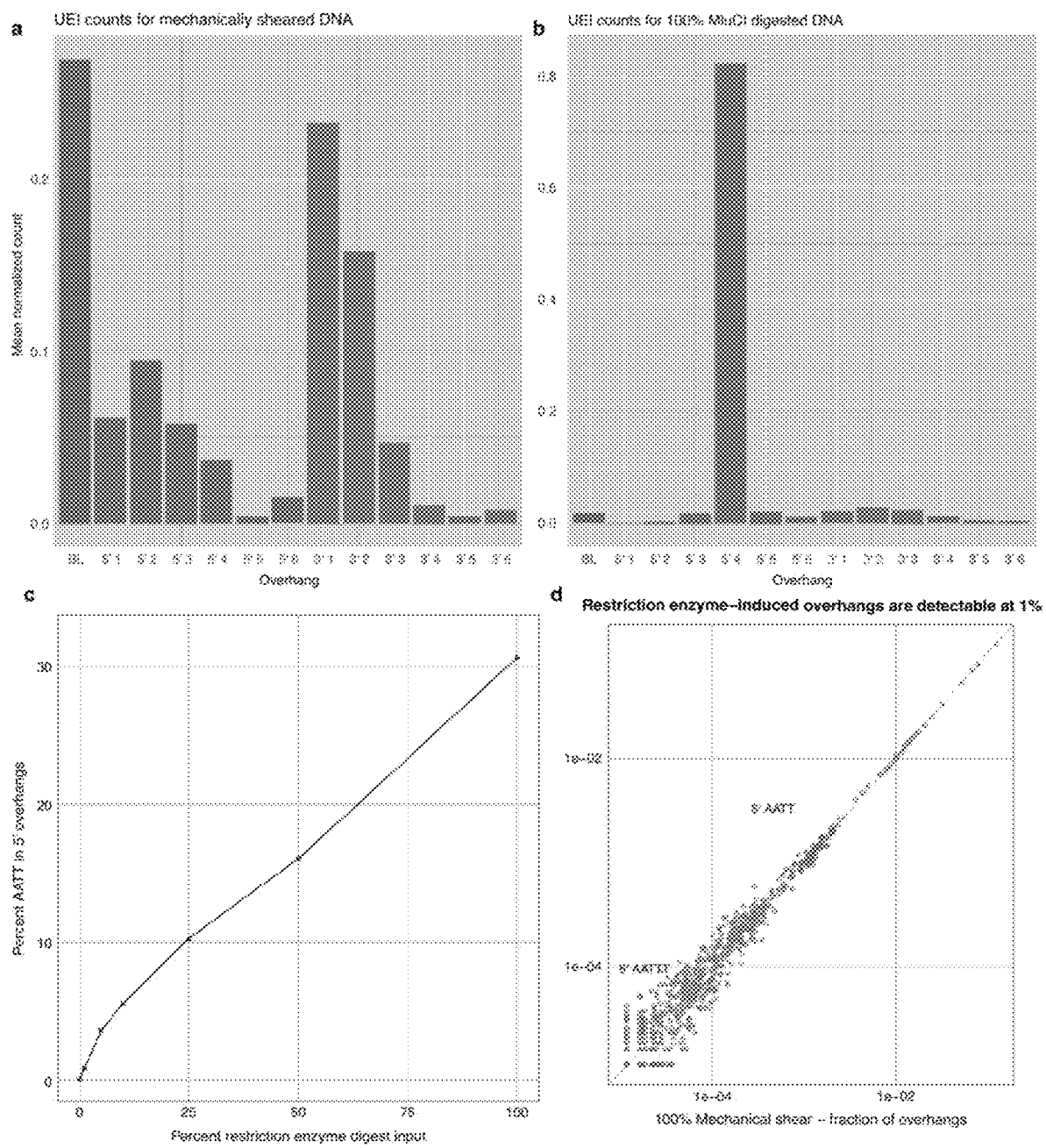

FIG. 15 shows results of sensitivity experiments. Overhang sequences are only considered if they occur on reverse reads. Panel A: overhang counts, divided by total per library, across two replicate libraries for 100% mechanically sheared DNA. Values are means across two libraries; error bars show maximum and minimum value. Panel B: overhang counts, divided by total per library, across two replicate libraries for 100% MluCI digested DNA. Values are means across two libraries; error bars show maximum and minimum value. Panel C: MluCI target sequence abundance with increasing concentration of MluCI. As the percent of MluCI digested DNA increases (x-axis), so does the frequency of its target sequence (AATT) among 5' overhang sequences (y-axis). Where replicate libraries were available, error bars show minimum and maximum values. Panel D: MluCI target sequence is identifiable even in 1% MluCI digested DNA. Points are counts of individual overhang sequences, divided by the sum of all such counts per library. Mean counts across two replicate libraries of only mechanically sheared DNA (x-axis) are shown against mean counts across two replicate libraries of 1% MluCI digested DNA (y-axis). The percent error of each count in 1% MluCI digested DNA was computed, using the count in mechanically sheared DNA as the expected value. All sequences for which this value, rounded to the thousandths place, fell at or above the 99.9th percentile of the distribution are shown. The target sequence (AATT) has the highest percent error (6.2%; 99.9th percentile; p<0.001).

Figure 16:
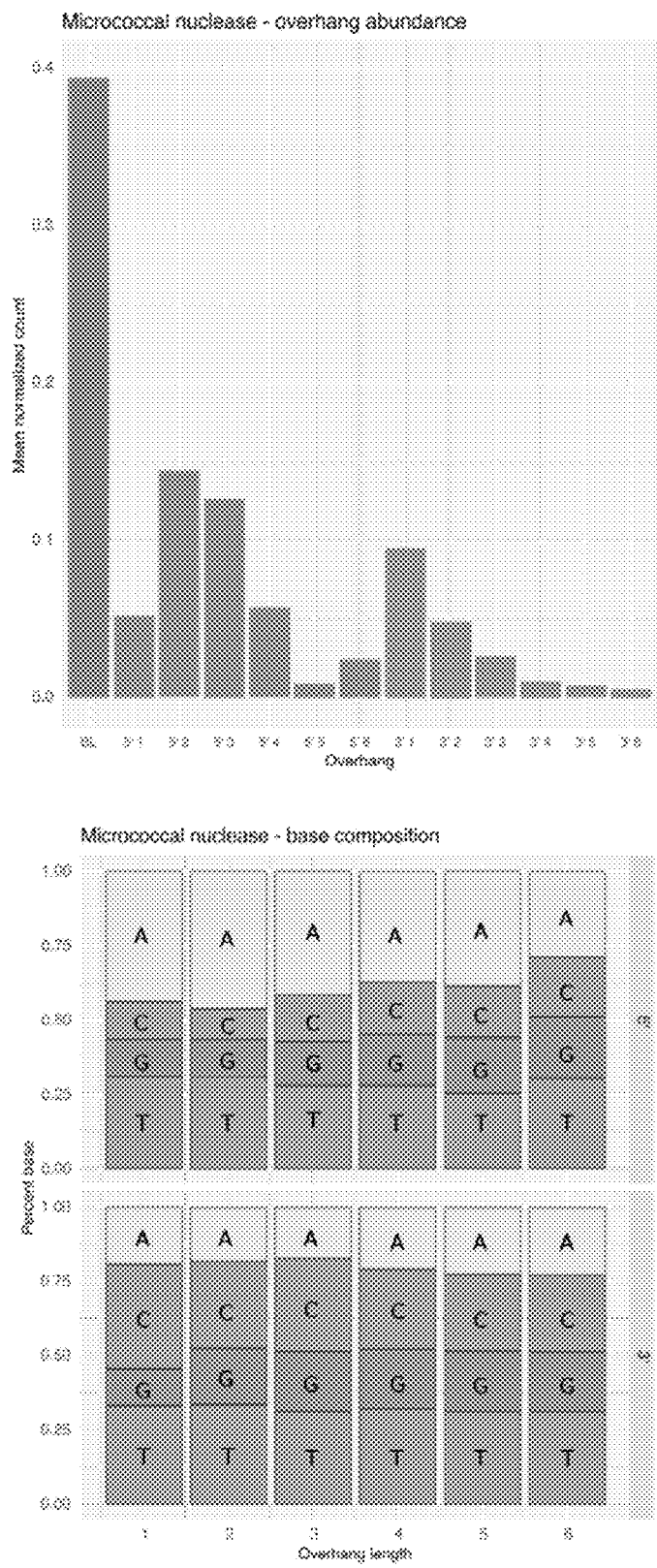

FIG. 16 shows overhang profile and base composition of overhangs created by a Micrococcal nuclease (restriction endonuclease MluCI). Results are the average of two independent libraries; error bars on the overhang abundance plot show maximum and minimum value. Input DNA for libraries is human genomic DNA extracted from GM12878 cells.

Figure 17:
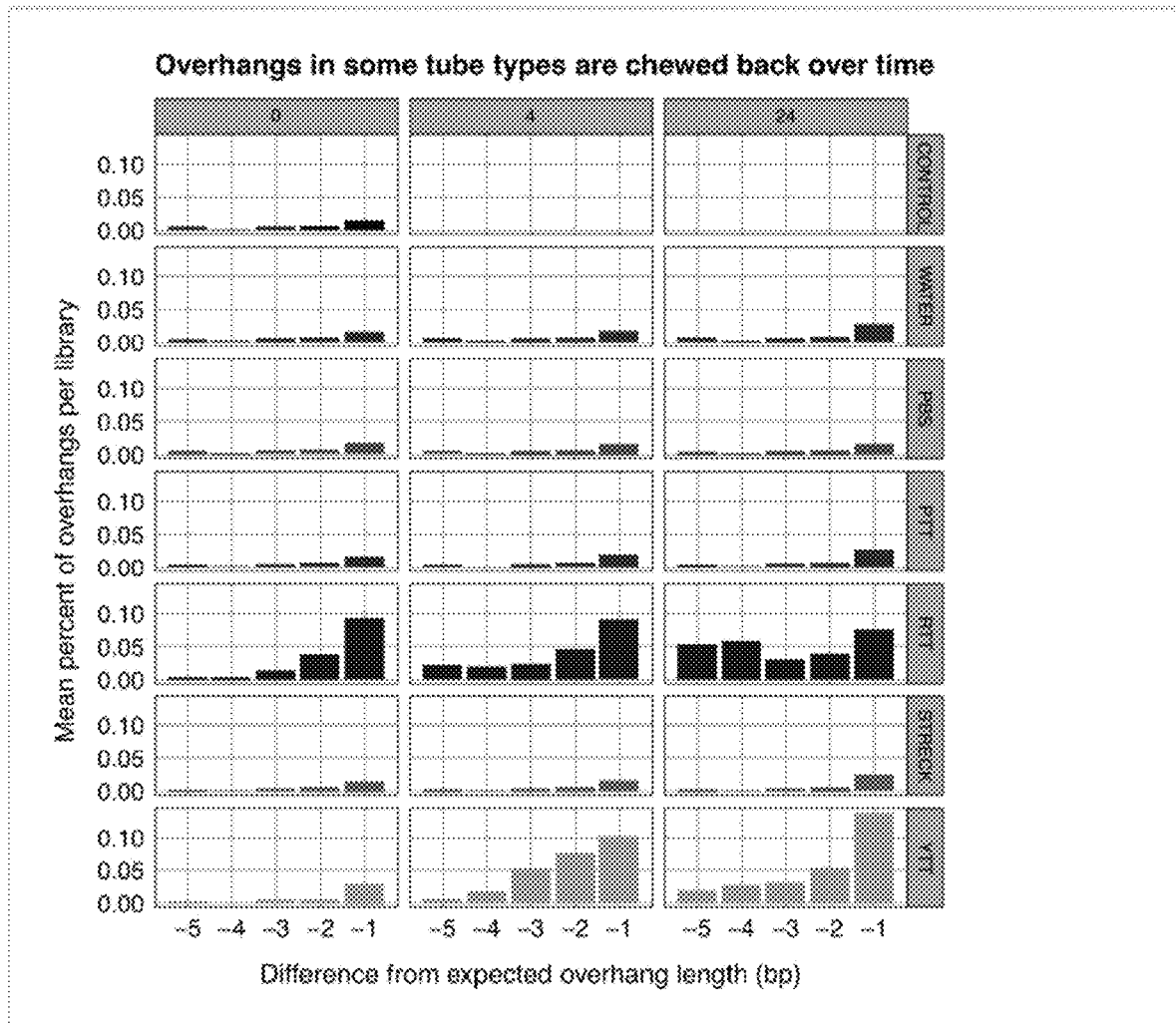

FIG. 17 shows effect of blood collection tubes on human cfDNA length and overhang profiles of control oligos. Difference between expected and observed control oligo overhang lengths demonstrate loss in overhang length in RTT by 4 hours and by 24 hours in YTT. Shown are frequencies of difference from expected length between −1 (chewed back by one base) and −5 (the 99th percentile of the distribution). PBS, Phosphate Buffer Saline pH 7.4 (control). RTT, red top tubes (serum). PTT, purple top tubes (potassium EDTA). YTT, yellow top tube (citrate). Control, control oligos without spiking or extraction.

Figure 18:
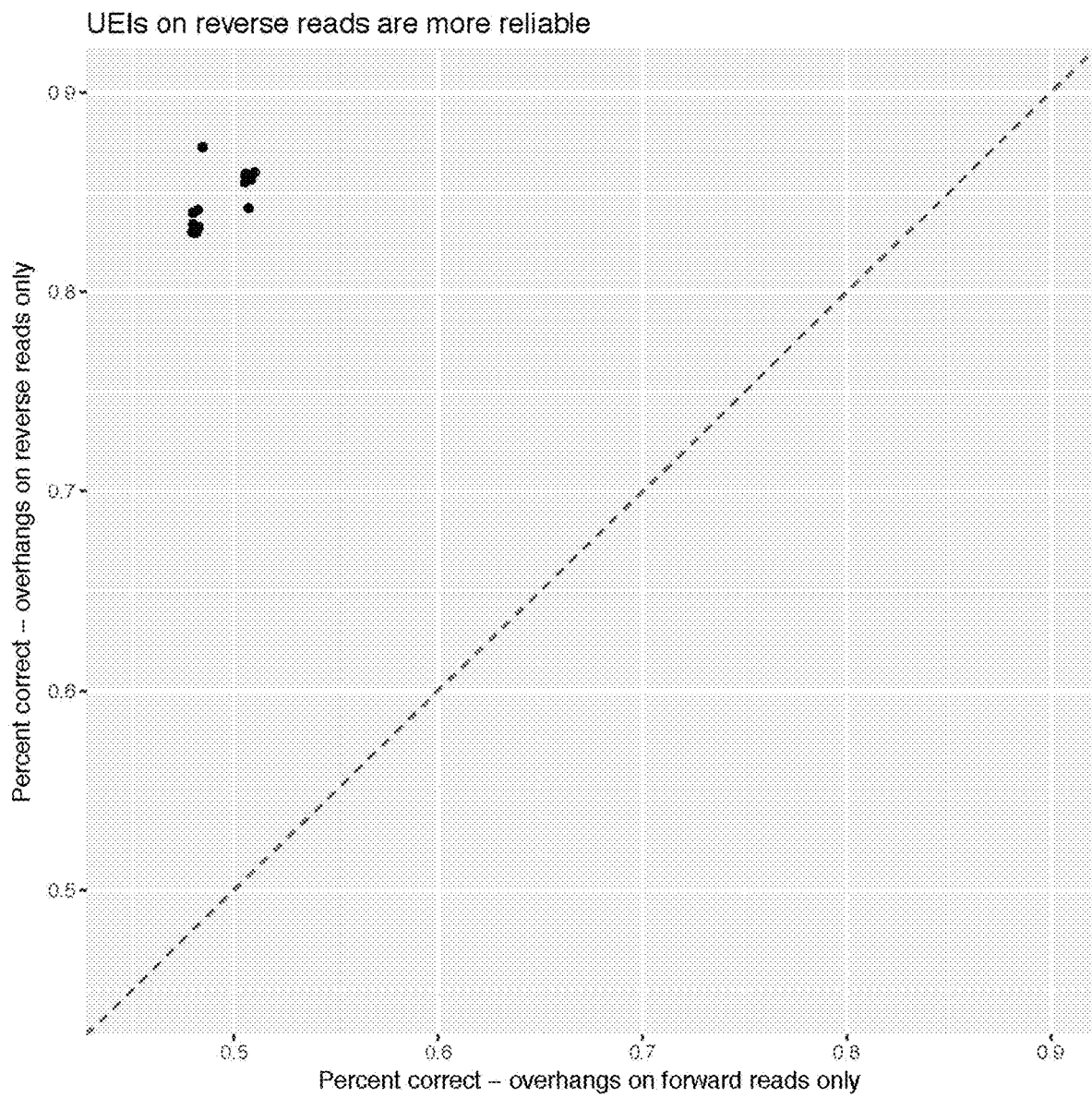

FIG. 18 shows accuracy in overhang determination. UEI data from reverse read only vs. UEI from forward read only. Accuracy in overhang determination is highest when only not-blunt UEIs on reverse reads are considered. X-axis: percent of UEIs ligated to the correct end of the correct control oligo, excluding non-blunt UEIs on reverse reads. Y-axis: same value, but excluding non-blunt UEIs on forward reads.

Figure 19:
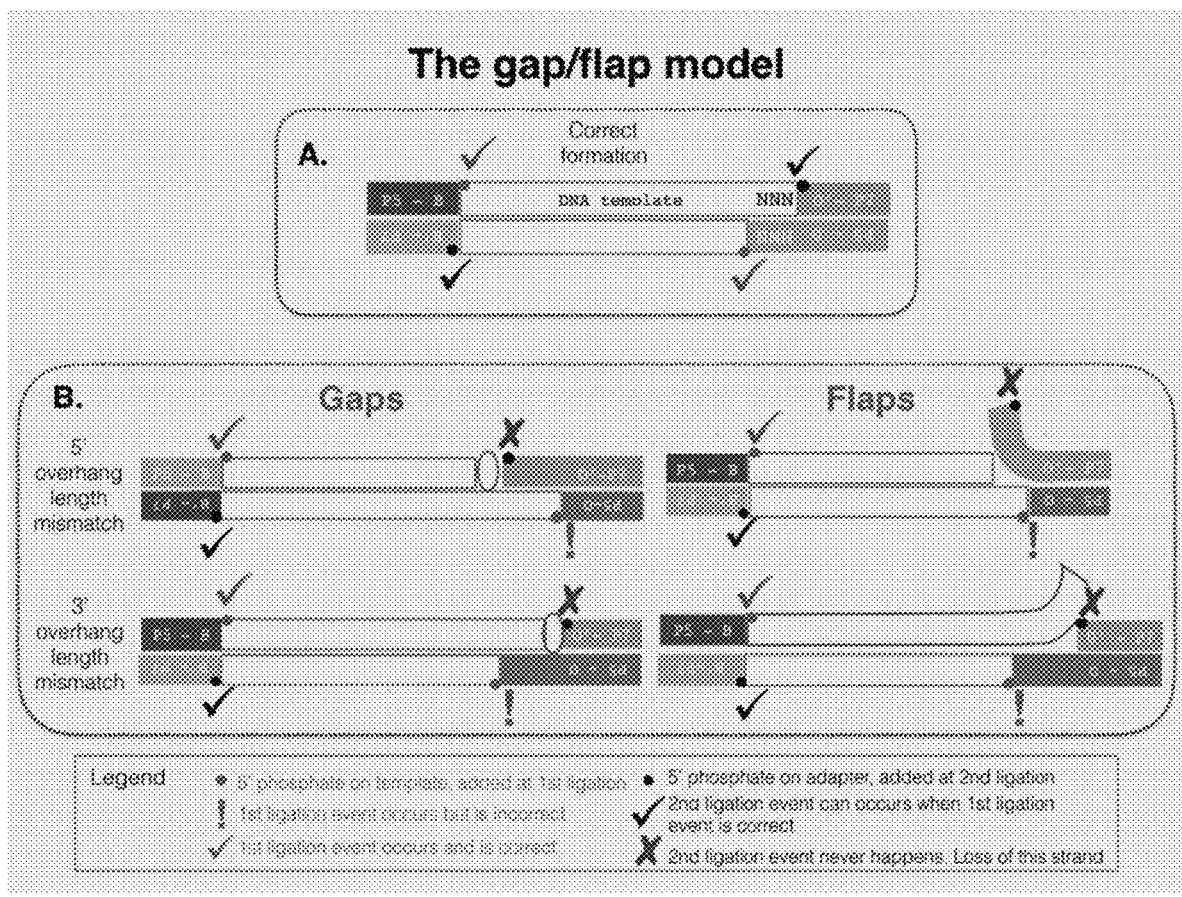

FIG. 19 shows a schematic of proposed gaps and flaps. The library preparation protocol completes ligation in two separate reactions. Black circles represent the 1$^{st}$ ligation, where the phosphates are present on the 5' end of the template. The adapters lack phosphates so a 2$^{nd}$ ligation event (white circles) is required to add phosphates to the 5' end of the adapter, permitting a fully formed double-stranded library molecule. P5 adapters are at forward reads, P7 adapters are at reverse reads. The following was observed: 1) an excess of only one of the two original strands, and 2) P5 UEIs are more inaccurate than P7 UEIs. Together these observations revealed the presence of several failure modes that may be caused by gaps and flaps of the overhangs during ligation. Given a template with one blunt end and one overhanging, as depicted, several failure modes during adapter ligation can cause one of the two strands to be lost. The top panel shows an error mode where a mismatch in the length of a 5' overhang causes a gap. The bottom panel shows an error mode where a mismatch in the length of a 3' overhang causes a flap. In both cases, these errors force an 'incorrect' covalent bond during the 1st ligation (black), inhibiting the 2nd ligation (white). This leads to conversion of only one strand and the loss of the other strand. Furthermore, in these cases the P5 UEI will report the wrong overhang length but the P7 UEI will be correct. A much higher accuracy of the P7 UEI was observed when they are blunt or overhangs; for this reason P7 UEIs were used during certain analyses. Although unlikely, if a gap at a 3' overhang, or a flap at a 5' overhang do occur, neither strand would convert into the library.

Figure 20:
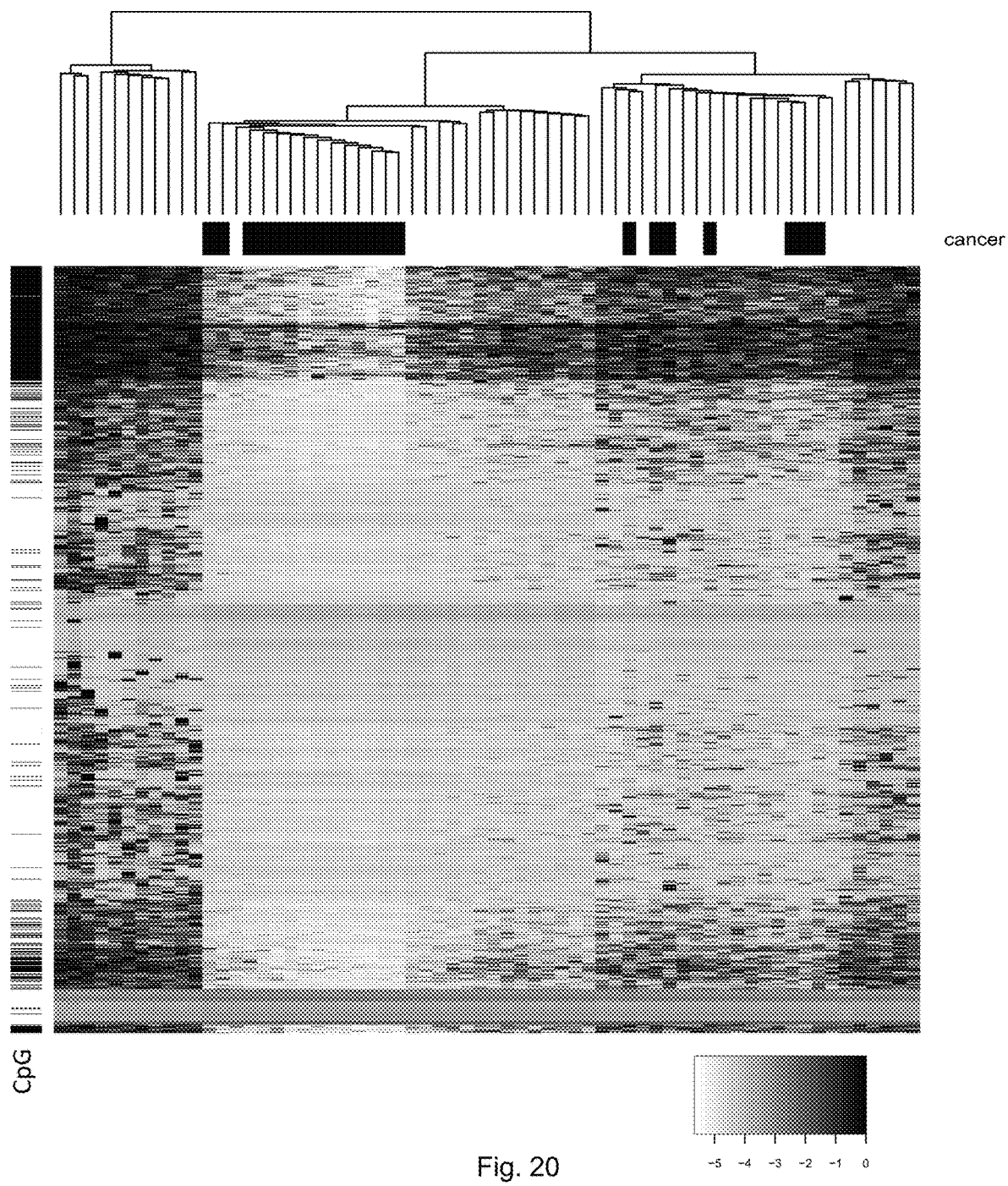

FIG. 20 shows a heat map generated from sequencing data of DNA overhangs present in each library produced using overhang adapters described herein. The heat map was generated using Ward's hierarchical clustering method. Each column represents a single cell-free DNA library from a cancer donor (black bar) or healthy donor (no bar). Each row represents a unique overhang (5' or 3') of length 1 to 6 nucleotides; rows (overhangs) containing at least one CG dinucleotide, or CpG, are indicated by a grey bar. Within the heat map matrix, the darker the color, the increasing proportion (log scaled) that overhang represents in the library. Lighter colors indicate depletion of that overhang. Scale on bottom of figure; N=50 no cancer reported; N=21 cancer.

FIG. 21 shows variables used in certain models.

Figure 22:
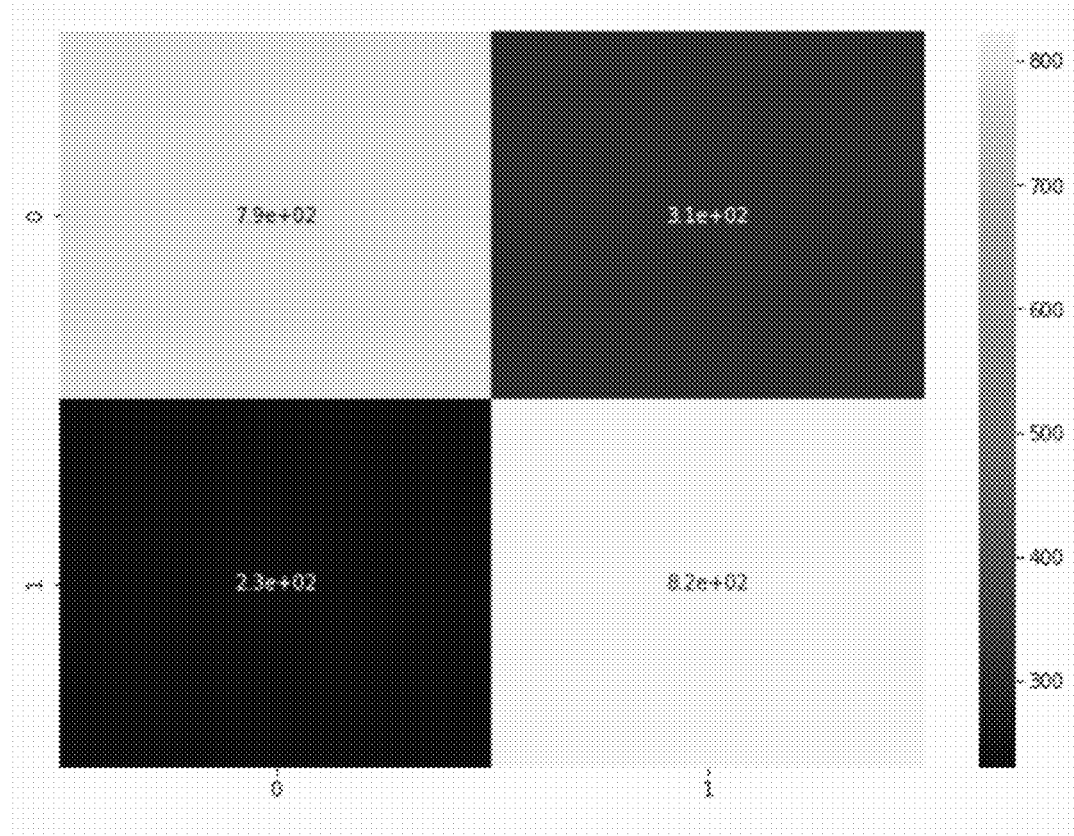

FIG. 22 shows a logistical regression classifier for cancer versus healthy samples.

Figure 23:
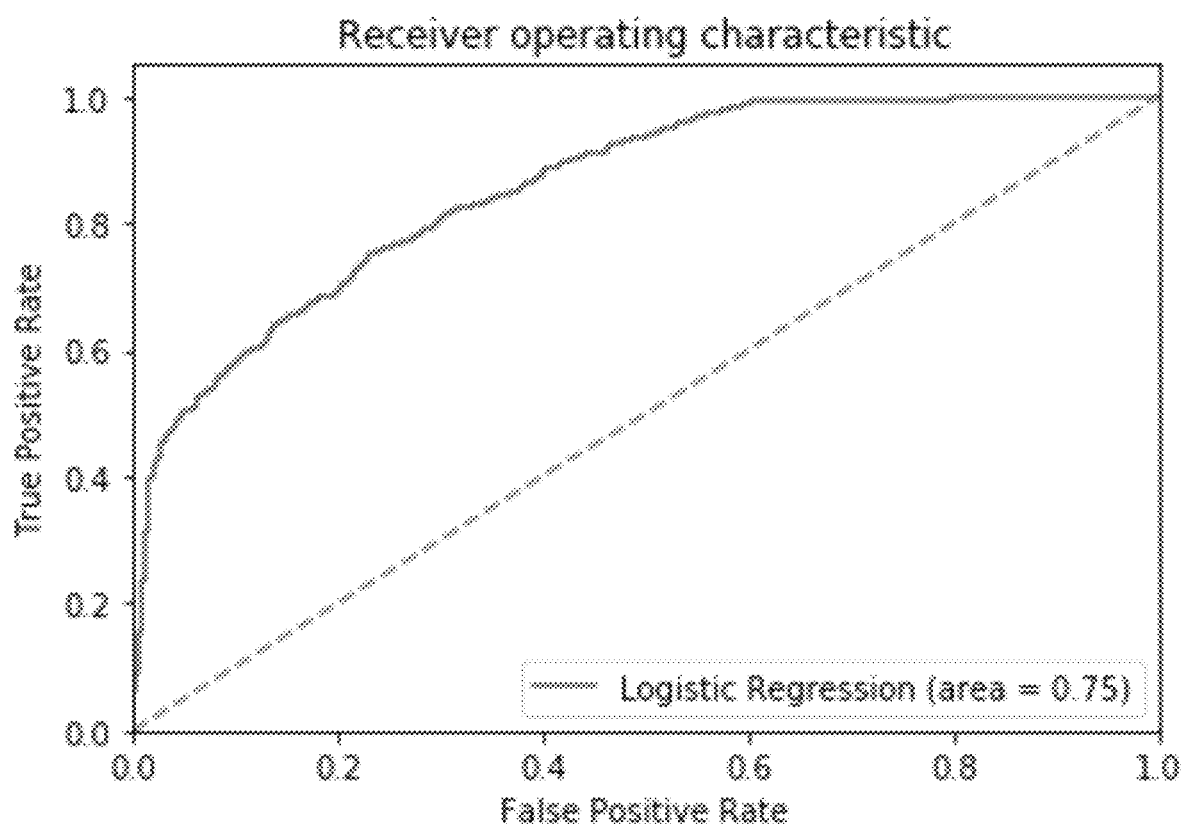

FIG. 23 shows a classification report and receiver operating characteristic (ROC) for cancer versus healthy samples.

FIG. 24 shows a model summary for gastrointestinal (GI) cancer versus healthy samples.

FIG. 25 shows a model summary for gastrointestinal (GI) cancer versus other samples (includes healthy and other cancer).

DETAILED DESCRIPTION

Provided herein are methods and compositions useful for analyzing nucleic acid. Also provided herein are methods and compositions useful for producing nucleic acid libraries. Also provided herein are methods and compositions useful for analyzing ends of nucleic acid fragments. In certain aspects, the methods include combining sample nucleic acid and oligonucleotides. In some embodiments, one or more oligonucleotides include an overhang capable of hybridizing to an overhang in a sample nucleic acid. In some embodiments, one or more oligonucleotides include a blunt end capable of ligating to a blunt end in a sample nucleic acid. In some embodiments, oligonucleotides each include at least one oligonucleotide overhang identification sequence. Oligonucleotides may comprise overhangs of different lengths and different sequences, and overhang identification sequences may be specific to the length of corresponding overhangs (and may be specific to other features of an overhang). In some embodiments, oligonucleotides include a cleavage site. In some embodiments, oligonucleotides are capable of forming a hairpin structure. In some embodiments, oligonucleotides comprise two strands, with an overhang at a first end and two non-complementary strands at a second end. In some embodiments, sample nucleic acid and oligonucleotides are combined under conditions in which overhangs in the oligonucleotides hybridize to overhangs in the sample nucleic acid having a corresponding length and complementary sequence, thereby forming hybridization products. In some embodiments, hybridization products include circularized nucleic acid fragments. In some embodiments, methods include generating blunt-ended nucleic acid fragments. Such hybridization products and/or blunt-ended nucleic acid fragments may be useful for producing a nucleic acid library and/or further analysis or processing, for example.

Nucleic Acid Ends

Provided herein are methods and compositions for analyzing nucleic acids. Methods may comprise modifying and/or analyzing nucleic acid ends. A nucleic acid end refers to the terminus of a nucleic acid fragment. Generally, a linear nucleic acid fragment contains two termini (i.e., a beginning and an end). Such termini are often referred to as a 5' end and a 3' end. A non-linear fragment may contain more than two termini (e.g., a forked fragment may contain 3 or more termini). For a double-stranded fragment, a nucleic acid end may contain an overhang or may be blunt ended (i.e., contains no overhang). The term overhang or overhang region generally refers to a single stranded portion at a nucleic acid end. For example, a nucleic acid fragment may include a double stranded or "duplex" region comprising one or more paired nucleotides (bases) and a single stranded or "overhang" region comprising one or more unpaired nucleotides (bases). Typically, an overhang refers to a single stranded region at an end of a nucleic acid molecule and not to a single stranded region flanked by double stranded regions. An overhang may be a 5' overhang or a 3' overhang. A 5' overhang generally refers to a single stranded region at the end of a nucleic acid molecule that reads according to conventional nucleic acid directionality in a 3' to 5' direction starting at the junction where the duplex portion ends and the single stranded portion begins and ending at the terminus (free end) of the overhang. A 3' overhang generally refers to a single stranded region at the end of a nucleic acid molecule that reads according to conventional nucleic acid directionality in a 5' to 3' direction starting at the junction where the duplex portion ends and the single stranded portion begins and ending at the terminus (free end) of the overhang.

Target nucleic acids may comprise an overhang (e.g., at end of a nucleic acid fragment) and may comprise two overhangs (e.g., at both ends of a nucleic acid fragment). Target nucleic acids may comprise two overhangs, one overhang and one blunt end, two blunt ends, or a combination of these. Target nucleic acids may comprise two 3' overhangs, two 5' overhangs, one 3' overhang and one 5' overhang, one 3' overhang and one blunt end, one 5' overhang and one blunt end, two blunt ends, or a combination of these. In some embodiments, overhangs in target nucleic acids are native overhangs. In some embodiments, target nucleic acid ends are native blunt ends. Native overhangs and native blunt ends generally refer to overhangs and blunt ends that have not been modified (e.g., have not been filled in, have not been cleaved or digested (e.g., by an endonuclease or exonuclease), have not been added or added to) prior to combining a sample composition with oligonucleotides described herein. Often, native overhangs and native blunt ends generally refer to overhangs and blunt ends that have not been modified ex vivo (e.g., have not been filled in ex vivo, have not been cleaved or digested ex vivo (e.g., by an endonuclease or exonuclease), have not been added or added to ex vivo) prior to combining a sample composition with oligonucleotides described herein. In certain instances, native overhangs and native blunt ends generally refer to overhangs and blunt ends that have not been modified after collection from a subject or source (e.g., have not been filled in after collection from a subject or source, have not been cleaved or digested after collection from a subject or source (e.g., by an endonuclease or exonuclease), have not been added or added to after collection from a subject or source). Native overhangs and native blunt ends generally do not include overhangs/ends created by contacting an isolated sample with a cleavage agent (e.g., endonuclease, exonuclease, restriction enzyme), and/or a polymerase. Native overhangs and native blunt ends generally do not include overhangs/ends created by mechanical shearing (e.g., ultrasonication (e.g., Adaptive Focused Acoustics™ (AFA) process by Covaris)). Native overhangs and native blunt ends generally do not include overhangs/ends created by contacting an isolated sample with an exonuclease (e.g., DNAse). Native overhangs and native blunt ends generally do not include overhangs/ends created by amplification (e.g., polymerase chain reaction). Native overhangs and native blunt ends generally do not include overhangs/ends attached to a solid support, conjugated to another molecule, or cloned into a vector. In some embodiments, native overhangs and native blunt ends may be subjected to dephosphorylation and may be referred to as dephosphorylated native overhangs and dephosphorylated native blunt ends. In some embodiments, native overhangs and native blunt ends may be subjected to phosphorylation and may be referred to as phosphorylated native overhangs and phosphorylated native blunt ends.

Oligonucleotides

In some embodiments, nucleic acids (e.g., nucleic acids from a sample; target nucleic acids) are combined with oligonucleotides. An oligonucleotide generally refers to a nucleic acid (e.g., DNA, RNA) polymer that is distinct from the target nucleic acids, and may be referred to as oligos, adapters, oligonucleotide adapters, and oligo adapters. Oligonucleotides may be short in length (e.g., less than 50 bp, less than 40 bp, less than 30 bp, less than 20 bp, less than 10 bp, less than 5 bp) and sometimes, but not always, are shorter than target nucleic acids. Oligonucleotides may be artificially synthesized. In some embodiments, nucleic acids (e.g., nucleic acids from a sample; target nucleic acids) are combined with a plurality or pool of oligonucleotide species. A pool of oligonucleotide species may be referred to as a set of oligonucleotide species, and may comprise a plurality of different oligonucleotide species. Methods and compositions herein may include more than one pool of oligonucleotide species (e.g., a first pool of oligonucleotide species and a second pool of oligonucleotide species). In such instances, oligonucleotides in a first pool may share a common feature and oligonucleotides in a second pool may share a different common feature. A common feature in a pool may include a particular domain and/or a particular modification. In some embodiments, a common feature in a pool includes a common primer binding domain.

A species of oligonucleotide generally contains a feature that is unique with respect to other oligonucleotide species. For example, an oligonucleotide species may contain a unique overhang feature. A unique overhang feature may include a unique overhang length, a unique overhang sequence, or a combination of a unique overhang sequence and overhang length. For example, an oligonucleotide species may contain a unique sequence for a particular overhang length with respect to other oligonucleotide species having the given overhang length. In some instances, an oligonucleotide species contains a unique sequence for a particular overhang length and type (e.g., 5' or 3') with respect to other oligonucleotide species having the given overhang length and type.

Oligonucleotides may comprise an overhang (e.g., at one end of the oligonucleotide) and may comprise two overhangs (e.g., at both ends of the oligonucleotide). In some embodiments, oligonucleotides comprise two overhangs, one overhang and one blunt end, two blunt ends, or a combination of these. In some embodiments, oligonucleotides comprise two 3' overhangs, two 5' overhangs, one 3' overhang and one 5' overhang, one 3' overhang and one blunt end, one 5' overhang and one blunt end, two blunt ends, or a combination of these. In some embodiments, oligonucleotides comprise two strands, with an overhang or blunt end at a first end and two non-complementary strands at a second end. For hairpin structure oligonucleotides described herein, such oligonucleotides (e.g., in the uncleaved state) generally comprise one overhang (e.g., a 5' overhang or a 3' overhang), and in certain instances, no overhang (i.e., a blunt end). Generally, an oligonucleotide overhang is capable of hybridizing to a target nucleic acid overhang. An oligonucleotide overhang may comprise a region that is complementary to a region in a target nucleic acid overhang. In some embodiments, the entire length of an oligonucleotide overhang is capable of hybridizing to the entire length of a target nucleic acid overhang. Thus, the entire oligonucleotide overhang may be complementary to the entire nucleic acid overhang.

Often, "complementary" or "complementarity" refers sequence complementarity, as described herein, and "non-complementary" or "non-complementarity" refers to sequence non-complementarity, as described herein. In certain aspects, "complementary" or "complementarity" may refer structural complementarity (e.g., overhang complementarity). For example, a target nucleic acid having a 5', 8 base-pair overhang may have structural complementarity with an oligonucleotide having a 5', 8 base-pair overhang. Structural complementarity may include non-specific base pairing. In certain embodiments, an oligonucleotide overhang comprises one or more nucleotides capable of non-specific base pairing to bases in the target nucleic acids. For example, a target nucleic acid having a 5', 8 base-pair overhang may have structural complementarity with an oligonucleotide having a 5', 8 base-pair overhang, where the oligonucleotide overhang comprises one or more nucleotides that can pair non-specifically with all or some of the base possibilities at a corresponding position in the target nucleic acid overhang. In certain embodiments, an oligonucleotide overhang comprises nucleotides that are all capable of non-specific base pairing to bases in the target nucleic acids. Nucleotides capable of non-specific base pairing may be referred to as "universal bases" which can replace any of the four typical bases described above (e.g., nitroindole, 5-nitroindole, 3-nitropyrrole, inosine, deoxyinosine, 2-deoxyinosine) or "degenerate/wobble bases" which can replace two or three (but not all) of the four typical bases (e.g., non-natural base P and K). In certain embodiments, an oligonucleotide overhang comprises one or more universal bases. In certain embodiments, an oligonucleotide overhang consists of universal bases.

In some embodiments, each oligonucleotide in a plurality or pool of oligonucleotide species comprises an oligonucleotide overhang identification sequence specific to one or more features of the oligonucleotide overhang. An oligonucleotide overhang identification sequence may be referred to as an overhang identification sequence, an identification sequence, an oligonucleotide overhang identification polynucleotide, an overhang identification polynucleotide, an identification polynucleotide, a barcode, a variable overhang barcode, a unique end identifier (UEI), an end identifier, or an identifier. An overhang identification sequence uniquely identifies the overhang present in its respective oligonucleotide, and can uniquely identify each type of overhang (e.g., length, 5' or 3', and/or the like) present in target nucleic acids to which the oligonucleotide overhangs specifically hybridize. In certain embodiments, an overhang identification sequence can uniquely identify each type of native overhang (e.g., length, 5' or 3', and/or the like) present in target nucleic acids to which the oligonucleotide overhangs specifically hybridize. Often, overhang identification sequences specific to oligonucleotide overhangs that hybridize to overhangs of different lengths are different from one another and are unique. Typically, overhang identification sequences specific to i) oligonucleotide overhangs that hybridize to overhangs of different lengths; and ii) oligonucleotide overhangs of different type (i.e., 3', 5'), are different from one another and are unique. Generally, no two overhang identification sequences specific to the length of an oligonucleotide overhang are in the plurality or pool of oligonucleotide species that have overhangs of a different length. In other words, a given overhang identification sequence (or set of sequences) that is specific to a given length of an oligonucleotide overhang will only be present in oligonucleotides having overhangs of such given length. Oligonucleotides having a different overhang length will include a different overhang identification sequence (or set of sequences). In some embodiments, there is one overhang identification sequence for all oligonucleotide species having an overhang of a specific length. In some embodiments, there are two overhang identification sequences for all oligonucleotide species having an overhang of a specific length such that one overhang identification sequence is specific to the given length for 5' overhangs and the other overhang identification sequence is specific to the given length for 3' overhangs. In some embodiments, there are one or two overhang identification sequence(s) for all oligonucleotide species having an overhang of a specific length, irrespective of the sequence of the overhang. In some embodiments, there is a subset of overhang identification sequences for oligonucleotide species having an overhang of a specific length, where different overhang identification sequences in the subset are specific to different overhang sequences in the oligonucleotides (e.g., in addition to being specific to the length and type (i.e., 5' or 3') of overhang). In some embodiments, an overhang identification sequence is specific to no overhang (i.e., a blunt ended oligonucleotide).

Generally, an overhang identification sequence is informative about the length and/or type of corresponding oligonucleotide overhang by way of the nucleotide sequence of the overhang identification sequence. The nucleotide sequence of the overhang identification sequence may be sequenced by a sequencing process and included in sequence reads for the oligonucleotide-target sequences. Thus, in certain embodiments, overhang identification sequences do not generate additional signals beyond reads of their nucleotide sequences. For example, overhang identification sequences may not require labeling (e.g., by fluorescent labels), conjugation (e.g., to solid supports, antibodies), or hybridization to a polynucleotide carrying a label or conjugated to a solid support, antibody, and the like, to generate a signal.

In some embodiments, oligonucleotides include one or more portions or domains other than the overhang and the overhang identification sequence. Such additional portions may be included, for example, to facilitate one or more downstream applications that utilize or further process the hybridization products or derivatives thereof, such as nucleic acid amplification, sequencing (e.g., high-throughput sequencing), or both. In certain embodiments, an additional portion includes one or more nucleic acid binding domains such as, for example, primer binding domains (also referred to as priming sequences), and/or a sequencing adapter or one or more components of a sequencing adapter (e.g., one or more components described herein). In some embodiments, an oligonucleotide comprises a unique molecular identifier (UMI). UMIs generally are used for estimating the number of unique starting molecules (e.g., starting molecules prior to amplification) and, in certain instances, evaluating the sensitivity of a ligation reaction.

In some embodiments, oligonucleotides include one or more primer binding domains. A primer binding domain is a polynucleotide to which a primer (e.g., an amplification primer) can anneal. A primer binding domain typically comprises a nucleotide sequence that is complementary or substantially complementary to the nucleotide sequence of a primer (e.g., an amplification primer). In some embodiments, different pools of oligonucleotide species may comprise oligonucleotides having primer binding domains, where each pool has its own primer binding domain. For example, oligonucleotides in pool A may comprise primer binding domain A, and oligonucleotides in pool B may comprise primer binding domain B, where primer binding domain A and primer binding domain B are different. Primer binding domain A and primer binding domain B may be considered different based on their nucleotide sequences being different. Primer binding domain A and primer binding domain B may be considered different based on the characteristic of primer A anneals to primer binding domain A and does not anneal to primer binding domain B, and primer B anneals to primer binding domain B and does not anneal to primer binding domain A.

In some embodiments, oligonucleotides include one overhang that hybridizes to target nucleic acid overhangs or includes a blunt end, and another overhang containing a sequence that does not hybridize to target nucleic acid overhangs. Such sequence that does not hybridize to target nucleic acid overhangs may contain a sequence that is generally not found in the target nucleic acid. Such sequence that does not hybridize to target nucleic acid overhangs also may contain a sequence that can hybridize to itself. For example, a sequence may include a palindromic sequence. Oligonucleotides containing overhangs having a palindromic sequence may hybridize to each end of a target nucleic acid by way of overhang hybridization, for example, and then hybridize to each other by way of palindromic sequence hybridization, forming a circular hybridization product.

In some embodiments, an oligonucleotide overhang comprises any suitable type of nucleotide (e.g., DNA nucleotides, RNA nucleotides, modified nucleotides, natural nucleotides), examples of which are provided herein. In some embodiments, an oligonucleotide overhang comprises one or more DNA nucleotides. In some embodiments, an oligonucleotide overhang consists of DNA nucleotides. In some embodiments, an oligonucleotide overhang comprises one or more RNA nucleotides. In some embodiments, an oligonucleotide overhang consists of RNA nucleotides. Oligonucleotide overhangs comprising or consisting of RNA nucleotides, for example, may hybridize to target nucleic acid overhangs comprising or consisting of DNA nucleotides, thereby forming an RNA-DNA duplex. An RNA ligase (e.g., T4 RNA ligase 2, SplintR® Ligase) may be used in such instances for ligation. In certain embodiments, unligated oligo dimer products (e.g., containing RNA-RNA duplexes) may be removed by digesting RNA-RNA duplexes (e.g., using an RNAse such as, for example RNAse III).

Y-Oligonucleotides

In some embodiments, oligonucleotides comprise two strands, with an overhang at a first end and two non-complementary strands at a second end. Such oligonucleotides may be referred to as Y-oligonucleotides, Y-adapters, Y-shaped oligonucleotides, Y-shaped adapters, and the like. In some embodiments, oligonucleotides (e.g., Y-adapters) comprise two strands, with either a blunt end or an overhang at a first end and two non-complementary strands at a second end. An oligonucleotide having a Y-shaped structure generally comprises a double-stranded duplex region, two single stranded "arms" at one end, and either a blunt end or an overhang at the other end.

Y-oligonucleotides may comprise a plurality of polynucleotides. In some embodiments, Y-oligonucleotides comprise a first polynucleotide and a second polynucleotide. In some embodiments, a first polynucleotide (of a first strand) is complementary to a second polynucleotide (of a second strand). In some embodiments, a portion of a first polynucleotide (of a first strand) is complementary to a portion of a second polynucleotide (of a second strand). In some embodiments, a first polynucleotide comprises a first region that is complementary to a first region in a second polynucleotide, and the first polynucleotide comprises a second region that is not complementary to a second region in the second polynucleotide. The complementary region often forms the duplex region of the Y-oligonucleotide and the non-complementary region often forms the arms, or parts thereof, of the Y-oligonucleotide. The first and second polynucleotides may comprise components of adapters described herein, such as, for example, amplification priming sites and/or specific sequencing adapters (e.g., P5, P7 adapters). In some embodiments, the first and second polynucleotides do not comprise certain components of adapters described herein, such as, for example, amplification priming sites and specific sequencing adapters (e.g., P5, P7 adapters).

In some embodiments, a Y-oligonucleotide comprises an overhang (e.g., 5' overhang, 3' overhang). The overhang of a Y-oligonucleotide typically is located adjacent to the double-stranded duplex portion and at the opposite end of the non-complementary strands (or "arms") portion. The overhang of a Y-oligonucleotide typically is complementary to an overhang in a target nucleic acid. Y-oligonucleotides may also comprise an overhang identification sequence. In some embodiments, a Y-oligonucleotide comprises a blunt end opposite to the non-complementary strands (or "arms") portion. In some embodiments, a plurality or pool of Y-oligonucleotide species comprises a mixture of: 1) oligonucleotides comprising an overhang; and 2) oligonucleotides comprising a blunt end.

Hairpins

In some embodiments, an oligonucleotide comprises one strand capable of forming a hairpin structure having a single-stranded loop. In some embodiments, an oligonucleotide consists of one strand capable of forming a hairpin structure having a single-stranded loop. An oligonucleotide having a hairpin structure generally comprises a double-stranded "stem" region and a single stranded "loop" region. In some embodiments, an oligonucleotide comprises one strand (i.e., one continuous strand) capable of adopting a hairpin structure. In some embodiments, an oligonucleotide consists essentially of one strand (i.e., one continuous strand) capable of adopting a hairpin structure. Consisting essentially of one strand means that the oligonucleotide does not include any additional strands of nucleic acid (e.g., hybridized to the oligonucleotides) that are not part of the continuous strand. Thus, "consisting essentially of" here refers to the number of strands in the oligonucleotides, and the oligonucleotides can include other features not essential to the number of strands (e.g., can include a detectable label, can include other regions). Oligonucleotides comprising or consisting essentially of one strand capable of forming a hairpin structure may be referred to herein as hairpins, hairpin oligonucleotides, or hairpin adapters.

Hairpin oligonucleotides may comprise a plurality of polynucleotides within the one strand. In some embodiments, hairpin adapters comprise a first polynucleotide and a second polynucleotide. In some embodiments, a first polynucleotide is complementary to a second polynucleotide. In some embodiments, a portion of a first polynucleotide is complementary to a portion of a second polynucleotide. In some embodiments, a first polynucleotide comprises a first region that is complementary to a first region in a second polynucleotide, and the first polynucleotide comprises a second region that is not complementary to a second region in the second polynucleotide. The complementary region often forms the stem of the hairpin adapter and the non-complementary region often forms the loop, or part thereof, of the hairpin adapter. The first and second polynucleotides may comprise components of adapters described herein, such as, for example, amplification priming sites and specific sequencing adapters (e.g., P5, P7 adapters). In some embodiments, the first and second polynucleotides do not comprise certain components of adapters described herein, such as, for example, amplification priming sites and specific sequencing adapters (e.g., P5, P7 adapters).

Hairpin oligonucleotides may comprise one or more cleavage sites capable of being cleaved under cleavage conditions. In some embodiments, a cleavage site is located between a first and second polynucleotide. Cleavage at a cleavage site often generates two separate strands from the hairpin oligonucleotide. In some embodiments, cleavage at a cleavage site generates a partially double stranded oligonucleotide with two unpaired strands forming a "Y" structure. Cleavage sites may include any suitable cleavage site, such as cleavage sites described herein, for example. In some embodiments, cleavage sites comprise RNA nucleotides and may be cleaved, for example, using an RNAse. In some embodiments, cleavage sites comprise uracil and/or deoxyuridine and may be cleaved, for example, using DNA glycosylase, endonuclease, RNAse, and the like and combinations thereof. In some embodiments, cleavage sites do not comprise uracil and/or deoxyuridine. In some embodiments, a method herein comprises after combining hairpin oligonucleotides with target nucleic acids, exposing one or more cleavage sites to cleavage conditions, thereby cleaving the oligonucleotides.

In some embodiments, a hairpin oligonucleotide comprises an overhang (e.g., 5' overhang, 3' overhang). The overhang of a hairpin oligonucleotide typically is located adjacent to the double-stranded stem portion and at the opposite end of the loop portion. The overhang of a hairpin oligonucleotide typically is complementary to an overhang in a target nucleic acid. Hairpin oligonucleotides may also comprise an overhang identification sequence. In some embodiments, a hairpin oligonucleotide comprises in a 5' to 3' orientation: a first overhang identification sequence, a first polynucleotide, one or more cleavage sites, a second polynucleotide, a second overhang identification sequence complementary to the first overhang identification sequence, and an overhang. In some embodiments, a hairpin oligonucleotide comprises in a 5' to 3' orientation: an overhang, a first overhang identification sequence, a first polynucleotide, one or more cleavage sites, a second polynucleotide, and an overhang identification sequence complementary to the first overhang identification sequence. In some embodiments, a plurality or pool of hairpin oligonucleotide species comprises a mixture of: 1) oligonucleotides comprising in a 5' to 3' orientation: a first overhang identification sequence, a first polynucleotide, one or more cleavage sites, a second polynucleotide, a second overhang identification sequence complementary to the first overhang identification sequence, and an overhang; and 2) oligonucleotides comprising in a 5' to 3' orientation: an overhang, a first overhang identification sequence, a first polynucleotide, one or more cleavage sites, a second polynucleotide, and an overhang identification sequence complementary to the first overhang identification sequence. In certain embodiments of the above, the first and second polynucleotides are ordered in a 5' to 3' orientation as follows: first portion of first polynucleotide, second portion of first polynucleotide, cleavage site, second portion of second polynucleotide and first portion of second polynucleotide, where the first portions of each polynucleotide are complementary and the second portions of each polynucleotide are not complementary. In some embodiments, a plurality or pool of hairpin oligonucleotide species comprises a mixture of: 1) oligonucleotides comprising an overhang; and 2) oligonucleotides comprising a blunt end.

Modified Nucleotides

In some embodiments, an oligonucleotide species comprises one or more modified nucleotides. Modified nucleotides may be referred to as modified bases and may include, for example, nucleotides conjugated to a member of a binding pair, blocked nucleotides, non-natural nucleotides, nucleotide analogues, peptide nucleic acid (PNA) nucleotides, Morpholino nucleotides, locked nucleic acid (LNA) nucleotides, bridged nucleic acid (BNA) nucleotides, glycol nucleic acid (GNA) nucleotides, threose nucleic acid (TNA) nucleotides, and the like and combinations thereof. In some embodiments, an oligonucleotide species comprises one or more modified nucleotides within a duplex region, within an overhang region, at one end, or at both ends of the oligonucleotide. In some embodiments, an oligonucleotide species comprises one or more unpaired modified nucleotides. In some embodiments, an oligonucleotide species comprises one or more unpaired modified nucleotides at one end of the oligonucleotide. In some embodiments, an oligonucleotide species comprises one or more unpaired modified nucleotides the end of the oligonucleotide opposite to the end that hybridizes to a target nucleic acid (e.g., an end comprising an oligonucleotide overhang). A modified nucleotide may be present at the end of the strand having a 3' terminus or at the end of the strand having a 5' terminus.

In some embodiments, an oligonucleotide species comprises one or more blocked nucleotides. For example, an oligonucleotide species may comprise one or more modified nucleotides that are capable of blocking hybridization to a nucleotide in a target nucleic acid. In some instances, the one or more modified nucleotides are capable of blocking ligation to a nucleotide in a target nucleic acid. In some embodiments, an oligonucleotide species comprises one or more modified nucleotides that are incapable of binding to a natural nucleotide. In some embodiments, one or more modified nucleotides comprise one or more of an isodeoxy-base, a dideoxy-base, an inverted dideoxy-base, a spacer, and an amino linker.

In some embodiments, one or more modified nucleotides comprise an isodeoxy-base. In some embodiments, one or more modified nucleotides comprise isodeoxy-guanine (iso-dG). In some embodiments, one or more modified nucleotides comprise isodeoxy-cytosine (iso-dC). Iso-dC and iso-dG are chemical variants of cytosine and guanine, respectively. Iso-dC can hydrogen bond with iso-dG but not with unmodified guanine (natural guanine). Iso-dG can base pair with Iso-dC but not with unmodified cytosine (natural cytosine). An oligonucleotide containing iso-dC can be designed so that it hybridizes to a complementary oligo containing iso-dG but cannot hybridize to any naturally occurring nucleic acid sequence.

In some embodiments, one or more modified nucleotides comprise a dideoxy-base. In some embodiments, one or more modified nucleotides comprise dideoxy-cytosine. In some embodiments, one or more modified nucleotides comprise an inverted dideoxy-base. In some embodiments, one or more modified nucleotides comprise inverted dideoxy-thymine. For example, an inverted dideoxy-thymine located at the 5' end of a sequence can prevent unwanted 5' ligations.

In some embodiments, one or more modified nucleotides comprise a spacer. In some embodiments, one or more modified nucleotides comprise a C3 spacer. A C3 spacer phosphoramidite can be incorporated internally or at the 5'-end of an oligonucleotide. Multiple C3 spacers can be added at either end of an oligonucleotide to introduce a long hydrophilic spacer arm (e.g., for the attachment of fluorophores or other pendent groups). Other spacers include, for example, photo-cleavable (PC) spacers, hexanediol, spacer 9, spacer 18, 1',2'-dideoxyribose (dSpacer), and the like.

In some embodiments, a modified nucleotide comprises a member of a binding pair. Binding pairs may include, for example, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group, digoxigenin moiety/anti-digoxigenin antibody, fluorescein moiety/anti-fluorescein antibody, steroid/steroid-binding protein, operator/repressor, nuclease/nucleotide, lectin/polysaccharide, active compound/active compound receptor, hormone/hormone receptor, enzyme/substrate, oligonucleotide or polynucleotide/its corresponding complement, the like or combinations thereof. In some embodiments, a modified nucleotide comprises biotin.

In some embodiments, a modified nucleotide comprises a first member of a binding pair (e.g., biotin); and a second member of a binding pair (e.g., streptavidin) is conjugated to a solid support or substrate. A solid support or substrate can be any physically separable solid to which a member of a binding pair can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™ polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, a solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, a solid support can be a collection of particles. In some embodiments, the particles can comprise silica, and the silica may comprise silica dioxide. In some embodiments, the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$). A member of a binding pair may be linked to a solid support by covalent bonds or by non-covalent interactions and may be linked to a solid support directly or indirectly (e.g., via an intermediary agent such as a spacer molecule or biotin).

Phosphorylation and Dephosphorylation

In some embodiments, a method herein comprises contacting a target nucleic acid composition with an agent comprising a phosphatase activity under conditions in which target nucleic acids are dephosphorylated, thereby generating a dephosphorylated target nucleic acid composition. In some embodiments, a method herein comprises contacting oligonucleotides with an agent comprising a phosphatase activity under conditions in which the oligonucleotides are dephosphorylated, thereby generating a plurality or pool of dephosphorylated oligonucleotide species. Generally, target nucleic acids and/or oligonucleotides are dephosphorylated prior to a combining step (i.e., prior to hybridization). Target nucleic acids may be dephosphorylated and then subsequently phosphorylated prior to a combining step (i.e., prior to hybridization). Oligonucleotides may be dephosphorylated and then subsequently phosphorylated prior to a combining step (i.e., prior to hybridization). Oligonucleotides may be dephosphorylated and then not phosphorylated prior to a combining step (i.e., prior to hybridization). Reagents and kits for carrying out dephosphorylation of nucleic acids are known and available. For example, target nucleic acids and/or oligonucleotides can be treated with a phosphatase (i.e., an enzyme that uses water to cleave a phosphoric acid monoester into a phosphate ion and an alcohol).

In some embodiments, a method herein comprises contacting a target nucleic acid composition with an agent comprising a phosphoryl transfer activity under conditions in which a 5' phosphate is added to a 5 end of target nucleic acids. In some embodiments, a method herein comprises contacting dephosphorylated target nucleic acids with an agent comprising a phosphoryl transfer activity under conditions in which a 5' phosphate is added to a 5' end of target nucleic acids. In some embodiments, a method herein comprises contacting oligonucleotides with an agent comprising a phosphoryl transfer activity under conditions in which a 5' phosphate is added to a 5' end of oligonucleotide species. In some embodiments, a method herein comprises contacting dephosphorylated oligonucleotides with an agent comprising a phosphoryl transfer activity under conditions in which a 5' phosphate is added to a 5 end of oligonucleotide species. Generally, target nucleic acids and/or oligonucleotides are phosphorylated prior to a combining step (i.e., prior to hybridization). 5' phosphorylation of nucleic acids can be conducted by a variety of techniques.

For example, target nucleic acids and/or oligonucleotides can be treated with a polynucleotide kinase (PNK) (e.g., T4 PNK), which catalyzes the transfer and exchange of Pi from the γ position of ATP to the 5'-hydroxyl terminus of polynucleotides (double- and single-stranded DNA and RNA) and nucleoside 3'-monophosphates. Suitable reaction conditions include, e.g., incubation of the nucleic acids with PNK in 1×PNK reaction buffer (e.g., 70 mM Tris-HCl, 10 mM $MgCl_2$, 5 mM DTT, pH 7.6 @25° C.) for 30 minutes at 37° C.; and incubation of the nucleic acids with PNK in T4 DNA ligase buffer (e.g., 50 mM Tris-HCl, 10 mM $MgCl_2$, 1 mM ATP, 10 mM DTT, pH 7.5 @25° C.) for 30 minutes at 37° C. Optionally, following the phosphorylation reaction, the PNK may be heat inactivated, e.g., at 65° C. for 20 minutes. In some embodiments, methods do not include producing the 5' phosphorylated nucleic acids by phosphorylating the 5' ends of nucleic acids from a nucleic acid sample. In certain instances, a nucleic acid sample comprises nucleic acids with natively phosphorylated 5' ends. In some embodiments, methods do not include producing the 5' phosphorylated oligonucleotides by phosphorylating the 5' ends of oligonucleotides.

Hybridization and Ligation

Nucleic acid fragments may be combined with oligonucleotides thereby generating combined products. Combining nucleic acid fragments with oligonucleotides may comprise one or more of overhang hybridization, ligation (e.g., ligation of hybridization products), and blunt-end ligation. A combined product may include a nucleic acid fragment connected to (e.g., hybridized to and/or ligated to) an oligonucleotide at one or both ends of the nucleic acid fragment. In some embodiments, target nucleic acids may be combined with oligonucleotides thereby generating combined products. In some embodiments, products from a cleavage step (i.e., cleaved products) may be combined with oligonucleotides thereby generating combined products. Certain methods herein comprise generating sets of combined products (e.g., a first set of combined products and a second set of combined products). In some embodiments, a first set of combined products includes target nucleic acids connected to (e.g., hybridized to and/or ligated to) oligonucleotides from a first pool of oligonucleotides. In some embodiments, a second set of combined products includes cleaved products connected to (e.g., hybridized to and/or ligated to) oligonucleotides from a second pool of oligonucleotides.

Target nucleic acids may be combined with oligonucleotides under hybridization conditions, thereby generating hybridization products. The conditions during the combining step are those conditions in which oligonucleotides (e.g., oligonucleotide overhangs) specifically hybridize to target nucleic acids having overhangs or overhang regions that are complementary in sequence and have corresponding lengths with respect to the oligonucleotide overhangs. In some embodiments, corresponding length generally refers to the same length (i.e., the same number of bases in the oligonucleotide overhang and the target nucleic acid overhang). Specific hybridization may be affected or influenced by factors such as the degree of complementarity between the oligonucleotide overhangs and the target nucleic acid overhangs, the length thereof, and the temperature at which the hybridization occurs, which may be informed by melting temperatures (Tm) of the overhangs. Melting temperature generally refers to the temperature at which half of the oligonucleotide overhangs/target nucleic acid overhangs remain hybridized and half of the oligonucleotide overhangs/target nucleic acid overhangs dissociate into single strands. The Tm of a duplex may be experimentally determined or predicted using the following formula $Tm=81.5+ 16.6(\log_{10}[Na+])+0.41$ (fraction G+C)−(60/N), where N is the chain length and [Na+] is less than 1 M.

In some embodiments, a method herein comprises exposing hybridization products to conditions under which an end of a target nucleic acid is joined to an end of an oligonucleotide species to which it is hybridized. Joining may be achieved by any suitable approach that permits covalent attachment of a target nucleic acid to the oligonucleotide to which it is hybridized. When one end of a target nucleic acid is joined to an end of the oligonucleotide to which it is hybridized, typically two attachment events are conducted: 1) the 3' end of one strand in the target nucleic acid to the 5' end of one strand in the oligonucleotide, and 2) the 5' end of the other strand in the target nucleic acid to the 3' end of the other strand in the oligonucleotide. When both ends of a target nucleic acid are each joined to an oligonucleotide to which it is hybridized, typically four attachment events are conducted: 1) the 3' end of one strand in the target nucleic acid to the 5' end of one strand in the oligonucleotide, 2) the 5' end of the other strand in the target nucleic acid to the 3' end of the other strand in the oligonucleotide; and 3) and 4): the same as (1) and (2) for the opposite end of the target nucleic acid attached to another oligonucleotide.

In some embodiments, a method herein comprises contacting hybridization products with an agent comprising a ligase activity under conditions in which an end of a target nucleic acid is covalently linked to an end of an oligonucleotide species to which the target nucleic acid is hybridized. Ligase activity may include, for example, blunt-end ligase activity, nick-sealing ligase activity, sticky end ligase activity, circularization ligase activity, cohesive end ligase activity, DNA ligase activity, and RNA ligase activity. Ligase activity may include ligating a 5' end of a target nucleic acid to a 3' end of an oligonucleotide hybridized thereto in a ligation reaction. Suitable reagents (e.g., ligases) and kits for performing ligation reactions are known and available. For example, Instant Sticky-end Ligase Master Mix available from New England Biolabs (Ipswich, Mass.) may be used. Ligases that may be used include, for example, T4 DNA ligase, T7 DNA Ligase, *E. coli* DNA Ligase, Electro Ligase®, RNA ligases, T4 RNA ligase 2, SplintR® Ligase, and the like and combinations thereof.

In some embodiments, hybridization products are contacted with a first agent comprising a first ligase activity and a second agent comprising a second ligase activity different than the first ligase activity. For example, the first ligase activity and the second ligase activity independently may be chosen from blunt-end ligase activity, nick-sealing ligase activity, sticky end ligase activity, circularization ligase activity, and cohesive end ligase activity. In some embodiments, certain oligonucleotides have no overhang. Such oligonucleotides may be blunt ended and may be joined (e.g., ligated) to one or more blunt ends of a target nucleic acid.

In some embodiments, a method herein comprises joining target nucleic acids to oligonucleotides via biocompatible attachments. Methods may include, for example, click chemistry or tagging, which include biocompatible reactions useful for joining biomolecules. In some embodiments, an end of each of the oligonucleotides comprises a first chemically reactive moiety and an end of each of the target nucleic acids includes a second chemically reactive moiety. In such embodiments, the first chemically reactive moiety typically is capable of reacting with the second chemically reactive moiety and forming a covalent bond between an oligonucleotide and a target nucleic acid to which the oligonucleotide is hybridized. In some embodiments, a method herein includes contacting target nucleic acids with one or more chemical agents under conditions in which the second chemically reactive moiety is incorporated at an end of each of the target nucleic acids. In some embodiments, a method herein includes exposing hybridization products to conditions in which the first chemically reactive moiety reacts with the second chemically reactive moiety forming a covalent bond between an oligonucleotide and a target nucleic acid to which the oligonucleotide is hybridized. In some embodiments, the first chemically reactive moiety is capable of reacting with the second chemically reactive moiety to form a 1,2,3-triazole between the oligonucleotide and the target nucleic acid to which the oligonucleotide is hybridized. In some embodiments, the first chemically reactive moiety is capable of reacting with the second chemically reactive moiety under conditions comprising copper. The first and second chemically reactive moieties may include any suitable pairings. For example, the first chemically reactive moiety may be chosen from an azide-containing moiety and 5-octadiynyl deoxyuracil, and the second chemically reactive moiety may be independently chosen from an azide-containing moiety, hexynyl and 5-octadiynyl deoxyuracil. In some embodiments, the azide-containing moiety is N-hydroxysuccinimide (NHS) ester-azide.

Cleavage

In some embodiments, oligonucleotides herein and/or hybridization products (e.g., oligonucleotides herein hybridized to target nucleic acids) are cleaved or sheared prior to, during, or after a method described herein. In some embodiments, oligonucleotides herein and/or hybridization products are cleaved or sheared at a cleavage site. In some embodiments, oligonucleotides herein and/or hybridization products are cleaved or sheared at a cleavage site within a hairpin loop. In some embodiments, oligonucleotides herein and/or hybridization products are cleaved or sheared at a cleavage site at an internal location in an oligonucleotide (e.g., within a duplex region of an oligonucleotide). In some embodiments, circular hybridization products are cleaved or sheared prior to, during, or after a method described herein. In some embodiments, nucleic acids, such as, for example, cellular nucleic acids and/or large fragments (e.g., greater than 500 base pairs in length) are cleaved or sheared prior to, during, or after a method described herein. Large fragments may be referred to as high molecular weight (HMW) nucleic acid or HMW DNA. HMW nucleic acid fragments may include fragments greater than about 500 bp, about 600 bp, about 700 bp, about 800 bp, about 900 bp, about 1000 bp, about 2000 bp, about 3000 bp, about 4000 bp, about 5000 bp, about 10,000 bp, or more. The term "shearing" or "cleavage" generally refers to a procedure or conditions in which a nucleic acid molecule may be severed into two (or more) smaller nucleic acid molecules. Such shearing or cleavage can be sequence specific, base specific, or nonspecific, and can be accomplished by any of a variety of methods, reagents or conditions, including, for example, chemical, enzymatic, and physical (e.g., physical fragmentation). Sheared or cleaved nucleic acids may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs.

Sheared or cleaved nucleic acids can be generated by a suitable method, non-limiting examples of which include physical methods (e.g., shearing, e.g., sonication, ultrasonication, French press, heat, UV irradiation, the like), enzymatic processes (e.g., enzymatic cleavage agents (e.g., a suitable nuclease, a suitable restriction enzyme), chemical methods (e.g., alkylation, DMS, piperidine, acid hydrolysis, base hydrolysis, heat, the like, or combinations thereof), ultraviolet (UV) light (e.g., at a photo-cleavable site (e.g., comprising a photo-cleavable spacer), the like or combinations thereof. The average, mean or nominal length of the resulting nucleic acid fragments can be controlled by selecting an appropriate fragment-generating method.

The term "cleavage agent" generally refers to an agent, sometimes a chemical or an enzyme that can cleave a nucleic acid at one or more specific or non-specific sites. Specific cleavage agents often cleave specifically according to a particular nucleotide sequence at a particular site, which may be referred to as a cleavage site. Cleavage agents may include enzymatic cleavage agents, chemical cleaving agents, and light (e.g., ultraviolet (UV) light).

Examples of enzymatic cleavage agents include without limitation endonucleases; deoxyribonucleases (DNase; e.g., DNase I, II); ribonucleases (RNase; e.g., RNAse A, RNAse E, RNAse F, RNAse H, RNAse III, RNAse L, RNAse P, RNAse PhyM, RNAse T1, RNAse T2, RNAse U2, and RNAse V); endonuclease VIII; CLEAVASE enzyme; TAQ DNA polymerase; E. coli DNA polymerase I; eukaryotic structure-specific endonucleases; murine FEN-1 endonucleases; nicking enzymes; type I, II or III restriction endonucleases (i.e., restriction enzymes) such as Acc I, Acil, Afl III, Alu I, Alw44 I, Apa I, Asn I, Ava I, Ava II, BamH I, Ban II, Bcl I, Bgl I. Bgl II, Bln I, Bsm I, BssH II, BstE II, BstUI, Cfo I, Cla I, Dde I, Dpn I, Dra I, EcIX I, EcoR I, EcoR I, EcoR II, EcoR V, Hae II, Hae II, Hhal, Hind II, Hind III, Hpa I, Hpa II, Kpn I, Ksp I, MaeII, McrBC, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase (e.g., hypoxanthine-DNA glycosylase, uracil DNA glycosylase (UDG), 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease I, exonuclease II, exonuclease III, exonuclease IV, exonuclease V, exonuclease VI, exonuclease VII, exonuclease VIII); 5' to 3' exonucleases (e.g. exonuclease II); 3' to 5' exonucleases (e.g. exonuclease I);

poly(A)-specific 3' to 5' exonucleases; ribozymes; DNAzymes; and the like and combinations thereof.

In some embodiments, a cleavage site (e.g., a cleavage site within a duplex portion of an oligonucleotide) comprises nucleotides chosen from uracil and deoxyuridine. In some embodiments, a cleavage agent comprises an endonuclease. In some embodiments, a cleavage agents comprises a DNA glycosylase. In some embodiments, cleavage agents comprise an endonuclease and a DNA glycosylase. In some embodiments, cleavage agents comprise a mixture of uracil DNA glycosylase (UDG) and endonuclease VIII.

In some embodiments, a cleavage site comprises a restriction enzyme recognition site. In some embodiments, a cleavage agent comprises a restriction enzyme. In some embodiments, a cleavage site comprises a rare-cutter restriction enzyme recognition site (e.g., a NotI recognition sequence). In some embodiments, a cleavage agent comprises a rare-cutter enzyme (e.g., a rare-cutter restriction enzyme). A rare-cutter enzyme generally refers to a restriction enzyme with a recognition sequence which occurs only rarely in a genome (e.g., a human genome). An example is NotI, which cuts after the first GC of a 5'-GCGGCCGC-3' sequence. Restriction enzymes with seven and eight base pair recognition sequences often are considered as rare-cutter enzymes.

Cleavage methods and procedures for selecting restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Enzymes often are used under conditions that will enable cleavage of the DNA with about 95%-100% efficiency, preferably with about 98%-100% efficiency.

In some embodiments, a cleavage site comprises one or more ribonucleic acid (RNA) nucleotides. In some embodiments, a cleavage site comprises a single stranded portion comprising one or more RNA nucleotides. In some embodiments, the singe stranded portion is flanked by duplex portions. In some embodiments, the singe stranded portion is a hairpin loop. In some embodiments, a cleavage site comprises one RNA nucleotide. In some embodiments, a cleavage site comprises two RNA nucleotides. In some embodiments, a cleavage site comprises three RNA nucleotides. In some embodiments, a cleavage site comprises four RNA nucleotides. In some embodiments, a cleavage site comprises five RNA nucleotides. In some embodiments, a cleavage site comprises more than five RNA nucleotides. In some embodiments, a cleavage site comprises one or more RNA nucleotides chosen from adenine (A), cytosine (C), guanine (G), and uracil (U). In some embodiments, a cleavage site comprises one or more RNA nucleotides chosen from adenine (A), cytosine (C), and guanine (G). In some embodiments, a cleavage site comprises no uracil (U). In some embodiments, a cleavage site comprises one or more RNA nucleotides comprising guanine (G). In some embodiments, a cleavage site comprises one or more RNA nucleotides consisting of guanine (G). In some embodiments, a cleavage site comprises one or more RNA nucleotides comprising cytosine (C). In some embodiments, a cleavage site comprises one or more RNA nucleotides consisting of cytosine (C). In some embodiments, a cleavage site comprises one or more RNA nucleotides comprising adenine (A). In some embodiments, a cleavage site comprises one or more RNA nucleotides consisting of adenine (A). In some embodiments, a cleavage site comprises one or more RNA nucleotides consisting of adenine (A), cytosine (C), and guanine (G). In some embodiments, a cleavage site comprises one or more RNA nucleotides consisting of adenine (A) and cytosine (C). In some embodiments, a cleavage site comprises one or more RNA nucleotides consisting of adenine (A) and guanine (G). In some embodiments, a cleavage site comprises one or more RNA nucleotides consisting of cytosine (C) and guanine (G). In some embodiments, a cleavage agent comprises a ribonuclease (RNAse). In some embodiments, an RNAse is an endoribonuclease. An RNAse may be chosen from one or more of RNAse A, RNAse E, RNAse F, RNAse H, RNAse III, RNAse L, RNAse P, RNAse PhyM, RNAse T1, RNAse T2, RNAse U2, and RNAse V.

In some embodiments, a cleavage site comprises a photo-cleavable spacer or photo-cleavable modification. Photo-cleavable modifications may contain, for example, a photo-labile functional group that is cleavable by ultraviolet (UV) light of specific wavelength (e.g., 300-350 nm). An example photo-cleavable spacer (available from Integrated DNA Technologies; product no. 1707) is a 10-atom linker arm that can only be cleaved when exposed to UV light within the appropriate spectral range. An oligonucleotide comprising a photo-cleavable spacer can have a 5' phosphate group that is available for subsequent ligase reactions. Photo-cleavable spacers can be placed between DNA bases or between an oligo and a terminal modification (e.g., a fluorophore). In such embodiments, ultraviolet (UV) light may be considered as a cleavage agent.

In some embodiments, a cleavage site comprises a diol. For example, a cleavage site may comprise vicinal diol incorporated in a 5' to 5' linkage. Cleavage sites comprising a diol may be chemically cleaved, for example, using a periodate. In some embodiments, a cleavage site comprises a blunt end restriction enzyme recognition site. Cleavage sites comprising a blunt end restriction enzyme recognition site may be cleaved by a blunt end restriction enzyme.

Nick Seal and Fill-In

In some embodiments, a method herein comprises performing a nick seal reaction (e.g., using a DNA ligase or other suitable enzyme, and, in certain instances, a kinase adapted to 5' phosphorylate nucleic acids (e.g., a polynucleotide kinase (PNK)). In some embodiments, a method herein comprises performing a fill-in reaction. For example, when oligonucleotides are present as duplexes, some or all of the duplexes may include an overhang at the end of the duplex opposite the end that hybridizes to the nucleic acids. When such duplex overhangs exist, subsequent to the combining, a method herein may further include filling in the overhangs formed by the duplexes. In some embodiments, a fill-in reaction is performed to generate a blunt-ended hybridization product. Any suitable reagent for carrying out a fill-in reaction may be used. Polymerases suitable for performing fill-in reactions include, e.g., DNA polymerase I, large (Klenow) fragment, *Bacillus stearothermophilus* (Bst) DNA polymerase, and the like. In some embodiments, a strand displacing polymerase is used (e.g., Bst DNA polymerase).

Exonuclease Treatment

In some embodiments, nucleic acid (e.g., hybridization products; circularized hybridization products) is treated with an exonuclease. Exonucleases are enzymes that work by cleaving nucleotides one at a time from the end of a polynucleotide chain through a hydrolyzing reaction that breaks phosphodiester bonds at either the 3' or the 5' end. Exonucleases include, for example, DNAses, RNAses (e.g., RNAseH), 5' to 3' exonucleases (e.g. exonuclease II), 3' to 5' exonucleases (e.g. exonuclease I), and poly(A)-specific 3' to 5' exonucleases. In some embodiments, hybridization products are treated with an exonuclease to remove contaminating nucleic acids such as, for example, single stranded oligonucleotides or nucleic acid fragments. In some embodiments, circularized hybridization products are treated with an exonuclease to remove any non-circularized hybridization products, non-hybridized oligonucleotides, non-hybridized target nucleic acids, oligonucleotide dimers, and the like and combinations thereof.

Second Pool of Oligonucleotides

Certain methods described herein comprise combining a target nucleic acid with a first pool of oligonucleotides (e.g., oligonucleotides comprising overhangs capable of hybridizing to target nucleic acid overhangs as described herein), cleaving the combined products to generate cleaved products, and combining the cleaved products with a second pool of oligonucleotides. Oligonucleotides in the second pool may comprise any feature described herein for oligonucleotides. However, oligonucleotides in the second pool generally do not comprise overhangs that are complementary to native overhangs in target nucleic acids, and generally do not comprise an overhang identification sequence.

In some embodiments, a method herein comprises attaching (e.g., annealing, hybridizing, ligating) an oligonucleotide from a second pool to at least one end of a cleaved target nucleic acid fragment (cleaved product). Generally, an oligonucleotide from a second pool attaches to a cleaved target nucleic acid fragment at a cleaved end and does not attach to a native end. In some embodiments, a cleaved target nucleic acid fragment undergoes end repair comprising one or more of blunt-end repair, 3' to 5' exonuclease treatment, 5' fill-in, A-tailing, and 5' phosphorylation, prior to combining with an oligonucleotide from a second pool. In some embodiments, a method herein comprises adding one or more unpaired nucleotides (e.g., A tail) to one or both ends of a cleaved product (i.e., at the cleaved end or ends). In some embodiments, an oligonucleotide from a second pool comprises one or more nucleotides (e.g., at the first end) that are complementary to the one or more nucleotides added to a cleaved product. In some embodiments, an end of an oligonucleotide from a second pool (e.g., a first end) is capable of being covalently linked to an end of a cleaved product to which the oligonucleotide is attached. In some embodiments, the 3' end of an oligonucleotide strand is capable of being covalently linked to the 5' end (e.g., phosphorylated 5' end) of a strand in the cleaved product to which the oligonucleotide is attached.

An oligonucleotide from a second pool may comprise a primer binding domain. A primer binding domain on an oligonucleotide from a second pool may be different from a primer binding domain on an oligonucleotide from a first pool. The primer binding domain may comprise any suitable primer binding sequence. In some embodiments, a primer binding domain comprises a P5 primer binding sequence. In some embodiments, a primer binding domain comprises a P7 primer binding sequence.

An oligonucleotide from a second pool may comprise a blunt end (e.g., at a first end), or may comprise a short (e.g., 1 bp, 2 bp, 3 bp) overhang at the first end. For example, an oligonucleotide from a second pool may comprise a single T, A, C, G or U overhang at the first end. In some embodiments, an oligonucleotide from a second pool comprises a single T overhang. Typically the overhang (e.g., T overhang) is on the 3' end of a strand at the first end.

An oligonucleotide from a second pool may comprise a phosphorothioate backbone modification (e.g., a phosphorothioate bond between the last two nucleotides on a strand). In some embodiments, an oligonucleotide from a second pool comprises a phosphorothioate backbone modification on a strand before an overhang (e.g., 3' T overhang). An oligonucleotide from a second pool may comprise one or more modified nucleotides, such as, for example, any modified nucleotide described herein. In some embodiments, an oligonucleotide from a second pool comprises a blocked nucleotide. An oligonucleotide from a second pool may be phosphorylated. An oligonucleotide from a second pool may be phosphorylated at the first end. Typically, an oligonucleotide from a second pool is phosphorylated at the 5' end of a strand at the first end.

Certain methods described herein comprise use of truncated oligonucleotides. In some embodiments, a second pool of oligonucleotides comprises truncated oligonucleotides. Truncated oligonucleotides may be referred to herein as specialized oligonucleotides, specialized adapters (e.g., specialized P5 adapters), shorty oligonucleotides, shorty adapters (e.g., shorty P5 adapters), and variations thereof. A truncated oligonucleotide generally comprise two nucleic acid strands (i.e., a first strand and a second strand), where one strand is shorter than the other strand. In some embodiments, the first strand is shorter than the second strand. In some embodiments, the first strand and the second strand are complementary at one end of the oligonucleotide (e.g., a first end) and the second strand comprises a single strand at the other end of the oligonucleotide (e.g., a second end). A truncated oligonucleotide may be designed such that the complement to the long strand is long enough to stay annealed, but is too short to be amplified (e.g., during index PCR). A truncated oligonucleotide may comprise any feature described herein for oligonucleotides. However, truncated oligonucleotides generally do not comprise overhangs that are complementary to native overhangs in target nucleic acids, and generally do not comprise an overhang identification sequence.

A truncated oligonucleotide may comprise an oligonucleotide identification sequence (e.g., barcode) specific to the truncated oligonucleotide. An oligonucleotide identification sequence may be used to identify a nucleic acid fragment end that is ligated to a truncated oligonucleotide. In some instances, an oligonucleotide identification sequence may be used to distinguish a nucleic acid fragment end that is ligated to a truncated oligonucleotide versus a nucleic acid fragment end that is ligated to a non-truncated oligonucleotide (e.g., an overhang oligonucleotide described herein). In some instances, an oligonucleotide identification sequence may be used to identify a non-native nucleic acid fragment end (e.g., a nucleic acid fragment end generated by shearing). In some embodiments, a truncated oligonucleotide comprises an oligonucleotide identification sequence that is about 5 bp to about 10 bp in length. For example, a truncated oligonucleotide may comprise an oligonucleotide identification sequence that is about 5 bp, 6 bp, 7 bp, 8 bp, 9 bp, or 10 bp in length. In some embodiments, a truncated oligonucleotide comprises an oligonucleotide identification sequence that is 8 bp in length.

A truncated oligonucleotide may comprise a primer binding domain. Generally, the primer binding domain is on the longer strand (e.g., the second strand). The primer binding domain may comprise any suitable primer binding sequence. In some embodiments, a primer binding domain comprises a P5 primer binding sequence. In some embodiments, a primer binding domain comprises a P7 primer binding sequence. Typically, the shorter strand (e.g., the first strand) comprises no primer binding domain.

A truncated oligonucleotide may comprise a blunt end (e.g., at the first end), or may comprise a short (e.g., 1 bp, 2 bp, 3 bp) overhang at the first end. For example, a truncated oligonucleotide may comprise a single T, A, C, G or U overhang at the first end. In some embodiments, a truncated oligonucleotide comprises a single T overhang. Typically the overhang (e.g., T overhang) is on the 3' end of the second strand.

A truncated oligonucleotide may comprise a phosphorothioate backbone modification (e.g., a phosphorothioate bond between the last two nucleotides on a strand). In some embodiments, a truncated oligonucleotide comprises a phosphorothioate backbone modification on the second strand. In some embodiments, a truncated oligonucleotide comprises a phosphorothioate backbone modification on the second strand before an overhang (e.g., 3' T overhang).

A truncated oligonucleotide may comprise one or more modified nucleotides, such as, for example, any modified nucleotide described herein. In some embodiments, a truncated oligonucleotide comprises a blocked nucleotide (e.g., a nucleotide comprising a C3 spacer). In some embodiments, a truncated oligonucleotide comprises a blocked nucleotide on the second strand. Typically, the blocked nucleotide is on the 5' end of the second strand. A truncated oligonucleotide may be phosphorylated. A truncated oligonucleotide may be phosphorylated at the first end. Typically, a truncated oligonucleotide is phosphorylated at the 5' end of the first strand.

Samples

Provided herein are methods and compositions for processing and/or analyzing nucleic acid. Nucleic acid or a nucleic acid mixture utilized in methods and compositions described herein may be isolated from a sample obtained from a subject (e.g., a test subject). A subject can be any living or non-living organism, including but not limited to a human, a non-human animal, a plant, a bacterium, a fungus, a protist or a pathogen. Any human or non-human animal can be selected, and may include, for example, mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, an infant, a child, an adult). A subject may be a cancer patient, a patient suspected of having cancer, a patient in remission, a patient with a family history of cancer, and/or a subject obtaining a cancer screen. A subject may be a patient having an infection or infectious disease or infected with a pathogen (e.g., bacteria, virus, fungus, protozoa, and the like), a patient suspected of having an infection or infectious disease or being infected with a pathogen, a patient recovering from an infection, infectious disease, or pathogenic infection, a patient with a history of infections, infectious disease, pathogenic infections, and/or a subject obtaining an infectious disease or pathogen screen. A subject may be a transplant recipient. A subject may be a patient undergoing a microbiome analysis. In some embodiments, a test subject is a female. In some embodiments, a test subject is a human female. In some embodiments, a test subject is a male. In some embodiments, a test subject is a human male.

A nucleic acid sample may be isolated or obtained from any type of suitable biological specimen or sample (e.g., a test sample). A nucleic acid sample may be isolated or obtained from a single cell, a plurality of cells (e.g., cultured cells), cell culture media, conditioned media, a tissue, an organ, or an organism (e.g., bacteria, yeast, or the like). In some embodiments, a nucleic acid sample is isolated or obtained from a cell(s), tissue, organ, and/or the like of an animal (e.g., an animal subject). In some embodiments, a nucleic acid sample is isolated or obtained from a source such as bacteria, yeast, insects (e.g., *drosophila*), mammals, amphibians (e.g., frogs (e.g., *Xenopus*)), viruses, plants, or any other mammalian or non-mammalian nucleic acid sample source.

A nucleic acid sample may be isolated or obtained from an extant organism or animal. In some instances, a nucleic acid sample may be isolated or obtained from an extinct (or "ancient") organism or animal (e.g., an extinct mammal; an extinct mammal from the genus Homo). In some instances, a nucleic acid sample may be obtained as part of a forensics analysis. In some instances, a nucleic acid sample may be obtained as part of a diagnostic analysis.

A sample or test sample may be any specimen that is isolated or obtained from a subject or part thereof (e.g., a human subject, a pregnant female, a cancer patient, a patient having an infection or infectious disease, a transplant recipient, a fetus, a tumor, an infected organ or tissue, a transplanted organ or tissue, a microbiome). A sample sometimes is from a pregnant female subject bearing a fetus at any stage of gestation (e.g., first, second or third trimester for a human subject), and sometimes is from a post-natal subject. A sample sometimes is from a pregnant subject bearing a fetus that is euploid for all chromosomes, and sometimes is from a pregnant subject bearing a fetus having a chromosome aneuploidy (e.g., one, three (i.e., trisomy (e.g., T21, T18, T13)), or four copies of a chromosome) or other genetic variation. Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo; cancer biopsy), celocentesis sample, cells (blood cells, placental cells, embryo or fetal cells, fetal nucleated cells or fetal cellular remnants, normal cells, abnormal cells (e.g., cancer cells)) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. A fluid or tissue sample from which nucleic acid is extracted may be acellular (e.g., cell-free). In some embodiments, a fluid or tissue sample may contain cellular elements or cellular remnants. In some embodiments, fetal cells or cancer cells may be included in the sample.

A sample can be a liquid sample. A liquid sample can comprise extracellular nucleic acid (e.g., circulating cell-free DNA). Non-limiting examples of liquid samples, include, blood or a blood product (e.g., serum, plasma, or the like), urine, biopsy sample (e.g., liquid biopsy for the detection of cancer), a liquid sample described above, the like or combinations thereof. In certain embodiments, a sample is a liquid biopsy, which generally refers to an assessment of a liquid sample from a subject for the presence, absence, progression or remission of a disease (e.g., cancer). A liquid biopsy can be used in conjunction with, or as an alternative to, a sold biopsy (e.g., tumor biopsy). In certain instances, extracellular nucleic acid is analyzed in a liquid biopsy.

In some embodiments, a biological sample may be blood, plasma or serum. The term "blood" encompasses whole blood, blood product or any fraction of blood, such as serum, plasma, buffy coat, or the like as conventionally defined. Blood or fractions thereof often comprise nucleosomes. Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3 to 40 milliliters, between 5 to 50 milliliters) often is collected and can be stored according to standard procedures prior to or after preparation.

An analysis of nucleic acid found in a subject's blood may be performed using, e.g., whole blood, serum, or plasma. An analysis of fetal DNA found in maternal blood, for example, may be performed using, e.g., whole blood, serum, or plasma. An analysis of tumor or cancer DNA found in a patient's blood, for example, may be performed using, e.g., whole blood, serum, or plasma. An analysis of pathogen DNA found in a patient's blood, for example, may be performed using, e.g., whole blood, serum, or plasma. An analysis of transplant DNA found in a transplant recipient's blood, for example, may be performed using, e.g., whole blood, serum, or plasma. Methods for preparing serum or plasma from blood obtained from a subject (e.g., a maternal subject; patient; cancer patient) are known. For example, a subject's blood (e.g., a pregnant woman's blood; patient's blood; cancer patient's blood) can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for nucleic acid extraction. In addition to the acellular portion of the whole blood, nucleic acid may also be recovered from the cellular fraction, enriched in the buffy coat portion, which can be obtained following centrifugation of a whole blood sample from the subject and removal of the plasma.

A sample may be a tumor nucleic acid sample (i.e., a nucleic acid sample isolated from a tumor). The term "tumor" generally refers to neoplastic cell growth and proliferation, whether malignant or benign, and may include pre-cancerous and cancerous cells and tissues. The terms "cancer" and "cancerous" generally refer to the physiological condition in mammals that is typically characterized by unregulated cell growth/proliferation. Examples of cancer include, but are not limited to, carcinoma, lymphoma, blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like.

A sample may be heterogeneous. For example, a sample may include more than one cell type and/or one or more nucleic acid species. In some instances, a sample may include (i) fetal cells and maternal cells, (ii) cancer cells and non-cancer cells, and/or (iii) pathogenic cells and host cells. In some instances, a sample may include (i) cancer and non-cancer nucleic acid, (ii) pathogen and host nucleic acid, (iii) fetal derived and maternal derived nucleic acid, and/or more generally, (iv) mutated and wild-type nucleic acid. In some instances, a sample may include a minority nucleic acid species and a majority nucleic acid species, as described in further detail below. In some instances, a sample may include cells and/or nucleic acid from a single subject or may include cells and/or nucleic acid from multiple subjects.

Nucleic Acid

Provided herein are methods and compositions for processing and/or analyzing nucleic acid. The terms nucleic acid(s), nucleic acid molecule(s), nucleic acid fragment(s), target nucleic acid(s), nucleic acid template(s), template nucleic acid(s), nucleic acid target(s), target nucleic acid(s), polynucleotide(s), polynucleotide fragment(s), target polynucleotide(s), polynucleotide target(s), and the like may be used interchangeably throughout the disclosure. The terms refer to nucleic acids of any composition from, such as DNA (e.g., complementary DNA (cDNA; synthesized from any RNA or DNA of interest), genomic DNA (gDNA), genomic DNA fragments, mitochondrial DNA (mtDNA), recombinant DNA (e.g., plasmid DNA), and the like), RNA (e.g., message RNA (mRNA), short inhibitory RNA (siRNA), ribosomal RNA (rRNA), transfer RNA (tRNA), microRNA, transacting small interfering RNA (ta-siRNA), natural small interfering RNA (nat-siRNA), small nucleolar RNA (snoRNA), small nuclear RNA (snRNA), long non-coding RNA (lncRNA), non-coding RNA (ncRNA), transfer-messenger RNA (tmRNA), precursor messenger RNA (pre-mRNA), small Cajal body-specific RNA (scaRNA), piwi-interacting RNA (piRNA), endoribonuclease-prepared siRNA (esiRNA), small temporal RNA (stRNA), signal recognition RNA, telomere RNA, RNA highly expressed by a fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, virus, bacterium, autonomously replicating sequence (ARS), mitochondria, centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense," "plus" strand or "minus" strand, "forward" reading frame or "reverse" reading frame) and double-stranded polynucleotides. The term "gene" refers to a section of DNA involved in producing a polypeptide chain; and generally includes regions preceding and following the coding region (leader and trailer) involved in the transcription/translation of the gene product and the regulation of the transcription/translation, as well as intervening sequences (introns) between individual coding regions (exons). A nucleotide or base generally refers to the purine and pyrimidine molecular units of nucleic acid (e.g., adenine (A), thymine (T), guanine (G), and cytosine (C)). For RNA, the base thymine is replaced with uracil. Nucleic acid length or size may be expressed as a number of bases.

Target nucleic acids may be any nucleic acids of interest. Nucleic acids may be polymers of any length composed of deoxyribonucleotides (i.e., DNA bases), ribonucleotides (i.e., RNA bases), or combinations thereof, e.g., 10 bases or longer, 20 bases or longer, 50 bases or longer, 100 bases or longer, 200 bases or longer, 300 bases or longer, 400 bases or longer, 500 bases or longer, 1000 bases or longer, 2000 bases or longer, 3000 bases or longer, 4000 bases or longer, 5000 bases or longer. In certain aspects, nucleic acids are polymers composed of deoxyribonucleotides (i.e., DNA bases), ribonucleotides (i.e., RNA bases), or combinations thereof, e.g., 10 bases or less, 20 bases or less, 50 bases or less, 100 bases or less, 200 bases or less, 300 bases or less, 400 bases or less, 500 bases or less, 1000 bases or less, 2000 bases or less, 3000 bases or less, 4000 bases or less, or 5000 bases or less.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of *E. Coli* RecA protein and/or by alteration of salt concentration, for example, using methods known in the art.

Nucleic acid (e.g., nucleic acid targets, oligonucleotides, overhangs) may be described herein as being complementary to another nucleic acid or having a complementarity region. The terms "complementary" or "complementarity" as used herein refer to a nucleotide sequence that base-pairs by non-covalent bonds to a region of a nucleic acid (e.g., target). In the canonical Watson-Crick base pairing, adenine (A) forms a base pair with thymine (T), and guanine (G) pairs with cytosine (C) in DNA. In RNA, thymine is replaced by uracil (U). As such, A is complementary to T and G is complementary to C. In RNA, A is complementary to U and vice versa. Typically, "complementary" or "complementarity" refers to a nucleotide sequence that is at least partially complementary. These terms may also encompass duplexes that are fully complementary such that every nucleotide in one strand is complementary to every nucleotide in the other strand in corresponding positions.

In certain instances, a nucleotide sequence may be partially complementary to a target, in which not all nucleotides are complementary to every nucleotide in the target nucleic acid in all the corresponding positions. For example, an oligonucleotide overhang may be perfectly (i.e., 100%) complementary to a target nucleic acid overhang, or an oligonucleotide overhang may share some degree of complementarity which is less than perfect (e.g., 70%, 75%, 85%, 90%, 95%, 99%).

In some embodiments, nucleic acids in a mixture of nucleic acids are analyzed. A mixture of nucleic acids can comprise two or more nucleic acid species having the same or different nucleotide sequences, different lengths, different origins (e.g., genomic origins, fetal vs. maternal origins, cell or tissue origins, cancer vs. non-cancer origin, tumor vs. non-tumor origin, host vs. pathogen, host vs. transplant, host vs. microbiome, sample origins, subject origins, and the like), different overhang lengths, different overhang types (e.g., 5' overhangs, 3' overhangs, no overhangs), or combinations thereof. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

In some embodiments, target nucleic acids comprise degraded DNA. Degraded DNA may be referred to as low-quality DNA or highly degraded DNA. Degraded DNA may be highly fragmented, and may include damage such as base analogs and abasic sites subject to miscoding lesions and/or intermolecular crosslinking. For example, sequencing errors resulting from deamination of cytosine residues may be present in certain sequences obtained from degraded DNA (e.g., miscoding of C to T and G to A).

Nucleic acid may be derived from one or more sources (e.g., biological sample, blood, cells, serum, plasma, buffy coat, urine, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as DNeasy®, RNeasy®, QIAprep®, QIAquick®, and QIAamp® (e.g., QIAamp® Circulating Nucleic Acid Kit, QiaAmp® DNA Mini Kit or QiaAmp® DNA Blood Mini Kit) nucleic acid isolation/purification kits by Qiagen, Inc. (Germantown, Md.); GenomicPrep™ Blood DNA Isolation Kit (Promega, Madison, Wis.); GFX™ Genomic Blood DNA Purification Kit (Amersham, Piscataway, N.J.); DNAzol®, ChargeSwitch®, Purelink®, GeneCatcher® nucleic acid isolation/purification kits by Life Technologies, Inc. (Carlsbad, Calif.); NucleoMag®, NucleoSpin®, and NucleoBond® nucleic acid isolation/purification kits by Clontech Laboratories, Inc. (Mountain View, Calif.); the like or combinations thereof. In certain aspects, the nucleic acid is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md.), the RecoverAll® Total Nucleic Acid Isolation kit for FFPE by Life Technologies, Inc. (Carlsbad, Calif.), and the NucleoSpin® FFPE kits by Clontech Laboratories, Inc. (Mountain View, Calif.).

In some embodiments, nucleic acid is extracted from cells using a cell lysis procedure. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. In some instances, a high salt and/or an alkaline lysis procedure may be utilized. In some instances, a lysis procedure may include a lysis step with EDTA/Proteinase K, a binding buffer step with high amount of salts (e.g., guanidinium chloride (GuHCl), sodium acetate) and isopropanol, and binding DNA in this solution to silica-based column. In some instances, a lysis protocol includes certain procedures described in Dabney et al., Proceedings of the National Academy of Sciences 110, no. 39 (2013): 15758-15763.

Nucleic acids can include extracellular nucleic acid in certain embodiments. The term "extracellular nucleic acid" as used herein can refer to nucleic acid isolated from a source having substantially no cells and also is referred to as "cell-free" nucleic acid (cell-free DNA, cell-free RNA, or both), "circulating cell-free nucleic acid" (e.g., CCF fragments, ccf DNA) and/or "cell-free circulating nucleic acid." Extracellular nucleic acid can be present in and obtained from blood (e.g., from the blood of a human subject). Extracellular nucleic acid often includes no detectable cells and may contain cellular elements or cellular remnants. Non-limiting examples of acellular sources for extracellular nucleic acid are blood, blood plasma, blood serum and urine. In certain aspects, cell-free nucleic acid is obtained from a body fluid sample chosen from whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion, and stool. As used herein, the term "obtain cell-free circulating sample nucleic acid" includes obtaining a sample directly (e.g., collecting a sample, e.g., a test sample) or obtaining a sample from another who has collected a sample. Extracellular nucleic acid may be a product of cellular secretion and/or nucleic acid release (e.g., DNA release). Extracellular nucleic acid may be a product of any form of cell death, for example. In some instances, extracellular nucleic acid is a product of any form of type I or type II cell death, including mitotic, oncotic, toxic, ischemic, and the like and combinations thereof. Without being limited by theory, extracellular nucleic acid may be a product of cell apoptosis and cell breakdown, which provides basis for extracellular nucleic acid often having a series of lengths across a spectrum (e.g., a "ladder"). In some instances, extracellular nucleic acid is a product of cell necrosis, necropoptosis, oncosis, entosis, pyrotosis, and the like and combinations thereof. In some embodiments, sample nucleic acid from a test subject is circulating cell-free nucleic acid. In some embodiments, circulating cell free nucleic acid is from blood plasma or blood serum from a test subject. In some aspects, cell-free nucleic acid is degraded. In some embodiments, cell-free nucleic acid comprises cell-free fetal nucleic acid (e.g., cell-free fetal DNA). In certain aspects, cell-free nucleic acid comprises circulating cancer nucleic acid (e.g., cancer DNA). In certain aspects, cell-free nucleic acid comprises circulating tumor nucleic acid (e.g., tumor DNA). In some embodiments, cell-free nucleic acid comprises infectious agent nucleic acid (e.g., pathogen DNA). In some embodiments, cell-free nucleic acid comprises nucleic acid (e.g., DNA) from a transplant. In some embodiments, cell-free nucleic acid comprises nucleic acid (e.g., DNA) from a microbiome (e.g., microbiome of gut, microbiome of blood, microbiome of mouth, microbiome of spinal fluid, microbiome of feces).

Extracellular nucleic acid can include different nucleic acid species, and therefore is referred to herein as "heterogeneous" in certain embodiments. For example, blood serum or plasma from a person having a tumor or cancer can include nucleic acid from tumor cells or cancer cells (e.g., neoplasia) and nucleic acid from non-tumor cells or non-cancer cells. In another example, blood serum or plasma from a pregnant female can include maternal nucleic acid and fetal nucleic acid. In another example, blood serum or plasma from a patient having an infection or infectious disease can include host nucleic acid and infectious agent or pathogen nucleic acid. In another example, a sample from a subject having received a transplant can include host nucleic acid and nucleic acid from the donor organ or tissue. In some instances, cancer nucleic acid, tumor nucleic acid, fetal nucleic acid, pathogen nucleic acid, or transplant nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is cancer, tumor, fetal, pathogen, transplant, or microbiome nucleic acid). In another example, heterogeneous nucleic acid may include nucleic acid from two or more subjects (e.g., a sample from a crime scene).

At least two different nucleic acid species can exist in different amounts in extracellular nucleic acid and sometimes are referred to as minority species and majority species. In certain instances, a minority species of nucleic acid is from an affected cell type (e.g., cancer cell, wasting cell, cell attacked by immune system). In certain embodiments, a genetic variation or genetic alteration (e.g., copy number alteration, copy number variation, single nucleotide alteration, single nucleotide variation, chromosome alteration, and/or translocation) is determined for a minority nucleic acid species. In certain embodiments, a genetic variation or genetic alteration is determined for a majority nucleic acid species. Generally, it is not intended that the terms "minority" or "majority" be rigidly defined in any respect. In one aspect, a nucleic acid that is considered "minority," for example, can have an abundance of at least about 0.1% of the total nucleic acid in a sample to less than 50% of the total nucleic acid in a sample. In some embodiments, a minority nucleic acid can have an abundance of at least about 1% of the total nucleic acid in a sample to about 40% of the total nucleic acid in a sample. In some embodiments, a minority nucleic acid can have an abundance of at least about 2% of the total nucleic acid in a sample to about 30% of the total nucleic acid in a sample. In some embodiments, a minority nucleic acid can have an abundance of at least about 3% of the total nucleic acid in a sample to about 25% of the total nucleic acid in a sample. For example, a minority nucleic acid can have an abundance of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total nucleic acid in a sample. In some instances, a minority species of extracellular nucleic acid sometimes is about 1% to about 40% of the overall nucleic acid (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% of the nucleic acid is minority species nucleic acid). In some embodiments, the minority nucleic acid is extracellular DNA. In some embodiments, the minority nucleic acid is extracellular DNA from apoptotic tissue. In some embodiments, the minority nucleic acid is extracellular DNA from tissue where some cells therein underwent apoptosis. In some embodiments, the minority nucleic acid is extracellular DNA from necrotic tissue. In some embodiments, the minority nucleic acid is extracellular DNA from tissue where some cells therein underwent necrosis. Necrosis may refer to a post-mortem process following cell death, in certain instances. In some embodiments, the minority nucleic acid is extracellular DNA from tissue affected by a cell proliferative disorder (e.g., cancer). In some embodiments, the minority nucleic acid is extracellular DNA from a tumor cell. In some embodiments, the minority nucleic acid is extracellular fetal DNA. In some embodiments, the minority nucleic acid is extracellular DNA from a pathogen. In some embodiments, the minority nucleic acid is extracellular DNA from a transplant. In some embodiments, the minority nucleic acid is extracellular DNA from a microbiome.

In another aspect, a nucleic acid that is considered "majority," for example, can have an abundance greater than 50% of the total nucleic acid in a sample to about 99.9% of the total nucleic acid in a sample. In some embodiments, a majority nucleic acid can have an abundance of at least about 60% of the total nucleic acid in a sample to about 99% of the total nucleic acid in a sample. In some embodiments, a majority nucleic acid can have an abundance of at least about 70% of the total nucleic acid in a sample to about 98% of the total nucleic acid in a sample. In some embodiments, a majority nucleic acid can have an abundance of at least about 75% of the total nucleic acid in a sample to about 97% of the total nucleic acid in a sample. For example, a majority nucleic acid can have an abundance of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the total nucleic acid in a sample. In some embodiments, the majority nucleic acid is extracellular DNA. In some embodiments, the majority nucleic acid is extracellular maternal DNA. In some embodiments, the majority nucleic acid is DNA from healthy tissue. In some embodiments, the majority nucleic acid is DNA from non-tumor cells. In some embodiments, the majority nucleic acid is DNA from host cells.

In some embodiments, a minority species of extracellular nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of extracellular nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of extracellular nucleic acid is of a length of about 250 base pairs or less (e.g., about 80, 85, 90, 91, 92, 93, 94, 95, 96, 97, 98, 99 or 100% of minority species nucleic acid is of a length of about 250 base pairs or less). In some embodiments, a minority species of extracellular nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of extracellular nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less). In some embodiments, a minority species of extracellular nucleic acid is of a length of about 100 base pairs or less (e.g., about 80, 85, 90, 91, 92, 93, 94, 95, 96, 97, 98, 99 or 100% of minority species nucleic acid is of a length of about 100 base pairs or less). In some embodiments, a minority species of extracellular nucleic acid is of a length of about 50 base pairs or less (e.g., about 80, 85, 90, 91, 92, 93, 94, 95, 96, 97, 98, 99 or 100% of minority species nucleic acid is of a length of about 50 base pairs or less).

Nucleic acid may be provided for conducting methods described herein with or without processing of the sample(s) containing the nucleic acid. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, small fragments of nucleic acid (e.g., 30 to 500 bp fragments) can be purified, or partially purified, from a mixture comprising nucleic acid fragments of different lengths. In certain examples, nucleosomes comprising smaller fragments of nucleic acid can be purified from a mixture of larger nucleosome complexes comprising larger fragments of nucleic acid. In certain examples, larger nucleosome complexes comprising larger fragments of nucleic acid can be purified from nucleosomes comprising smaller fragments of nucleic acid. In certain examples, small fragments of fetal nucleic acid (e.g., 30 to 500 bp fragments) can be purified, or partially purified, from a mixture comprising both fetal and maternal nucleic acid fragments. In certain examples, nucleosomes comprising smaller fragments of fetal nucleic acid can be purified from a mixture of larger nucleosome complexes comprising larger fragments of maternal nucleic acid. In certain examples, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid. In some embodiments, nucleic acid is provided for conducting methods described herein without prior processing of the sample(s) containing the nucleic acid. For example, nucleic acid may be analyzed directly from a sample without prior extraction, purification, partial purification, and/or amplification.

Nucleic acids may be amplified under amplification conditions. The term "amplified" or "amplification" or "amplification conditions" as used herein refers to subjecting a target nucleic acid in a sample to a process that linearly or exponentially generates amplicon nucleic acids having the same or substantially the same nucleotide sequence as the target nucleic acid, or part thereof. In certain embodiments, the term "amplified" or "amplification" or "amplification conditions" refers to a method that comprises a polymerase chain reaction (PCR). In certain instances, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule).

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a sequence analysis.

In some embodiments, target nucleic acids are not modified in length prior to combining with the oligonucleotides herein. In this context, "not modified" means that target nucleic acids are isolated from a sample and then combined with oligonucleotides without modifying the length of the target nucleic acids. For example, target nucleic acids are not shortened (e.g., they are not contacted with a restriction enzyme or nuclease or physical condition that reduces length (e.g., shearing condition, cleavage condition)) and are not increased in length by one or more nucleotides (e.g., ends are not filled in at overhangs; no nucleotides are added to the ends). Adding a phosphate or chemically reactive group to one or both ends of a target nucleic acid generally is not considered modifying the length of the nucleic acid.

In some embodiments, native ends of target nucleic acids are not modified in length prior to combining with the oligonucleotides herein. In this context, "not modified" means that target nucleic acids are isolated from a sample and then combined with oligonucleotides without modifying the length of the native ends of target nucleic acids. For example, target nucleic acids are not shortened (e.g., they are not contacted with a restriction enzyme or nuclease or physical condition that reduces length (e.g., shearing condition, cleavage condition) to generate non-native ends) and are not increased in length by one or more nucleotides (e.g., native ends are not filled in at overhangs; no nucleotides are added to the native ends). Adding a phosphate or chemically reactive group to one or both native ends of a target nucleic acid generally is not considered modifying the length of the nucleic acid.

In some embodiments, target nucleic acids are not contacting with a cleavage agent (e.g., endonuclease, exonuclease, restriction enzyme) and/or a polymerase prior to combining with the oligonucleotides herein. In some embodiments, target nucleic acids are not subjected to mechanical shearing (e.g., ultrasonication (e.g., Adaptive Focused Acoustics™ (AFA) process by Covaris)) prior to combining with the oligonucleotides herein. In some embodiments, target nucleic acids are not contacting with an exonuclease (e.g., DNAse) prior to combining with the oligonucleotides herein. In some embodiments, target nucleic acids are not amplified prior to combining with the oligonucleotides herein. In some embodiments, target nucleic acids are not attached to a solid support prior to combining with the oligonucleotides herein. In some embodiments, target nucleic acids are not conjugated to another molecule prior to combining with the oligonucleotides herein. In some embodiments, target nucleic acids are not cloned into a vector prior to combining with the oligonucleotides herein. In some embodiments, target nucleic acids may be subjected to dephosphorylation prior to combining with the oligonucleotides herein. In some embodiments, target nucleic acids may be subjected to phosphorylation prior to combining with the oligonucleotides herein.

In some embodiments, combining target nucleic acids with the oligonucleotides herein comprises isolating the target nucleic acids, and combing the isolated target nucleic acids with the oligonucleotides herein. In some embodiments, combining target nucleic acids with the oligonucleotides herein comprises isolating the target nucleic acids, phosphorylating the isolated target nucleic acids, and combing the phosphorylated target nucleic acids with the oligonucleotides herein. In some embodiments, combining target nucleic acids with the oligonucleotides herein comprises isolating the target nucleic acids, dephosphorylating the oligonucleotides, and combing the isolated target nucleic acids with the dephosphorylated oligonucleotides herein. In some embodiments, combining target nucleic acids with the oligonucleotides herein comprises isolating the target nucleic acids, dephosphorylating the isolated target nucleic acids, phosphorylating the dephosphorylated target nucleic acids, and combing the phosphorylated target nucleic acids with the oligonucleotides herein. In some embodiments, combining target nucleic acids with the oligonucleotides herein comprises isolating the target nucleic acids, dephosphorylating the isolated target nucleic acids, phosphorylating the dephosphorylated target nucleic acids, dephosphorylating the oligonucleotides, and combing the phosphorylated target nucleic acids with the dephosphorylated oligonucleotides herein.

In some embodiments, combining target nucleic acids with the oligonucleotides herein consists of isolating the target nucleic acids, and combing the isolated target nucleic acids with the oligonucleotides herein. In some embodiments, combining target nucleic acids with the oligonucleotides herein consists of isolating the target nucleic acids, phosphorylating the isolated target nucleic acids, and combing the phosphorylated target nucleic acids with the oligonucleotides herein. In some embodiments, combining target nucleic acids with the oligonucleotides herein consists of isolating the target nucleic acids, dephosphorylating the oligonucleotides, and combing the isolated target nucleic acids with the dephosphorylated oligonucleotides herein. In some embodiments, combining target nucleic acids with the oligonucleotides herein consists of isolating the target nucleic acids, dephosphorylating the isolated target nucleic acids, phosphorylating the dephosphorylated target nucleic acids, and combing the phosphorylated target nucleic acids with the oligonucleotides herein. In some embodiments, combining target nucleic acids with the oligonucleotides herein consists of isolating the target nucleic acids, dephosphorylating the isolated target nucleic acids, phosphorylating the dephosphorylated target nucleic acids, dephosphorylating the oligonucleotides, and combing the phosphorylated target nucleic acids with the dephosphorylated oligonucleotides herein.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, cancer nucleic acid, tumor nucleic acid, patient nucleic acid, host nucleic acid, pathogen nucleic acid, transplant nucleic acid, microbiome nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample. In certain embodiments, nucleic acid from normal tissue (e.g., non-cancer cells, host cells) is selectively removed (partially, substantially, almost completely or completely) from the sample. In certain embodiments, maternal nucleic acid is selectively removed (partially, substantially, almost completely or completely) from the sample. In certain embodiments, enriching for a particular low copy number species nucleic acid (e.g., cancer, tumor, fetal, pathogen, transplant, microbiome nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, the entire content of each is incorporated herein by reference, including all text, tables, equations and drawings.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art.

Non-limiting examples of methods for enriching for a nucleic acid subpopulation in a sample include methods that exploit epigenetic differences between nucleic acid species (e.g., methylation-based fetal nucleic acid enrichment methods described in U.S. Patent Application Publication No. 2010/0105049, which is incorporated by reference herein); restriction endonuclease enhanced polymorphic sequence approaches (e.g., such as a method described in U.S. Patent Application Publication No. 2009/0317818, which is incorporated by reference herein); selective enzymatic degradation approaches; massively parallel signature sequencing (MPSS) approaches; amplification (e.g., PCR)-based approaches (e.g., loci-specific amplification methods, multiplex SNP allele PCR approaches; universal amplification methods); pull-down approaches (e.g., biotinylated ultramer pull-down methods); extension and ligation-based methods (e.g., molecular inversion probe (MIP) extension and ligation); and combinations thereof.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from a nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a part or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci, or a particular sequence in a nucleic acid target. In certain embodiments, a hybridization-based method (e.g., using oligonucleotide arrays) can be used to enrich for fragments containing certain nucleic acid sequences. Thus, in some embodiments, a nucleic acid sample is optionally enriched by capturing a subset of fragments using capture oligonucleotides complementary to, for example, selected sequences in sample nucleic acid. In certain instances, captured fragments are amplified. For example, captured fragments containing adapters may be amplified using primers complementary to the adapter oligonucleotides to form collections of amplified fragments, indexed according to adapter sequence. In some embodiments, nucleic acid is enriched for fragments from a select genomic region (e.g., chromosome, a gene) by amplification of one or more regions of interest using oligonucleotides (e.g., PCR primers) complementary to sequences in fragments containing the region(s) of interest, or part(s) thereof.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain instances, length-based separation approaches can include selective sequence tagging approaches, fragment circularization, chemical treatment (e.g., formaldehyde, polyethylene glycol (PEG) precipitation), mass spectrometry and/or size-specific nucleic acid amplification, for example.

In some aspects, a method comprises enriching for a species of target nucleic acid. For example, a method herein may comprise enriching for a species of target nucleic acid having a particular overhang feature (e.g., length, type (5', 3'), sequence). Enrichment for a species of target nucleic acid having a particular overhang feature may be achieved according to a particular overhang identification sequence. For example, certain target nucleic acids complexed with oligonucleotides described herein may be separated from the rest of the target nucleic acids according to a particular overhang identification sequence (e.g., according to the sequence, or according to another feature (e.g., modification) of the overhang identification sequence). In some embodiments, a method comprises associating complexes (target nucleic acids joined to oligonucleotides herein) with one or more binding agents that specifically hybridize to a particular overhang identification sequence, thereby generating enriched complexes. For the term "specifically hybridize," specific, or specificity, generally refers to the binding or hybridization of one molecule to another molecule (e.g., a polynucleotide strand to a complementary strand). That is, specific or specificity refers to the recognition, contact, and formation of a stable complex between two molecules, as compared to substantially less recognition, contact, or complex formation of either of those two molecules with other molecules. The term hybridize generally refers to the formation of a stable complex between two molecules.

In some aspects, a polynucleotide complementary to a particular overhang identification sequence comprises a member of a binding pair. In some aspects, one or more nucleotides (e.g., one or more modified nucleotides) in a particular overhang identification sequence comprises a member of a binding pair. Binding pairs may include, for example, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group, digoxigenin moiety/anti-digoxigenin antibody, fluorescein moiety/anti-fluorescein antibody, steroid/steroid-binding protein, operator/repressor, nuclease/nucleotide, lectin/polysaccharide, active compound/active compound receptor, hormone/hormone receptor, enzyme/substrate, oligonucleotide or polynucleotide/its corresponding complement, the like or combinations thereof.

In some embodiments, one or more binding agents that specifically hybridize to a particular overhang identification sequence may be attached to a solid support (e.g., bead or any suitable solid support described herein or known in the art). Enrichment for target nucleic acids having a particular species of overhang may be subsequently achieved according to any suitable method for separating biomolecules (e.g., pull down assays, use of solid supports, and the like).

Length-Based Separation

In some embodiments, a method herein comprises separating target nucleic acids according to fragment length. For example, target nucleic acids may be enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also may be referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In some embodiments, length-based separation approaches can include fragment circularization, chemical treatment (e.g., formaldehyde, polyethylene glycol (PEG)), mass spectrometry and/or size-specific nucleic acid amplification, for example. In some embodiments, length based-separation is performed using Solid Phase Reversible Immobilization (SPRI) beads.

In some embodiments, nucleic acid fragments of a certain length, range of lengths, or lengths under or over a particular threshold or cutoff are separated from the sample. In some embodiments, fragments having a length under a particular threshold or cutoff (e.g., 500 bp, 400 bp, 300 bp, 200 bp, 150 bp, 100 bp) are referred to as "short" fragments and fragments having a length over a particular threshold or cutoff (e.g., 500 bp, 600 bp, 700 bp, 800 bp, 900 bp, 1000 bp) are referred to as "long" fragments, large fragments, and/or high molecular weight (HMW) fragments. In some embodiments, fragments of a certain length, range of lengths, or lengths under or over a particular threshold or cutoff are retained for analysis while fragments of a different length or range of lengths, or lengths over or under the threshold or cutoff are not retained for analysis. In some embodiments, fragments that are less than about 500 bp are retained. In some embodiments, fragments that are less than about 400 bp are retained. In some embodiments, fragments that are less than about 300 bp are retained. In some embodiments, fragments that are less than about 200 bp are retained. In some embodiments, fragments that are less than about 150 bp are retained. For example, fragments that are less than about 190 bp, 180 bp, 170 bp, 160 bp, 150 bp, 140 bp, 130 bp, 120 bp, 110 bp or 100 bp are retained. In some embodiments, fragments that are about 100 bp to about 200 bp are retained. For example, fragments that are about 190 bp, 180 bp, 170 bp, 160 bp, 150 bp, 140 bp, 130 bp, 120 bp or 110 bp are retained. In some embodiments, fragments that are in the range of about 100 bp to about 200 bp are retained. For example, fragments that are in the range of about 110 bp to about 190 bp, 130 bp to about 180 bp, 140 bp to about 170 bp, 140 bp to about 150 bp, 150 bp to about 160 bp, or 145 bp to about 155 bp are retained.

In some embodiments, target nucleic acids having fragment lengths of less than about 1000 bp are combined with a plurality or pool of oligonucleotide species described herein. In some embodiments, target nucleic acids having fragment lengths of less than about 500 bp are combined with a plurality or pool of oligonucleotide species described herein. In some embodiments, target nucleic acids having fragment lengths of less than about 400 bp are combined with a plurality or pool of oligonucleotide species described herein. In some embodiments, target nucleic acids having fragment lengths of less than about 300 bp are combined with a plurality or pool of oligonucleotide species described herein. In some embodiments, target nucleic acids having fragment lengths of less than about 200 bp are combined with a plurality or pool of oligonucleotide species described herein. In some embodiments, target nucleic acids having fragment lengths of less than about 100 bp are combined with a plurality or pool of oligonucleotide species described herein.

In some embodiments, target nucleic acids having fragment lengths of about 100 bp or more are combined with a plurality or pool of oligonucleotide species described herein. In some embodiments, target nucleic acids having fragment lengths of about 200 bp or more are combined with a plurality or pool of oligonucleotide species described herein. In some embodiments, target nucleic acids having fragment lengths of about 300 bp or more are combined with a plurality or pool of oligonucleotide species described herein. In some embodiments, target nucleic acids having fragment lengths of about 400 bp or more are combined with a plurality or pool of oligonucleotide species described herein. In some embodiments, target nucleic acids having fragment lengths of about 500 bp or more are combined with a plurality or pool of oligonucleotide species described herein. In some embodiments, target nucleic acids having fragment lengths of about 1000 bp or more are combined with a plurality or pool of oligonucleotide species described herein.

In some embodiments, target nucleic acids having any fragment length or any combination of fragment lengths are combined with a plurality or pool of oligonucleotide species described herein. For example, target nucleic acids having fragment lengths of less than 500 bp and fragments lengths of 500 bp or more may be combined with a plurality or pool of oligonucleotide species described herein.

Certain length-based separation methods that can be used with methods described herein employ a selective sequence tagging approach, for example. In such methods, a fragment size species (e.g., short fragments) nucleic acids are selectively tagged in a sample that includes long and short nucleic acids. Such methods typically involve performing a nucleic acid amplification reaction using a set of nested primers which include inner primers and outer primers. In some embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another length-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Nucleic Acid Library

Methods herein may include preparing a nucleic acid library and/or modifying nucleic acids for a nucleic acid library. In some embodiments, ends of nucleic acid fragments are modified such that the fragments, or amplified products thereof, may be incorporated into a nucleic acid library. Generally, a nucleic acid library refers to a plurality of polynucleotide molecules (e.g., a sample of nucleic acids) that are prepared, assembled and/or modified for a specific process, non-limiting examples of which include immobilization on a solid phase (e.g., a solid support, a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments, a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigenin moiety and an anti-digoxigenin antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments, a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, an overhang identification sequence (i.e., unique end identifier (UEI)) described herein, a unique molecular identifier (UMI) described herein, a palindromic sequence described herein, the like or combinations thereof. Polynucleotides of known sequence can be added at a suitable position, for example on the 5' end, 3' end or within a nucleic acid sequence. Polynucleotides of known sequence can be the same or different sequences. In some embodiments, a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments, a library of nucleic acid can comprise chromosome-specific tags, capture sequences, labels and/or adapters (e.g., oligonucleotide adapters described herein). In some embodiments, a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments, a library of nucleic acids comprises hybridized oligonucleotides. In certain embodiments hybridized oligonucleotides are labeled probes. In some embodiments, a library of nucleic acids comprises hybridized oligonucleotide probes prior to immobilization on a solid phase.

In some embodiments, a polynucleotide of known sequence comprises a universal sequence. A universal sequence is a specific nucleotide sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using cell-free DNA).

In certain embodiments, a ligation-based library preparation method is used (e.g., ILLUMINA TRUSEQ, Illumina, San Diego Calif.). Ligation-based library preparation methods often make use of an adapter (e.g., a methylated adapter) design which can incorporate an index sequence (e.g., a sample index sequence to identify sample origin for a nucleic acid sequence) at the initial ligation step and often can be used to prepare samples for single-read sequencing, paired-end sequencing and multiplexed sequencing. For example, nucleic acids (e.g., fragmented nucleic acids or cell-free DNA) may be end repaired by a fill-in reaction, an exonuclease reaction or a combination thereof. In some embodiments, the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments, end repair is omitted and adapter oligonucleotides (e.g., oligonucleotides described herein) are ligated directly to the native ends of nucleic acids (e.g., fragmented nucleic acids or cell-free DNA).

In some embodiments, nucleic acid library preparation comprises ligating an adapter oligonucleotide (e.g., to a sample nucleic acid, to a sample nucleic acid fragment, to a template nucleic acid, to a target nucleic acid), such as an adapter oligonucleotide described herein. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). In some embodiments, an adapter oligonucleotide comprises one or more of primer annealing polynucleotide, also referred to herein as priming sequence or primer binding domain, (e.g., for annealing to flow cell attached oligonucleotides and/or to free amplification primers), an index polynucleotide (e.g., sample index sequence for tracking nucleic acid from different samples; also referred to as a sample ID), an overhang identification sequence (also referred to herein as and a unique end identifier (UEI)) barcode polynucleotide (e.g., single molecule barcode (SMB) for tracking individual molecules of sample nucleic acid that are amplified prior to sequencing; also referred to as a molecular barcode or a unique molecular identifier (UMI)). In some embodiments, a primer annealing component (or priming sequence or primer binding domain) of an adapter oligonucleotide comprises one or more universal sequences (e.g., sequences complementary to one or more universal amplification primers). In some embodiments, an index polynucleotide (e.g., sample index; sample ID) is a component of an adapter oligonucleotide. In some embodiments, an index polynucleotide (e.g., sample index; sample ID) is a component of a universal amplification primer sequence.

In some embodiments, adapter oligonucleotides when used in combination with amplification primers (e.g., universal amplification primers) are designed generate library constructs comprising one or more of: universal sequences, molecular barcodes, sample ID sequences, spacer sequences, and a sample nucleic acid sequence. In some embodiments, adapter oligonucleotides when used in combination with universal amplification primers are designed generate library constructs comprising an ordered combination of one or more of: universal sequences, molecular barcodes, sample ID sequences, spacer sequences, and a sample nucleic acid sequence. For example, a library construct may comprise a first universal sequence, followed by a second universal sequence, followed by first molecular barcode, followed by a spacer sequence, followed by a template sequence (e.g., sample nucleic acid sequence), followed by a spacer sequence, followed by a second molecular barcode, followed by a third universal sequence, followed by a sample ID, followed by a fourth universal sequence. In some embodiments, adapter oligonucleotides when used in combination with amplification primers (e.g., universal amplification primers) are designed generate library constructs for each strand of a template molecule (e.g., sample nucleic acid molecule). In some embodiments, adapter oligonucleotides are duplex adapter oligonucleotides.

An identifier can be a suitable detectable label incorporated into or attached to a nucleic acid (e.g., a polynucleotide) that allows detection and/or identification of nucleic acids that comprise the identifier. In some embodiments, an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments, an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, apparatus or machine, non-limiting examples of which include flow cytometry, quantitative polymerase chain reaction (qPCR), gel electrophoresis, a luminometer, a fluorometer, a spectrophotometer, a suitable genechip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a nucleic acid library or parts thereof are amplified (e.g., amplified by a PCR-based method) under amplification conditions. In some embodiments, a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments, a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support. In some embodiments, modified nucleic acid (e.g., nucleic acid modified by addition of adapters) is amplified.

In some embodiments, solid phase amplification comprises a nucleic acid amplification reaction comprising only one species of oligonucleotide primer immobilized to a surface. In certain embodiments, solid phase amplification comprises a plurality of different immobilized oligonucleotide primer species. In some embodiments, solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., U.S. Patent Application Publication No. 2013/0012399), the like or combinations thereof.

Nucleic Acid Sequencing

In some embodiments, nucleic acid (e.g., nucleic acid fragments, sample nucleic acid, cell-free nucleic acid) is sequenced. In some embodiments, nucleic acid targets hybridized to oligonucleotides provided herein ("hybridization products") are sequenced by a sequencing process. In some embodiments, hybridization products are amplified by an amplification process, and the amplification products are sequenced by a sequencing process. In some embodiments, the sequencing process generates sequence reads (or sequencing reads). In some embodiments, a method herein comprises determining the sequence of an overhang for target nucleic acids based on the sequence reads. In some embodiments, a method herein comprises determining a sequence of an overhang identification sequence or unique end identifier (UEI) based on the sequence reads. In some embodiments, a method herein comprises determining the sequence of elements comprising an overhang identification sequence or unique end identifier (UEI) and an overhang for target nucleic acids based on the sequence reads. In some embodiments, a method herein comprises determining the sequence of elements consisting of an overhang identification sequence or unique end identifier (UEI) and an overhang for target nucleic acids based on the sequence reads. In some embodiments, a method herein comprises determining lengths of the overhangs for target nucleic acids according to the sequence reads.

For certain sequencing platforms (e.g., paired-end sequencing), generating sequence reads may include generating forward sequence reads and generating reverse sequence reads. For example, sequencing using certain paired-end sequencing platforms sequence each nucleic acid fragment from both directions, generally resulting in two reads per nucleic acid fragment, with the first read in a forward orientation (forward read) and the second read in a reverse-complement orientation (reverse read). For certain platforms, a forward read is generated off a particular primer within a sequencing adapter (e.g., Illumina adapter, P5 primer), and a reverse read is generated off a different primer within a sequencing adapter (e.g., Illumina adapter, P7 primer).

In some embodiments, a method herein comprises analyzing (e.g., quantifying, processing) a subset of sequence reads. In some embodiments, a method herein comprises analyzing (e.g., quantifying, processing) a subset of sequence reads and omitting another subset of sequence reads from the analysis. In some embodiments, a method herein comprises analyzing or processing overhang information for a subset of sequence reads. In some embodiments, a method herein comprises analyzing (e.g., quantifying, processing) reverse sequence reads. In some embodiments, a method herein comprises analyzing or processing overhang information for reverse sequence reads. In some embodiments, a method herein comprises analyzing or processing overhang information associated with overhang identification sequences for reverse sequence reads. In some embodiments, a method herein comprises analyzing (e.g., quantifying, processing) P7 sequence reads. In some embodiments, a method herein comprises analyzing (e.g., quantifying, processing) overhang information generated from P7 sequence reads. In some embodiments, a method herein comprises analyzing (e.g., quantifying, processing) overhang information associated with overhang identification sequences generated from P7 sequence reads.

In some embodiments, a method herein comprises omitting forward sequence reads from an analysis. In some embodiments, a method herein comprises omitting overhang information generated from forward sequence reads from an analysis. In some embodiments, a method herein comprises omitting overhang information associated with overhang identification sequences generated from forward sequence reads from an analysis. In some embodiments, a method herein comprises omitting P5 sequence reads from an analysis. In some embodiments, a method herein comprises omitting overhang information generated from P5 sequence reads from an analysis. In some embodiments, a method herein comprises omitting overhang information associated with overhang identification sequences generated from P5 sequence reads from an analysis.

In some embodiments, forward reads as a whole are not excluded entirely. For example, the overhang identification sequence of a forward read may be ignored and thus the overhang inferred from the forward read overhang identification sequence is excluded from an overhang analysis; and only overhangs from the reverse reads are analyzed. In such instances, other aspects of the forward reads may be included in an analysis, for example, to infer fragment length, determine GC content, identify single nucleotide variants, or identify blunt ends.

In some embodiments, a method herein comprises analyzing or processing overhang information associated with overhang identification sequences that indicate no overhang (i.e., blunt end) for reverse sequence reads. In some embodiments, a method herein comprises analyzing or processing overhang information associated with overhang identification sequences that indicate no overhang (i.e., blunt end) for forward sequence reads. In some embodiments, a method herein comprises analyzing or processing overhang information associated with overhang identification sequences that indicate no overhang (i.e., blunt end) for forward and reverse sequence reads. Thus, in some embodiments, where an overhang identification sequence indicates no overhang (i.e., blunt end), no information about the blunt end is omitted from the analysis.

In some embodiments, a method herein comprises analyzing or processing overhang information associated with overhang identification sequences that indicate no overhang (i.e., blunt end) for forward and reverse sequence reads, analyzing or processing overhang information associated with overhang identification sequences that indicate presence of an overhang for reverse sequence reads, and omitting overhang information associated with overhang identification sequences that indicate presence of an overhang for forward sequence reads from the analysis. Thus, an analysis of nucleic acid ends (e.g., native nucleic acid ends) may include analysis of nucleic acid end blunt end information generated from both forward and reverse sequence reads, and nucleic acid overhang information generated from reverse reads only.

Nucleic acid may be sequenced using any suitable sequencing platform including a Sanger sequencing platform, a high throughput or massively parallel sequencing (next generation sequencing (NGS)) platform, or the like, such as, for example, a sequencing platform provided by Illumina® (e.g., HiSeq™, MiSeq™ and/or Genome Analyzer™ sequencing systems); Oxford Nanopore™ Technologies (e.g., MinION sequencing system), Ion Torrent™ (e.g., Ion PGM™ and/or Ion Proton™ sequencing systems); Pacific Biosciences (e.g., PACBIO RS II sequencing system); Life Technologies™ (e.g., SOLiD sequencing system); Roche (e.g., 454 GS FLX+ and/or GS Junior sequencing systems); or any other suitable sequencing platform. In some embodiments, the sequencing process is a highly multiplexed sequencing process. In certain instances, a full or substantially full sequence is obtained and sometimes a partial sequence is obtained. Nucleic acid sequencing generally produces a collection of sequence reads. As used herein, "reads" (e.g., "a read," "a sequence read") are short sequences of nucleotides produced by any sequencing process described herein or known in the art. Reads can be generated from one end of nucleic acid fragments (single-end reads), and sometimes are generated from both ends of nucleic acid fragments (e.g., paired-end reads, double-end reads). In some embodiments, a sequencing process generates short sequencing reads or "short reads." In some embodiments, the nominal, average, mean or absolute length of short reads sometimes is about 10 continuous nucleotides to about 250 or more contiguous nucleotides. In some embodiments, the nominal, average, mean or absolute length of short reads sometimes is about 50 continuous nucleotides to about 150 or more contiguous nucleotides.

The length of a sequence read is often associated with the particular sequencing technology utilized. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length of about 1000 bp or more. In some embodiments sequence reads are of a mean, median, average or absolute length of about 1500, 2000, 2500, 3000, 3500, 4000, 4500, or 5000 bp or more. In some embodiments, sequence reads are of a mean, median, average or absolute length of about 100 bp to about 200 bp.

In some embodiments. the nominal, average, mean or absolute length of single-end reads sometimes is about 10 continuous nucleotides to about 250 or more contiguous nucleotides, about 15 contiguous nucleotides to about 200 or more contiguous nucleotides, about 15 contiguous nucleotides to about 150 or more contiguous nucleotides, about 15 contiguous nucleotides to about 125 or more contiguous nucleotides, about 15 contiguous nucleotides to about 100 or more contiguous nucleotides, about 15 contiguous nucleotides to about 75 or more contiguous nucleotides, about 15 contiguous nucleotides to about 60 or more contiguous nucleotides, 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length. In certain embodiments the nominal, average, mean or absolute length of single-end reads is about 20 to about 200 bases, about 100 to about 200 bases, or about 140 to about 160 bases in length. In certain embodiments the nominal, average, mean or absolute length of single-end reads is about 30, 40, 50, 60, 70, 80, 90, 100, 110, 120, 130, 140, 150, 160, 170, 180, 190, or about 200 bases or more in length. In certain embodiments, the nominal, average, mean or absolute length of paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides. In certain embodiments, the nominal, average, mean or absolute length of paired-end reads sometimes is about 25 contiguous nucleotides to about 400 contiguous nucleotides or more (e.g., about 25, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 nucleotides in length or more), about 50 contiguous nucleotides to about 350 contiguous nucleotides or more, about 100 contiguous nucleotides to about 325 contiguous nucleotides, about 150 contiguous nucleotides to about 325 contiguous nucleotides, about 200 contiguous nucleotides to about 325 contiguous nucleotides, about 275 contiguous nucleotides to about 310 contiguous nucleotides, about 100 contiguous nucleotides to about 200 contiguous nucleotides, about 100 contiguous nucleotides to about 175 contiguous nucleotides, about 125 contiguous nucleotides to about 175 contiguous nucleotides, and sometimes is about 140 contiguous nucleotides to about 160 contiguous nucleotides. In certain embodiments, the nominal, average, mean, or absolute length of paired-end reads is about 150 contiguous nucleotides, and sometimes is 150 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from a sample from a subject can be reads from a mixture of a minority nucleic acid and a majority nucleic acid. For example, sequence reads obtained from the blood of a cancer patient can be reads from a mixture of cancer nucleic acid and non-cancer nucleic acid. In another example, sequence reads obtained from the blood of a pregnant female can be reads from a mixture of fetal nucleic acid and maternal nucleic acid. In another example, sequence reads obtained from the blood of a patient having an infection or infectious disease can be reads from a mixture of host nucleic acid and pathogen nucleic acid. In another example, sequence reads obtained from the blood of a transplant recipient can be reads from a mixture of host nucleic acid and transplant nucleic acid. In another example, sequence reads obtained from a sample can be reads from a mixture of nucleic acid from microorganisms collectively comprising a microbiome (e.g., microbiome of gut, microbiome of blood, microbiome of mouth, microbiome of spinal fluid, microbiome of feces) in a subject. In another example, sequence reads obtained from a sample can be reads from a mixture of nucleic acid from microorganisms collectively comprising a microbiome (e.g., microbiome of gut, microbiome of blood, microbiome of mouth, microbiome of spinal fluid, microbiome of feces), and nucleic acid from the host subject. A mixture of relatively short reads can be transformed by processes described herein into a representation of genomic nucleic acid present in the subject, and/or a representation of genomic nucleic acid present in a tumor, a fetus, a pathogen, a transplant, or a microbiome.

In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, some or all nucleic acids in a sample are enriched and/or amplified (e.g., non-specifically, e.g., by a PCR based method) prior to or during sequencing. In certain embodiments, specific nucleic acid species or subsets in a sample are enriched and/or amplified prior to or during sequencing. In some embodiments, a species or subset of a pre-selected pool of nucleic acids is sequenced randomly. In some embodiments, nucleic acids in a sample are not enriched and/or amplified prior to or during sequencing.

In some embodiments, a representative fraction of a genome is sequenced and is sometimes referred to as "coverage" or "fold coverage." For example, a 1-fold coverage indicates that roughly 100% of the nucleotide sequences of the genome are represented by reads. In some instances, fold coverage is referred to as (and is directly proportional to) "sequencing depth." In some embodiments, "fold coverage" is a relative term referring to a prior sequencing run as a reference. For example, a second sequencing run may have 2-fold less coverage than a first sequencing run. In some embodiments, a genome is sequenced with redundancy, where a given region of the genome can be covered by two or more reads or overlapping reads (e.g., a "fold coverage" greater than 1, e.g., a 2-fold coverage). In some embodiments, a genome (e.g., a whole genome) is sequenced with about 0.01-fold to about 100-fold coverage, about 0.1-fold to 20-fold coverage, or about 0.1-fold to about 1-fold coverage (e.g., about 0.015-, 0.02-, 0.03-, 0.04-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold or greater coverage). In some embodiments, specific parts of a genome (e.g., genomic parts from targeted methods) are sequenced and fold coverage values generally refer to the fraction of the specific genomic parts sequenced (i.e., fold coverage values do not refer to the whole genome). In some instances, specific genomic parts are sequenced at 1000-fold coverage or more. For example, specific genomic parts may be sequenced at 2000-fold, 5,000-fold, 10,000-fold, 20,000-fold, 30,000-fold, 40,000-fold or 50,000-fold coverage. In some embodiments, sequencing is at about 1,000-fold to about 100,000-fold coverage. In some embodiments, sequencing is at about 10,000-fold to about 70,000-fold coverage. In some embodiments, sequencing is at about 20,000-fold to about 60,000-fold coverage. In some embodiments, sequencing is at about 30,000-fold to about 50,000-fold coverage.

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments, a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments, the number of samples analyzed in a given flow cell lane is dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8-lane flow cell. Similarly, multiplexing using 48 identifiers, for example, allows simultaneous analysis of 384 samples (e.g., equal to the number of wells in a 384 well microwell plate) in an 8-lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first-generation technology, such as, for example, Sanger sequencing methods including automated Sanger sequencing methods, including microfluidic Sanger sequencing, can be used in a method provided herein. In some embodiments, sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments, MPS sequencing methods utilize a targeted approach, where specific chromosomes, genes or regions of interest are sequenced. In certain embodiments, a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments, a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g., Illumina's Genome Analyzer; Genome Analyzer II; HISEQ 2000; HISEQ 2500 (Illumina, San Diego Calif.)). With this technology, millions of nucleic acid (e.g., DNA) fragments can be sequenced in parallel. In one example of this type of sequencing technology, a flow cell is used which contains an optically transparent slide with 8 individual lanes on the surfaces of which are bound oligonucleotide anchors (e.g., adapter primers).

Sequencing by synthesis generally is performed by iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments, reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof.

Any suitable MPS method, system or technology platform for conducting methods described herein can be used to obtain nucleic acid sequence reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, U.S. Patent Application Publication No. 2013/0012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, the like or combinations thereof. Other sequencing methods that may be used to conduct methods herein include digital PCR, sequencing by hybridization, nanopore sequencing, chromosome-specific sequencing (e.g., using DANSR (digital analysis of selected regions) technology.

In some embodiments, nucleic acid is sequenced and the sequencing product (e.g., a collection of sequence reads) is processed prior to, or in conjunction with, an analysis of the sequenced nucleic acid. For example, sequence reads may be processed according to one or more of the following: aligning, mapping, filtering, counting, normalizing, weighting, generating a profile, and the like, and combinations thereof. Certain processing steps may be performed in any order and certain processing steps may be repeated.

Mapping Reads

Sequence reads can be mapped and the number of reads mapping to a specified nucleic acid region (e.g., a chromosome or portion thereof) are referred to as counts. In certain embodiments, sequence reads comprising overhang sequence information can be mapped and the number of reads comprising overhang sequence information are mapping to a specified nucleic acid region. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped," as "a mapped sequence read" or as "a mapped read." In certain embodiments, a mapped sequence read is referred to as a "hit" or "count." In some embodiments, mapped sequence reads are grouped together according to various parameters and assigned to particular genomic portions, which are discussed in further detail below.

The terms "aligned," "alignment," or "aligning" generally refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand (e.g., sense or antisense strand). In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP, BWA or SEQMAP, or variations thereof or combinations thereof. In some embodiments, sequence reads can be aligned with sequences in a reference genome. In some embodiments, sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search identified sequences against a sequence database. Search hits can then be used to sort the identified sequences into appropriate portions (described hereafter), for example.

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at World Wide Web URL ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, mappability is assessed for a genomic region (e.g., portion, genomic portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

For paired-end sequencing, reads may be mapped to a reference genome by use of a suitable mapping and/or alignment program, non-limiting examples of which include BWA (Li H. and Durbin R. (2009) *Bioinformatics* 25, 1754-60), Novoalign [Novocraft (2010)], Bowtie (Langmead B, et al., (2009) *Genome Biol.* 10:R25), SOAP2 (Li R, et al., (2009) *Bioinformatics* 25, 1966-67), BFAST (Homer N, et al., (2009) *PLoS ONE* 4, e7767), GASSST (Rizk, G. and Lavenier, D. (2010) *Bioinformatics* 26, 2534-2540), and MPscan (Rivals E., et al. (2009) *Lecture Notes in Computer Science* 5724, 246-260), and the like. Paired-end reads may be mapped and/or aligned using a suitable short read alignment program. Non-limiting examples of short read alignment programs include BarraCUDA, BFAST, BLASTN, BLAT, Bowtie, BWA, CASHX, CUDA-EC, CUSHAW, CUSHAW2, drFAST, ELAND, ERNE, GNUMAP, GEM, GensearchNGS, GMAP, Geneious Assembler, iSAAC, LAST, MAQ, mrFAST, mrsFAST, MOSAIK, MPscan, Novoalign, NovoalignCS, Novocraft, NextGENe, Omixon, PALMapper, Partek, PASS, PerM, QPalma, RazerS, REAL, cREAL, RMAP, rNA, RTG, Segemehl, SeqMap, Shrec, SHRiMP, SLIDER, SOAP, SOAP2, SOAP3, SOCS, SSAHA, SSAHA2, Stampy, SToRM, Subread, Subjunc, Taipan, UGENE, VelociMapper, TimeLogic, XpressAlign, ZOOM, the like or combinations thereof. Paired-end reads are often mapped to opposing ends of the same polynucleotide fragment, according to a reference genome. In some embodiments, read mates are mapped independently. In some embodiments, information from both sequence reads (i.e., from each end) is factored in the mapping process. A reference genome is often used to determine and/or infer the sequence of nucleic acids located between paired-end read mates. The term "discordant read pairs" as used herein refers to a paired-end read comprising a pair of read mates, where one or both read mates fail to unambiguously map to the same region of a reference genome defined, in part, by a segment of contiguous nucleotides. In some embodiments discordant read pairs are paired-end read mates that map to unexpected locations of a reference genome. Non-limiting examples of unexpected locations of a reference genome include (i) two different chromosomes, (ii) locations separated by more than a predetermined fragment size (e.g., more than 300 bp, more than 500 bp, more than 1000 bp, more than 5000 bp, or more than 10,000 bp), (iii) an orientation inconsistent with a reference sequence (e.g., opposite orientations), the like or a combination thereof. In some embodiments discordant read mates are identified according to a length (e.g., an average length, a predetermined fragment size) or expected length of template polynucleotide fragments in a sample. For example, read mates that map to a location that is separated by more than the average length or expected length of polynucleotide fragments in a sample are sometimes identified as discordant read pairs. Read pairs that map in opposite orientation are sometimes determined by taking the reverse complement of one of the reads and comparing the alignment of both reads using the same strand of a reference sequence. Discordant read pairs can be identified by any suitable method and/or algorithm known in the art or described herein (e.g., SVDetect, Lumpy, BreakDancer, BreakDancerMax, CREST, DELLY, the like or combinations thereof).

Sequence Read Quantification

Sequence reads that are mapped or partitioned based on a selected feature or variable can be quantified to determine the amount or number of reads that are mapped to one or more portions (e.g., portion of a reference genome). In some embodiments, sequence reads comprising overhang information that are mapped or partitioned based on a selected feature or variable can be quantified to determine the amount or number of reads comprising overhang information that are mapped to one or more portions. In certain embodiments, the quantity of sequence reads that are mapped to a portion or segment is referred to as a count or read density.

A count often is associated with a genomic portion. In some embodiments a count is determined from some or all of the sequence reads mapped to (i.e., associated with) a portion. In certain embodiments, a count is determined from some or all of the sequence reads mapped to a group of portions (e.g., portions in a segment or region).

A count can be determined by a suitable method, operation or mathematical process. A count sometimes is the direct sum of all sequence reads mapped to a genomic portion or a group of genomic portions corresponding to a segment, a group of portions corresponding to a sub-region of a genome (e.g., copy number variation region, copy number alteration region, copy number duplication region, copy number deletion region, microduplication region, microdeletion region, chromosome region, autosome region, sex chromosome region) and/or sometimes is a group of portions corresponding to a genome. A read quantification sometimes is a ratio, and sometimes is a ratio of a quantification for portion(s) in region a to a quantification for portion(s) in region b. Region a sometimes is one portion, segment region, copy number variation region, copy number alteration region, copy number duplication region, copy number deletion region, microduplication region, microdeletion region, chromosome region, autosome region and/or sex chromosome region. Region b independently sometimes is one portion, segment region, copy number variation region, copy number alteration region, copy number duplication region, copy number deletion region, microduplication region, microdeletion region, chromosome region, autosome region, sex chromosome region, a region including all autosomes, a region including sex chromosomes and/or a region including all chromosomes.

In some embodiments, a count is derived from raw sequence reads and/or filtered sequence reads. In certain embodiments a count is an average, mean or sum of sequence reads mapped to a genomic portion or group of genomic portions (e.g., genomic portions in a region). In some embodiments, a count is associated with an uncertainty value. A count sometimes is adjusted. A count may be adjusted according to sequence reads associated with a genomic portion or group of portions that have been weighted, removed, filtered, normalized, adjusted, averaged, derived as a mean, derived as a median, added, or combination thereof.

A sequence read quantification sometimes is a read density. A read density may be determined and/or generated for one or more segments of a genome. In certain instances, a read density may be determined and/or generated for one or more chromosomes. In some embodiments a read density comprises a quantitative measure of counts of sequence reads mapped to a segment or portion of a reference genome. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. A read density may be a density estimation derived from a suitable probability density function. A density estimation is the construction of an estimate, based on observed data, of an underlying probability density function. In some embodiments a read density comprises a density estimation (e.g., a probability density estimation, a kernel density estimation). A read density may be generated according to a process comprising generating a density estimation for each of the one or more portions of a genome where each portion comprises counts of sequence reads. A read density may be generated for normalized and/or weighted counts mapped to a portion or segment. In some instances, each read mapped to a portion or segment may contribute to a read density, a value (e.g., a count) equal to its weight obtained from a normalization process described herein. In some embodiments read densities for one or more portions or segments are adjusted. Read densities can be adjusted by a suitable method. For example, read densities for one or more portions can be weighted and/or normalized.

Reads quantified for a given portion or segment can be from one source or different sources. In one example, reads may be obtained from nucleic acid from a subject having cancer or suspected of having cancer. In such circumstances, reads mapped to one or more portions often are reads representative of both healthy cells (i.e., non-cancer cells) and cancer cells (e.g., tumor cells). In certain embodiments, some of the reads mapped to a portion are from cancer cell nucleic acid and some of the reads mapped to the same portion are from non-cancer cell nucleic acid. In another example, reads may be obtained from a nucleic acid sample from a pregnant female bearing a fetus. In such circumstances, reads mapped to one or more portions often are reads representative of both the fetus and the mother of the fetus (e.g., a pregnant female subject). In certain embodiments some of the reads mapped to a portion are from a fetal genome and some of the reads mapped to the same portion are from a maternal genome.

Assays

Techniques of the present disclosure can be used to perform a variety of assays. In some cases, a sample can be assayed for some, many, or all of the overhangs present in the sample nucleic acids. This information can be used to generate an overall overhang profile for the sample, indicating the number or frequency of the overhangs present. In some cases, a sample can be assayed for a panel of one or more particular overhangs present in the sample. In some cases, a sample can be assayed for one or more features of the overhangs present in the sample. In some cases, a sample can be assayed for bunt-ended fragments (e.g., target nucleic acid (e.g., DNA) that is blunt-ended on one side or blunt-ended on both sides).

An overhang profile for a sample may be generated by analyzing and/or quantifying certain features of the overhangs present in the sample. In certain instances, profiles may additionally or alternatively include features of the target/template nucleic acids themselves (e.g., with or without overhang information). In certain instances, overhang profiles exclude features of the target/template nucleic acids. Thus, in certain embodiments, overhang profiles consist of overhang features. Overhang/template features may be analyzed or quantified using any suitable quantification method, clustering method, statistical algorithm, classifier or model including, but not limited to, regression (e.g., logistic regression, linear regression, multivariate regression, least squares regression), hierarchical clustering (e.g., Ward's hierarchical clustering), supervised learning algorithm (e.g., support vector machine (SVM)), multivariate model (e.g., principal component analysis (PCA)), linear discriminant analysis, quadratic discriminant analysis, bagging, neural networks, support vector machine models, random forests, classification tree models, K-nearest neighbors, and the like, and/or any suitable mathematical and/or statistical manipulation.

Overhang/template features that may be analyzed or quantified include, but are not limited to, dinucleotide count (e.g., presence/absence of a particular dinucleotide in the overhang or read (e.g., number of overhangs in the sample having a particular dinucleotide, number of template+overhangs in the sample having a particular dinucleotide, or number of template minus overhangs in the sample having a particular dinucleotide) and/or a count of the instances of a particular dinucleotide within an overhang or read); trinucleotide count (e.g., presence/absence of a particular trinucleotide in the overhang or read (e.g., number of overhangs in the sample having a particular trinucleotide, number of template+overhangs in the sample having a particular trinucleotide, or number of template minus overhangs in the sample having a particular trinucleotide) and/or a count of the instances of a particular trinucleotide within an overhang or read); tetranucleotide count (e.g., presence/absence of a particular tetranucleotide in the overhang or read (e.g., number of overhangs in the sample having a particular tetranucleotide, number of template+overhangs in the sample having a particular tetranucleotide, or number of template minus overhangs in the sample having a particular tetranucleotide) and/or a count of the instances of a particular tetranucleotide within an overhang or read); dinucleotide percent (e.g., percent of overhangs in the sample having a particular dinucleotide, percent of template+overhangs in the sample having a particular dinucleotide, or percent of template minus overhangs in the sample having a particular dinucleotide; number of dinucleotides in the overhang normalized by the overhang length; the proportion of the dinucleotide that is of that particular overhang; comparison across all overhangs regardless of length); trinucleotide percent (e.g., percent of overhangs in the sample having a particular trinucleotide, percent of template+overhangs in the sample having a particular trinucleotide, or percent of template minus overhangs in the sample having a particular trinucleotide; number of trinucleotides in the overhang normalized by the overhang length; the proportion of the trinucleotide that is of that particular overhang; comparison across all overhangs regardless of length); tetranucleotide percent (e.g., percent of overhangs in the sample having a particular tetranucleotide, percent of template+overhangs in the sample having a particular tetranucleotide, or percent of template minus overhangs in the sample having a particular tetranucleotide; number of tetranucleotides in the overhang normalized by the overhang length; the proportion of the tetranucleotide that is of that particular overhang; comparison across all overhangs regardless of length); full length of template; length category (e.g., for cfDNA: subnucleosome, mononucleosome, multinucleosome); overhang length (e.g., 1 base, 2 bases, 3 bases, 4 bases, 5 bases, 6 bases, 7 bases, 8 bases, 9 bases, 10 bases, or more); overhang type (e.g., 5' overhang, 3' overhang, blunt); GC content (e.g., overhang GC content, template+overhang GC content, or template minus overhang GC content); overhang percent (e.g., log 2 percent of overhang sequence/total overhangs); overhang count (e.g., counts of particular overhang sequence); percent length (e.g., length of overhang/full length of template); dinucleotide count in overhang vs. entire sequence of template molecule; trinucleotide count in overhang vs. entire sequence of template molecule; tetranucleotide count in overhang vs. entire sequence of template molecule; Boolean variables which may include whether an overhang overlaps with, is contained in, and/or starts or ends in a particular region (e.g., coding regions, CpG islands, transcription factor binding sites (e.g., CCCTC-binding factor (CTCF) binding site), DNAse hypersensitive sites, sequences denoting open chromatin (e.g., ATAC-seq peaks); promoter regions, enhancer regions, hypermethylated regions, other regions of interest, and the like); genome coordinates; mean fragment length or distribution of molecules with a given overhang type and length; mean fragment length or distribution of molecules with a given overhang sequence; delta between libraries (e.g., identification of correlations in the data between variables (e.g., detect correlation between X feature and Y feature such as the mean of the fragment length distribution vs X variable (e.g., mean length or distribution of fragments with a given overhang sequence vs. its X, where X=any feature/variable above))); and the like and combinations thereof. Example dinucleotides include AA, AT, AC, AG, TT, TA, TC, TG, CC, CG, CA, CT, GG, GA, GC, and GT. Trinucleotides include $4^3$ possible nucleotide combinations, and tetranucleotides include $4^4$ possible nucleotide combinations. In some embodiments, presence of a dinucleotide in the overhangs in a sample is analyzed. In some embodiments, presence of a CG dinucleotide in the overhangs in a sample is analyzed. In some embodiments, presence of a GG dinucleotide in the overhangs in a sample is analyzed. In some embodiments, presence of a GC dinucleotide in the overhangs in a sample is analyzed.

Overhang profiles, including overall overhang profiles, overhang panels, and overhang features, can be indicative of various characteristics of a sample or a source (e.g., organism) from which a sample was taken. These characteristics can include, but are not limited to, nuclease activity and/or content, topoisomerase activity and/or content, disease (e.g., cancer type, cancer stage, infection, organ disease or failure, neurodegenerative disease, ischemia, stroke, cardiovascular disease), cell death (e.g., increased or decreased rate of cell death systemically, increased or decreased rate of cell death in a particular organ or cell type, increased or decreased rate of certain modes of cell death (e.g., apoptosis, autophagy, necrosis, mitotic catastrophe, anoikis, cornification, excitotoxicity, ferroptosis, Wallerian degeneration, activation-induced cell death (AICD), ischemic cell death, oncosis, immunogenic cell death or apoptosis, pyroptosis), dysregulation of apoptosis or other cell death modes), microbiome profile (e.g., gut microbiome, blood microbiome, mouth microbiome, skin microbiome, environmental microbiome (such as soil microbiome, water microbiome)), and radiation exposure type and/or amount (e.g., ultraviolet (A and B), ionizing radiation (e.g., cosmic rays, alpha particles, beta particles, gamma rays, X-rays), neutron radiation). In some embodiments, overhang profiles, including overall overhang profiles, overhang panels, and overhang features, are indicative of cancer. In some embodiments, overhang profiles, including overall overhang profiles, overhang panels, and overhang features, are indicative of gastrointestinal cancer.

Overhang profiles, including overall overhang profiles, overhang panels, and overhang features, can be indicative of nuclease (e.g., DNase) activity, such as endogenous nuclease activity. Nuclease (e.g., DNase) activity can be indicative of various characteristics of a sample or a source discussed herein, including but not limited to cancer. In some cases, the overhangs of naturally present nucleic acids in a sample can be assayed. In some cases, nucleic acids (e.g., synthesized nucleic acids) can be introduced into a sample, where they can then be acted on by nucleases present in the sample. Use of a known nucleic acid population can produce an overhang profile that is compared to those from different samples. The different overhangs produced on the known nucleic acids can be informative of the nuclease profile of the sample. Tissue-specific nuclease activity can be assayed in vitro. For example, cell lines from different organs, tissues, or cell types can be cultured and cell death can be induced, followed by an assay of overhang profiles. Overhang profiles also can be assayed for a particular enzyme (e.g., nuclease) or group of enzymes. A particular enzyme or group of enzymes can be used to digest a population of nucleic acids, and the resulting overhang profile can be assayed. For example, CRISPR/Cas-system proteins or other nucleic acid-guided nucleases can be assayed to determine the type of ends (e.g., blunt ends, 1-bp staggered ends, other overhangs) they produce. In some applications, overhang profile assays may be used to monitor the efficacy of particular treatments and targeted therapies that aim to alter the activity of DNAse activity (e.g., vitamins C and K3; topoisomerase inhibitors used in anti-cancer therapies; and the like).

In some cases, nucleases in a subject or a sample can be inhibited to preserve a particular overhang profile. For example, cellular processes may produce one overhang profile (e.g., from lysis, cell death, and/or post-mortem intracellular processes), while nucleases present outside the cell (e.g., in a bodily fluid such as blood) may further alter the first overhang profile of the cell. Nucleases, such as those outside the cell, can be inhibited or deactivated (e.g., temporarily) to preserve the initial overhang profile for assaying. Nuclease activity can be inhibited (e.g., with actin) ahead of the sample collection. In an example, two populations of overhangs are assayed, those from diseased cells (D) and those from healthy cells (H); after release of DNA from the cells, nucleases in the blood may further alter the overhangs, resulting in modified overhang populations D' and H'; inhibiting the nucleases (e.g., DNases) present in the blood can allow assaying of overhang populations that are not modified or are less modified (e.g., D and H, or closer to D and H than would be observed without inhibition). Other enzymes affecting overhang profiles can also be inhibited. For example, topoisomerase excisions can cleave nucleic acids resulting in particular overhang profiles. Topoisomerase inhibitors can be introduced to preserve these overhangs (e.g., by preventing re-ligation) to allow assaying of these profiles.

Overhang profiles can be assayed by a variety of techniques. Overhangs can be assayed by nucleic acid sequencing, including as disclosed herein. Overhangs can be assayed by binding or hybridization. For example, overhangs can be bound to binding agents that specifically hybridize particular overhangs. Binding agents can be located on a substrate, such as an array or a bead. Binding events can be detected (e.g., fluorescence or other optical signal, electrical signal) and the overhang profile can be determined. Prior to an assay, or as part of an assay, particular species of nucleic acids (e.g., those with a particular overhang or with one or more overhangs from a panel of overhangs) can be enriched, including as disclosed herein.

Classifications and Uses Thereof

Methods described herein can provide an outcome indicative of one or more characteristics of a sample or source described above. Methods described herein sometimes provide an outcome indicative of a phenotype and/or presence or absence of a medical condition for a test sample (e.g., providing an outcome determinative of the presence or absence of a medical condition and/or phenotype). An outcome often is part of a classification process, and a classification (e.g., classification of one or more characteristics of a sample or source; and/or presence or absence of a genotype, phenotype, genetic variation and/or medical condition for a test sample) sometimes is based on and/or includes an outcome. An outcome and/or classification sometimes is based on and/or includes a result of data processing for a test sample that facilitates determining one or more characteristics of a sample or source and/or presence or absence of a genotype, phenotype, genetic variation, genetic alteration, and/or medical condition in a classification process (e.g., a statistic value). An outcome and/or classification sometimes includes or is based on a score determinative of, or a call of, one or more characteristics of a sample or source and/or presence or absence of a genotype, phenotype, genetic variation, genetic alteration, and/or medical condition. In certain embodiments, an outcome and/or classification includes a conclusion that predicts and/or determines one or more characteristics of a sample or source and/or presence or absence of a genotype, phenotype, genetic variation, genetic alteration, and/or medical condition in a classification process.

Any suitable expression of an outcome and/or classification can be provided. An outcome and/or classification sometimes is based on and/or includes one or more numerical values generated using a processing method described herein in the context of one or more considerations of probability. Non-limiting examples of values that can be utilized include a sensitivity, specificity, standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, ploidy value, fitted minority species fraction, area ratio, median level, the like or combination thereof. In some embodiments, an outcome and/or classification comprises an overhang profile, a read density, a read density profile and/or a plot (e.g., a profile plot). In certain embodiments, multiple values are analyzed together, sometimes in a profile for such values (e.g., z-score profile, p-value profile, chi value profile, phi value profile, result of a t-test, value profile, the like, or combination thereof). A consideration of probability can facilitate determining one or more characteristics of a sample or source and/or whether a subject is at risk of having, or has, a genotype, phenotype, genetic variation and/or medical condition, and an outcome and/or classification determinative of the foregoing sometimes includes such a consideration.

In certain embodiments, an outcome and/or classification is based on and/or includes a conclusion that predicts and/or determines a risk or probability of the presence or absence of a genotype, phenotype, genetic variation and/or medical condition for a test sample. A conclusion sometimes is based on a value determined from a data analysis method described herein (e.g., a statistics value indicative of probability, certainty and/or uncertainty (e.g., standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, sensitivity, specificity, the like or combination thereof). An outcome and/or classification sometimes is expressed in a laboratory test report for particular test sample as a probability (e.g., odds ratio, p-value), likelihood, or risk factor, associated with the presence or absence of a genotype, phenotype, genetic variation and/or medical condition. An outcome and/or classification for a test sample sometimes is provided as "positive" or "negative" with respect a particular genotype, phenotype, genetic variation and/or medical condition. For example, an outcome and/or classification sometimes is designated as "positive" in a laboratory test report for a particular test sample where presence of a genotype, phenotype, genetic variation and/or medical condition is determined, and sometimes an outcome and/or classification is designated as "negative" in a laboratory test report for a particular test sample where absence of a genotype, phenotype, genetic variation and/or medical condition is determined. An outcome and/or classification sometimes is determined and sometimes includes an assumption used in data processing.

There typically are four types of classifications generated in a classification process: true positive, false positive, true negative and false negative. The term "true positive" as used herein refers to presence of a genotype, phenotype, genetic variation, or medical condition correctly determined for a test sample. The term "false positive" as used herein refers to presence of a genotype, phenotype, genetic variation, or medical condition incorrectly determined for a test sample. The term "true negative" as used herein refers to absence of a genotype, phenotype, genetic variation, or medical condition correctly determined for a test sample. The term "false negative" as used herein refers to absence of a genotype, phenotype, genetic variation, or medical condition incorrectly determined for a test sample. Two measures of performance for a classification process can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, a laboratory test report generated for a classification process includes a measure of test performance (e.g., sensitivity and/or specificity) and/or a measure of confidence (e.g., a confidence level, confidence interval). A measure of test performance and/or confidence sometimes is obtained from a clinical validation study performed prior to performing a laboratory test for a test sample. In certain embodiments, one or more of sensitivity, specificity and/or confidence are expressed as a percentage. In some embodiments, a percentage expressed independently for each of sensitivity, specificity or confidence level, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). A confidence interval expressed for a particular confidence level (e.g., a confidence level of about 90% to about 99.9% (e.g., about 95%)) can be expressed as a range of values, and sometimes is expressed as a range or sensitivities and/or specificities for a particular confidence level. Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome and/or classification is not due to chance) in certain embodiments is expressed as a standard score (e.g., z-score), a p-value, or result of a t-test. In some embodiments, a measured variance, confidence level, confidence interval, sensitivity, specificity and the like (e.g., referred to collectively as confidence parameters) for an outcome and/or classification can be generated using one or more data processing manipulations described herein.

An outcome and/or classification for a test sample often is ordered by, and often is provided to, a health care professional or other qualified individual (e.g., physician or assistant) who transmits an outcome and/or classification to a subject from whom the test sample is obtained. In certain embodiments, an outcome and/or classification is provided using a suitable visual medium (e.g., a peripheral or component of a machine, e.g., a printer or display). A classification and/or outcome often is provided to a healthcare professional or qualified individual in the form of a report. A report typically comprises a display of an outcome and/or classification (e.g., a value, one or more characteristics of a sample or source, or an assessment or probability of presence or absence of a genotype, phenotype, genetic variation and/or medical condition), sometimes includes an associated confidence parameter, and sometimes includes a measure of performance for a test used to generate the outcome and/or classification. A report sometimes includes a recommendation for a follow-up procedure (e.g., a procedure that confirms the outcome or classification). A report sometimes includes a visual representation of a chromosome or portion thereof (e.g., a chromosome ideogram or karyogram), and sometimes shows a visualization of a duplication and/or deletion region for a chromosome (e.g., a visualization of a whole chromosome for a chromosome deletion or duplication; a visualization of a whole chromosome with a deleted region or duplicated region shown; a visualization of a portion of chromosome duplicated or deleted; a visualization of a portion of a chromosome remaining in the event of a deletion of a portion of a chromosome) identified for a test sample.

A report can be displayed in a suitable format that facilitates determination of presence or absence of a genotype, phenotype, genetic variation and/or medical condition by a health professional or other qualified individual. Non-limiting examples of formats suitable for use for generating a report include digital data, a graph, a 2D graph, a 3D graph, and 4D graph, a picture (e.g., a jpg, bitmap (e.g., bmp), pdf, tiff, gif, raw, png, the like or suitable format), a pictograph, a chart, a table, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, or combination of the foregoing.

A report may be generated by a computer and/or by human data entry, and can be transmitted and communicated using a suitable electronic medium (e.g., via the internet, via computer, via facsimile, from one network location to another location at the same or different physical sites), or by another method of sending or receiving data (e.g., mail service, courier service and the like). Non-limiting examples of communication media for transmitting a report include auditory file, computer readable file (e.g., pdf file), paper file, laboratory file, medical record file, or any other medium described in the previous paragraph. A laboratory file or medical record file may be in tangible form or electronic form (e.g., computer readable form), in certain embodiments. After a report is generated and transmitted, a report can be received by obtaining, via a suitable communication medium, a written and/or graphical representation comprising an outcome and/or classification, which upon review allows a healthcare professional or other qualified individual to make a determination as to one or more characteristics of a sample or source, or presence or absence of a genotype, phenotype, genetic variation and/or or medical condition for a test sample.

An outcome and/or classification may be provided by and obtained from a laboratory (e.g., obtained from a laboratory file). A laboratory file can be generated by a laboratory that carries out one or more tests for determining one or more characteristics of a sample or source and/or presence or absence of a genotype, phenotype, genetic variation and/or medical condition for a test sample. Laboratory personnel (e.g., a laboratory manager) can analyze information associated with test samples (e.g., test profiles, reference profiles, test values, reference values, level of deviation, patient information) underlying an outcome and/or classification. For calls pertaining to presence or absence of a genotype, phenotype, genetic variation and/or medical condition that are close or questionable, laboratory personnel can re-run the same procedure using the same (e.g., aliquot of the same sample) or different test sample from a test subject. A laboratory may be in the same location or different location (e.g., in another country) as personnel assessing the presence or absence of a genotype, phenotype, genetic variation and/or a medical condition from the laboratory file. For example, a laboratory file can be generated in one location and transmitted to another location in which the information for a test sample therein is assessed by a healthcare professional or other qualified individual, and optionally, transmitted to the subject from which the test sample was obtained. A laboratory sometimes generates and/or transmits a laboratory report containing a classification of presence or absence of genomic instability, a genotype, phenotype, a genetic variation and/or a medical condition for a test sample. A laboratory generating a laboratory test report sometimes is a certified laboratory, and sometimes is a laboratory certified under the Clinical Laboratory Improvement Amendments (CLIA).

An outcome and/or classification sometimes is a component of a diagnosis for a subject, and sometimes an outcome and/or classification is utilized and/or assessed as part of providing a diagnosis for a test sample. For example, a healthcare professional or other qualified individual may analyze an outcome and/or classification and provide a diagnosis based on, or based in part on, the outcome and/or classification. In some embodiments, determination, detection or diagnosis of a medical condition, disease, syndrome or abnormality comprises use of an outcome and/or classification determinative of presence or absence of a genotype, phenotype, genetic variation and/or medical condition. Thus, provided herein are methods for diagnosing presence or absence of a genotype, phenotype, a genetic variation and/or a medical condition for a test sample according to an outcome or classification generated by methods described herein, and optionally according to generating and transmitting a laboratory report that includes a classification for presence or absence of the genotype, phenotype, a genetic variation and/or a medical condition for the test sample.

Machines, Software and Interfaces

Certain processes and methods described herein (e.g., selecting a subset of reads, generating an overhang profile, processing overhang data, processing overhang quantifications, determining one or more characteristics of a sample based on overhang data or an overhang profile) often cannot be performed without a computer, microprocessor, software, module or other machine. Methods described herein may be computer-implemented methods, and one or more portions of a method sometimes are performed by one or more processors (e.g., microprocessors), computers, systems, apparatuses, or machines (e.g., microprocessor-controlled machine).

Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Provided herein are computer readable storage media with an executable program stored thereon, where the program instructs a microprocessor to perform a method described herein. Provided also are computer readable storage media with an executable program module stored thereon, where the program module instructs a microprocessor to perform part of a method described herein. Also provided herein are systems, machines, apparatuses and computer program products that include computer readable storage media with an executable program stored thereon, where the program instructs a microprocessor to perform a method described herein. Provided also are systems, machines and apparatuses that include computer readable storage media with an executable program module stored thereon, where the program module instructs a microprocessor to perform part of a method described herein.

Also provided are computer program products. A computer program product often includes a computer usable medium that includes a computer readable program code embodied therein, the computer readable program code adapted for being executed to implement a method or part of a method described herein. Computer usable media and readable program code are not transmission media (i.e., transmission signals per se). Computer readable program code often is adapted for being executed by a processor, computer, system, apparatus, or machine.

In some embodiments, methods described herein (e.g., (e.g., selecting a subset of reads, generating an overhang profile, processing overhang data, processing overhang quantifications, determining one or more characteristics of a sample based on overhang data or an overhang profile) are performed by automated methods. In some embodiments, one or more steps of a method described herein are carried out by a microprocessor and/or computer, and/or carried out in conjunction with memory. In some embodiments, an automated method is embodied in software, modules, microprocessors, peripherals and/or a machine comprising the like, that perform methods described herein. As used herein, software refers to computer readable program instructions that, when executed by a microprocessor, perform computer operations, as described herein.

Machines, software and interfaces may be used to conduct methods described herein. Using machines, software and interfaces, a user may enter, request, query or determine options for using particular information, programs or processes (e.g., processing overhang data, processing overhang quantifications, and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by suitable hardware media (e.g., flash drive), and/or a user may send a data set from one system to another for subsequent processing and/or providing an outcome (e.g., send sequence read data from a sequencer to a computer system for overhang sequence processing; send processed overhang data to a computer system for further processing and/or yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine an outcome from the sequence reads (e.g., a characteristic of a sample).

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, inkjet, impact, black and white or color printer), or other output useful for providing visual, auditory and/or hardcopy output of information (e.g., outcome and/or report).

In a system, input and output components may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, overhang information (e.g., overhang features such as length, type, sequence) may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process or part of a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein. A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to a machine, peripheral, component or another module. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. Sequence read quantifications (e.g., counts) and/or overhang data sometimes are accessed by a microprocessor that executes instructions configured to carry out a method described herein. Sequence read quantifications and/or overhang data that are accessed by a microprocessor can be within memory of a system, and the counts and/or overhang data can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module (e.g., one or more modules). A machine comprising a module often is capable of receiving and transferring one or more of data and/or information to and from other modules.

In certain embodiments, a machine comprises peripherals and/or components. In certain embodiments, a machine can comprise one or more peripherals or components that can transfer data and/or information to and from other modules, peripherals and/or components. In certain embodiments, a machine interacts with a peripheral and/or component that provides data and/or information. In certain embodiments, peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash memory devices (e.g., flash drives), RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining one or more characteristics of a sample.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

Provided herein, in certain embodiments, are systems, machines and apparatuses comprising one or more microprocessors and memory, which memory comprises instructions executable by the one or more microprocessors and which instructions executable by the one or more microprocessors are configured to generate an overhang profile of nucleic acid overhangs of a population of nucleic acids in a sample, and, based on the overhang profile, determine one or more characteristics of the sample.

Provided herein, in certain embodiments, are systems, machines and apparatuses comprising one or more microprocessors and memory, which memory comprises instructions executable by the one or more microprocessors and which instructions executable by the one or more microprocessors are configured to analyze overhang information associated with overhang identification sequences that indicate presence of an overhang for reverse sequence reads, thereby generating an analysis, and omitting from the analysis overhang information associated with overhang identification sequences that indicate presence of an overhang for forward sequence reads.

Provided herein, in certain embodiments, are machines comprising one or more microprocessors and memory, which memory comprises instructions executable by the one or more microprocessors and which memory comprises overhang data for nucleic acid overhangs of a population of nucleic acids in a sample, and which instructions executable by the one or more microprocessors are configured to generate an overhang profile of the nucleic acid overhangs, and, based on the overhang profile, determine one or more characteristics of the sample.

Provided herein, in certain embodiments, are machines comprising one or more microprocessors and memory, which memory comprises instructions executable by the one or more microprocessors and which memory comprises forward sequence reads and reverse sequence reads generated by a sequencing process, and which instructions executable by the one or more microprocessors are configured to analyze overhang information associated with overhang identification sequences that indicate presence of an overhang for the reverse sequence reads, thereby generating an analysis, and omitting from the analysis overhang information associated with overhang identification sequences that indicate presence of an overhang for the forward sequence reads.

Provided herein, in certain embodiments, are non-transitory computer-readable storage media with an executable program stored thereon, where the program instructs a microprocessor to perform the following: (a) access overhang data for nucleic acid overhangs of a population of nucleic acids in a sample, and (b) generate an overhang profile of the nucleic acid overhangs, and (c) based on the overhang profile, determine one or more characteristics of the sample.

Provided herein, in certain embodiments, are non-transitory computer-readable storage media with an executable program stored thereon, where the program instructs a microprocessor to perform the following: (a) access forward sequence reads and reverse sequence reads generated by a sequencing process, and (b) analyze overhang information associated with overhang identification sequences that indicate presence of an overhang for the reverse sequence reads, thereby generating an analysis, and omitting from the analysis overhang information associated with overhang identification sequences that indicate presence of an overhang for the forward sequence reads.

Kits

Provided in certain embodiments are kits. The kits may include any components and compositions described herein (e.g., oligonucleotides, oligonucleotide components/regions, target nucleic acids, enzymes) useful for performing any of the methods described herein, in any suitable combination. Kits may further include any reagents, buffers, or other components useful for carrying out any of the methods described herein. For example, a kit may include one or more of a plurality or pool of oligonucleotide species, a kinase adapted to 5' phosphorylate nucleic acids of a nucleic acid sample (e.g., a polynucleotide kinase (PNK)), a DNA ligase, a cleavage agent, an enzyme (e.g., polymerase) suitable for performing a fill-in and/or strand displacement reaction, and any combination thereof.

Components of a kit may be present in separate containers, or multiple components may be present in a single container. Suitable containers include a single tube (e.g., vial), one or more wells of a plate (e.g., a 96-well plate, a 384-well plate, and the like), and the like.

Kits may also comprise instructions for performing one or more methods described herein and/or a description of one or more components described herein. For example, a kit may include instructions for using a composition described herein to modify ends of nucleic acid fragments and/or to produce a nucleic acid library. Instructions and/or descriptions may be in printed form and may be included in a kit insert. In some embodiments, instructions and/or descriptions are provided as an electronic storage data file present on a suitable computer readable storage medium, e.g., portable flash drive, DVD, CD-ROM, diskette, and the like. A kit also may include a written description of an internet location that provides such instructions or descriptions.

EXAMPLES

The examples set forth below illustrate certain embodiments and do not limit the technology.

Example 1: RNAse-Cleavable Hairpin Adapters

Figure 1A:
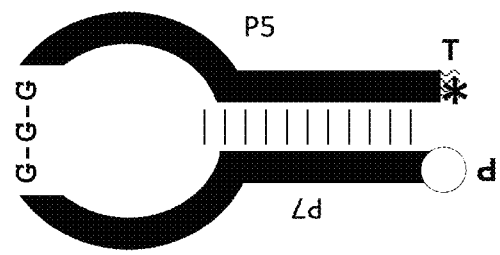
FIG. 1A to FIG. 1C show examples of hairpin adapter configurations.
Figure 1B:
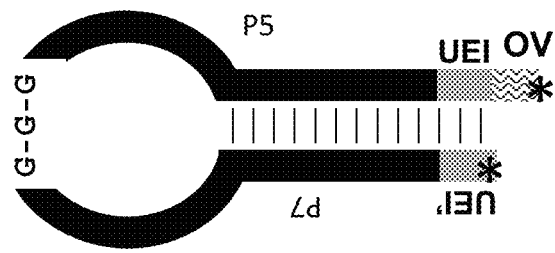
Figure 1C:
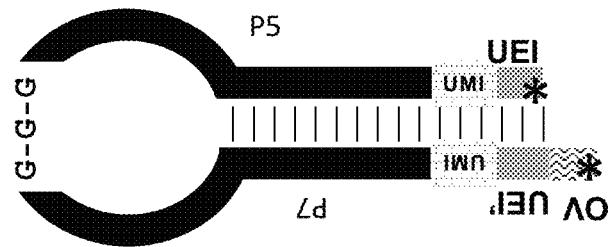

One form of damage in degraded DNA molecules (e.g., ancient DNA) is the deamination of cytosine (C) into uracil. DNA sequencing adapters in the form of hairpin structure that contain a deoxyuridine in the loop require the use of a uracil-DNA-glycosylase and an endonuclease to cut the single strand. One potential consequence of using these enzymes is cleavage at damaged sites within DNA fragments of interest, rendering the fragments inaccessible to library conversion. Certain substrates similar to ancient DNA, such as, for example, circulating cell-free DNA, may accumulate damaged bases during the process of release and clearance from the body. This could limit the use of sequencing adapters containing deoxyuridine for circulating cell-free DNA library preparations. Use of hairpin adapters having RNA bases within the loop of the hairpin in conjunction with use of an RNAse during library preparation could obviate such challenges for DNA library preparation. Use of an RNAse during library preparation also can be useful for reducing certain contaminants prior to sequencing. Example hairpin adapter configurations are shown in FIG. 1A, FIG. 1B and FIG. 1C.

Methods

Sequencing libraries were prepared by ligating template DNA to a DNA/RNA adapter having a stem-loop structure, where the double-stranded stem was created by the complementarity of several DNA bases universal to Illumina sequencing adapters, and the single-stranded loop contained unique, non-complementary DNA bases of P5 and P7 (forward and reverse) primer sites. Three guanine RNA bases were positioned within loop, which served as a cleavage site for T1 RNAse. Following cleavage, a double-stranded DNA molecule was formed that that could directly be amplified and sequenced.

A commercially available Illumina library preparation kit that performs A-tailing during end repair was used for comparison. The RNAse-cleavable hairpin adapters tested in this Example were designed to have a single T-overhang to accommodate the A-tailed template and had a 5' phosphate.

The performance of the RNAse-cleavable hairpin adapter was evaluated by replicating the preparation of standard Illumina libraries, and substituting the RNAse-cleavable hairpin adapter for the commercial kit's uracil adapter. Four sources of DNA were used as template: 1) cell-free DNA isolated from blood plasma, 2) cell-free DNA isolated from urine, 3) human formalin-fixed paraffin-embedded (FFPE) sample, and 4) DNA isolated from a 30 kya bison bone. Library prep was performed as described in the manual and paired-end sequencing was performed on MiSeq using a v2 nano flow cell or v3 reagent kit.

Results

The results in Table 1 show that the RNAse-cleavable hairpin adapter performed just as well as the commercially available uracil adapter, with most gains observed for the cell free DNA from urine and the fragmented FFPE sample. In six of the eight experiments below, the RNAse-cleavable hairpin adapter showed a slightly lower duplication rate.

TABLE 1

Comparison of commercial kit adapter with RNA-cleavable adapter. Values in bold show the higher of the two comparisons.

| type | sample | total reads (not phiX or discarded) | % human mapped of all reads that are not phiX or discarded | perc_dup |
|---|---|---|---|---|
| kit | urine1 | 822,307 | 32.49% | 0.0921% |
| RNA hairpin | urine1 | 449,756 | 41.94% | 0.0504% |
| kit | plasma1 | 3,166,878 | 91.27% | 0.0085% |
| RNA hairpin | plasma1 | 3,090,306 | 91.36% | 0.0107% |
| kit | plasma2 | 3,281,333 | 89.33% | 0.0364% |
| RNA hairpin | plasma2 | 3,148,270 | 89.63% | 0.0249% |
| kit | plasma3 | 3,301,742 | 91.47% | 0.0219% |
| RNA hairpin | plasma3 | 2,927,874 | 91.61% | 0.0134% |
| kit | plasma4 | 3,053,505 | 91.72% | 0.0235% |
| RNA hairpin | plasma4 | 3,462,353 | 91.76% | 0.0127% |
| kit | ffpe1-fragmented | 170,776 | 93.46% | 0.0000% |
| RNA hairpin | ffpe1-fragmented | 165,126 | 97.20% | 0.0006% |
| kit | ffpe1 | 30,566 | 83.12% | 0.0039% |
| RNA hairpin | ffpe1 | 20,300 | 83.46% | 0.0118% |
| kit | bison | 1,992,301 | 15.57% | 0.005% |
| RNA hairpin | bison | 1,467,088 | 15.00% | 0.005% |

Example 2: Unique End Identifiers (UEIs) and Unique Molecular Identifiers (UMIs)

Events such as DNA release, various forms of cell-death, and postmortem cellular processes are characterized by distinct morphological features and molecular pathways.

Signals found in the DNA termini following a double-strand break may reflect unique patterns of DNA degradation and may provide information about causative processes and potential pathological processes. To investigate this, RNAse-cleavable adapters were designed to capture single-stranded overhangs when present in native DNA termini (see e.g., FIG. 1B).

Such adapters were generated by ligating synthetic DNA that contains at least two parts: 1) a 5' or 3' single-stranded overhang of length N, and 2) a unique end identifier (UEI) adjacent to the overhang. A UEI is a double-stranded barcode that conveys the type and length of that overhang, if any. Generally, UEIs and UEI adapters are not phosphorylated to avoid hybridization and formation of dimers. In some instances, UEIs and UEI adapters are phosphorylated.

In certain iterations of this hairpin design, as well as designs of other adapters, a unique molecular identifier (UMI) also is included adjacent to the UEI or elsewhere within the adapter structure (see e.g., FIG. 1C). UMIs serve a different purpose than the UEIs in that they allow an estimation of the number of unique starting molecules and evaluate the sensitivity of the ligation reaction.

Example 3: Double-Sided Oligos with Unique End Identifiers (UEIs) for Tagging DNA Ends Unique end identifiers (UEIs) also can be used for tagging DNA ends. In order to provide flexible options for other sequencing platforms or downstream analyses, UEIs can function as stand-alone ligation components (i.e., without sequencer-specific adapter sequences). This process encodes/keeps intact the native ends of overhanging DNA for conversion into any library type or analysis. The product of such ligation may be a double-stranded blunt ended molecule.

One design is depicted in FIG. 2A, which allows ligation on either side of a UEI to a corresponding DNA overhang. This oligo, which may be referred to as a double-sided UEI oligo, has internal uracil(s) (or deoxyuridine) on forward and reverse strands which serve as cleavage sites for the Uracil-Specific Excision Reagent (USER) enzyme (i.e., a mixture of uracil DNA glycosylase (UDG) and the DNA glycosylase-lyase endonuclease VIII). Certain oligo designs include two to twelve random bases between UEIs, with one or two uracils. FIG. 2A shows example oligonucleotides, and an example workflow is illustrated in FIG. 2B. Briefly, after ligation, an enzyme cocktail cuts uracils at both strands, separating any unligated material or adjacent ligation product. After cleavage, a template DNA molecule remains with UEIs ligated on both sides. Fill-in is performed to repair the nicks remaining in the molecule. After fill-in, a double-stranded, blunt-ended molecule remains, ready for library preparation.

To test the performance of the above oligo design, double-sided UEI oligos were ligated (20× oligo:template ratio) to 5 ng of cell-free DNA isolated from plasma from two individuals. Often, two fractions of cell-free DNA fragment sizes isolated from plasma were observed. To address this, the DNA extract was fractionated to separate fragments larger than 500 bp ("high") from those smaller than 500 bp ("low"). Library preparation was performed as described above, the template was phosphorylated, double-sided UEI oligos were ligated, uracils were cleaved, and fill-in was performed. The resulting DNA product was then subjected to library preparation using a NEB Ultra II library preparation kit for Illumina. Paired-end sequencing (2×150) was performed using MiSeq v2 Nano flowcell.

Results

This approach generated more adapter dimers compared to other designs, which lowered the sequencing output. Between 30,000 and 150,000 reads per library were generated. DNA that was mappable to the human genome was the expected size distribution of cell-free DNA, around 167 bp, or the length of DNA wrapped around a nucleosome (see FIG. 3 and FIG. 4). Very few reads from the "high" fractions of extract, APN 307 and APN 310, were short enough to merge, and were well above the size of one nucleosome (FIG. 3, panels C and F). The "high" fraction libraries had too few data for any visual display (FIG. 4, panels C and F). The "low" or "all" (i.e., not size fractionated) portions of the libraries generated libraries; however, most DNA fragments of intended size were ligated to only one double-sided UEI oligo or none of the double-sided UEI oligonucleotides (FIG. 4, panels A, B, D, E).

In certain instances, it is advantageous for each template DNA molecule to receive two UEI oligonucleotides. Often, molecules with only one ligated UEI oligo or no ligated UEI oligo will still be converted into a standard library molecule downstream. For purposes of characterizing the native ends of DNA, fragments having no UEI oligonucleotides are not useful, and fragments with one UEI oligo are not ideal. To address this challenge, biotinylated dNTPs are incorporated into the strand during the fill-in step. By immobilizing only those template fragments that have been successfully filled-in (i.e., successfully ligated), DNA molecules with no UEI oligo ligation events are excluded from downstream processing. This approach is applicable to any design that prepares DNA fragments with UEI oligos (i.e., double-sided UEI oligos) before sequencing preparation.

Example 4: Blocked One-Sided Oligos with Unique End Identifiers (UEIs) for Tagging DNA Ends Rather than using a design that encourages ligation on either end of a UEI oligo, a single blocking, modified base is placed on the 3' end of a UEI oligo to ensure ligation in a specific direction. One design, shown in FIG. 5, blocks the 3' end of the UEI oligos such that they are forced to ligate unidirectionally. An isodeoxy-base was selected as a blocker. Isodeoxy-G and isodeoxy-C have a hydrogen-bonding pattern that is different than natural bases. As such, they cannot bond with any natural base. Typically, isoG can only pair with isoC. By using only one of these two modified bases, either isoG or isoC, no ligation or hybridization should occur on the 'incorrect' end of the UEI oligo, forcing the correct orientation of the ligation event.

Because only the template DNA is phosphorylated (and not the oligo), a nick remains in the molecule on both the forward and reverse strand following ligation. Fill-in using a strand displacing polymerase completes the double-stranded molecule, and removes the strand of the UEI oligo having the modified base (see FIG. 6).

Example 5: Dephosphorylation of Synthetic and Biological DNA

Library preparation described in certain Examples above omits a conventional end repair step, which generally chews back 3' overhangs and fills-in 5' overhangs, and prepares the template for A-tailing or blunt-end ligation. The methods described above typically do not include use of a nuclease or polymerase to prepare template DNA, and instead phosphorylate the template with T4 PNK before ligation.

In certain instances, a pre-treatment was performed on oligos, including adapters and controls, and/or template DNA to remove all 3' and 5' terminal phosphates, recessed or otherwise. The phosphatase rSAP (1 unit/1 pmol of DNA) was used for the pre-treatment.

Tapestation data in FIG. 7A, FIG. 7B and FIG. 7C demonstrate the improvement of library generation after treating the cell-free DNA template (FIG. 7B) and cell-free DNA and adapters (FIG. 7C) with rSAP. Improvements following rSAP treatments are considered as a reduction of adapter dimer peak and an increase of DNA-sized peaks. FIG. 7A shows a library made of almost exclusively adapter dimer, a nearly complete loss of DNA when the template is not treated with rSAP.

Significant improvements also were observed when synthetic 50 bp double-stranded control oligos were dephosphorylated before the first step with T4 PNK. This indicates that even when unphosphorylated oligos or adapters are purchased from a commercial outfit, some DNA termini are not amenable to end modification, including phosphorylation with T4 PNK, and thus perform poorly during ligation.

Example 6: Mate Pair Library

Genomic or other DNA that is longer than the recommended fragment length for library conversion is typically sheared, either mechanically or enzymatically, before library preparation. After shearing, conventional library preparation begins with an end repair step. Both shearing and end repair prevent access to, and thus observation of, the native DNA termini.

A portion of cell-free DNA fragments can be larger than is ideal for generating usable sequencing data (e.g., above 500 bp to 700 bp). The high molecular weight (HMW) portion of cell-free DNA containing large fragments may be the result of release following non-apoptotic cell death or necrosis, and the ends of such fragments may provide a source of useful information. One design for retaining and characterizing the native ends of long DNA fragments from HMW DNA, and successfully converting the preserved ends into a sequencing library, is a modification of a mate pair library or a circularization of DNA fragments.

The mate pair modification first includes ligating long, e.g., >500 bp, 5' phosphorylated DNA fragments to a pool of biotinylated double-stranded (ds) oligonucleotides. Each ds oligo is designed to include a long palindromic single-stranded overhang on one side (can be placed as either a 5' overhang or a 3' overhang; shown in FIG. 8A as a 5' overhang), and on the other side, all combinations of 5' or 3' single-stranded overhangs composed of a random sequence varied up to length N, preceded by a unique sequence that identifies the length and type (5' or 3') of the overhang, referred to as a unique end identifier (UEI). A few examples of oligonucleotides with varying 5' and 3' overhang lengths are illustrated in FIG. 8A. The long palindromic sequence generally is not found or predicted in the human genome nor is commonly observed in bacteria often associated with human microbiome. High Delta G values estimated for hairpin formation suggest that self-dimers, rather than hairpins, will preferentially form, as desired, promoting circularization. Native 3' and 5' overhangs present on the dsDNA template, if any, will ligate to the available overhanging ends of the oligonucleotide set. Natively blunt dsDNA templates can ligate to the blunt-ended oligonucleotides in the set. Self-dimers produced by long palindromic sequences of complementary oligonucleotides permits circularization of the long fragments in the presence of ligase. In some instances, a polynucleotide kinase is used with or before the ligase to repair nicks and complete the double strand. In some instances, the oligonucleotides are prepared with a 5' phosphate.

After oligonucleotide and template DNA is ligated and circularized, an exonuclease removes any non-circularized DNA or excess oligonucleotides. Circularized DNA is then sheared (e.g., using an ultrasonicator (Covaris) or by enzymatic fragmentation) to generate molecules suitable for short read high throughput sequencers. Generally, only the DNA ends of interest are captured by immobilizing all DNA fragments that are ligated to biotinylated oligonucleotides on streptavidin-coated beads. These steps reduce generating library molecules from pieces of high molecular weight (HMW) DNA that did not originate from the native ends. After fractioning both low molecular weight (LMW) and molecular weight (HMW) nucleic acid after DNA extraction, the circularization strategy for long DNA fragments can be paired with an approach, like those described above, for shorter DNA fragments. The datasets resulting from these two strategies can be bioinformatically merged or analyzed separately for comparative purposes to explore how native DNA ends differ depending on overall DNA fragment length.

The mate-pair or circularization method is generally performed as follows: 1) pre-treat template DNA with phosphatase; 2) phosphorylate template DNA; 3) ligate overhanging UEI oligonucleotide pool to template; repair nicks if necessary; 4) treat with exonuclease; 5) shear; 6) immobilize biotinylated fragments on beads; 7) begin library preparation of choice.

For methods described above, if a particular overhanging end pattern is significant for biological (e.g. human endogenous or tissue-specific nuclease function), biomedical (e.g. pathological or treatment-induced cell death, tumor formation), or forensic (e.g. biological vs. taphonomic degradation) discovery, overhanging oligo/adapters with built-in UEI sequences can be used as a targeted enrichment strategy, with or without biotin.

Example 7: Additional Adapter Examples

Additional adapter examples are shown in FIGS. 9A and 9B (panel A). FIG. 9A shows an example method for attaching a unique end identifier (UEI) sequence in a first phase using strand-displacing polymerase, and a sequencer-specific sequence (e.g., sequencing adapter) in a second phase. Thus the adapters shown in FIG. 9A, panel A, do not contain sequencer-specific adapter sequences (e.g., P5, P7). Panel A of FIG. 9A shows a Y adapter (left) and a hairpin adapter (right) composed of a unique end identifier (UEI) sequence (shown in gray) and random sequence (shown in black). In some instances, the Y adapter is a cleaved version of the hairpin adapter. The hairpin adapter includes a cleavage site ("X"), which can include one or more RNA nucleotides as described in Example 1. Panel B of FIG. 9A shows ligation of the adapters to a target nucleic acid. The hairpin adapter ligation product can be cleaved at the cleavage site. After cleavage, the ligation product is the same as the Y-adapter ligation product. Panel C of FIG. 9A shows a fill-in step at nicks with a strand-displacing polymerase to create a fully complementary double-stranded, blunt-ended fragment. Panel D of FIG. 9A shows a nucleic acid fragment that is ready for any sequencing library preparation of choice (second phase).

FIG. 9B shows an example method for attaching a Y adapter or a hairpin adapter to the ends of a native nucleic acid fragment. Panel A shows a Y adapter (left) and a hairpin adapter (right) composed of an overhang, a unique end identifier (UEI) sequence (shown in gray), and priming sequences (priming sequence 1 (e.g., Illumina P5 priming sequence) and priming sequence 2 (e.g., Illumina P7 priming sequence); priming region shown in black). Panel B shows ligation of the adapters to a target nucleic acid. Because the adapters are not phosphorylated, the ligation only occurs at the 5' end of the template, leaving nicks. Panel C shows that the nicks are repaired once the 5' adapter strand is phosphorylated and ligates the 3' end of the adapter. After nick repair, the hairpin adapter ligation product can be cleaved at the cleavage site. After cleavage, the ligation product is the same as the Y-adapter ligation product. This method generates a double-stranded nucleic acid fragment that is ready for any sequencing library preparation of choice (second phase) and/or sequencer of choice, which may depend on the priming sequences used.

Example 8: Fragment Size Selection

Rather than perform size selection after library preparation using beads, gel excision or automated methods like the Pippen Prep machine, a size fractionation is performed on the DNA extract, in some instances, controlling the size of DNA that will be converted into library molecules. There are certain practical and biological motives for fractionation. Practically, fractionation reduces the presence of fragments too long for efficient sequencing using certain sequencing platforms (e.g., Illumina platforms). Biologically, fractionation separates and retains fragments that could be the products of differing biological processes. Cell-free DNA (cfDNA) fragment lengths generally are around the size of one, two, or a few nucleosomes, ~170, ~340, ~510 bp and the fragments are generally considered a product of cell apoptosis. Larger fragments include genomic DNA (gDNA) contaminants, in certain instances. Larger fragments also may include cfDNA fragments (e.g., fragments larger than a nucleosome, for example fragments at different stages of breakdown, or fragments derived from a process other than apoptosis (e.g., necrosis)).

Fractionation is performed using Solid Phase Reversible Immobilization (SPRI) beads to separate and retain both short and long DNA fragments, which are defined as <500 bp and >500 bp, respectively. Carboxylated beads are prepared in a solution of varying PEG-8000 (18%, 20% and 38%) and NaCl (0.5M, 1M, 2M) concentrations. The DNA extract is incubated with the solution, and the beads are collected using a magnetic particle separator. The supernatant is either discarded or retained, depending on desired effect. After washing the beads with ethanol, DNA is released from beads into an elution buffer of neutral pH, like water, 10 mM Tris-HCl, TE buffer, or TE with TWEEN-20 (TET).

The length of DNA fragments that will immobilize on SPRI beads in the solution is dependent on the concentration of PEG, which translates to the ratio of beads to DNA. Generally, the lower the ratio, the longer DNA fragments will be captured on beads, resulting in shorter DNA remaining in the supernatant. To retain the short fragments from the supernatant, a higher ratio of beads to DNA is used. In one example, dual size selection was performed on plasma DNA extractions, and each DNA extract was incubated with 0.4-0.5× ratio of SPRI beads solution (final 18% PEG, 1M NaCl) for 15 minutes at room temperature (i.e., 20 ul of DNA, 8 ul of beads). After 15 minutes, the supernatant was collected and set aside. The beads were washed twice with 80% ethanol and eluted in 15 ul of TET buffer. This fraction generally excludes short DNA fragments.

A 2× ratio of SPRI beads were added to the supernatant. Incubation, washing and elution were performed as described above. After elution, this fraction generally contained short DNA fragments. The short fragments are then used in various Illumina overhanging library preparation methods, some of which are described in certain Examples above.

Example 9: Oligonucleotide Adapters with RNA Overhangs

This Example describes a method that uses RNA bases as the substrate for single-stranded overhangs in oligonucleotide adapters. An adapter with an RNA overhang can be structured for library preparation in numerous configurations, e.g., Y, hairpin, duplex, duplex with blocking modifications (see e.g., FIG. 10A). Like all other iterations described herein, a unique end identifier (UEI) indicating the length of overhang and type of overhang (e.g., 5' overhang or 3' overhang) is incorporated into the duplex portion of the oligonucleotide. In some instances, Illumina-specific adapter sequences (e.g., P5, P7) are included in the UEI-adapters. In some instances, Illumina-specific adapter sequences (e.g., P5, P7) are not included in the UEI-adapters.

Certain ligases or combinations of ligases, such as T4 RNA ligase 2 or SplintR® Ligase, can, under certain conditions, ligate RNA to DNA when DNA is annealed to an RNA template. By creating adapters with single-stranded overhangs of RNA bases, hybridization with native DNA template will result in a RNA-DNA duplex that can be ligated.

To address a potential problem of oligonucleotide adapters forming dimers (e.g., through overhang hybridization forming RNA-RNA duplexes), digestion of adapter dimers is performed using a ribonuclease (RNAse) that targets double-stranded RNA (dsRNA) structures. RNAse III is an example RNAse that targets dsRNA structures. Most ribonucleases require a long substrate to function well. However, shorter dsRNA adapter dimers are eliminated via digestion or cleavage provided the 5' end ('leader') of the adapter design (e.g., minimum length of substrate and a permissive leader sequence) satisfies the canonical requirements for a particular ribonuclease (e.g., RNAse III).

An example workflow includes the following components: 1) dephosphorylate DNA template; 2) phosphorylate DNA template; 3) hybridize template with a plurality of (completely or partially, depending on design) double-stranded DNA adapter oligonucleotide species each having a UEI and a single-stranded overhang with random RNA bases of length 1 to N; a blunt adapter (no overhang) also included; 4) ligate with one or a combination of ligases; 5) if necessary, cleave the hairpin structure; 6) complete double-stranded molecule—nick seal or fill-in at nick using strand displacing polymerase, depending on adapter configuration; 7) SPRI purify to remove adapter dimers based on size, removing excess adapters and dimers under 100 bp; enzymatic digestion also is used in certain instances; 8) continue to Illumina preparation, if necessary.

Example 10: Oligonucleotide Adapters for High Molecular Weight (HMW) DNA

This Example describes oligonucleotide adapters and methods for collecting overhang information from high molecular weight (HMW) DNA utilizing short read next generation sequencing (NGS; e.g., high-throughput sequencing).

Certain oligonucleotide adapters and methods described in the Examples above may be useful for obtaining information on the length and orientation of overhangs for double stranded DNA (dsDNA) that has a length of less than 500 bp (e.g., using short read NGS sequencers). Certain strategies discussed above rely on ligating a pool of barcoded Y (or hairpin) oligonucleotide adapters, containing random single-stranded N-mers at either the 5' terminus or the 3' terminus, onto dsDNA. After next generation sequencing a unique barcode present on each type of adapter relays the correct length and orientation of the overhang, if any, present on each DNA molecule. In certain protocols, one computational approach uses the barcode at the beginning of read 2 of sequencing data (e.g., obtained using the Illumina platform), due to the specifics of the molecular biology involved.

Generally, in the methods described above, dsDNA ends are unaltered. Use of short-read sequencers generally requires that high molecular weight (HMW) DNA (e.g., DNA greater than 500 bp in length) be sheared to smaller fragment sizes prior to sequencing. Shearing of HMW DNA typically results in native ends being lost. Provided below are oligonucleotide adapters and methods for sequencing DNA of any size, whether naked or bound to chromatin, on short read sequencers while retaining information on the overhangs of the original DNA molecule. Such adapters and methods may be useful for high throughput methods for analyzing overhang information of DNA naturally larger than about 500 bp, for example, including but not limited to DNA from formalin-fixed, paraffin-embedded tissue (FFPE DNA), DNA damaged by in vivo and/or in vitro endogenous means (UV, methylation, bulky adducts, and the like), and DNA from cell culture extracts. Other uses may include interrogating medically designed DNA damaging and chemotherapeutic agents, in cell culture in vitro or in vivo; a replacement for the current TUNEL assay; screening of novel nucleases; and the like.

A first method is shown in FIG. 11. DNA molecules of their native fragment length go through a partial sequencing library prep where a non-phosphorylated degenerate barcoded first adapter (e.g., P7 adapter) with overhang length information is ligated to phosphorylated genomic DNA (gDNA). The first adapter (e.g., P7 adapter) may be modified using any suitable modification to discourage adapter dimers from occurring and preventing adapter chaining (see e.g., FIG. 12).

After an appropriate solid phase reversible immobilization (SPRI) clean-up to remove un-ligated adapters, ligated adapters go through phosphorylation and nick repair as described in certain Examples above. If a partial first adapter (e.g., P7 adapter) strategy is used, the adapter is filled in (e.g., using Bst DNA polymerase). After an appropriate SPRI clean-up to remove adapter dimers, DNA is sheared to an appropriate sequencing length for short read sequencers using mechanical or enzymatic methods. DNA molecules then undergo end repair and A-tailing using suitable end repair and A-tailing techniques. After A tailing, a modified second adapter (e.g., modified P5 adapter), with a 5' phosphorylation modification on the correct end and ligation blocking modifications on the other free ends, is ligated to the remaining DNA fragments.

The library is then PCR amplified up using primers designed according to the first and second adapters (e.g., a P5/P7 amplification strategy). This strategy ensures enrichment for the native DNA overhangs since only molecules with a modified first adapter (e.g., P7 adapter) are amplified in the final pool. This strategy with the modifications only on the first adapter (e.g., P7 adapter) also ensures enrichment for the correct ligation event to be read on read 2 of an Illumina Sequencer as per the specifics in the assay.

A second method is shown in FIG. 14. This method of capturing ends of high molecular weight DNA molecules may be performed on naked DNA or on chromatin bound DNA. First, a pool of overhanging Y-adapters is ligated to free dsDNA ends. The overhanging Y-adapters may be blocked (e.g., using C3 spacers; blocked modification is indicated by Xs in FIG. 14). DNA is then sheared (in case of chromatin bound DNA, the DNA is treated with proteinase K before shearing). After DNA is fragmented to a size suitable for sequencing, the library is completed by performing an end repair step (with or without A-tailing) and ligating a specialized adapter (e.g., specialized P5 adapter; referred to as special shorty P5* in FIG. 14) to the newly free ends, in order to enrich for the correctly formed molecule. DNA that is shorter than is amenable to shearing will still make a library molecule—but will have normal (i.e., not specialized) adapters and corresponding barcodes on both sides. The cleaved products may undergo an end repair process that performs blunt-end repair and A-tailing. For this step a commercially available enzyme mix may be used. Such enzyme mix may include a polynucleotide kinase that performs 5' phosphorylation, a polymerase that performs 5' fill-in (e.g., T4 polymerase), an enzyme with 3' to 5' exonuclease (e.g., T4 polymerase), and a polymerase that performs A-tailing (e.g., Taq polymerase).

The specialized adapter (e.g., specialized P5 adapter) is designed such that the complement to the long strand (e.g., P5) is long enough to stay annealed, but is too short to be amplified during index PCR and thus only one strand will be properly formed and copied. Information from an overhang is considered if it is on the P7 side. Accordingly, that strand is enriched. The specialized adapter (e.g., specialized P5 adapter) has a unique 8 bp barcode to recognize the molecules that were once HMW. The specialized adapter may be blocked (indicated by Xs in FIG. 14), minimizing interactions in the wrong direction. In certain instances, the specialized adapters are phosphorylated and blocked with C3 spacers. One of the two strands may have a phosphorothioate backbone modification before the T-overhang (see FIG. 14; phosphorothioate backbone modification is indicated by an asterisk "*" in the pool of specialized P5 adapters).

An example specialized P5 adapter includes the following nucleotide sequences:

(SEQ ID NO: 1)
5' /5Phos/GGGTAGCAAGATCGGAA/3SpC3/ 3'

(SEQ ID NO: 2)
5' /5SpC3/ACACTCTTTCCCTACACGACGCTCTTCCGATCTTGCTACC C*T 3'

Preliminary testing of this method was performed and the results indicated the method successfully captured the ends of high molecular weight DNA molecules.

Example 11: NGS Library Preparation Method to Characterize Native Termini of Fragmented DNA In this Example, a ligation-based next-generation sequencing (NGS) library approach is described that provides comprehensive information about the native state of fragmentary DNA termini. By omitting the standard DNA end repair step, libraries generated using this method can encode the type of break at each molecule terminus using custom sequencing adapters. The end result of this library preparation method is a high-throughput NGS assay that provides genome-wide nucleotide resolution DNA fragmentation. This method for generating Illumina-compatible double-stranded DNA (dsDNA) sequencing libraries introduces into the sequencing adapter a unique identifier that encodes the type (3', 5', or blunt) and length of single-stranded overhangs, if any, present on each original template molecule, as well as length and sequence of the remaining overhang, if present, on each DNA fragment. The accuracy of this method is demonstrated using 1) a population of control oligos with known single-stranded overhangs; and 2) DNA digestion products from specific restriction enzymes. The distribution of native termini of dsDNA fragments produced by common methods of mechanical and enzymatic shearing using the Diagenode Bioruptor, NEB Fragmentase, DNaseI, and Micrococcal nuclease also is described. Finally, using this method, it is shown that common procedures for collecting human blood vary in their ability to protect circulating cell-free DNA fragments from degradation by nucleases present in the blood.

Materials and Methods

Nucleic Acid Template Acquisition and Preparation

Synthetic control oligos (Table 2) were designed using a random sequence generator at 50% GC content; sequences matching any known organism in public databases were removed. Each control molecule (n=12) is a unique 50 bp sequence of double-stranded DNA with one blunt-end, and one 3' or 5' single-stranded overhang of random sequence, 1 to 6 nucleotides in length. Because each control is a unique sequence, it serves as its own barcode indicating the structure of the oligo. Oligos were synthesized using standard desalting purification and duplexed by Integrated DNA Technologies (IDT); all random nucleotides were 'hand-mixed' to reduce synthesis bias. Control oligos were pooled together in an equimolar ratio. Before adapter ligation, up to 1 pmol of pooled control oligos were dephosphorylated in a 20 µl reaction using rapid Shrimp Alkaline Phosphatase (New England Biolabs) incubated at 37° C. for 30 minutes followed by a 10-minute heat inactivation at 65° C. Control oligos were then 5' phosphorylated by bringing the heat inactivated 20 µl Shrimp Alkaline Phosphatase reaction up to 40 µl using T4 Polynucleotide Kinase (New England Biolabs), supplemented with ATP. The phosphorylation reaction was carried out at 37° C. for 30 minutes followed by a 30-minute heat inactivation step at 65° C. Oligos were then ready for adapter ligation. Oligo concentration was calculated by taking the original input pmol divided by 40 µl.

TABLE 2

Synthetic oligo design

| Overhang type | Sequence 1 | SEQ ID NO: | Sequence 2 | SEQ ID NO: |
|---|---|---|---|---|
| 3' 1 bp | CCATACTGTGGTCGTCACCTATTA CCCCGCGTAAAGGTAGGCTATGT CATN$_1$ | 3 | ATGACATAGCCTACCTTTACGCGG GGTAATAGGTGACGACCACAGTAT GG | 15 |
| 3' 2 bp | GTGAATTGTTGATGTCCTGGGTGC CTCGTCCCAAAAGCTGTCCTCACG ACN$_2$ | 4 | GTCGTGAGGACAGCTTTTGGGACG AGGCACCCAGGACATCAACAATTC AC | 16 |
| 3' 3 bp | GCTTCTCGAACCCGCGATCCGGC CGATCCGGCATAATGGGTTGATTT AGAN$_3$ | 5 | TCTAAATCAACCCATTATGCCGGAT CGGCCGGATCGCGGGTTCGAGAA GC | 17 |
| 3' 4 bp | CGACACGGATATTCCATCAAGAGA CGGGCCTATGGTCCCTGTGATGAT GTN$_4$ | 6 | ACATCATCACAGGGACCATAGGCC CGTCTCTTGATGGAATATCCGTGTC G | 18 |
| 3' 5 bp | ACCTTGTGTGTTGCTGAAGCAAAG CCGCGTGACCGTTTTAACCAGCGA ACN$_5$ | 7 | GTTCGCTGGTTAAAACGGTCACGC GGCTTTGCTTCAGCAACACACAAG GT | 19 |
| 3' 6 bp | ATTTTACCACGAGTTCCTTACGAC GGCTGTGATGCCACGGTAGGCAG GTAN$_6$ | 8 | TACCTGCCTACCGTGGCATCACAG CCGTCGTAAGGAACTCGTGGTAAA AT | 20 |
| 5' 1 bp | N$_1$CGCTTTACGGGTCCTGGGCCG GGGTGCGATACCTTGCAGAAATC GAGGCC | 9 | GGCCTCGATTTCTGCAAGGTATCG CACCCCGGCCCAGGACCCGTAAAG CG | 21 |
| 5' 2 bp | N$_2$AGGACTCTGCCGTCGACGAGTT CGTTAATTCACGGCATCACGTGCG TAGT | 10 | ACTACGCACGTGATGCCGTGAATT AACGAACTCGTCGACGGCAGAGTC CT | 22 |
| 5' 3 bp | N$_3$ACCTCCGTCGCGCTATGTTCTG TTGCATTCGACCTTCTCCGTTCTG TGGG | 11 | CCCACAGAACGGAGAAGGTCGAAT GCAACAGAACATAGCGCGACGGAG GT | 23 |

TABLE 2-continued

Synthetic oligo design

| Overhang type | Sequence 1 | SEQ ID NO: | Sequence 2 | SEQ ID NO: |
|---|---|---|---|---|
| 5' 4 bp | $N_4$ACAAGAGGAGCATCCGTATTAC CGCCTATATCGCCTACGTTTAGAG CATT | 12 | AATGCTCTAAACGTAGGCGATATAG GCGGTAATACGGATGCTCCTCTTG T | 24 |
| 5' 5 bp | $N_5$GTAAATCCCACACAGCTGTCGG CTTATATGGTCATTGGACGGCGTA ATAG | 13 | CTATTACGCCGTCCAATGACCATAT AAGCCGACAGCTGTGTGGGATTTA C | 25 |
| 5' 6 bp | $N_6$CCAGACAGCCATAGAGGTTACA AGCATAGCAATTTGCATCAGTTCG CAGA | 14 | TCTGCGAACTGATGCAAATTGCTAT GCTTGTAACCTCTATGGCTGTCTGG | 26 |

NA12878 gDNA was purchased from the Coriell Institute for Medical Research, was prepared for adapter ligation in several ways. Mechanical shearing: NA12878 was sheared to an average length of 350 bp using a Bioruptor Pico (Diagenode) and manufacturer's instructions. Sheared DNA was then size selected from 200-600 bp using a Pippen Prep dye free 2% gel (Sage Sciences) following manufacturer's instructions. Restriction enzyme digest: 1 µg of NA12878 was digested in a 50 µl reaction using 10 units of MluCI (New England Biolabs) at 37° C. for 1 hour. Digested DNA was purified using 2× AMPURE beads (Beckman Coulter) following manufacturer's instructions. After purification DNA was size-selected from 200-600 bp using a Pippen Prep dye free 2% gel (Sage Sciences) and manufacturer's instructions. Enzymatic shearing: 1 µg of NA12878 was digested in a 20 µl reaction with NEBNext® dsDNA Fragmentase® (New England Biolabs) at 37° C. for 25 minutes and stopped with 0.1 mM EDTA. The reaction was then brought up to 50 µl and purified as above. DNase I: 1 µg of NA12878 was digested in a 50 µl reaction using 0.01 units of DNase I (New England Biolabs) at 37° C. for 10 minutes and stopped with 0.1 mM EDTA; DNA was purified as above. Micrococcal nuclease: 1 µg of NA12878 was digested in a 50 µl reaction using 2 units of Micrococcal nuclease (New England Biolabs) at 37° C. for 5 minutes and stopped with 0.1 mM EDTA; DNA was purified as above.

All NA12878 reactions: After NA12878 gDNA was prepared using any of the above methods, it was end prepared for adapter ligation by dephosphorylation followed by 5' phosphorylation using the same protocol detailed above for the control oligos.

For human plasma and cell-free DNA preparation, whole blood from deidentified donors was obtained for in-vitro investigational use from the Stanford Blood Center in Palo Alto, Calif. Blood was drawn into one of several tube types (Table 3). Blood plasma was extracted from whole blood by spinning the blood collection tubes at 1800 g for 10 minutes at 4° C. Without disturbing the cell layer, the supernatant was transferred to microfuge tubes under sterile conditions in 2 ml aliquots and spun again at 16000 g for 10 minutes at 4° C. to remove cell debris, and stored at −80° C. as 1 ml aliquots. cfDNA was extracted from 1 ml plasma using the Circulating Cell-free DNA kit (Qiagen) following manufacturer's protocol. Purified cfDNA was measured for double-stranded DNA (dsDNA) concentration using the QUANT-IT high sensitivity dsDNA Assay Kit and a Qubit Fluorometer (ThermoFisher). Purified cfDNA was analyzed for size distribution using the Agilent TapeStation 4200 and associated D1000 and D5000 high sensitivity products. Cell-free DNA was end prepared for adapter ligation by dephosphorylation followed by 5' phosphorylation using the same protocol detailed above for the control oligos.

TABLE 3

Blood collection tubes used in synthetic spike experiments

| Blood Collection Tube | Anti-coagulant | Nuclease inhibited |
|---|---|---|
| Red top tube | None | No - Additional nucleases released during clotting |
| Yellow top tube | Sodium Citrate | No - Citrate has no nuclease inhibition function |
| Purple top tube | Potassium EDTA | Maybe - EDTA can inhibit nuclease function |
| Streck DNA tube | Potassium EDTA | Yes - contains nuclease and cell lysis inhibitors |

For the control-spike experiments, approximately 40 ml of whole blood was obtained per donor in five blood collection tubes (Table 3). Blood from each tube was divided into three aliquots. To accurately evaluate the effect of blood nucleases on overhang profile, a pool of control oligos (1 pmol total per ml of whole blood) was added under sterile conditions. In the case of serum tubes, because coagulation initiates from the time of blood draw, the clot was separated at the start of the experiment and the control oligo pool was added to 1 ml of the supernatant prior to serum preparation. The plasma-oligo mixtures were incubated for 0, 4, or 24 hours. Immediately following each time point, plasma extraction and cfDNA preparation were performed following the protocol described above. Water and 1×PBS pH7.4 were used as negative controls, substituting for control oligos; DNA extractions were performed similar to the whole blood aliquots. The bead binding buffer, proteinase K and magnetic bead volumes were scaled according to the input plasma volume. DNA end preparation of control-spiked cfDNA was performed as described above, followed by library preparation.

Adapter Ligation and Sequencing Library Preparation

Each adapter contains Illumina sequencer-specific priming sites and a Unique-End-Identifier (UEI)—a barcode sequence that indicates the length and identity (5' or 3') of the overhang, if any, present in the original molecule (Table 4). The adapters were synthesized using standard desalting purification and duplexed by Integrated DNA Technologies (IDT). For purposes of this study the 13 adapter set includes six with 3' overhangs (1 to 6 nt in length), six with 5' overhangs (1-6 nt in length), and a single blunt adapter (i.e., no overhang). Adapters were not phosphorylated and thus were discouraged from forming dimers. All 13 duplexed adapters were pooled in equimolar ratio and prepared for ligation by end dephosphorylation using the following 20 µl reaction: 1 pmol of pooled adapters, 10 units of rapid Shrimp Alkaline Phosphatase (New England Biolabs), 1× Cutsmart Buffer, incubated at 37° C. for 30 minutes followed by a 10 minute heat inactivation at 65° C. Multiple dephosphorylation reactions were combined over a single QIAQUICK Nucleotide Removal column (Qiagen) and purified according to manufacturer's instructions. Adapter molarity was calculated using DNA concentration (Qubit Fluorometric Quantitation) and known length. Adapters were then ready for ligation.

minutes. Nick repair was followed by a 2× AMPURE bead clean and elution in 20 µl of low TE (10 mM Tris pH 8, 0.1 mM EDTA).

For index PCR, 10 µl of purified adapter-ligated DNA was combined with 1× Kapa HiFi HotStart ReadyMix (Roche) and 0.4 mM final concentration of IS4 and 0.4 mM final concentration of an index primer2 in a 50 µl reaction and amplified using the following thermal cycling conditions: 3 minutes at 98° C. for initial denaturation followed by 15 cycles for control/NA12878 or 18 cycles for cfDNA at 98° C. for 20 seconds, 68° C. for 30 seconds, 72° C. for 30 seconds, and finally an elongation step of 1 minute at 72° C. After index PCR, DNA was purified with either a 1.5×

TABLE 4

Adapter design

| Adapter | Sequence 1 | SEQ ID NO: | Sequence 2 | SEQ ID NO: |
|---|---|---|---|---|
| Blunt | /5SpC3/ACACTCTTTCCCTACACGA CGCTCTTCCGATCTataccgc | 27 | gcggtatAGATCGGAAGAGCACACGT CTGAACTCCAGTCAC/3SPC3/ | 40 |
| 3' 1 bp | /5SpC3/ACACTCTTTCCCTACACGA CGCTCTTCCGATCTgatatcg*$N_1$ | 28 | cgatatcAGATCGGAAGAGCACACGT CTGAACTCCAGTCAC/3SPC3/ | 41 |
| 3' 2 bp | /5SpC3/ACACTCTTTCCCTACACGA CGCTCTTCCGATCTgtctgac$N_1$*$N_1$ | 29 | gtcagacAGATCGGAAGAGCACACG TCTGAACTCCAGTCAC/3SPC3/ | 42 |
| 3' 3 bp | /5SpC3/ACACTCTTTCCCTACACGA CGCTCTTCCGATCTgagccaa$N_2$*$N_1$ | 30 | ttggctcAGATCGGAAGAGCACACGT CTGAACTCCAGTCAC/3SPC3/ | 43 |
| 3' 4 bp | /5SpC3/ACACTCTTTCCCTACACGA CGCTCTTCCGATCTcgccata$N_3$*$N_1$ | 31 | tatggcgAGATCGGAAGAGCACACGT CTGAACTCCAGTCAC/3SPC3/ | 44 |
| 3' 5 bp | /5SpC3/ACACTCTTTCCCTACACGA CGCTCTTCCGATCTcgtatat$N_4N_1$ | 32 | atatacgAGATCGGAAGAGCACACGT CTGAACTCCAGTCAC/3SPC3/ | 45 |
| 3' 6 bp | /5SpC3/ACACTCTTTCCCTACACGA CGCTCTTCCGATCTgactaag$N_5$*$N_1$ | 33 | cttagtcAGATCGGAAGAGCACACGT CTGAACTCCAGTCAC/3SPC3/ | 46 |
| 5' 1 bp | /5SpC3/ACACTCTTTCCCTACACGA CGCTCTTCCGATCTagtacgg | 34 | $N_1$*ccgtactAGATCGGAAGAGCACAC GTCTGAACTCCAGTCAC/3SPC3/ | 47 |
| 5' 2 bp | /5SpC3/ACACTCTTTCCCTACACGA CGCTCTTCCGATCTagcagcg | 35 | $N_1$*$N_1$cgctgctAGATCGGAAGAGCAC ACGTCTGAACTCCAGTCAC/3SPC3/ | 48 |
| 5' 3 bp | /5SpC3/ACACTCTTTCCCTACACGA CGCTCTTCCGATCTccatatg | 36 | $N_1$*$N_2$catatggAGATCGGAAGAGCAC ACGTCTGAACTCCAGTCAC/3SPC3/ | 49 |
| 5' 4bp | /5SpC3/ACACTCTTTCCCTACACGA CGCTCTTCCGATCTagcctgg | 37 | $N_1$*$N_3$ccaggctAGATCGGAAGAGCAC ACGTCTGAACTCCAGTCAC/3SPC3/ | 50 |
| 5' 5bp | /5SpC3/ACACTCTTTCCCTACACGA CGCTCTTCCGATCTatacgcg | 38 | $N_1$*$N_4$cgcgtatAGATCGGAAGAGCAC ACGTCTGAACTCCAGTCAC/3SPC3/ | 51 |
| 5' 6bp | /5SpC3/ACACTCTTTCCCTACACGA CGCTCTTCCGATCTgctaggc | 39 | $N_1$*$N_5$gcctagcAGATCGGAAGAGCAC ACGTCTGAACTCCAGTCAC/3SPC3/ | 52 |

Adapter ligation included an initial ligation step followed by a subsequent nick repair ligation step prior to index PCR. 0.05 pmol of substrate DNA (control/NA12878/cfDNA) was combined with 1 pmol of adapters in a 60 µl ligation reaction with 800 units of T4 DNA ligase (New England Biolabs) and incubated at 20° C. for 1 hour, followed by either a 2× AMPURE clean for control oligos, or a 1.2× AMPURE clean for NA12878 or cfDNA. After DNA purification, DNA was phosphorylated with 20 units of T4 Polynucleotide Kinase (New England Biolabs) and 1× T4 DNA ligase buffer in a 48.8 µl reaction and incubated at 37° C. After 30 minutes, 480 units of T4 DNA ligase was added to the reaction and the temperature reduced to 20° C. for 15

AMPURE clean for control oligos, or a 1.2× AMPURE clean for NA12878/cfDNA. For each sequencing DNA library, final molarity estimates were calculated using fragment length distribution and dsDNA concentration (Agilent Tapestation 4200 and Qubit Fluorometric Quantitation unit). Samples were then pooled and run 2×150 bp cycles on an Illumina MISEQ benchtop sequencer (following manufacturer's instructions) to a depth of approximately 100,000 read-pairs per sample.

Informatic Analysis

Mapping UEI-barcoded read pairs poses a bioinformatic challenge when template molecules are shorter than the sum of the lengths of the forward and reverse reads plus a single 7-nt barcode. This challenge exists because each read can extend through its mate's barcode sequence and possibly beyond into the Illumina adapter sequence. One approach in studies where short template molecules are expected, such as in the field of ancient DNA, is to simultaneously remove adapter sequences and merge reads. This process includes collapsing forward and reverse reads into single sequences, based on sequence similarity, while trimming ends of reads that match known Illumina adapter sequences using SEQPREP (github.com/jstjohn/SeqPrep). When UEIs are present, however, these merged reads can have a 7-nt UEI on both ends, one of which will be reverse-complemented.

To simplify mapping, adapter trimming and read merging were conditioned on the presence of UEI sequences. For each read, the presence of a known UEI on both the forward and reverse read in each pair was checked. UEIs were allowed to contain up to one "N" base, but no other base mismatches were allowed. If both reads had a known UEI sequence, it was checked whether reads merged by searching each sequence for the reverse complement of its mate's UEI. If neither read met this criterion, both reads were output unchanged, since a read can only include adapter sequence if it extends through its mate's UEI sequence. If both reads contained their mate's reverse-complemented UEI sequence, and the positions at which the mates' UEIs were encountered matched, then both reads were truncated at the position where their mates' UEIs were encountered. If the positions did not match, both reads were discarded.

Rather than storing all merged read pairs as collapsed sequences, they were kept as truncated read pairs, so that UEI sequences of mates would not interfere with mapping to reference genomes. For the sake of control oligo experiments, in which relatively short sequences were expected, collapsed sequences for read pairs that merged using the above criteria also were stored. For such sequences, the bases within the merged region were allowed to contain at most one mismatch (the chosen base at mismatching positions was the base with the higher quality, or a random base in the case of a tie).

To reduce the risk of contamination of the sequencing data by the Illumina sequencing control DNA—phiX—due to index misassignment, all of the raw data was first aligned to the phiX genome using bwa mem with default parameters. Reads that did not map (samtools fastq-f 12) were extracted and used for downstream analyses.

Because it was found that overhanging adapters were less reliable when encountered on forward (P5) rather than reverse (P7) reads, the analyses ignored forward reads that began with an overhanging adapter. Blunt adapters were allowed on both the forward and reverse reads. In all cases, this filtering step was applied only when computing results (all reads were included when processing, merging, and aligning, but overhanging adapters on forward reads were not allowed to affect results).

A code was used that identifies overhangs using "Unique End Identifying-UEI" barcodes. The algorithm included the following features:

1. a data structure that contains a list of UEI barcode sequences that indicate the type and length of an overhang, or a blunt end;
2. take first 7 bases of each read (7=length of barcode);
3. see if these match a known barcode;
4. if there is one N, see if converting it to a base makes it match a known barcode;
5. if it matches a barcode, look up that barcode's overhang by taking from the read the number of bases indicated by the barcode; and
6. ignore forward reads, unless barcode is blunt.

Control Oligo Experiments

Control oligos were short (50 bp) sequences of synthetic double-stranded DNA, one end of which was synthesized to have a single-stranded overhang and the other end of which was intended to be blunt. When processing, all properly formed sequences were expected to merge using the criteria above, except in cases where control oligos chained together. Two ways of assessing control oligo experiments were defined, one to measure sensitivity and the other to measure specificity.

To measure sensitivity, the percent of legitimate (non-chained) control oligo ends that were correctly identified using the adapters was computed. First, all reads that merged using the criteria above were considered. When a mismatching base was encountered while merging a read pair, the base with the higher quality score was chosen; if quality scores were tied, the base was chosen randomly. Next, a reference sequence comprising all control oligo sequences and their reverse complements was constructed, separated by runs of "N" bases equal in length to the longest control oligo overhang. To determine the control oligo type of each merged read, merged reads were aligned to this reference sequence using the Edlib C++ sequence alignment library, allowing gaps at the beginning and end of the read in the alignment and allowing up to one base mismatch, letting "N" match any base with no penalty. If the best alignment fell within the coordinates of a single control oligo sequence (a non-chimeric alignment), that control oligo was chosen as the correct sequence. A control oligo was considered correct if the barcode for the correct overhang was ligated to the overhang end of the oligo and the barcode for blunt adapters was ligated to the opposite end.

To measure specificity, the percent of UEI sequences that were ligated to the correct end of the control oligo with the matching overhang was computed. In this case, it was not assessed whether control oligos formed chains, thereby assessing any DNA end available for ligation. For every paired-end read (truncated as described above, but not merged), the sequence following the UEI was aligned to a reference sequence containing all control oligo sequences, separated by runs of "N" bases equal to the length of the longest overhang. The best alignment, allowing up to one mismatch and with "N" matching any base, was used to determine the correct control oligo sequence, if the alignment was non-chimeric (within the coordinates of a single control oligo sequence). Specificity was then defined as the percent of reads for which the UEI at the beginning of the read was followed by the correct type of control oligo end, in the correct orientation.

For determining nucleotide composition of overhang sequence, all bases between the end of a UEI sequence and the beginning of a control oligo sequence were considered to be the true sequence of the overhang. When assessing the base composition of overhang sequences, all adapters were required to be ligated to the correct type of control oligo.

Human DNA

Paired-end reads that remain after filtering were truncated if necessary and aligned to the hg19 human reference genome downloaded from the UCSC genome browser. For alignment, bwa aln and bwa sample with default parameters were used, skipping the UEI sequences at the beginning of the reads (-B parameter). Duplicate reads were then removed using samtools rmdup. Reads were counted as mapped only when in proper pairs with a minimum map quality of 20 (samtools view-c-f66-q20), except in the case of the restriction enzyme experiments, in which the requirement for proper pairing (samtools view-c-f64-q20) was removed due to the possibility of chaining fragments causing chimeric alignments.

To count UEI types in mapped reads, the BAM files were scanned using HTSLib's BAM parser and obtained UEI sequences from the BC tag. Overhang sequences were obtained by taking a number of bases from the beginning of each read equal to the overhang length indicated by the UEI.

Some sequencing libraries contained human DNA spiked with control oligos. To analyze these libraries, all sequencing reads were first processed as if the libraries contained only human DNA. Then, non-human sequences were extracted from the alignments to the human reference genome, by selecting unmapped reads and reads with map quality less than 10 (using a custom technique that can re-append barcodes to extracted read sequences, unlike samtools fastq). These reads, which were mostly control oligos, were then processed the same way as other control oligo libraries.

Results

Library Construction

The method in this Example assayed fragmented and degraded dsDNA termini following a library preparation workflow. Each adapter for this method included three parts: P5/P7 Illumina-based sequencing and index priming sites, a 7 base pair (bp) Unique End Identifier (UEI; a barcode encoding the termini type), and a blunt end or a single-stranded overhang that hybridizes and ligates to the substrate's overhang, when present. The overhangs were synthesized with equal proportions of random sequence of length N (here up to 6 nucleotides (nt) long). Adapters were included in excess to ensure that every template dsDNA type has access to a compatible adapter. In this way, adapters were introduced in a competitive reaction that provided enough compatible sequences to hybridize with all possible sticky-ended template molecules. However, the overhangs of the adapters create the potential for self-hybridization and ligation, and therefore were not phosphorylated to prevent adapter dimer formation.

During the initial step of this method, template DNA was treated with polynucleotide kinase so as to phosphorylate 5' termini. Aside from the phosphorylation, template DNA termini are not altered. Next, a two-step ligation was performed. First the 5' phosphorylated template DNA was ligated to a pool of unphosphorylated, UEI-containing adapters. This first ligation occurs only at the forward (P5) adapter ends of both template strands. Next, purification was performed to remove excess, unligated adapters. Finally, the 5' ends of the adapters were phosphorylated and a second ligation was performed—this time at the reverse (P7) adapter ends—in order to complete the dsDNA library molecule. Fully formed molecules were then indexed and amplified using a universal P5 primer and a uniquely indexed P7 primer. Following paired-end sequencing on an Illumina sequencer, the UEI was used to classify sequence reads by the type, length, and sequence of the overhang.

Assessing Accuracy of DNA Termini Identification

Accuracy

To determine the accuracy of the assay described in this Example, a pool of 12 synthetic double-stranded control oligos were constructed, each with a known length and type (3' or 5') of single-stranded overhang. Each control oligo contained a unique and identifiable 50 bp core and a common structure: blunt terminus on one side, and a 5' or 3' overhang of a specific length (1 to 6 nt) on the other side. After sequencing libraries, the UEIs on the reverse read (P7) were used to quantify the assay's accuracy by comparing how often the overhang indicated by the adapter UEI correctly matched the overhang engineered on the dsDNA control template. Analysis was limited to reverse reads because the UEI present on the reverse adapter was more accurate in predicting the correct overhang than when the UEI present on both adapters was included, or when only the forward adapter was included (FIG. 18). A model to explain this phenomenon is provided in FIG. 19.

The specificity of the assay in this Example was measured in two ways using the control oligo pools. First, the dataset was limited to correctly formed library molecules (i.e., monomeric control oligos that have a sequence within an edit distance 1 of a true control oligo sequence) and how often the correct overhang type and length was captured was calculated. For each control oligo, the most commonly observed adapter UEI was the correct adapter in all overhang types (3' and 5') and lengths (1 to 6-nt) tested. However, a minor fraction of library molecules was observed whose UEI did not correspond to the known overhang length or type for these control oligos. The overall UEI accuracy over each overhang type and length was 84.94%+/−0.72% (95% C.I.). Next, the specificity of each UEI was measured by counting the times each UEI adapter was observed ligated to each type of synthetic oligo. For all 3' UEIs and blunt UEI, the most common ligation event was the correct one. For all 5' UEIs other than the 5' 1-nt overhang, the most common ligation event was the correct one. However, taken together as a group, the 5' overhangs have lower accuracy than that of the 3' overhangs. Errors most often occurred ±1-nt in distance from the correct length, notably in the 5' 1-nt, 5' 3-nt, and 5' 5-nt controls.

Base Composition

To determine if ligation accuracy or efficiency is influenced by the base composition of the overhangs, sequence data and UEI data were used to determine the nucleotide sequence of each recovered single-stranded overhang. Due to the architecture of the libraries, the bases present in the 5' overhangs derived from the insert template molecule, which was in this case the control oligo, whereas 3' overhangs were derived from the DNA overhang of the adapter itself. A uniform distribution of nucleotides was observed for each overhang type and length except for 5' 1-nt overhangs, where an excess of cytosine was observed. To evaluate whether this cytosine bias was a product of the oligo synthesis process, standard end repaired libraries were prepared (NEB Ultra II) with the synthetic control oligos. The end repair step removed 3' overhangs and filled-in 5' overhangs via polymerase activity, allowing characterization of the base composition of the synthetic DNA 5' overhangs. Within the standard end repaired libraries of the control oligos, an elevated read count of 5' 1-nt cytosines was observed. Therefore, this observation is likely to derive from biases in the custom oligo synthesis and not from biases introduced during ligation.

Table 5) was calculated. Overall, there was concordance between the known MluCI fraction in the library pool and that observed as correct 5' 4 nucleotide overhangs with the correct AATT overhang within the sequenced data. Libraries with higher fractions of MluCI-digested DNA (100%-10%) showed fewer than expected 5' AATT overhangs, likely due to the overabundance of compatible sticky template ends, whereas the lower dilution libraries generated more accurate estimates of the known MluCI fraction.

TABLE 5

Sequencing data for sensitivity experiments

| Sample Type | Number of Read Pairs Sequenced | % Reads Mapped to hg19 | Number of Overhangs on R2 Observed | Number of 5' AATT Observed in R2 Overhangs | % of 5' AATT in R2 Overhangs |
|---|---|---|---|---|---|
| 100% Mechanical Shear | 138921 | 91 | 91011 | 41 | 0.05 |
| 1% RE Digest | 132516 | 90 | 86052 | 647 | 0.75 |
| 5% RE Digest | 134791 | 90 | 88194 | 2977 | 3.38 |
| 10% RE Digest | 129736 | 90 | 85432 | 4268 | 5.00 |
| 25% RE Digest | 106698 | 88 | 68811 | 6499 | 9.44 |
| 50% RE Digest | 125340 | 86 | 75954 | 12211 | 16.08 |
| 100% RE Digest | 97724 | 76 | 44139 | 17523 | 39.70 |

Sensitivity

To evaluate the ability of the adapters herein to detect the presence of a specific terminus type in a background of extraneous DNA molecules, a dilution series was performed in which DNA with a single known overhang sequence was mixed into a pool of diverse overhangs. The pool of diverse termini was created by sonication (Diagenode Bioruptor) and size selection of NA12878 genomic DNA (gDNA). The DNA with a single known overhang was created by digesting NA12878 gDNA with the restriction endonuclease MluCI, which creates 5' 4-nt overhangs of the sequence AATT, followed by size selection.

First, libraries generated from the sonicated template and from the MluCI-digested template DNA were sequenced to characterize termini in both samples. The overhang length distribution for the sonicated sample (FIG. 15, panel A) showed that sonication shearing of DNA creates a nonrandom profile characterized by a prevalence of blunt termini followed by 1 to 4-nt overhangs that occur on both the 5' and 3' termini with an excess for 3' 1-nt and 3' 2-nt overhangs. As expected for MluCI, the length distribution for the MluCI-digested DNA showed an overwhelming excess of 5' 4-nt overhangs (FIG. 15, panel B).

To perform the dilution series, defined amounts of the MluCI-digested DNA were mixed with the sonicated DNA sample, and then libraries were generated from the pooled mixtures. The pools contained from 1% up to 50% MluCI-digested DNA. The percent of sequence reads in each library that were attributed to 5' AATT overhangs (FIG. 15, panel C;

Next, to estimate at what concentration of MluCI-digested DNA the 5' AATT signal is lost, the sonicated libraries containing titrated amounts of MluCI-digested DNA were compared to the control sonicated library that contained no spiked 5' AATT overhangs. Even at the lowest dilution in the series (1% MluCI) the occurrence of 5' AATT overhangs was detected over all other overhangs, p<0.001 (FIG. 15, panel D). This observation indicates the assay in this Example, when compared to an appropriate control library, is sufficiently sensitive to discover overhang motifs that make up less than 1% of a library. Mapping the precise genomic location of DNA ends sheared by sonication and digested by MluCI showed a random distribution of overhangs and an overabundance of expected 5' 4-nt overhangs, respectively.

Overhang Profile of Common DNA Shearing Mechanisms

Fragmentation, or shearing, of high molecular weight DNA typically is a necessary step in creating short-read, e.g. Illumina, sequencing libraries. Popular means of shearing DNA include sonication and enzymatic digestion. To explore whether mechanical shearing via sonication biases or otherwise affects the quality of NGS libraries, several studies have compared the consequences of shearing methods, including one that used a cloning based approach to examine termini created by DNA sonication, and another that analyzed 5' overhangs in standard end repaired NGS libraries to find evidence for non-random shearing by DNA sonication. To explore the consequences of enzymatic shearing, several studies have used molecular, microarray, and sequencing-based methods to describe the digestion preferences of DNaseI as well as the cut preferences of Micrococcal Nuclease but in low resolution. Because libraries generated using adapters described herein can assess the microstructure of all free DNA ends in an unbiased high-throughput way, the assay described in this Example was used to characterize the DNA end profiles of naked NA12878 genomic DNA fragmented via both sonication and enzymatic shearing (Table 6).

TABLE 6

Sequencing data for common shearing mechanisms and nucleases

| Sample Type | Number of Read Pairs Sequenced | % Molecules that Contain UEIs | % UEI Molecules Mapped to hg19 |
|---|---|---|---|
| Bioruptor Shear | 147,613 ± 30,695 | 94.7 | 89 |
| NEB dsFragmentase | 184,975 ± 66,401 | 94 | 86 |
| DNaseI | 184,938 ± 27,744 | 92 | 66 |
| Micrococcal Nuclease | 178,653 ± 30,933 | 95 | 82 |

Sonication

To interrogate the overhangs produced by sonication in greater detail, data generated from libraries sheared with a Diagenode Bioruptor was examined, as introduced above (see Sensitivity section). The overhang length and sequence motif distributions for the sonicated sample showed that sonication of DNA creates a higher prevalence of blunt ends followed by 1 to 4-nt overhangs that occur on both the 5' and 3' ends, but with a preference for 3' 1-nt and 3' 2-nt overhangs. The base composition profiles of the Bioruptor-sonicated DNA showed a balanced spectrum except for when a 1-nt overhang forms. The occurrence of a 1-nt DSB most often leaves a single cytosine overhang, a phenomenon observed previously on 5'1-nt overhangs.

Enzymatic Shearing

To interrogate the overhangs produced by enzymatic shearing, libraries were generated using three endonucleases, dsFragmentase (New England Biolabs, NEB), DNaseI and Micrococcal nuclease (MNase). The NEB product dsFragmentase is a cocktail of two enzymes designed specifically for NGS DNA fragmentation. The overhang length distribution from the dsFragmentase-digested sample created more molecules with overhangs and fewer blunt ended molecules when compared to sonication. The dsFragmentase also created a more random shearing profile than the Bioruptor, based on the variation in overhang lengths observed between library replicates. The adapters used in this study extend only to 6-nt. The sheer number of molecules containing 6-nt overhangs indicates dsFragmentase creates overhangs that are longer than 6-nt. The motif distribution for the dsFragmentase overhangs showed an even distribution between the generation of 5' and 3' overhangs. The base composition of the dsFragmentase overhangs was similar to that of the Bioruptor, but with more cytosines in overhangs of 2-nt to 6-nt in length.

Next, the overhangs produced by endonucleases DNaseI and Micrococcal Nuclease (MNase) was interrogated. The overhang length plot for DNaseI-digested naked DNA showed a prevalence of 3' 2-nt overhangs, as well as 5' 2-nt to 4-nt overhangs. Of the latter, overhangs of 3 or more nucleotides were GC-rich. Based on the relative abundance of 6-nt overhangs in the overhang length distribution plot, it is likely that DNaseI creates overhangs greater than 6-nt in length. The overhang base composition profile of DNaseI digested DNA showed a decreasing preference for cytosine in the 5' overhang as the length of the overhang increased, and a slight preference for 3'1-nt thymine. The base composition of nucleotides upstream of DNaseI cut sites showed a preference for the cutting of DNA at A/T sites in the −1 position of 5' overhangs.

The overhang length plot for MNase digested DNA (FIG. 16, top panel) showed that MNase has a strong preference for the creation of blunt DNA termini (39.5% of the overhang data), with longer overhangs becoming decreasingly likely. When an overhang is produced, MNase showed an overall preference for A/T rich 5' overhangs (excluding 1-nt overhangs) (FIG. 16, bottom panel). The base composition of nucleotides upstream of MNase cut sites shows that, although the actual 3' overhangs produced by MNase are not as A/T rich as 5' overhangs, the −1 position of 3' overhangs is overwhelmingly A/T rich.

These results show that the method described in this Example is able to reproduce the outcomes of previous studies that characterized the preferences and biases of various DNA shearing methods. These results also highlight the potential benefits of utilizing this method in the characterization of novel nucleases.

Recovery of Ends Generated by In Vivo Nuclease Activity in Whole Blood

Recently, circulating cell-free DNA (cfDNA) profiling has garnered considerable attention for use in non-invasive prenatal testing and cancer diagnostics. Obtaining high quality DNA from blood plasma begins with blood collection itself. Blood coagulation or clotting is a process associated with increased nuclease activity and the type of blood collection tube (BCT) may affect the quantity and quality of a cfDNA extract. Here, how common BCTs maintain cfDNA integrity was assayed by constructing libraries of cfDNA extracted from various BCTs spiked with known control oligos (described above). BCTs containing commonly used anticoagulants were included (Table 3), and a control tube without anticoagulants (red top tube; RTT) was included.

Before extracting plasma (or serum) and isolating cfDNA as described above, control oligos were spiked into each of four tube types. Mixtures of control oligos and cfDNA were extracted at 0, 4, and 24 hours following the oligo spike-in and converted into libraries using adapters described herein. In Streck® BCTs (SBCTs), which contain additives that inhibit nuclease activity and cell lysis, the human cfDNA fragment length profile or abundance did not change over time. Conversely, multi-nucleosome fragments appeared in YTTs (anticoagulant—citrate), and PTTs (anticoagulant—Potassium EDTA) at 24 hours, reminiscent of apoptotic cellular gDNA. In the RTTs, multi-nucleosome fragments were seen as early as 0 hours suggesting that apoptotic processes may be initiated during blood coagulation that are associated with release of endo- and exo-nucleases.

The incubation of whole blood containing control oligos prior to cfDNA extraction allowed the quantification of the amount of loss or change of known DNA ends due to nuclease(s) that remained active following the blood draw. No significant loss nor change to the control DNA end profiles was observed in the SBCTs, the PTTs, or the negative controls (FIG. 17). In YTTs, which do not contain any known nuclease inhibitors, changes in both 3' and 5' overhang profiles were observed. These changes indicated the presence of one or more active circulating exonucleases (FIG. 17). By 24 hours the 3' overhang signal of control oligos was significantly diminished in YTTs, suggesting the 3' to 5' exonuclease(s) may be more processive than the 5' to 3' exonuclease(s). In the RTTs, the complete loss of 3' overhang counts was observed within 4 hours, as well as depletion of true blunt-ends, identified by the generation of new overhangs on formerly blunt molecules. By 24 hours, the control oligos were no longer visible in RTTs, as was expected in a highly active nuclease environment. In sum, these observations show that the method described in this Example discerns changes in overhang patterns of cfDNA and can be used to investigate the effect(s) of circulating nucleases in the blood.

more features of the overhangs (e.g., quantification of certain overhang types (e.g., 5', 3', blunt), quantification of certain overhang lengths, quantification of certain overhang sequence features, and the like). In certain instances, features of the template molecules may be considered. Based on the overhang profile and/or certain template features, one or more characteristics of the sample may be determined.

Provided in Table 7 are example feature variables (e.g., overhang features; template features) that may be used to determine one or more characteristics of a sample.

TABLE 7

Example feature variables

| Feature | Examples |
|---|---|
| presence/absence of dinucleotide/trinucleotide/tetranucleotide* | overhang<br>template + overhang<br>template minus overhang |
| dinucleotide/trinucleotide/tetranucleotide* count | overhang<br>template + overhang<br>template minus overhang |
| dinucleotide/trinucleotide/tetranucleotide* percent | overhang<br>template + overhang<br>template minus overhang |
| full length of template | |
| length category (e.g., for cfDNA) | subnucleosome<br>mononucleosome<br>multinucleosome |
| length of overhang | |
| overhang type | 5' overhang<br>3' overhang<br>blunt (no overhang) |
| GC content | overhang<br>template + overhang<br>template minus overhang |
| overhang percent | log 2 percent of overhang sequence/total overhangs |
| overhang count | counts of particular overhang sequence |
| percent overhang length | length of overhang/full length of template |
| dinucleotide/trinucleotide/tetranucleotide* count in overhang vs. entire sequence of template | |
| Boolean variables: whether overhang overlaps with/is contained in/starts or ends in particular regions | coding regions<br>CpG islands<br>transcription factor binding sites (e.g., CCCTC-binding factor (CTCF) binding site)<br>DNAse hypersensitive sites<br>ATAC-seq peaks (e.g., open chromatin)<br>promoter regions<br>enhancer regions<br>hypermethylated regions |
| genome coordinate | |
| mean fragment length or distribution of molecules with a given overhang type and length | |
| mean fragment length or distribution of molecules with a given overhang sequence | |
| delta between libraries | mean length or distribution of fragments with a given overhang sequence vs. its X**<br>difference between library A and library B, where A has mean fragment length of 200 (or any X variable) and 0 count of GC dinucleotide (or any Y variable) compared to B with mean fragment length of 100 and 10 GC dinucleotide |

*Example dinucleotides include AA, AT, AC, AG, TT, TA, TC, TG, CC, CG, CA, CT, GG, GA, GC, GT; $4^3$ possible trinucleotide combinations; $4^4$ possible tetranucleotide combinations
**X = any feature above

Example 12: Analysis of Overhang Sequencing Datasets

Nucleic acid overhangs of a population of nucleic acids in a sample may be interrogated (e.g., using bioinformatic analyses) to generate an overhang profile comprising one or more An example of certain bioinformatic analyses of overhang data and the relation to a sample characteristic is described below.

Heat Map of Overhang Data

Libraries were generated using Y-shaped overhang adapters described herein (see e.g., the Y-shaped adapter and method shown in FIG. 9B) for cell-free DNA from donors having cancer ("cancer donors") and healthy donors. A heat map (FIG. 20) was generated from sequencing data of DNA overhangs present in each library using Ward's hierarchical clustering method. Each column of the heat map shown in FIG. 20 represents a single cell-free DNA library from a cancer donor (black bar) or healthy donor (no bar). Each row of the heat map shown in FIG. 20 represents a unique overhang (5' or 3') of length 1 to 6 nucleotides; rows (overhangs) containing at least one CG dinucleotide, or CpG, are indicated by a grey bar. Within the heat map matrix shown in FIG. 20, the darker the color, the increasing proportion (log scaled) that overhang represents in the library. Lighter colors indicate depletion of that overhang.

As shown in FIG. 20, the majority of CpG-containing overhangs are clustered towards one end of the tree, with a few smaller clusters throughout. One primary cluster of cancer donors was observed (FIG. 20, second clade from top left), the majority (12 of 13) of which had GI cancers. These samples showed a lower percent of the libraries having CG-containing overhangs (depletion), whereas healthy donors tended to have a higher percentage of libraries having CG-containing overhangs (enrichment). Thus, with respect to CG-containing overhangs, a pattern of depletion was observed in certain clusters of cancer cell-free DNA libraries.

Machine Learning Approaches Using Overhang Sequence Data

A Logistic Regression and a supervised learning algorithm (support vector machine (SVM)) were performed classifying cancer and healthy samples with variables including CG count, overhang length, full molecule length, and other variables as set forth in FIG. 21. Both SVM and Logistic Regression had an accuracy of 75%, with precision and recall above 75% (precision—ability of model to label sample as truly positive; recall—ability of model to find all positive samples).

Variables used in the models are provided in FIG. 21. After Recursive Feature Elimination all variables were considered a best performing feature after repeating the process of creating the model with different subsets—recursing on these with smaller and smaller sets of features.

Logistical Regression Classifier (Cancer Vs. Healthy—Confusion Matrix)

The predicted accuracy of the logistic regression classifier on the test set was 75%, with a better split between true positives, false positives, true negatives and false negatives—790+823 correct predictions and 308+230 incorrect predictions (FIG. 22).

SVM Classifier (Cancer Vs. Healthy—Classification Report and ROC)

There was a 73% ability of model to label sample as truly positive (precision) and 78% ability of model to find all positive samples (recall). The final model split the data into 30% test set and 70% train set. The f1-score is the harmonic mean between precision and recall and support is the number of samples taken into account from the test set. The accuracy of the classification was 75%.

GI Cancer Vs. Healthy—Model Summary

The odds of a patient having cancer increases by 120% if the overhang contains the CG dinucleotide sequence. The odds of a patient having cancer increases by 105% if the overhang contains the GG dinucleotide sequence, and 50% if the overhang contains the GC dinucleotide sequence. All feature variables had significant p-values, P>|z|, in final model—given a cut-off of 0.05.

GI Cancer Vs. Other (Includes Healthy and Other Cancer)—Model Summary

The odds of a patient having cancer increases by 94% if the overhang contains the CG dinucleotide sequence. All feature variables had significant p-values, P>|z|, in final model—given a cut-off of 0.05.

Example Classifier

Cancer vs healthy

In [1]:
import pandas as pd
import numpy as np
from sklearn import preprocessing
import matplotlib.pyplot as plt
from sklearn.linear_model import LogisticRegression
from sklearn.model_selection import train_test_split
import dask.dataframe as dd In [2]:
dt=pd.read_csv('APN_cpg_out.csv', sep=',', header=None, dtype={0: str, 1: str, 2: int, 3: str, 4: str, 5: int, 6: int, 7: object, 8: int, 9: str, 10: str, 11: float})
dt.columns=['barcode', 'overhang_type', 'overhang_length', 'overhang_seq', 'aligned_seq', 'start', 'end', 'aligned_len', 'full_len', 'chr', 'lib_name','cpg_island']

In [3]:
dt.loc[(dt['lib_name']=='APN1047')|(dt['lib_name']=='APN1048')|(dt['lib_name']=='APN1049')|(dt['lib_name']=='APN1050')|(dt['lib_name']=='APN1051')|(dt['lib_name']=='APN1052')|(dt['lib_name']=='APN1053')|(dt['lib_name']=='APN1054')|(dt['lib_name']=='APN1055')|(dt['lib_name']=='APN1056')|(dt['lib_name']=='APN1057')|(dt['lib_name']=='APN1058')|(dt['lib_name']=='APN816')|(dt['lib_name']=='APN1021')|(dt['lib_name']=='APN1022')|(dt['lib_name']=='APN1026')|(dt['lib_name']=='APN1027')|(dt['lib_name']=='APN1028')|(dt['lib_name']=='APN1029'), 'y']='1' dt.loc[(dt['lib_name']=='APN815')|(dt['lib_name']=='APN823')|(dt['lib_name']=='APN824')|(dt['lib_name']=='APN825')|(dt['lib_name']=='APN826')|(dt['lib_name']=='APN827')|(dt['lib_name']=='APN828')|(dt['lib_name']=='APN829')|(dt['lib_name']=='APN830')|(dt['lib_name']=='APN831')|(dt['lib_name']=='APN832')|(dt['lib_name']=='APN833')|(dt['lib_name']=='APN834')|(dt['lib_name']=='APN835')|(dt['lib_name']=='APN886')|(dt['lib_name']=='APN887')|(dt['lib_name']=='APN888')|(dt['lib_name']=='APN890')|(dt['lib_name']=='APN908')|(dt['lib_name']=='APN909')|(dt['lib_name']=='APN911')|(dt['lib_name']=='APN709')|(dt['lib_name']=='APN710')|(dt['lib_name']=='APN711')|(dt['lib_name']=='APN713')|(dt['lib_name']=='APN716')|(dt['lib_name']=='APN717')|(dt['lib_name']=='APN718')|(dt['lib_name']=='APN719')|(dt['lib_name']=='APN720')|(dt['lib_name']=='APN721')|(dt['lib_name']=='APN722')|(dt['lib_name']=='APN723')|(dt['lib_name']=='APN724')|(dt['lib_name']=='APN725')|(dt['lib_name']=='APN726')|(dt['lib_name']=='APN727')|(dt['lib_name']=='APN728')|(dt['lib_name']=='APN729')|(dt['lib_name']=='APN730')|(dt['lib_name']=='APN731')|(dt['lib_name']=='APN732')|(dt['lib_name']=='APN735')|(dt['lib_name']=='APN807')|(dt['lib_name']=='APN808')|(dt['lib_name']=='APN809')|(dt['lib_name']=='APN810')|(dt['lib_name']=='APN811')|(dt['lib_name']=='APN812')|(dt['lib_name']=='APN913')|(dt['lib_name']=='APN914')|(dt['lib_name']=='APN915')|(dt['lib_name']=='APN916')|(dt['lib_name']=='APN917')|(dt['lib_name']=='APN918')|(dt['lib_name']=='APN919')|(dt['lib_name']==

'APN920')|(dt['lib_name']=='APN921')|(dt['lib_name']=='APN922')|(dt['lib_name']=='APN923')|(dt['lib_name']=='APN924')|(dt['lib_name']=='APN925')|(dt['lib_name']=='APN926')|(dt['lib_name']=='APN927')|(dt['lib_name']=='APN1017')|(dt['lib_name']=='APN1018')|(dt['lib_name']=='APN1019')|(dt['lib_n ame']=='APN1020')|(dt['lib_name']=='APN1023')|(dt['lib_name']=='APN1024')|(dt['lib_name']=='APN1025'), 'y']='0'

In [4]:
dt['overhang_count']=dt.groupby('overhang_seq')['overhang_seq'].transform('count')
dt.loc[dt.overhang_type=="5'", 'otype']=1
dt.loc[dt.overhang_type=="3'", 'otype']=0
dt.loc[dt.overhang_type=="BL", 'otype']=0
dt.loc[dt.full_len<120, 'len_cat']=0
dt.loc[120<=dt.full_len, 'len_cat']=1

In [5]:
dt['AA_count_oh']=dt['overhang_seq'].str.count('AA')
dt['AC_count_oh']=dt['overhang_seq'].str.count('AC')
dt['AT_count_oh']=dt['overhang_seq'].str.count('AT')
dt['AG_count_oh']=dt['overhang_seq'].str.count('AG')
dt['CA_count_oh']=dt['overhang_seq'].str.count('CA')
dt['CC_count_oh']=dt['overhang_seq'].str.count('CC')
dt['CT_count_oh']=dt['overhang_seq'].str.count('CT')
dt['CG_count_oh']=dt['overhang_seq'].str.count('CG')
dt['TA_count_oh']=dt['overhang_seq'].str.count('TA')
dt['TC_count_oh']=dt['overhang_seq'].str.count('TC')
dt['TT_count_oh']=dt['overhang_seq'].str.count('TT')
dt['TG_count_oh']=dt['overhang_seq'].str.count('TG')
dt['GA_count_oh']=dt['overhang_seq'].str.count('GA')
dt['GC_count_oh']=dt['overhang_seq'].str.count('GC')
dt['GT_count_oh']=dt['overhang_seq'].str.count('GT')
dt['GG_count_oh']=dt['overhang_seq'].str.count('GG')

In [9]:
dt['y']=pd.to_numeric(dt['y'])

In [10]:
data=dt.groupby('overhang_seq').mean()
data.loc[(data['y']>=0.5), 'y']=1
data.loc[(data['y']<0.5), 'y']=0

In [13]:
data['perc_len']=np.log 2(data['overhang_length']/data['full_len'])
data['AA_perc']=(data['AA_count_oh']/data['overhang_ length'])*100
data['AC_perc']=(data['AC_count_oh']/data['overhang_length'])*100
data['AT_perc']=(data['AT_count_oh']/data['overhang_length'])*100
data['AG_perc']=(data['AG_count_oh']/data['overhang_ length'])*100
data['CA_perc']=(data['CA_count_oh']/data['overhang_length'])*100
data['CC_perc']=(data['CC_count_oh']/data['overhang_length'])*100
data['CT_perc']=(data['CT_count_oh']/data['overhang_length'])*100
data['CG_perc']=(data['CG_count_oh']/data['overhang_length'])*100
data['TA_perc']=(data['TA_count_oh']/data['overhang_length'])*100
data['TC_perc']=(data['TC_count_oh']/data['overhang_length'])*100
data['TT_perc']=(data['TT_count_oh']/data['overhang_length'])*100
data['TG_perc']=(data['TG_count_oh']/data['overhang_length'])*100
data['GA_perc']=(data['GA_count_oh']/data['overhang_ length'])*100
data['GC_perc']=(data['GC_count_oh']/data['overhang_length'])*100
data['GT_perc']=(data['GT_count_oh']/data['overhang_length'])*100
data['GG_perc']=(data['GG_count_oh']/data['overhang_ length'])*100
data['overhang_perc']=np.log 2(data['overhang_count']/len(data.columns))
data.head( )

In [14]:
data.fillna(0, inplace=True)
np.any(np.isnan(data))

In [16]:
len(list(data.keys( )))

In [17]:
X=data.loc[:, data.columns!='y']
y=data.loc[:, data.columns=='y']

In [18]:
from imblearn.over sampling import SMOTE
os=SMOTE(random_state=0)
X_train, X_test, y_train, y_test=train_test_split(X, y, test_size=0.3, random_state=0)
columns=X_train.columns In [19]:
os_data_X, os_data_y=os.fit_sample(X_train, y_train.values.ravel( ))
os_data_X=pd.DataFrame(data=os_data_X, columns=columns)
os_data_y=pd.DataFrame(data=os_data_y,columns=['y'])

In [20]:
data_final_vars=dt.columns.values.tolist( )
y=['y']
X=[i for i in data_final_vars if i not in y]

In [21]:
logreg=LogisticRegression( )

In [22]:
from sklearn.feature_selection import RFE
rfe=RFE(logreg,56)
rfe=rfe.fit(os_data_X, os_data_y.values.ravel( ))
print(rfe.support_)
print(rfe.ranking_)

In [32]:
cols=['overhang_length',
'start',
'end',
'full_len',
'overhang_count',
'AT_count_oh',
'TA_count_oh',
'TG_count_oh',
'GT_count_oh',
'AC_count_al',
'AT_count_al',
'AG_count_al',
'CA_count_al',
'CC_count_al',
'CT_count_al',
'CG_count_al',
'TA_count_al',
'TC_count_al',
'TT_count_al',
'GA_count_al',
'GC_count_al',
'perc_len',

```
'AG_perc',
'TA_perc',
'TG_perc',
'GA_perc',
'GC_perc',
'GT_perc',
'overhang_perc']
X=os_data_X[cols]
y=os_data_y['y']
logit_model=sm.Logit(y,X)
result=logit_model.fit( )
print(result.summary2( ))
In [33]:
from sklearn.linear_model import LogisticRegression
from sklearn import metrics
X_train, X_test, y_train, y_test=train_test_split(X, y,
   test_size=0.3, random_state=0)
logreg=LogisticRegression( )
logreg.fit(X_train, y_train)
In [34]:
y_pred=logreg.predict(X_test)
print('Accuracy of logistic regression classifier on test set:
   {:.2f}'.format(logreg.score(X_test y_test)))
In [35]:
import seaborn as sn
from sklearn.metrics import confusion_matrix
confusion_matrix=confusion_matrix(y_test, y_pred)
print(confusion_matrix)
plt.figure(figsize=(10,7))
sn.heatmap(confusion_matrix, annot=True)
In [36]:
from sklearn.metrics import classification_report
print(classification_report(y_test, y_pred))
In [37]:
from sklearn.metrics import roc_auc_score
from sklearn.metrics import roc_curve
logit_roc_auc=roc_auc_score(y_test,    logreg.predict
   (X_test))
fpr, tpr, thresholds=roc_curve(y_test, logreg.predict_
   proba(X_test)[:,1])
plt.figure( )
plt.plot(fpr, tpr, label='Logistic Regression (area=%0.2f'
   % logit_roc_auc)
plt.plot([0, 1], [0, 1],'r--')
plt.xlim([0.0, 1.0])
plt.ylim([0.0, 1.05])
plt.xlabel('False Positive Rate')
plt.ylabel('True Positive Rate')
plt.title('Receiver operating characteristic')
plt.legend(loc="lower right")
plt.savefig('Log_ROC')
plt.show( )
```

Example 13: Examples of Embodiments

The examples set forth below illustrate certain embodiments and do not limit the technology.

A1. A method for producing a nucleic acid library, comprising:
(a) combining a nucleic acid composition comprising target nucleic acids and a plurality of oligonucleotide species, wherein:
   (i) each oligonucleotide species in the plurality of oligonucleotide species comprises one strand capable of forming a hairpin structure having a single-stranded loop, wherein the loop comprises one or more ribonucleic acid (RNA) nucleotides,
   (ii) some or all of the target nucleic acids comprise an overhang,
   (iii) some or all of the oligonucleotides in the plurality of oligonucleotide species comprise an overhang capable of hybridizing to a target nucleic acid overhang, wherein each oligonucleotide species has a unique overhang sequence and length,
   (iv) each oligonucleotide in the plurality of oligonucleotide species comprises an oligonucleotide overhang identification sequence specific to one or more features of the oligonucleotide overhang, and
   (v) the nucleic acid composition and the plurality of oligonucleotide species is combined under conditions in which oligonucleotide overhangs hybridize to target nucleic acid overhangs having a corresponding length, thereby forming hybridization products; and
(b) contacting the hybridization products under cleavage conditions with one or more cleavage agents capable of cleaving the hybridization products within the hairpin loop at the RNA nucleotide(s), thereby forming cleaved hybridization products.

A2. The method of embodiment A1, wherein each oligonucleotide in the plurality of oligonucleotide species consists of one strand capable of forming a hairpin structure having a single-stranded loop.

A3. The method of embodiment A1 or A2, wherein the loop comprises two RNA nucleotides.

A4. The method of embodiment A1 or A2, wherein the loop comprises three RNA nucleotides.

A5. The method of embodiment A1 or A2, wherein the loop comprises four RNA nucleotides.

A6. The method of any one of embodiments A1 to A5, wherein the loop comprises one or more ribonucleic acid (RNA) nucleotides chosen from adenine (A), cytosine (C), and guanine (G).

A7. The method of any one of embodiments A1 to A6, wherein the RNA nucleotides comprise guanine (G).

A8. The method of any one of embodiments A1 to A6, wherein the RNA nucleotides consist of guanine (G).

A9. The method of any one of embodiments A1 to A6, wherein the RNA nucleotides comprise cytosine (C).

A10. The method of any one of embodiments A1 to A6, wherein the RNA nucleotides consist of cytosine (C).

A11. The method of any one of embodiments A1 to A6, wherein the RNA nucleotides comprise adenine (A).

A12. The method of any one of embodiments A1 to A6, wherein the RNA nucleotides consist of adenine (A).

A13. The method of any one of embodiments A1 to A6, wherein the RNA nucleotides consist of adenine (A), cytosine (C), and guanine (G).

A14. The method of any one of embodiments A1 to A6, wherein the RNA nucleotides consist of adenine (A) and cytosine (C).

A15. The method of any one of embodiments A1 to A6, wherein the RNA nucleotides consist of adenine (A) and guanine (G).

A16. The method of any one of embodiments A1 to A6, wherein the RNA nucleotides consist of cytosine (C) and guanine (G).

A17. The method of any one of embodiments A1 to A16, wherein the plurality of oligonucleotide species comprises oligonucleotides having a 5' overhang and oligonucleotides having a 3' overhang.

A18. The method of any one of embodiments A1 to A17, wherein the plurality of oligonucleotide species comprises oligonucleotides having a 5' overhang, oligonucleotides having a 3' overhang, and oligonucleotides having no overhang.

A19. The method of any one of embodiments A1 to A18, wherein the oligonucleotides that comprise an overhang comprise a single-stranded loop, a duplex portion, and a single-stranded overhang.

A20. The method of any one of embodiments A1 to A19, wherein the oligonucleotide overhang comprises 1, 2, 3, 4, 5, 6, 7, 8, 9, 10, 11, 12, 13, 14, 15, 16, 17, 18, 19 or 20 nucleotides.

A21. The method of any one of embodiments A1 to A20, wherein the oligonucleotides in the plurality of oligonucleotide species comprise oligonucleotide overhangs having different sequences for a particular overhang length.

A22. The method of embodiment A21, wherein the oligonucleotides in the plurality of oligonucleotide species comprise all possible overhang sequence combinations for a particular overhang length.

A23. The method of embodiment A22, wherein the oligonucleotides in the plurality of oligonucleotide species comprise all possible overhang sequence combinations for each overhang length.

A24. The method of embodiment A21, A22 or A23, wherein the oligonucleotide overhang sequences are random.

A25. The method of any one of embodiments A1 to A18, wherein the oligonucleotides that comprise no overhang comprise a single-stranded loop and a duplex portion.

A26. The method of any one of embodiments A1 to A25, wherein an end of an oligonucleotide is capable of being covalently linked to an end of a target nucleic acid to which the oligonucleotide is hybridized in the hybridization products.

A27. The method of embodiment A26, wherein the 3' end of an oligonucleotide strand is capable of being covalently linked to the 5' end of a strand in the target nucleic acid to which the oligonucleotide is hybridized in a hybridization product.

A28. The method of any one of embodiments A1 to A27, wherein the hybridization products comprise a duplex region and at least one single-stranded loop.

A29. The method of any one of embodiments A1 to A28, wherein the hybridization products comprise a duplex region and a single-stranded loop at each end.

A30. The method of embodiment A28 or A29, wherein the one or more cleavage agents are capable of cleaving the hybridization products within the hairpin loop at the RNA nucleotide(s) and are not capable of cleaving the hybridization products within the duplex region.

A31. The method of any one of embodiments A1 to A30, wherein the one or more cleavage agents comprise a ribonuclease (RNAse).

A32. The method of embodiment A31, wherein the RNAse is an endoribonuclease.

A33. The method of embodiment A31 or A32, wherein the RNAse is chosen from one or more of RNAse A, RNAse E, RNAse F, RNAse H, RNAse III, RNAse L, RNAse P, RNAse PhyM, RNAse T1, RNAse T2, RNAse U2, and RNAse V.

A34. The method of any one of embodiments A1 to A33, wherein the oligonucleotide overhang identification sequence is specific to length of the oligonucleotide overhang.

A35. The method of any one of embodiments A1 to A34, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

A36. The method of any one of embodiments A1 to A35, wherein some of the target nucleic acids comprise no overhang.

A37. The method of any one of embodiments A1 to A36, wherein an oligonucleotide species comprises no overhang and comprises an oligonucleotide overhang identification sequence specific to having no overhang.

A38. The method of any one of embodiments A1 to A37, wherein the target nucleic acids comprising an overhang comprise a duplex region and a single-stranded overhang.

A39. The method of any one of embodiments A1 to A38, wherein each target nucleic acid comprising an overhang comprises an overhang at one end or an overhang at both ends.

A40. The method of any one of embodiments A1 to A39, wherein an end, or both ends, of each target nucleic acid comprising an overhang independently comprises a 5' overhang or a 3' overhang.

A41. The method of any one of embodiments A1 to A40, wherein the target nucleic acids comprise deoxyribonucleic acid (DNA) fragments.

A42. The method of embodiment A41, wherein the DNA fragments are obtained from cells.

A43. The method of embodiment A41 or A42, wherein the DNA fragments comprise genomic DNA fragments.

A44. The method of any one of embodiments A1 to A40, wherein the target nucleic acids comprise ribonucleic acid (RNA) fragments.

A45. The method of embodiment A44, wherein the RNA fragments are obtained from cells.

A46. The method of any one of embodiments A1 to A45, wherein the target nucleic acids comprise cell-free nucleic acid fragments.

A47. The method of any one of embodiments A1 to A46, wherein the target nucleic acids comprise circulating cell-free nucleic acid fragments.

A48. The method of any one of embodiments A1 to A47, wherein the overhangs in target nucleic acids are native overhangs.

A49. The method of any one of embodiments A1 to A48, wherein the overhangs in target nucleic acids are unmodified overhangs.

A50. The method of any one of embodiments A1 to A49, wherein the target nucleic acids are not modified in length prior to combining with the plurality of oligonucleotide species.

A51. The method of any one of embodiments A1 to A50, comprising preparing the nucleic acid composition prior to (a), by a process consisting essentially of isolating nucleic acid from a sample, thereby generating the nucleic acid composition.

A52. The method of any one of embodiments A1 to A51, comprising exposing the hybridization products to conditions under which an end of the target nucleic acid is joined to an end of the oligonucleotide to which it is hybridized.

A53. The method of embodiment A52, comprising contacting the hybridization products with an agent comprising a ligase activity under conditions in which an end of a target nucleic acid is covalently linked to an end of the oligonucleotide to which the target nucleic acid is hybridized.

A54. The method of any one of embodiments A1 to A53, comprising prior to (a), contacting the target nucleic acid composition with an agent comprising a phosphatase activity under conditions in which target nucleic acids are dephosphorylated, thereby generating a dephosphorylated target nucleic acid composition.

A55. The method of embodiment A54, comprising prior to (a), contacting the dephosphorylated target nucleic acid composition with an agent comprising a phosphoryl transfer activity under conditions in which a 5' phosphate is added to a 5' end of target nucleic acids.

A56. The method of any one of embodiments A1 to A55, comprising prior to (a), contacting the plurality of oligonucleotide species with an agent comprising a phosphatase activity under conditions in which the oligonucleotides are dephosphorylated, thereby generating a plurality of dephosphorylated oligonucleotide species.

A57. The method of embodiment A56, comprising prior to (a), contacting the dephosphorylated oligonucleotide species with an agent comprising a phosphoryl transfer activity under conditions in which a 5' phosphate is added to a 5' end of oligonucleotide species.

A58. The method of any one of embodiments A1 to A57, wherein the target nucleic acids are obtained from a sample from a subject.

A59. The method of embodiment A58, wherein the subject is a human.

A60. The method of any one of embodiments A1 to A59, comprising prior to (a), separating the target nucleic acids according to fragment length.

A61. The method of embodiment A60, wherein target nucleic acids having fragment lengths of less than about 500 bp are combined with the plurality of oligonucleotide species.

A62. The method of embodiment A60, wherein target nucleic acids having fragment lengths of about 500 bp or more are combined with the plurality of oligonucleotide species.

A63. The method of any one of embodiments A1 to A62, wherein the oligonucleotide overhang comprises DNA nucleotides.

A64. The method of any one of embodiments A1 to A62, wherein the oligonucleotide overhang consists of DNA nucleotides.

A65. The method of any one of embodiments A1 to A62, wherein the oligonucleotide overhang comprises RNA nucleotides.

A66. The method of any one of embodiments A1 to A62, wherein the oligonucleotide overhang consists of RNA nucleotides.

A67. The method of embodiment A65 or A66, comprising contacting the hybridization products with an agent comprising a RNA ligase activity under conditions in which an end of a target nucleic acid is covalently linked to an end of the oligonucleotide to which the target nucleic acid is hybridized.

A68. The method of any one of embodiments A65 to A67, comprising contacting the hybridization products with an agent comprising an RNAse activity under conditions in which double-stranded RNA duplexes are digested.

B1. A composition comprising a plurality of oligonucleotide species, wherein:
  (a) each oligonucleotide in the plurality of oligonucleotide species comprises one strand capable of forming a hairpin structure having a single-stranded loop, wherein the loop comprises one or more ribonucleic acid (RNA) nucleotides;
  (b) some or all of the oligonucleotides in the plurality of oligonucleotide species comprise an overhang capable of hybridizing to an overhang in a target nucleic acid, wherein each oligonucleotide species has a unique overhang sequence and length; and
  (c) each oligonucleotide in the plurality of oligonucleotide species comprises an oligonucleotide overhang identification sequence specific to one or more features of the oligonucleotide overhang.

B2. The composition of embodiment B1, wherein each oligonucleotide in the plurality of oligonucleotide species consists of one strand capable of forming a hairpin structure having a single-stranded loop.

B3. The composition of embodiment B1 or B2, wherein the loop comprises two RNA nucleotides.

B4. The composition of embodiment B1 or B2, wherein the loop comprises three RNA nucleotides.

B5. The composition of embodiment B1 or B2, wherein the loop comprises four RNA nucleotides.

B6. The composition of any one of embodiments B1 to B5, wherein the loop comprises one or more ribonucleic acid (RNA) nucleotides chosen from adenine (A), cytosine (C), and guanine (G).

B7. The composition of any one of embodiments B1 to B6, wherein the RNA nucleotides comprise guanine (G).

B8. The composition of any one of embodiments B1 to B6, wherein the RNA nucleotides consist of guanine (G).

B9. The composition of any one of embodiments B1 to B6, wherein the RNA nucleotides comprise cytosine (C).

B10. The composition of any one of embodiments B1 to B6, wherein the RNA nucleotides consist of cytosine (C).

B11. The composition of any one of embodiments B1 to B6, wherein the RNA nucleotides comprise adenine (A).

B12. The composition of any one of embodiments B1 to B6, wherein the RNA nucleotides consist of adenine (A).

B13. The composition of any one of embodiments B1 to B6, wherein the RNA nucleotides consist of adenine (A), cytosine (C), and guanine (G).

B14. The composition of any one of embodiments B1 to B6, wherein the RNA nucleotides consist of adenine (A) and cytosine (C).

B15. The composition of any one of embodiments B1 to B6, wherein the RNA nucleotides consist of adenine (A) and guanine (G).

B16. The composition of any one of embodiments B1 to B6, wherein the RNA nucleotides consist of cytosine (C) and guanine (G).

B17. The composition of any one of embodiments B1 to B16, wherein the plurality of oligonucleotide species comprises oligonucleotides having a 5' overhang and oligonucleotides having a 3' overhang.

B18. The composition of any one of embodiments B1 to B17, wherein the plurality of oligonucleotide species comprises oligonucleotides having a 5' overhang, oligonucleotides having a 3' overhang, and oligonucleotides having no overhang.

B19. The composition of any one of embodiments B1 to B18, wherein the oligonucleotides that comprise an overhang comprise a single-stranded loop, a duplex portion, and a single-stranded overhang.

B20. The composition of any one of embodiments B1 to B19, wherein the oligonucleotide overhang comprises 1, 2, 3, 4, 5, 6, 7, 8, 9, 10, 11, 12, 13, 14, 15, 16, 17, 18, 19 or 20 nucleotides.

B21. The composition of any one of embodiments B1 to B20, wherein the oligonucleotides in the plurality of oligonucleotide species comprise oligonucleotide overhangs having different sequences for a particular overhang length.

B22. The composition of embodiment B21, wherein the oligonucleotides in the plurality of oligonucleotide species comprise all possible overhang sequence combinations for a particular overhang length.

B23. The composition of embodiment B22, wherein the oligonucleotides in the plurality of oligonucleotide species comprise all possible overhang sequence combinations for each overhang length.

B24. The composition of embodiment B21, B22 or B23, wherein the oligonucleotide overhang sequences are random.

B25. The composition of any one of embodiments B1 to B18, wherein the oligonucleotides that comprise no overhang comprise a single-stranded loop and a duplex portion.

B26. The composition of any one of embodiments B1 to B25, wherein the oligonucleotide overhang identification sequence is specific to length of the oligonucleotide overhang.

B27. The composition of any one of embodiments B1 to B26, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

B28. The composition of any one of embodiments B1 to B27, wherein an oligonucleotide species comprises no overhang and comprises an oligonucleotide overhang identification sequence specific to having no overhang.

B29. The composition of any one of embodiments B1 to B28, wherein the oligonucleotide overhang comprises DNA nucleotides.

B30. The composition of any one of embodiments B1 to B28, wherein the oligonucleotide overhang consists of DNA nucleotides.

B31. The composition of any one of embodiments B1 to B28, wherein the oligonucleotide overhang comprises RNA nucleotides.

B32. The composition of any one of embodiments B1 to B28, wherein the oligonucleotide overhang consists of RNA nucleotides.

C1. A method for modifying nucleic acid ends, comprising:
 (a) combining a nucleic acid composition comprising target nucleic acids and a plurality of oligonucleotide species, wherein:
  (i) each oligonucleotide in the plurality of oligonucleotide species comprises one or more cleavage sites capable of being cleaved under cleavage conditions,
  (ii) some or all of the target nucleic acids comprise an overhang,
  (iii) some or all of the oligonucleotides in the plurality of oligonucleotide species comprise two strands and a first overhang and a second overhang, wherein each overhang is capable of hybridizing to a target nucleic acid overhang, wherein each oligonucleotide species has a unique overhang sequence and length,
  (iv) each oligonucleotide in the plurality of oligonucleotide species comprises at least two oligonucleotide overhang identification sequences specific to one or more features of the first and second oligonucleotide overhangs, and
  (v) the nucleic acid composition and the plurality of oligonucleotide species is combined under conditions in which oligonucleotide overhangs hybridize to target nucleic acid overhangs having a corresponding length, thereby forming hybridization products;
 (b) contacting the hybridization products under cleavage conditions with one or more cleavage agents capable of cleaving the hybridization products at the one or more cleavage sites, thereby forming cleaved hybridization products; and
 (c) contacting the cleaved hybridization products with a strand-displacing polymerase, thereby forming blunt-ended nucleic acid fragments.

C2. The method of embodiment C1, wherein (c) comprises contacting the cleaved hybridization products with a strand-displacing polymerase and modified nucleotides, thereby forming blunt-ended nucleic acid fragments comprising one or more modified nucleotides.

C3. The method of embodiment C2, wherein the one or more modified nucleotides comprise a nucleotide conjugated to a member of a binding pair.

C4. The method of embodiment C2, wherein the one or more modified nucleotides comprise a nucleotide conjugated to biotin.

C5. The method of any one of embodiments C1 to C4, wherein the one or more cleavage sites comprise nucleotides chosen from uracil and deoxyuridine.

C6. The method of any one of embodiments C1 to C5, wherein the one or more cleavage agents comprise an endonuclease.

C7. The method of any one of embodiments C1 to C5, wherein the one or more cleavage agents comprise a DNA glycosylase.

C8. The method of any one of embodiments C1 to C7, wherein the one or more cleavage agents comprise an endonuclease and a DNA glycosylase.

C9. The method of embodiment C8, wherein the one or more cleavage agents comprise a mixture of uracil DNA glycosylase (UDG) and endonuclease VIII.

C10. The method of any one of embodiments C1 to C4, wherein the one or more cleavage sites comprise a restriction enzyme recognition site.

C11. The method of embodiment C10, wherein the one or more cleavage agents comprise a restriction enzyme.

C12. The method of embodiment C10, wherein the one or more cleavage agents comprise a rare-cutter restriction enzyme.

C13. Reserved.

C14. Reserved.

C15. The method of any one of embodiments C1 to C4, wherein the one or more cleavage sites comprise one or more RNA nucleotides.

C16. The method of any one of embodiments C1 to C4, wherein the one or more cleavage sites comprise a single stranded portion comprising one or more RNA nucleotides.

C17. The method of embodiment C15 or C16, wherein the one or more cleavage agents comprise a ribonuclease (RNAse).

C18. The method of embodiment C17, wherein the RNAse is an endoribonuclease.

C19. The method of embodiment C17 or C18, wherein the RNAse is chosen from one or more of RNAse A, RNAse E, RNAse F, RNAse H, RNAse III, RNAse L, RNAse P, RNAse PhyM, RNAse T1, RNAse T2, RNAse U2, and RNAse V.

C20. The method of any one of embodiments C1 to C4, wherein the one or more cleavage sites comprise a photocleavable spacer.

C21. The method of embodiment C20, wherein the one or more cleavage agents comprise ultraviolet (UV) light.

C22. The method of any one of embodiments C1 to C21, wherein the plurality of oligonucleotide species comprises oligonucleotides having a 5' overhang and oligonucleotides having a 3' overhang.

C23. The method of any one of embodiments C1 to C22, wherein the plurality of oligonucleotide species comprises oligonucleotides having a 5' overhang, oligonucleotides having a 3' overhang, and oligonucleotides having no overhang.

C24. The method of any one of embodiments C1 to C23, wherein the oligonucleotides that comprise an overhang comprise a duplex portion, and a single-stranded overhang on each end.

C25. The method of any one of embodiments C1 to C24, wherein the oligonucleotides that comprise an overhang comprise a duplex portion, and a single-stranded overhang on each end, wherein the single-stranded overhang on the first end is identical in length and identical in sequence to the overhang on the second end.

C26. The method of any one of embodiments C1 to C25, wherein the oligonucleotide overhang comprises 1, 2, 3, 4, 5, 6, 7, 8, 9, 10, 11, 12, 13, 14, 15, 16, 17, 18, 19 or 20 nucleotides.

C27. The method of any one of embodiments C1 to C26, wherein the oligonucleotides in the plurality of oligonucleotide species comprise oligonucleotide overhangs having different sequences for a particular overhang length.

C28. The method of embodiment C27, wherein the oligonucleotides in the plurality of oligonucleotide species comprise all possible overhang sequence combinations for a particular overhang length.

C29. The method of embodiment C28, wherein the oligonucleotides in the plurality of oligonucleotide species comprise all possible overhang sequence combinations for each overhang length.

C30. The method of embodiment C27, C28 or C29, wherein the oligonucleotide overhang sequences are random.

C31. The method of any one of embodiments C1 to C30, wherein the oligonucleotides that comprise no overhang comprise a dual blunt-ended duplex portion.

C32. The method of any one of embodiments C1 to C31, wherein an end of an oligonucleotide is capable of being covalently linked to an end of a target nucleic acid to which the oligonucleotide is hybridized in the hybridization products.

C33. The method of embodiment C32, wherein the 3' end of an oligonucleotide strand is capable of being covalently linked to the 5' end of a strand in the target nucleic acid to which the oligonucleotide is hybridized in a hybridization product.

C34. The method of any one of embodiments C1 to C33, wherein the oligonucleotide overhang identification sequence is specific to length of the oligonucleotide overhang.

C35. The method of any one of embodiments C1 to C34, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

C36. The method of any one of embodiments C1 to C35, wherein some of the target nucleic acids comprise no overhang.

C37. The method of any one of embodiments C1 to C36, wherein an oligonucleotide species comprises no overhang and comprises an oligonucleotide overhang identification sequence specific to having no overhang.

C38. The method of any one of embodiments C1 to C37, wherein the target nucleic acids comprising an overhang comprise a duplex region and a single-stranded overhang.

C39. The method of any one of embodiments C1 to C38, wherein each target nucleic acid comprising an overhang comprises an overhang at one end or an overhang at both ends.

C40. The method of any one of embodiments C1 to C39, wherein an end, or both ends, of each target nucleic acid comprising an overhang independently comprises a 5' overhang or a 3' overhang.

C41. The method of any one of embodiments C1 to C40, wherein the target nucleic acids comprise deoxyribonucleic acid (DNA) fragments.

C42. The method of embodiment C41, wherein the DNA fragments are obtained from cells.

C43. The method of embodiment C41 or C42, wherein the DNA fragments comprise genomic DNA fragments.

C44. The method of any one of embodiments C1 to C40, wherein the target nucleic acids comprise ribonucleic acid (RNA) fragments.

C45. The method of embodiment C44, wherein the RNA fragments are obtained from cells.

C46. The method of any one of embodiments C1 to C45, wherein the target nucleic acids comprise cell-free nucleic acid fragments.

C47. The method of any one of embodiments C1 to C46, wherein the target nucleic acids comprise circulating cell-free nucleic acid fragments.

C48. The method of any one of embodiments C1 to C47, wherein the overhangs in target nucleic acids are native overhangs.

C49. The method of any one of embodiments C1 to C48, wherein the overhangs in target nucleic acids are unmodified overhangs.

C50. The method of any one of embodiments C1 to C49, wherein the target nucleic acids are not modified in length prior to combining with the plurality of oligonucleotide species.

C51. The method of any one of embodiments C1 to C50, comprising preparing the nucleic acid composition prior to (a), by a process consisting essentially of isolating nucleic acid from a sample, thereby generating the nucleic acid composition.

C52. The method of any one of embodiments C1 to C51, comprising exposing the hybridization products to conditions under which an end of the target nucleic acid is joined to an end of the oligonucleotide to which it is hybridized.

C53. The method of embodiment C52, comprising contacting the hybridization products with an agent comprising a ligase activity under conditions in which an end of a target nucleic acid is covalently linked to an end of the oligonucleotide to which the target nucleic acid is hybridized.

C54. The method of any one of embodiments C1 to C53, comprising prior to (a), contacting the target nucleic acid composition with an agent comprising a phosphatase activity under conditions in which target nucleic acids are dephosphorylated, thereby generating a dephosphorylated target nucleic acid composition.

C55. The method of embodiment C54, comprising prior to (a), contacting the dephosphorylated target nucleic acid composition with an agent comprising a phosphoryl transfer activity under conditions in which a 5' phosphate is added to a 5' end of target nucleic acids.

C56. The method of any one of embodiments C1 to C55, comprising prior to (a), contacting the plurality of oligonucleotide species with an agent comprising a phosphatase activity under conditions in which the oligonucleotides are dephosphorylated, thereby generating a plurality of dephosphorylated oligonucleotide species.

C57. The method of embodiment C56, comprising prior to (a), contacting the dephosphorylated oligonucleotide species with an agent comprising a phosphoryl transfer activity under conditions in which a 5' phosphate is added to a 5' end of oligonucleotide species.

C58. The method of any one of embodiments C1 to C57, wherein the target nucleic acids are obtained from a sample from a subject.

C59. The method of embodiment C58, wherein the subject is a human.

C60. The method of any one of embodiments C1 to C59, comprising prior to (a), separating the target nucleic acids according to fragment length.

C61. The method of embodiment C60, wherein target nucleic acids having fragment lengths of less than about 500 bp are combined with the plurality of oligonucleotide species.

C62. The method of embodiment C60, wherein target nucleic acids having fragment lengths of about 500 bp or more are combined with the plurality of oligonucleotide species.

C63. The method of any one of embodiments C1 to C62, wherein the oligonucleotide overhang comprises DNA nucleotides.

C64. The method of any one of embodiments C1 to C62, wherein the oligonucleotide overhang consists of DNA nucleotides.

C65. The method of any one of embodiments C1 to C62, wherein the oligonucleotide overhang comprises RNA nucleotides.

C66. The method of any one of embodiments C1 to C62, wherein the oligonucleotide overhang consists of RNA nucleotides.

C67. The method of embodiment C65 or C66, comprising contacting the hybridization products with an agent comprising a RNA ligase activity under conditions in which an end of a target nucleic acid is covalently linked to an end of the oligonucleotide to which the target nucleic acid is hybridized.

C68. The method of any one of embodiments C65 to C67, comprising contacting the hybridization products with an agent comprising an RNAse activity under conditions in which double-stranded RNA duplexes are digested.

D1. A composition comprising a plurality of oligonucleotide species, wherein:
  (a) each oligonucleotide in the plurality of oligonucleotide species comprises one or more cleavage sites capable of being cleaved under cleavage conditions;
  (b) some or all of the oligonucleotides in the plurality of oligonucleotide species comprise two strands and a first overhang and a second overhang, wherein each overhang is capable of hybridizing to a target nucleic acid overhang, wherein each oligonucleotide species has a unique overhang sequence and length; and
  (c) each oligonucleotide in the plurality of oligonucleotide species comprises at least two oligonucleotide overhang identification sequences specific to one or more features of the first and second oligonucleotide overhangs.

D2. The composition of embodiment D1, wherein the one or more cleavage sites comprise nucleotides chosen from uracil and deoxyuridine.

D3. The composition of embodiment D1, wherein the one or more cleavage sites comprise a restriction enzyme recognition site.

D4. The composition of embodiment D1, wherein the one or more cleavage sites comprise one or more RNA nucleotides.

D5. The composition of embodiment D4, wherein the one or more cleavage sites comprise a single stranded portion comprising one or more RNA nucleotides.

D6. The composition of embodiment D1, wherein the one or more cleavage sites comprise a photo-cleavable spacer.

D7. The composition of any one of embodiments D1 to D6, wherein the plurality of oligonucleotide species comprises oligonucleotides having a 5' overhang and oligonucleotides having a 3' overhang.

D8. The composition of any one of embodiments D1 to D7, wherein the plurality of oligonucleotide species comprises oligonucleotides having a 5' overhang, oligonucleotides having a 3' overhang, and oligonucleotides having no overhang.

D9. The composition of any one of embodiments D1 to D8, wherein the oligonucleotides that comprise an overhang comprise a duplex portion, and a single-stranded overhang on each end.

D10. The composition of any one of embodiments D1 to D9, wherein the oligonucleotides that comprise an overhang comprise a duplex portion, and a single-stranded overhang on each end, wherein the single-stranded overhang on the first end is identical in length and identical in sequence to the overhang on the second end.

D11. The composition of any one of embodiments D1 to D10, wherein the oligonucleotide overhang comprises 1, 2, 3, 4, 5, 6, 7, 8, 9, 10, 11, 12, 13, 14, 15, 16, 17, 18, 19 or 20 nucleotides.

D12. The composition of any one of embodiments D1 to D11, wherein the oligonucleotides in the plurality of oligonucleotide species comprise oligonucleotide overhangs having different sequences for a particular overhang length.

D13. The composition of embodiment D12, wherein the oligonucleotides in the plurality of oligonucleotide species comprise all possible overhang sequence combinations for a particular overhang length.

D14. The composition of embodiment D13, wherein the oligonucleotides in the plurality of oligonucleotide species comprise all possible overhang sequence combinations for each overhang length.

D15. The composition of embodiment D12, D13 or D14, wherein the oligonucleotide overhang sequences are random.

D16. The composition of any one of embodiments D1 to D15, wherein the oligonucleotides that comprise no overhang comprise a dual blunt-ended duplex portion.

D17. The composition of any one of embodiments D1 to D16, wherein the oligonucleotide overhang identification sequence is specific to length of the oligonucleotide overhang.

D18. The composition of any one of embodiments D1 to D17, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

D19. The composition of any one of embodiments D1 to D18, wherein an oligonucleotide species comprises no overhang and comprises an oligonucleotide overhang identification sequence specific to having no overhang.

D20. The composition of any one of embodiments D1 to D19, wherein the oligonucleotide overhang comprises DNA nucleotides.

D21. The composition of any one of embodiments D1 to D19, wherein the oligonucleotide overhang consists of DNA nucleotides.

D22. The composition of any one of embodiments D1 to D19, wherein the oligonucleotide overhang comprises RNA nucleotides.

D23. The composition of any one of embodiments D1 to D19, wherein the oligonucleotide overhang consists of RNA nucleotides.

E1. A method for modifying nucleic acid ends, comprising:
  (a) combining a nucleic acid composition comprising target nucleic acids and a plurality of oligonucleotide species, wherein:
    (i) some or all of the oligonucleotides in the plurality of oligonucleotide species comprise two strands and an overhang at a first end and one or more modified nucleotides at a second end, wherein the overhang is capable of hybridizing to a target nucleic acid overhang, wherein each oligonucleotide species has a unique overhang sequence and length,
    (ii) some or all of the target nucleic acids comprise an overhang,
    (iii) each oligonucleotide in the plurality of oligonucleotide species comprises an oligonucleotide overhang identification sequence specific to one or more features of the oligonucleotide overhang, and
    (iv) the nucleic acid composition and the plurality of oligonucleotide species is combined under conditions in which oligonucleotide overhangs hybridize to target nucleic acid overhangs having a corresponding length, thereby forming hybridization products; and
  (b) contacting the hybridization products with a strand-displacing polymerase, thereby forming blunt-ended nucleic acid fragments.

E2. The method of embodiment E1, wherein the oligonucleotides having one or more modified nucleotides at a second end comprise an unpaired modified nucleotide at the second end.

E3. The method of embodiment E1 or E2, wherein the oligonucleotides having one or modified nucleotides at a second end comprise the one or more modified nucleotides at the end of the strand having a 3' terminus.

E4. The method of embodiment E1 or E2, wherein the oligonucleotides having one or modified nucleotides at a second end comprise the one or more modified nucleotides at the end of the strand having a 5' terminus.

E5. The method of any one of embodiments E1 to E4, wherein the one or more modified nucleotides are capable of blocking hybridization to a nucleotide in a target nucleic acid.

E6. The method of any one of embodiments E1 to E5, wherein the one or more modified nucleotides are capable of blocking ligation to a nucleotide in a target nucleic acid.

E7. The method of any one of embodiments E1 to E6, wherein the one or more modified nucleotides comprise a modified nucleotide incapable of binding to a natural nucleotide.

E8. The method of any one of embodiments E1 to E7, wherein the one or more modified nucleotides comprise one or more modified nucleotides chosen from an isodeoxy-base, a dideoxy-base, an inverted dideoxy-base, a spacer, and an amino linker.

E9. The method of any one of embodiments E1 to E8, wherein the one or more modified nucleotides comprise an isodeoxy-base.

E10. The method of embodiment E9, wherein the one or more modified nucleotides comprise isodeoxy-guanine (iso-dG).

E11. The method of embodiment E10, wherein the one or more modified nucleotides comprise isodeoxy-cytosine (iso-dC).

E12. The method of any one of embodiments E1 to E8, wherein the one or more modified nucleotides comprise a dideoxy-base.

E13. The method of embodiment E12, wherein the one or more modified nucleotides comprise dideoxy-cytosine.

E14. The method of any one of embodiments E1 to E8, wherein the one or more modified nucleotides comprise an inverted dideoxy-base.

E15. The method of embodiment E14, wherein the one or more modified nucleotides comprise inverted dideoxy-thymine.

E16. The method of any one of embodiments E1 to E8, wherein the one or more modified nucleotides comprise a spacer.

E17. The method of embodiment E16, wherein the one or more modified nucleotides comprise a C3 spacer.

E18. The method of any one of embodiments E1 to E17, wherein the blunt-ended nucleic acid fragments formed in (b) comprise no modified nucleotides.

E19. The method of any one of embodiments E1 to E18, wherein the plurality of oligonucleotide species comprises oligonucleotides having a 5' overhang and oligonucleotides having a 3' overhang.

E20. The method of any one of embodiments E1 to E19, wherein the plurality of oligonucleotide species comprises oligonucleotides having a 5' overhang, oligonucleotides having a 3' overhang, and oligonucleotides having no overhang.

E21. The method of any one of embodiments E1 to E20, wherein the oligonucleotides that comprise an overhang comprise a duplex portion, an overhang at the first end and at least one unpaired modified nucleotide at the second end.

E22. The method of any one of embodiments E1 to E21, wherein the oligonucleotide overhang comprises 1, 2, 3, 4, 5, 6, 7, 8, 9, 10, 11, 12, 13, 14, 15, 16, 17, 18, 19 or 20 nucleotides.

E23. The method of any one of embodiments E1 to E22, wherein the oligonucleotides in the plurality of oligonucleotide species comprise oligonucleotide overhangs having different sequences for a particular overhang length.

E24. The method of embodiment E23, wherein the oligonucleotides in the plurality of oligonucleotide species comprise all possible overhang sequence combinations for a particular overhang length.

E25. The method of embodiment E24, wherein the oligonucleotides in the plurality of oligonucleotide species comprise all possible overhang sequence combinations for each overhang length.

E26. The method of embodiment E23, E24 or E25, wherein the oligonucleotide overhang sequences are random.

E27. The method of any one of embodiments E1 to E26, wherein the oligonucleotides that comprise no overhang comprise a duplex portion having a blunt end at a first end and at least one unpaired modified nucleotide at a second end.

E28. The method of any one of embodiments E1 to E27, wherein an end of an oligonucleotide is capable of being covalently linked to an end of a target nucleic acid to which the oligonucleotide is hybridized in the hybridization products.

E29. The method of embodiment E28, wherein the 3' end of an oligonucleotide strand is capable of being covalently linked to the 5' end of a strand in the target nucleic acid to which the oligonucleotide is hybridized in a hybridization product.

E30. The method of any one of embodiments E1 to E29, wherein the oligonucleotide overhang identification sequence is specific to length of the oligonucleotide overhang.

E31. The method of any one of embodiments E1 to E30, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

E32. The method of any one of embodiments E1 to E31, wherein some of the target nucleic acids comprise no overhang.

E33. The method of any one of embodiments E1 to E32, wherein an oligonucleotide species comprises no overhang and comprises an oligonucleotide overhang identification sequence specific to having no overhang.

E34. The method of any one of embodiments E1 to E33, wherein the target nucleic acids comprising an overhang comprise a duplex region and a single-stranded overhang.

E35. The method of any one of embodiments E1 to E34, wherein each target nucleic acid comprising an overhang comprises an overhang at one end or an overhang at both ends.

E36. The method of any one of embodiments E1 to E35, wherein an end, or both ends, of each target nucleic acid comprising an overhang independently comprises a 5' overhang or a 3' overhang.

E37. The method of any one of embodiments E1 to E36, wherein the target nucleic acids comprise deoxyribonucleic acid (DNA) fragments.

E38. The method of embodiment E37, wherein the DNA fragments are obtained from cells.

E39. The method of embodiment E37 or E38, wherein the DNA fragments comprise genomic DNA fragments.

E40. The method of any one of embodiments E1 to E36, wherein the target nucleic acids comprise ribonucleic acid (RNA) fragments.

E41. The method of embodiment E40, wherein the RNA fragments are obtained from cells.

E42. The method of any one of embodiments E1 to E41, wherein the target nucleic acids comprise cell-free nucleic acid fragments.

E43. The method of any one of embodiments E1 to E42, wherein the target nucleic acids comprise circulating cell-free nucleic acid fragments.

E44. The method of any one of embodiments E1 to E43, wherein the overhangs in target nucleic acids are native overhangs.

E45. The method of any one of embodiments E1 to E44, wherein the overhangs in target nucleic acids are unmodified overhangs.

E46. The method of any one of embodiments E1 to E45, wherein the target nucleic acids are not modified in length prior to combining with the plurality of oligonucleotide species.

E47. The method of any one of embodiments E1 to E46, comprising preparing the nucleic acid composition prior to (a), by a process consisting essentially of isolating nucleic acid from a sample, thereby generating the nucleic acid composition.

E48. The method of any one of embodiments E1 to E47, comprising exposing the hybridization products to conditions under which an end of the target nucleic acid is joined to an end of the oligonucleotide to which it is hybridized.

E49. The method of embodiment E48, comprising contacting the hybridization products with an agent comprising a ligase activity under conditions in which an end of a target nucleic acid is covalently linked to an end of the oligonucleotide to which the target nucleic acid is hybridized.

E50. The method of any one of embodiments E1 to E49, comprising prior to (a), contacting the target nucleic acid composition with an agent comprising a phosphatase activity under conditions in which target nucleic acids are dephosphorylated, thereby generating a dephosphorylated target nucleic acid composition.

E51. The method of embodiment E50, comprising prior to (a), contacting the dephosphorylated target nucleic acid composition with an agent comprising a phosphoryl transfer activity under conditions in which a 5' phosphate is added to a 5' end of target nucleic acids.

E52. The method of any one of embodiments E1 to E51, comprising prior to (a), contacting the plurality of oligonucleotide species with an agent comprising a phosphatase activity under conditions in which the oligonucleotides are dephosphorylated, thereby generating a plurality of dephosphorylated oligonucleotide species.

E53. The method of embodiment E52, comprising prior to (a), contacting the dephosphorylated oligonucleotide species with an agent comprising a phosphoryl transfer activity under conditions in which a 5' phosphate is added to a 5' end of oligonucleotide species.

E54. The method of any one of embodiments E1 to E53, wherein the target nucleic acids are obtained from a sample from a subject.

E55. The method of embodiment E54, wherein the subject is a human.

E56. The method of any one of embodiments E1 to E55, comprising prior to (a), separating the target nucleic acids according to fragment length.

E57. The method of embodiment E56, wherein target nucleic acids having fragment lengths of less than about 500 bp are combined with the plurality of oligonucleotide species.

E58. The method of embodiment E56, wherein target nucleic acids having fragment lengths of about 500 bp or more are combined with the plurality of oligonucleotide species.

E59. The method of any one of embodiments E1 to E58, wherein the oligonucleotide overhang comprises DNA nucleotides.

E60. The method of any one of embodiments E1 to E58, wherein the oligonucleotide overhang consists of DNA nucleotides.

E61. The method of any one of embodiments E1 to E58, wherein the oligonucleotide overhang comprises RNA nucleotides.

E62. The method of any one of embodiments E1 to E58, wherein the oligonucleotide overhang consists of RNA nucleotides.

E63. The method of embodiment E61 or E62, comprising contacting the hybridization products with an agent comprising a RNA ligase activity under conditions in which an end of a target nucleic acid is covalently linked to an end of the oligonucleotide to which the target nucleic acid is hybridized.

E64. The method of any one of embodiments E61 to E63, comprising contacting the hybridization products with an agent comprising an RNAse activity under conditions in which double-stranded RNA duplexes are digested.

F1. A composition comprising a plurality of oligonucleotide species, wherein:
  (a) some or all of the oligonucleotides in the plurality of oligonucleotide species comprise two strands and an overhang at a first end and one or more modified nucleotides at a second end, wherein the overhang is capable of hybridizing to a target nucleic acid overhang, wherein each oligonucleotide species has a unique overhang sequence and length; and
  (b) each oligonucleotide in the plurality of oligonucleotide species comprises an oligonucleotide overhang identification sequence specific to one or more features of the oligonucleotide overhang.

F2. The composition of embodiment F1, wherein the oligonucleotides having one or more modified nucleotides at a second end comprise an unpaired modified nucleotide at the second end.

F3. The composition of embodiment F1 or F2, wherein the oligonucleotides having one or modified nucleotides at a second end comprise the one or more modified nucleotides at the end of the strand having a 3' terminus.

F4. The composition of embodiment F1 or F2, wherein the oligonucleotides having one or more modified nucleotides at a second end comprise the one or more modified nucleotides at the end of the strand having a 5' terminus.

F5. The composition of any one of embodiments F1 to F4, wherein the one or more modified nucleotides are capable of blocking hybridization to a nucleotide in a target nucleic acid.

F6. The composition of any one of embodiments F1 to F5, wherein the one or more modified nucleotides are capable of blocking ligation to a nucleotide in a target nucleic acid.

F7. The composition of any one of embodiments F1 to F6, wherein the one or more modified nucleotides comprise a modified nucleotide incapable of binding to a natural nucleotide.

F8. The composition of any one of embodiments F1 to F7, wherein the one or more modified nucleotides comprise one or more modified nucleotides chosen from an isodeoxy-base, a dideoxy-base, an inverted dideoxy-base, a spacer, and an amino linker.

F9. The composition of any one of embodiments F1 to F8, wherein the one or more modified nucleotides comprise an isodeoxy-base.

F10. The composition of embodiment F9, wherein the one or more modified nucleotides comprise isodeoxy-guanine (iso-dG).

F11. The composition of embodiment F9, wherein the one or more modified nucleotides comprise isodeoxy-cytosine (iso-dC).

F12. The composition of any one of embodiments F1 to F8, wherein the one or more modified nucleotides comprise a dideoxy-base.

F13. The composition of embodiment F12, wherein the one or more modified nucleotides comprise dideoxy-cytosine.

F14. The composition of any one of embodiments F1 to F8, wherein the one or more modified nucleotides comprise an inverted dideoxy-base.

F15. The composition of embodiment F14, wherein the one or more modified nucleotides comprise inverted dideoxy-thymine.

F16. The composition of any one of embodiments F1 to F8, wherein the one or more modified nucleotides comprise a spacer.

F17. The composition of embodiment F16, wherein the one or more modified nucleotides comprise a C3 spacer.

F18. The composition of any one of embodiments F1 to F17, wherein the plurality of oligonucleotide species comprises oligonucleotides having a 5' overhang and oligonucleotides having a 3' overhang.

F19. The composition of any one of embodiments F1 to F18, wherein the plurality of oligonucleotide species comprises oligonucleotides having a 5' overhang, oligonucleotides having a 3' overhang, and oligonucleotides having no overhang.

F20. The composition of any one of embodiments F1 to F19, wherein the oligonucleotides that comprise an overhang comprise a duplex portion, an overhang at the first end and at least one unpaired modified nucleotide at the second end.

F21. The composition of any one of embodiments F1 to F20, wherein the oligonucleotide overhang comprises 1, 2, 3, 4, 5, 6, 7, 8, 9, 10, 11, 12, 13, 14, 15, 16, 17, 18, 19 or 20 nucleotides.

F22. The composition of any one of embodiments F1 to F21, wherein the oligonucleotides in the plurality of oligonucleotide species comprise oligonucleotide overhangs having different sequences for a particular overhang length.

F23. The composition of embodiment F22, wherein the oligonucleotides in the plurality of oligonucleotide species comprise all possible overhang sequence combinations for a particular overhang length.

F24. The composition of embodiment F23, wherein the oligonucleotides in the plurality of oligonucleotide species comprise all possible overhang sequence combinations for each overhang length.

F25. The composition of embodiment F22, F23 or F24, wherein the oligonucleotide overhang sequences are random.

F26. The composition of any one of embodiments F1 to F25, wherein the oligonucleotides that comprise no overhang comprise a duplex portion having a blunt end at a first end and at least one unpaired modified nucleotide at a second end.

F27. The composition of any one of embodiments F1 to F26, wherein the oligonucleotide overhang identification sequence is specific to length of the oligonucleotide overhang.

F28. The composition of any one of embodiments F1 to F27, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

F29. The composition of any one of embodiments F1 to F28, wherein an oligonucleotide species comprises no overhang and comprises an oligonucleotide overhang identification sequence specific to having no overhang.

F30. The composition of any one of embodiments F1 to F29, wherein the oligonucleotide overhang comprises DNA nucleotides.

F31. The composition of any one of embodiments F1 to F29, wherein the oligonucleotide overhang consists of DNA nucleotides.

F32. The composition of any one of embodiments F1 to F29, wherein the oligonucleotide overhang comprises RNA nucleotides.

F33. The composition of any one of embodiments F1 to F29, wherein the oligonucleotide overhang consists of RNA nucleotides.

G1. A method for modifying nucleic acid ends, comprising:
- (a) combining a nucleic acid composition comprising target nucleic acids and a plurality of oligonucleotide species, wherein:
  - (i) the oligonucleotides in the plurality of oligonucleotide species comprise two strands and an overhang at a first end, wherein the first end overhang comprises a palindromic sequence;
  - (ii) some or all of the oligonucleotides in the plurality of oligonucleotide species comprise an overhang at a second end, wherein the second end overhang is capable of hybridizing to a target nucleic acid overhang, wherein each oligonucleotide species has a unique second end overhang sequence and length,
  - (iii) some or all of the target nucleic acids comprise an overhang,
  - (iv) each oligonucleotide in the plurality of oligonucleotide species comprises an oligonucleotide overhang identification sequence specific to one or more features of the second end overhang,
  - (v) each oligonucleotide in the plurality of oligonucleotide species comprises one or more modified nucleotides, and
  - (vi) the nucleic acid composition and the plurality of oligonucleotide species is combined under conditions in which first end overhangs hybridize to other first end overhangs and second end overhangs hybridize to target nucleic acid overhangs having a corresponding length, thereby forming circular hybridization products;
- (b) contacting the hybridization products with an exonuclease, thereby generating exonuclease-treated hybridization products;
- (c) shearing the exonuclease-treated hybridization products, thereby generating sheared exonuclease-treated hybridization products; and
- (d) separating fragments comprising a sequence in the oligonucleotide species from fragments not comprising a sequence in the oligonucleotide species, thereby generating separated, sheared, exonuclease-treated hybridization products.

G2. The method of embodiment G1, wherein the one or more modified nucleotides comprise a nucleotide conjugated to a first member of a binding pair.

G3. The method of embodiment G1 or G2, wherein the one or more modified nucleotides comprise a nucleotide conjugated to biotin.

G4. The method of any one of embodiments G1 to G3, wherein the first end overhang comprises the one or more modified nucleotides.

G5. The method of any one of embodiments G1 to G4, wherein the separating in (d) comprises contacting the sheared exonuclease-treated hybridization products with a second member of a binding pair.

G6. The method of embodiment G5, wherein the second member of a binding pair is streptavidin conjugated to a solid support.

G7. The method of any one of embodiments G1 to G6, wherein the plurality of oligonucleotide species comprises oligonucleotides having a 5' overhang and oligonucleotides having a 3' overhang, and combinations thereof.

G8. The method of any one of embodiments G1 to G7, wherein one or more oligonucleotide species have a 5' overhang at a first end.

G9. The method of any one of embodiments G1 to G8, wherein one or more oligonucleotide species have a 3' overhang at a first end.

G10. The method of any one of embodiments G1 to G9, wherein one or more oligonucleotide species have a 5' overhang at a second end.

G11. The method of any one of embodiments G1 to G10, wherein one or more oligonucleotide species have a 3' overhang at a second end.

G12. The method of any one of embodiments G1 to G11, wherein one or more oligonucleotide species have no overhang at a second end.

G13. The method of any one of embodiments G1 to G12, wherein the plurality of oligonucleotide species comprises oligonucleotides independently having a first end 5' overhang or a first end 3' overhang, and a second end 5' overhang, a second end 3' overhang, or a second end comprising no overhang.

G14. The method of any one of embodiments G1 to G13, wherein the second end overhang comprises 1, 2, 3, 4, 5, 6, 7, 8, 9, 10, 11, 12, 13, 14, 15, 16, 17, 18, 19 or 20 nucleotides.

G15. The method of any one of embodiments G1 to G14, wherein the oligonucleotides in the plurality of oligonucleotide species comprise second end overhangs having different sequences for a particular overhang length.

G16. The method of embodiment G15, wherein the second end overhangs in the plurality of oligonucleotide species comprise all possible overhang sequence combinations for a particular overhang length.

G17. The method of embodiment G16, wherein the second end overhangs in the plurality of oligonucleotide species comprise all possible overhang sequence combinations for each overhang length.

G18. The method of embodiment G15, G16 or G17, wherein the second end overhang sequences are random.

G19. The method of any one of embodiments G1 to G18, wherein an end of an oligonucleotide is capable of being covalently linked to an end of a target nucleic acid to which the oligonucleotide is hybridized in the hybridization products.

G20. The method of any one of embodiments G1 to G19, wherein an end of a first end overhang is capable of being covalently linked to an end of an oligonucleotide species comprising a first end to which the first end overhang is hybridized in the hybridization products.

G21. The method of embodiment G20, wherein the 3' end of an oligonucleotide strand is capable of being covalently linked to the 5' end of a strand in the target nucleic acid to which the oligonucleotide is hybridized in a hybridization product.

G22. The method of any one of embodiments G1 to G21, wherein the oligonucleotide overhang identification sequence is specific to length of the second end overhang.

G23. The method of any one of embodiments G1 to G22, wherein the oligonucleotide overhang identification sequence is specific to length of the second end overhang and is specific to one or more features of the second end overhang chosen from (i) a 5' overhang, (ii) a 3' overhang, (iii) a particular sequence, (iv) a combination of (i) and (iii), or (v) a combination of (ii) and (iii).

G24. The method of any one of embodiments G1 to G23, wherein some of the target nucleic acids comprise no overhang.

G25. The method of any one of embodiments G1 to G24, wherein an oligonucleotide species comprises no second end overhang and comprises an oligonucleotide overhang identification sequence specific to having no overhang.

G26. The method of any one of embodiments G1 to G25, wherein the target nucleic acids comprising an overhang comprise a duplex region and a single-stranded overhang.

G27. The method of any one of embodiments G1 to G26, wherein each target nucleic acid comprising an overhang comprises an overhang at one end or an overhang at both ends.

G28. The method of any one of embodiments G1 to G27, wherein an end, or both ends, of each target nucleic acid comprising an overhang independently comprises a 5' overhang or a 3' overhang.

G29. The method of any one of embodiments G1 to G28, wherein the target nucleic acids comprise deoxyribonucleic acid (DNA) fragments.

G30. The method of embodiment G29, wherein the DNA fragments are obtained from cells.

G31. The method of embodiment G29 or G30, wherein the DNA fragments comprise genomic DNA fragments.

G32. The method of any one of embodiments G1 to G28, wherein the target nucleic acids comprise ribonucleic acid (RNA) fragments.

G33. The method of embodiment G32, wherein the RNA fragments are obtained from cells.

G34. The method of any one of embodiments G1 to G33, wherein the target nucleic acids comprise cell-free nucleic acid fragments.

G35. The method of any one of embodiments G1 to G34, wherein the target nucleic acids comprise circulating cell-free nucleic acid fragments.

G36. The method of any one of embodiments G1 to G35, wherein the overhangs in target nucleic acids are native overhangs.

G37. The method of any one of embodiments G1 to G36, wherein the overhangs in target nucleic acids are unmodified overhangs.

G38. The method of any one of embodiments G1 to G37, wherein the target nucleic acids are not modified in length prior to combining with the plurality of oligonucleotide species.

G39. The method of any one of embodiments G1 to G38, comprising preparing the nucleic acid composition prior to (a), by a process consisting essentially of isolating nucleic acid from a sample, thereby generating the nucleic acid composition.

G40. The method of any one of embodiments G1 to G39, comprising exposing the hybridization products to conditions under which an end of the target nucleic acid is joined to an end of the oligonucleotide to which it is hybridized.

G41. The method of embodiment G40, comprising contacting the hybridization products with an agent comprising a ligase activity under conditions in which an end of a target nucleic acid is covalently linked to an end of the oligonucleotide to which the target nucleic acid is hybridized.

G42. The method of any one of embodiments G1 to G41, comprising prior to (a), contacting the target nucleic acid composition with an agent comprising a phosphatase activity under conditions in which target nucleic acids are dephosphorylated, thereby generating a dephosphorylated target nucleic acid composition.

G43. The method of embodiment G42, comprising prior to (a), contacting the dephosphorylated target nucleic acid composition with an agent comprising a phosphoryl transfer activity under conditions in which a 5' phosphate is added to a 5' end of target nucleic acids.

G44. The method of any one of embodiments G1 to G43, comprising prior to (a), contacting the plurality of oligonucleotide species with an agent comprising a phosphatase activity under conditions in which the oligonucleotides are dephosphorylated, thereby generating a plurality of dephosphorylated oligonucleotide species.

G45. The method of embodiment G44, comprising prior to (a), contacting the dephosphorylated oligonucleotide species with an agent comprising a phosphoryl transfer activity under conditions in which a 5' phosphate is added to a 5' end of oligonucleotide species.

G46. The method of any one of embodiments G1 to G45, wherein the target nucleic acids are obtained from a sample from a subject.

G47. The method of embodiment G46, wherein the subject is a human.

G48. The method of any one of embodiments G1 to G47, comprising prior to (a), separating the target nucleic acids according to fragment length.

G49. The method of embodiment G48, wherein target nucleic acids having fragment lengths of less than about 500 bp are combined with the plurality of oligonucleotide species.

G50. The method of embodiment G48, wherein target nucleic acids having fragment lengths of about 500 bp or more are combined with the plurality of oligonucleotide species.

G51. The method of any one of embodiments G1 to G50, wherein the second end overhang comprises DNA nucleotides.

G52. The method of any one of embodiments G1 to G50, wherein the second end overhang consists of DNA nucleotides.

G53. The method of any one of embodiments G1 to G50, wherein the second end overhang comprises RNA nucleotides.

G54. The method of any one of embodiments G1 to G50, wherein the second end overhang consists of RNA nucleotides.

G55. The method of embodiment G53 or G54, comprising contacting the hybridization products with an agent comprising a RNA ligase activity under conditions in which an end of a target nucleic acid is covalently linked to an end of the oligonucleotide to which the target nucleic acid is hybridized.

G56. The method of any one of embodiments G53 to G55, comprising contacting the hybridization products with an agent comprising an RNAse activity under conditions in which double-stranded RNA duplexes are digested.

H1. A composition comprising a plurality of oligonucleotide species, wherein:
  (a) the oligonucleotides in the plurality of oligonucleotide species comprise two strands and an overhang at a first end, wherein the first end overhang comprises a palindromic sequence;
  (b) some or all of the oligonucleotides in the plurality of oligonucleotide species comprise an overhang at a second end, wherein the second end overhang is capable of hybridizing to a target nucleic acid overhang, wherein each oligonucleotide species has a unique second end overhang sequence and length;

(c) each oligonucleotide in the plurality of oligonucleotide species comprises an oligonucleotide overhang identification sequence specific to one or more features of the second end overhang; and (d) each oligonucleotide in the plurality of oligonucleotide species comprises one or more modified nucleotides.

H2. The composition of embodiment H1, wherein the one or more modified nucleotides comprise a nucleotide conjugated to a first member of a binding pair.

H3. The composition of embodiment H1 or H2, wherein the one or more modified nucleotides comprise a nucleotide conjugated to biotin.

H4. The composition of any one of embodiments H1 to H3, wherein the first end overhang comprises the one or more modified nucleotides.

H5. The composition of any one of embodiments H1 to H4, wherein the separating in (d) comprises contacting the sheared exonuclease-treated hybridization products with a second member of a binding pair.

H6. The composition of embodiment H5, wherein the second member of a binding pair is streptavidin conjugated to a solid support.

H7. The composition of any one of embodiments H1 to H6, wherein the plurality of oligonucleotide species comprises oligonucleotides having a 5' overhang and oligonucleotides having a 3' overhang, and combinations thereof.

H8. The composition of any one of embodiments H1 to H7, wherein one or more oligonucleotide species have a 5' overhang at a first end.

H9. The composition of any one of embodiments H1 to H8, wherein one or more oligonucleotide species have a 3' overhang at a first end.

H10. The composition of any one of embodiments H1 to H9, wherein one or more oligonucleotide species have a 5' overhang at a second end.

H11. The composition of any one of embodiments H1 to H10, wherein one or more oligonucleotide species have a 3' overhang at a second end.

H12. The composition of any one of embodiments H1 to H11, wherein one or more oligonucleotide species have no overhang at a second end.

H13. The composition of any one of embodiments H1 to H12, wherein the plurality of oligonucleotide species comprises oligonucleotides independently having a first end 5' overhang or a first end 3' overhang, and a second end 5' overhang, a second end 3' overhang, or a second end comprising no overhang.

H14. The composition of any one of embodiments H1 to H13, wherein the second end overhang comprises 1, 2, 3, 4, 5, 6, 7, 8, 9, 10, 11, 12, 13, 14, 15, 16, 17, 18, 19 or 20 nucleotides.

H15. The composition of any one of embodiments H1 to H14, wherein the oligonucleotides in the plurality of oligonucleotide species comprise second end overhangs having different sequences for a particular overhang length.

H16. The composition of embodiment H15, wherein the second end overhangs in the plurality of oligonucleotide species comprise all possible overhang sequence combinations for a particular overhang length.

H17. The composition of embodiment H16, wherein the second end overhangs in the plurality of oligonucleotide species comprise all possible overhang sequence combinations for each overhang length.

H18. The composition of embodiment H15, H16 or H17, wherein the second end overhang sequences are random.

H19. The composition of any one of embodiments H1 to H18, wherein the oligonucleotide overhang identification sequence is specific to length of the second end overhang.

H20. The composition of any one of embodiments H1 to H19, wherein the oligonucleotide overhang identification sequence is specific to length of the second end overhang and is specific to one or more features of the second end overhang chosen from (i) a 5' overhang, (ii) a 3' overhang, (iii) a particular sequence, (iv) a combination of (i) and (iii), or (v) a combination of (ii) and (iii).

H21. The composition of any one of embodiments H1 to H20, wherein an oligonucleotide species comprises no second end overhang and comprises an oligonucleotide overhang identification sequence specific to having no overhang.

H22. The composition of any one of embodiments H1 to H21, wherein the second end overhang comprises DNA nucleotides.

H23. The composition of any one of embodiments H1 to H21, wherein the second end overhang consists of DNA nucleotides.

H24. The composition of any one of embodiments H1 to H21, wherein the second end overhang comprises RNA nucleotides.

H25. The composition of any one of embodiments H1 to H21, wherein the second end overhang consists of RNA nucleotides.

I1. A method for modifying nucleic acid ends, comprising:

(a) combining a nucleic acid composition comprising target nucleic acids and a plurality of oligonucleotide species, wherein:

(i) some or all of the oligonucleotides in the plurality of oligonucleotide species comprise (1) two strands and an overhang at a first end and two non-complementary strands at a second end, or (2) one strand capable of forming a hairpin structure having a single-stranded loop and an overhang; wherein the overhang is capable of hybridizing to a target nucleic acid overhang, wherein each oligonucleotide species has a unique overhang sequence and length, (ii) some or all of the target nucleic acids comprise an overhang, (iii) each oligonucleotide in the plurality of oligonucleotide species comprises an oligonucleotide overhang identification sequence specific to one or more features of the oligonucleotide overhang, and (iv) the nucleic acid composition and the plurality of oligonucleotide species is combined under conditions in which oligonucleotide overhangs hybridize to target nucleic acid overhangs having a corresponding length, thereby forming hybridization products; and (b) contacting the hybridization products with a strand-displacing polymerase, thereby forming blunt-ended nucleic acid fragments.

I2. The method of embodiment I1, wherein each oligonucleotide in the plurality of oligonucleotide species consists of one strand capable of forming a hairpin structure having a single-stranded loop.

I3. The method of embodiment I1 or I2, wherein the single stranded loop comprises a cleavage site.

I4. The method of embodiment I3, wherein the cleavage site comprises one or more RNA nucleotides.

I5. The method of embodiment I4, wherein the loop comprises two RNA nucleotides.

I6. The method of embodiment I4, wherein the loop comprises three RNA nucleotides.

I7. The method of embodiment I4, wherein the loop comprises four RNA nucleotides.

I8. The method of any one of embodiments I4 to I7, wherein the loop comprises one or more ribonucleic acid (RNA) nucleotides chosen from adenine (A), cytosine (C), guanine (G), and uracil (U).

I9. The method of any one of embodiments I4 to I8, wherein the RNA nucleotides comprise guanine (G).

I10. The method of any one of embodiments I4 to I8, wherein the RNA nucleotides consist of guanine (G).

I11. The method of any one of embodiments I4 to I8, wherein the RNA nucleotides comprise cytosine (C).

I12. The method of any one of embodiments I4 to I8, wherein the RNA nucleotides consist of cytosine (C).

I13. The method of any one of embodiments I4 to I8, wherein the RNA nucleotides comprise adenine (A).

I14. The method of any one of embodiments I4 to I8, wherein the RNA nucleotides consist of adenine (A).

I15. The method of any one of embodiments I4 to I8, wherein the RNA nucleotides consist of adenine (A), cytosine (C), and guanine (G).

I16. The method of any one of embodiments I4 to I8, wherein the RNA nucleotides consist of adenine (A) and cytosine (C).

I17. The method of any one of embodiments I4 to I8, wherein the RNA nucleotides consist of adenine (A) and guanine (G).

I18. The method of any one of embodiments I4 to I8, wherein the RNA nucleotides consist of cytosine (C) and guanine (G).

I19. The method of any one of embodiments I1 to I18, wherein the plurality of oligonucleotide species comprises oligonucleotides having a 5' overhang and oligonucleotides having a 3' overhang.

I20. The method of any one of embodiments I1 to I19, wherein the plurality of oligonucleotide species comprises oligonucleotides having a 5' overhang, oligonucleotides having a 3' overhang, and oligonucleotides having no overhang.

I21. The method of any one of embodiments I1 to I20, wherein the oligonucleotides that comprise an overhang comprise a single-stranded loop, a duplex portion, and a single-stranded overhang.

I22. The method of any one of embodiments I1 to I20, wherein the oligonucleotides that comprise an overhang comprise an overhang at a first end, a duplex portion, and two non-complementary strands at a second end.

I23. The method of any one of embodiments I1 to I22, wherein the oligonucleotide overhang comprises 1, 2, 3, 4, 5, 6, 7, 8, 9, 10, 11, 12, 13, 14, 15, 16, 17, 18, 19 or 20 nucleotides.

I24. The method of any one of embodiments I1 to I23, wherein the oligonucleotides in the plurality of oligonucleotide species comprise oligonucleotide overhangs having different sequences for a particular overhang length.

I25. The method of embodiment I24, wherein the oligonucleotides in the plurality of oligonucleotide species comprise all possible overhang sequence combinations for a particular overhang length.

I26. The method of embodiment I25, wherein the oligonucleotides in the plurality of oligonucleotide species comprise all possible overhang sequence combinations for each overhang length.

I27. The method of embodiment I24, I25 or I26, wherein the oligonucleotide overhang sequences are random.

I28. The method of any one of embodiments I1 to I27, wherein the oligonucleotides that comprise no overhang comprise a single-stranded loop and a duplex portion.

I29. The method of any one of embodiments I1 to I27, wherein the oligonucleotides that comprise no overhang comprise a blunt-ended first end, a duplex portion, and two non-complementary strands at a second end.

I30. The method of any one of embodiments I1 to I29, wherein an end of an oligonucleotide is capable of being covalently linked to an end of a target nucleic acid to which the oligonucleotide is hybridized in the hybridization products.

I31. The method of embodiment I30, wherein the 3' end of an oligonucleotide strand is capable of being covalently linked to the 5' end of a strand in the target nucleic acid to which the oligonucleotide is hybridized in a hybridization product.

I32. The method of any one of embodiments I1 to I31, wherein the hybridization products comprise a duplex region and at least one single-stranded loop.

I33. The method of any one of embodiments I1 to I32, wherein the hybridization products comprise a duplex region and a single-stranded loop at each end.

I34. The method of any one of embodiments I1 to I31, wherein the hybridization products comprise a duplex region and at least one end comprising two non-complementary strands.

I35. The method of any one of embodiments I1 to I31 and I134, wherein the hybridization products comprise a duplex region and two non-complementary strands at each end.

I36. The method of any one of embodiments I3 to I35, comprising contacting the hybridization products under cleavage conditions with one or more cleavage agents capable of cleaving the hybridization products within the hairpin loop at the cleavage site, thereby forming cleaved hybridization products.

I37. The method of any one of embodiments I4 to I36, comprising contacting the hybridization products under cleavage conditions with one or more cleavage agents capable of cleaving the hybridization products within the hairpin loop at the RNA nucleotide(s), thereby forming cleaved hybridization products.

I38. The method of embodiment I37, wherein the one or more cleavage agents are capable of cleaving the hybridization products within the hairpin loop at the RNA nucleotide(s) and are not capable of cleaving the hybridization products within the duplex region.

I39. The method of any one of embodiments I36 to I38, wherein the one or more cleavage agents comprise a ribonuclease (RNAse).

I40. The method of embodiment I39, wherein the RNAse is an endoribonuclease.

I41. The method of embodiment I39 or I40, wherein the RNAse is chosen from one or more of RNAse A, RNAse E, RNAse F, RNAse H, RNAse III, RNAse L, RNAse P, RNAse PhyM, RNAse T1, RNAse T2, RNAse U2, and RNAse V.

I42. The method of any one of embodiments I1 to I41, wherein the oligonucleotide overhang identification sequence is specific to length of the oligonucleotide overhang.

I43. The method of any one of embodiments I1 to I42, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

I44. The method of any one of embodiments I1 to I43, wherein some of the target nucleic acids comprise no overhang.

I45. The method of any one of embodiments I1 to I44, wherein an oligonucleotide species comprises no overhang and comprises an oligonucleotide overhang identification sequence specific to having no overhang.

I46. The method of any one of embodiments I1 to I45, wherein the target nucleic acids comprising an overhang comprise a duplex region and a single-stranded overhang.

I47. The method of any one of embodiments I1 to I46, wherein each target nucleic acid comprising an overhang comprises an overhang at one end or an overhang at both ends.

I48. The method of any one of embodiments I1 to I47, wherein an end, or both ends, of each target nucleic acid comprising an overhang independently comprises a 5' overhang or a 3' overhang.

I49. The method of any one of embodiments I1 to I48, wherein the target nucleic acids comprise deoxyribonucleic acid (DNA) fragments.

I50. The method of embodiment I49, wherein the DNA fragments are obtained from cells.

I51. The method of embodiment I49 or I50, wherein the DNA fragments comprise genomic DNA fragments.

I52. The method of any one of embodiments I1 to I48, wherein the target nucleic acids comprise ribonucleic acid (RNA) fragments.

I53. The method of embodiment I52, wherein the RNA fragments are obtained from cells.

I54. The method of any one of embodiments I1 to I53, wherein the target nucleic acids comprise cell-free nucleic acid fragments.

I55. The method of any one of embodiments I1 to I54, wherein the target nucleic acids comprise circulating cell-free nucleic acid fragments.

I56. The method of any one of embodiments I1 to I55, wherein the overhangs in target nucleic acids are native overhangs.

I57. The method of any one of embodiments I1 to I56, wherein the overhangs in target nucleic acids are unmodified overhangs.

I58. The method of any one of embodiments I1 to I57, wherein the target nucleic acids are not modified in length prior to combining with the plurality of oligonucleotide species.

I59. The method of any one of embodiments I1 to I58, comprising preparing the nucleic acid composition prior to (a), by a process consisting essentially of isolating nucleic acid from a sample, thereby generating the nucleic acid composition.

I60. The method of any one of embodiments I1 to I59, comprising exposing the hybridization products to conditions under which an end of the target nucleic acid is joined to an end of the oligonucleotide to which it is hybridized.

I61. The method of embodiment I60, comprising contacting the hybridization products with an agent comprising a ligase activity under conditions in which an end of a target nucleic acid is covalently linked to an end of the oligonucleotide to which the target nucleic acid is hybridized.

I62. The method of any one of embodiments I1 to I61, comprising prior to (a), contacting the target nucleic acid composition with an agent comprising a phosphatase activity under conditions in which target nucleic acids are dephosphorylated, thereby generating a dephosphorylated target nucleic acid composition.

I63. The method of embodiment I62, comprising prior to (a), contacting the dephosphorylated target nucleic acid composition with an agent comprising a phosphoryl transfer activity under conditions in which a 5' phosphate is added to a 5' end of target nucleic acids.

I64. The method of any one of embodiments I1 to I63, comprising prior to (a), contacting the plurality of oligonucleotide species with an agent comprising a phosphatase activity under conditions in which the oligonucleotides are dephosphorylated, thereby generating a plurality of dephosphorylated oligonucleotide species.

I65. The method of embodiment I64, comprising prior to (a), contacting the dephosphorylated oligonucleotide species with an agent comprising a phosphoryl transfer activity under conditions in which a 5' phosphate is added to a 5' end of oligonucleotide species.

I66. The method of any one of embodiments I1 to I65, wherein the target nucleic acids are obtained from a sample from a subject.

I67. The method of embodiment I66, wherein the subject is a human.

I68. The method of any one of embodiments I1 to I67, comprising prior to (a), separating the target nucleic acids according to fragment length.

I69. The method of embodiment I68, wherein target nucleic acids having fragment lengths of less than about 500 bp are combined with the plurality of oligonucleotide species.

I70. The method of embodiment I68, wherein target nucleic acids having fragment lengths of about 500 bp or more are combined with the plurality of oligonucleotide species.

I71. The method of any one of embodiments I1 to I70, wherein the oligonucleotide overhang comprises DNA nucleotides.

I72. The method of any one of embodiments I1 to I70, wherein the oligonucleotide overhang consists of DNA nucleotides.

I73. The method of any one of embodiments I1 to I70, wherein the oligonucleotide overhang comprises RNA nucleotides.

I74. The method of any one of embodiments I1 to I70, wherein the oligonucleotide overhang consists of RNA nucleotides.

I75. The method of embodiment I73 or I74, comprising contacting the hybridization products with an agent comprising a RNA ligase activity under conditions in which an end of a target nucleic acid is covalently linked to an end of the oligonucleotide to which the target nucleic acid is hybridized.

I76. The method of any one of embodiments I73 to I75, comprising contacting the hybridization products with an agent comprising an RNAse activity under conditions in which double-stranded RNA duplexes are digested.

J1. A composition comprising a plurality of oligonucleotide species, wherein:
(a) some or all of the oligonucleotides in the plurality of oligonucleotide species comprise (i) two strands and an overhang at a first end and two non-complementary strands at a second end, or (ii) one strand capable of forming a hairpin structure having a single-stranded loop and an overhang; wherein the overhang is capable of hybridizing to a target nucleic acid overhang, wherein each oligonucleotide species has a unique overhang sequence and length; and (b) each oligonucleotide in the plurality of oligonucleotide species comprises an oligonucleotide overhang identification sequence specific to one or more features of the oligonucleotide overhang.

J2. The composition of embodiment J1, wherein each oligonucleotide in the plurality of oligonucleotide species consists of one strand capable of forming a hairpin structure having a single-stranded loop.

J3. The composition of embodiment J1 or J2, wherein the single stranded loop comprises a cleavage site.

J4. The composition of embodiment J3, wherein the cleavage site comprises one or more RNA nucleotides.

J5. The composition of embodiment J4, wherein the loop comprises two RNA nucleotides.

J6. The composition of embodiment J4, wherein the loop comprises three RNA nucleotides.

J7. The composition of embodiment J4, wherein the loop comprises four RNA nucleotides.

J8. The composition of any one of embodiments J4 to J7, wherein the loop comprises one or more ribonucleic acid (RNA) nucleotides chosen from adenine (A), cytosine (C), guanine (G), and uracil (U).

J9. The composition of any one of embodiments J4 to J8, wherein the RNA nucleotides comprise guanine (G).

J10. The composition of any one of embodiments J4 to J8, wherein the RNA nucleotides consist of guanine (G).

J11. The composition of any one of embodiments J4 to J8, wherein the RNA nucleotides comprise cytosine (C).

J12. The composition of any one of embodiments J4 to J8, wherein the RNA nucleotides consist of cytosine (C).

J13. The composition of any one of embodiments J4 to J8, wherein the RNA nucleotides comprise adenine (A).

J14. The composition of any one of embodiments J4 to J8, wherein the RNA nucleotides consist of adenine (A).

J15. The composition of any one of embodiments J4 to J8, wherein the RNA nucleotides consist of adenine (A), cytosine (C), and guanine (G).

J16. The composition of any one of embodiments J4 to J8, wherein the RNA nucleotides consist of adenine (A) and cytosine (C).

J17. The composition of any one of embodiments J4 to J8, wherein the RNA nucleotides consist of adenine (A) and guanine (G).

J18. The composition of any one of embodiments J4 to J8, wherein the RNA nucleotides consist of cytosine (C) and guanine (G).

J19. The composition of any one of embodiments J1 to J18, wherein the plurality of oligonucleotide species comprises oligonucleotides having a 5' overhang and oligonucleotides having a 3' overhang.

J20. The composition of any one of embodiments J1 to J19, wherein the plurality of oligonucleotide species comprises oligonucleotides having a 5' overhang, oligonucleotides having a 3' overhang, and oligonucleotides having no overhang.

J21. The composition of any one of embodiments J1 to J20, wherein the oligonucleotides that comprise an overhang comprise a single-stranded loop, a duplex portion, and a single-stranded overhang.

J22. The composition of any one of embodiments J1 to J21, wherein the oligonucleotides that comprise an overhang comprise an overhang at a first end, a duplex portion, and two non-complementary strands at a second end.

J23. The composition of any one of embodiments J1 to J22, wherein the oligonucleotide overhang comprises 1, 2, 3, 4, 5, 6, 7, 8, 9, 10, 11, 12, 13, 14, 15, 16, 17, 18, 19 or 20 nucleotides.

J24. The composition of any one of embodiments J1 to J23, wherein the oligonucleotides in the plurality of oligonucleotide species comprise oligonucleotide overhangs having different sequences for a particular overhang length.

J25. The composition of embodiment J24, wherein the oligonucleotides in the plurality of oligonucleotide species comprise all possible overhang sequence combinations for a particular overhang length.

J26. The composition of embodiment J25, wherein the oligonucleotides in the plurality of oligonucleotide species comprise all possible overhang sequence combinations for each overhang length.

J27. The composition of embodiment J24, J25 or J26, wherein the oligonucleotide overhang sequences are random.

J28. The composition of any one of embodiments J1 to J27, wherein the oligonucleotides that comprise no overhang comprise a single-stranded loop and a duplex portion.

J29. The composition of any one of embodiments J1 to J27, wherein the oligonucleotides that comprise no overhang comprise a blunt-ended first end, a duplex portion, and two non-complementary strands at a second end.

J30. The composition of any one of embodiments J1 to J29, wherein the oligonucleotide overhang identification sequence is specific to length of the oligonucleotide overhang.

J31. The composition of any one of embodiments J1 to J30, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

J32. The composition of any one of embodiments J1 to J31, wherein an oligonucleotide species comprises no overhang and comprises an oligonucleotide overhang identification sequence specific to having no overhang.

J33. The composition of any one of embodiments J1 to J32, wherein the oligonucleotide overhang comprises DNA nucleotides.

J34. The composition of any one of embodiments J1 to J32, wherein the oligonucleotide overhang consists of DNA nucleotides.

J35. The composition of any one of embodiments J1 to J32, wherein the oligonucleotide overhang comprises RNA nucleotides.

J36. The composition of any one of embodiments J1 to J32, wherein the oligonucleotide overhang consists of RNA nucleotides.

K1. A kit, comprising:
the composition of any one of embodiments B1 to B32; and
instructions for using the composition to produce a nucleic acid library.

K2. The kit of embodiment K1, further comprising an agent comprising a phosphatase activity.

K3. The kit of embodiment K1 or K2, further comprising an agent comprising a phosphoryl transfer activity.

K4. The kit of any one of embodiments K1 to K3, further comprising an agent comprising a ligase activity.

K5. The kit of any one of embodiments K1 to K4, further comprising one or more cleavage agents.

K6. The kit of embodiment K5, wherein the one or more cleavage agents comprise a ribonuclease (RNAse).

K7. The kit of embodiment K6, wherein the RNAse is an endoribonuclease.

L1. A kit, comprising:
the composition of any one of embodiments D1 to D23; and
instructions for using the composition to modify nucleic acid ends.

L2. The kit of embodiment L1, further comprising an agent comprising a phosphatase activity.

L3. The kit of embodiment L1 or L2, further comprising an agent comprising a phosphoryl transfer activity.

L4. The kit of any one of embodiments L1 to L3, further comprising an agent comprising a ligase activity.

L5. The kit of any one of embodiments L1 to L4, further comprising one or more cleavage agents.

L6. The kit of any one of embodiments L1 to L5, wherein the one or more cleavage agents comprise an endonuclease.

L7. The kit of any one of embodiments L1 to L5, wherein the one or more cleavage agents comprise a DNA glycosylase.

L8. The kit of any one of embodiments L1 to L7, wherein the one or more cleavage agents comprise an endonuclease and a DNA glycosylase.

L9. The kit of embodiment L8, wherein the one or more cleavage agents comprise a mixture of uracil DNA glycosylase (UDG) and endonuclease VIII.

L10. The kit of any one of embodiments L1 to L9, further comprising a strand-displacing polymerase.

L11. The kit of any one of embodiments L1 to L10, further comprising modified nucleotides.

L12. The kit of embodiment L11, wherein the modified nucleotides comprise a nucleotide conjugated to a first member of a binding pair.

L13. The kit of embodiment L11 or L12, wherein the modified nucleotides comprise a nucleotide conjugated to biotin.

L14. The kit of embodiment L12 or L13, further comprising a second member of a binding pair conjugated to a solid support.

L15. The kit of embodiment L14, wherein the second member of a binding pair is streptavidin.

M1. A kit, comprising:
the composition of any one of embodiments F1 to F33; and
instructions for using the composition to modify nucleic acid ends.

M2. The kit of embodiment M1, further comprising an agent comprising a phosphatase activity.

M3. The kit of embodiment M1 or M2, further comprising an agent comprising a phosphoryl transfer activity.

M4. The kit of any one of embodiments M1 to M3, further comprising an agent comprising a ligase activity.

M5. The kit of any one of embodiments M1 to M4, further comprising a strand-displacing polymerase.

N1. A kit, comprising:
the composition of any one of embodiments H1 to H25; and
instructions for using the composition to modify nucleic acid ends.

N2. The kit of embodiment N1, further comprising an agent comprising a phosphatase activity.

N3. The kit of embodiment N1 or N2, further comprising an agent comprising a phosphoryl transfer activity.

N4. The kit of any one of embodiments N1 to N3, further comprising an agent comprising a ligase activity.

N5. The kit of any one of embodiments N1 to N4, further comprising an exonuclease.

N6. The kit of any one of embodiments N1 to N5, further comprising a shearing agent.

N7. The kit of any one of embodiments N1 to N6, further comprising a member of a binding pair conjugated to a solid support.

N8. The kit of embodiment N7, the member of a binding pair is streptavidin.

O1. A kit comprising:
the composition of any one of embodiments J1 to J36; and
instructions for using the composition to modify nucleic acid ends.

O2. The kit of embodiment O1, further comprising an agent comprising a phosphatase activity.

O3. The kit of embodiment O1 or O2, further comprising an agent comprising a phosphoryl transfer activity.

O4. The kit of any one of embodiments O1 to O3, further comprising an agent comprising a ligase activity.

O5. The kit of any one of embodiments O1 to O4, further comprising a strand-displacing polymerase.

O6. The kit of any one of embodiments O1 to O5, further comprising one or more cleavage agents.

O7. The kit of embodiment O6, wherein the one or more cleavage agents comprise a ribonuclease (RNAse).

O8. The kit of embodiment O7, wherein the RNAse is an endoribonuclease.

P1. A method of assaying a population of nucleic acids, comprising:
assaying nucleic acid overhangs of a population of nucleic acids in a sample, thereby generating an overhang profile of the population; and
based on the overhang profile, determining one or more characteristics of the sample.

P2. The method of embodiment P1, wherein the assaying comprises contacting oligonucleotides to the population of nucleic acids.

P2.1 The method of embodiment P2, wherein some or all of the oligonucleotides comprise an overhang capable of hybridizing to a nucleic acid overhang, wherein each oligonucleotide species has a unique overhang sequence and length.

P3. The method of embodiment P2 or P2.1, wherein the oligonucleotides comprise overhang identification sequences.

P3.1 The method of embodiment P3, wherein each overhang identification sequence is specific to one or more features of the oligonucleotide overhang.

P3.2 The method of any one of embodiments P2 to P3.1, wherein some or all of the oligonucleotides comprise two strands, and an overhang at a first end and two non-complementary strands at a second end.

P3.3. The method of any one of embodiments P2 to P3.1, wherein some or all of the oligonucleotides comprise one strand capable of forming a hairpin structure having a single-stranded loop and an overhang.

P4. The method of any one of embodiments P1 to P3.3, wherein the one or more characteristics of the sample comprise a disease state.

P5. The method of embodiment P4, wherein the disease state comprises a cancer type or a cancer stage.

P5.1 The method of embodiment P5, wherein the cancer type is gastrointestinal cancer.

P6. The method of embodiment P4, wherein the disease state comprises a change in a rate or mode of cell death.

P7. The method of embodiment P6, wherein the change is associated with a particular cell type or organ type.

P8. The method of any one of embodiments P1 to P3.3, wherein the one or more characteristics of the sample comprise a microbiome profile.

P9. The method of any one of embodiments P1 to P3.3, wherein the one or more characteristics of the sample comprise radiation exposure.

P10. The method of any one of embodiments P1 to P3.3, wherein the one or more characteristics of the sample comprise nuclease activity.

P11. The method of embodiment P10, wherein the nuclease activity comprises nucleic acid-guided nuclease activity.

P12. The method of embodiment P11, wherein the nucleic acid-guided nuclease activity comprises CRISPR/Cas-system protein activity.

P13. The method of any one of embodiments P1 to P3.3, wherein the one or more characteristics of the sample comprise topoisomerase activity.

P14. The method of any one of embodiments P1 to P13, further comprising, prior to the assaying, inhibiting enzyme activity.

P15. The method of embodiment P14, wherein the enzyme activity comprises nuclease activity.

P16. The method of any one of embodiments P1 to P15, wherein the assaying comprises hybridization, thereby generating hybridization products.

P17. The method of any one of embodiments P1 to P16, wherein the assaying comprises sequencing the hybridization products, or amplification products thereof, by a sequencing process, thereby generating sequence reads.

P18. The method of embodiment P17, wherein the sequence reads comprise forward sequence reads and reverse sequence reads.

P19. The method of embodiment P18, comprising quantifying the sequence reads thereby generating a sequence read quantification, wherein the reverse sequence reads are quantified, and the forward sequence reads are excluded from the quantification.

P20. The method of embodiment P18 or P19, wherein the overhang profile is generated according to the reverse sequence reads.

P21. The method of embodiment P18, comprising analyzing overhang information associated with overhang identification sequences that indicate presence of an overhang for the reverse sequence reads, thereby generating an analysis.

P22. The method of embodiment P21, comprising omitting from the analysis overhang information associated with overhang identification sequences that indicate presence of an overhang for the forward sequence reads.

P23. The method of embodiment P21 or P22, comprising analyzing overhang information associated with overhang identification sequences that indicate no overhang for the forward sequence reads and the reverse sequence reads.

P24. The method of any one of embodiments P1 to P23, wherein the overhang profile comprises one or more overhang features.

P25. The method of embodiment P24, wherein the one or more overhang features are chosen from one or more of overhang length, overhang type, dinucleotide count, trinucleotide count, tetranucleotide count, dinucleotide percent, trinucleotide percent, tetranucleotide percent, GC content, overhang percent, overhang count, percent overhang length, and genome coordinate.

P26. The method of embodiment P24, wherein the one or more overhang features comprise presence of a particular dinucleotide.

P27. The method of embodiment P26, wherein the one or more overhang features comprise presence of a CG dinucleotide.

P28. The method of any one of embodiments P1 to P27, further comprising comparing the overhang profile to a reference overhang profile.

P29. The method of any one of embodiments P1 to P27, further comprising comparing the overhang profile to a second overhang profile of a second sample, wherein the second sample is from the same source as the sample at a different time point.

P30. The method of any one of embodiments P1 to P29, wherein one or more steps are performed by a microprocessor.

P31. The method of any one of embodiments P1 to P29, comprising one or more features of any one of embodiments A1 to A68, C1 to C68, E1 to E64, G1 to G56, I1 to I76, Q1 to Q42, T1 to T58, and W1 to W59.

Q1. A method for modifying nucleic acid ends, comprising:
  combining a nucleic acid composition comprising target nucleic acids and a plurality of oligonucleotide species, wherein:
    (a) some or all of the oligonucleotides in the plurality of oligonucleotide species comprise at least one overhang comprising RNA nucleotides, wherein the overhang is capable of hybridizing to a target nucleic acid overhang, wherein each oligonucleotide species has a unique overhang sequence and length,
    (b) some or all of the target nucleic acids comprise an overhang,
    (c) each oligonucleotide in the plurality of oligonucleotide species comprises an oligonucleotide overhang identification sequence specific to one or more features of the oligonucleotide overhang, and
    (d) the nucleic acid composition and the plurality of oligonucleotide species is combined under conditions in which oligonucleotide overhangs hybridize to target nucleic acid overhangs having a corresponding length, thereby forming hybridization products.

Q2. The method of embodiment Q1, wherein the oligonucleotide overhang consists of RNA nucleotides.

Q3. The method of embodiment Q1 or Q2, wherein the plurality of oligonucleotide species comprises oligonucleotides having a 5' overhang and oligonucleotides having a 3' overhang.

Q4. The method of any one of embodiments Q1 to Q3, wherein the plurality of oligonucleotide species comprises oligonucleotides having a 5' overhang, oligonucleotides having a 3' overhang, and oligonucleotides having no overhang.

Q5. The method of any one of embodiments Q1 to Q4, wherein the oligonucleotide overhang comprises 1, 2, 3, 4, 5, 6, 7, 8, 9, 10, 11, 12, 13, 14, 15, 16, 17, 18, 19 or 20 nucleotides.

Q6. The method of any one of embodiments Q1 to Q5, wherein the oligonucleotides in the plurality of oligonucleotide species comprise oligonucleotide overhangs having different sequences for a particular overhang length.

Q7. The method of embodiment Q6, wherein the oligonucleotides in the plurality of oligonucleotide species comprise all possible overhang sequence combinations for a particular overhang length.

Q8. The method of embodiment Q7, wherein the oligonucleotides in the plurality of oligonucleotide species comprise all possible overhang sequence combinations for each overhang length.

Q9. The method of embodiment Q6, Q7 or Q8, wherein the oligonucleotide overhang sequences are random.

Q10. The method of any one of embodiments Q1 to Q9, wherein an end of an oligonucleotide is capable of being covalently linked to an end of a target nucleic acid to which the oligonucleotide is hybridized in the hybridization products.

Q11. The method of embodiment Q10, wherein the 3' end of an oligonucleotide strand is capable of being covalently linked to the 5' end of a strand in the target nucleic acid to which the oligonucleotide is hybridized in a hybridization product.

Q12. The method of any one of embodiments Q1 to Q11, wherein the oligonucleotide overhang identification sequence is specific to length of the oligonucleotide overhang.

Q13. The method of any one of embodiments Q1 to Q12, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

Q14. The method of any one of embodiments Q1 to Q13, wherein some of the target nucleic acids comprise no overhang.

Q15. The method of any one of embodiments Q1 to Q14, wherein an oligonucleotide species comprises no overhang and comprises an oligonucleotide overhang identification sequence specific to having no overhang.

Q16. The method of any one of embodiments Q1 to Q15, wherein the target nucleic acids comprising an overhang comprise a duplex region and a single-stranded overhang.

Q17. The method of any one of embodiments Q1 to Q16, wherein each target nucleic acid comprising an overhang comprises an overhang at one end or an overhang at both ends.

Q18. The method of any one of embodiments Q1 to Q17, wherein an end, or both ends, of each target nucleic acid comprising an overhang independently comprises a 5' overhang or a 3' overhang.

Q19. The method of any one of embodiments Q1 to Q18, wherein the target nucleic acids comprise deoxyribonucleic acid (DNA) fragments.

Q20. The method of embodiment Q19, wherein the DNA fragments are obtained from cells.

Q21. The method of embodiment Q19 or Q20, wherein the DNA fragments comprise genomic DNA fragments.

Q22. The method of any one of embodiments Q1 to Q18, wherein the target nucleic acids comprise ribonucleic acid (RNA) fragments.

Q23. The method of embodiment Q22, wherein the RNA fragments are obtained from cells.

Q24. The method of any one of embodiments Q1 to Q23, wherein the target nucleic acids comprise cell-free nucleic acid fragments.

Q25. The method of any one of embodiments Q1 to Q24, wherein the target nucleic acids comprise circulating cell-free nucleic acid fragments.

Q26. The method of any one of embodiments Q1 to Q25, wherein the overhangs in target nucleic acids are native overhangs.

Q27. The method of any one of embodiments Q1 to Q26, wherein the overhangs in target nucleic acids are unmodified overhangs.

Q28. The method of any one of embodiments Q1 to Q27, wherein the target nucleic acids are not modified in length prior to combining with the plurality of oligonucleotide species.

Q29. The method of any one of embodiments Q1 to Q28, comprising preparing the nucleic acid composition prior to (a), by a process consisting essentially of isolating nucleic acid from a sample, thereby generating the nucleic acid composition.

Q30. The method of any one of embodiments Q1 to Q29, comprising exposing the hybridization products to conditions under which an end of the target nucleic acid is joined to an end of the oligonucleotide to which it is hybridized.

Q31. The method of embodiment Q30, comprising contacting the hybridization products with an agent comprising a ligase activity under conditions in which an end of a target nucleic acid is covalently linked to an end of the oligonucleotide to which the target nucleic acid is hybridized.

Q32. The method of embodiment Q30, comprising contacting the hybridization products with an agent comprising an RNA ligase activity under conditions in which an end of a target nucleic acid is covalently linked to an end of the oligonucleotide to which the target nucleic acid is hybridized.

Q33. The method of any one of embodiments Q1 to Q32, comprising prior to combining, contacting the target nucleic acid composition with an agent comprising a phosphatase activity under conditions in which target nucleic acids are dephosphorylated, thereby generating a dephosphorylated target nucleic acid composition.

Q34. The method of embodiment Q33, comprising prior to combining, contacting the dephosphorylated target nucleic acid composition with an agent comprising a phosphoryl transfer activity under conditions in which a 5' phosphate is added to a 5' end of target nucleic acids.

Q35. The method of any one of embodiments Q1 to Q34, comprising prior to combining, contacting the plurality of oligonucleotide species with an agent comprising a phosphatase activity under conditions in which the oligonucleotides are dephosphorylated, thereby generating a plurality of dephosphorylated oligonucleotide species.

Q36. The method of embodiment Q35, comprising prior to combining, contacting the dephosphorylated oligonucleotide species with an agent comprising a phosphoryl transfer activity under conditions in which a 5' phosphate is added to a 5' end of oligonucleotide species.

Q37. The method of any one of embodiments Q1 to Q36, wherein the target nucleic acids are obtained from a sample from a subject.

Q38. The method of embodiment Q37, wherein the subject is a human.

Q39. The method of any one of embodiments Q1 to Q38, comprising prior combining, separating the target nucleic acids according to fragment length.

Q40. The method of embodiment Q39, wherein target nucleic acids having fragment lengths of less than about 500 bp are combined with the plurality of oligonucleotide species.

Q41. The method of embodiment Q39, wherein target nucleic acids having fragment lengths of about 500 bp or more are combined with the plurality of oligonucleotide species.

Q42. The method of any one of embodiments Q1 to Q41, comprising contacting the hybridization products with an agent comprising an RNAse activity under conditions in which double-stranded RNA duplexes are digested.

R1. A composition comprising a plurality of oligonucleotide species, wherein:
  (a) some or all of the oligonucleotides in the plurality of oligonucleotide species comprise at least one overhang comprising RNA nucleotides, wherein the overhang is capable of hybridizing to a target nucleic acid overhang, wherein each oligonucleotide species has a unique overhang sequence and length; and (b) each oligonucleotide in the plurality of oligonucleotide species comprises an oligonucleotide overhang identification sequence specific to one or more features of the oligonucleotide overhang.

R2. The composition of embodiment R1, wherein the oligonucleotide overhang consists of RNA nucleotides.

R3. The composition of embodiment R1 or R2, wherein the plurality of oligonucleotide species comprises oligonucleotides having a 5' overhang and oligonucleotides having a 3' overhang.

R4. The composition of any one of embodiments R1 to R3, wherein the plurality of oligonucleotide species comprises oligonucleotides having a 5' overhang, oligonucleotides having a 3' overhang, and oligonucleotides having no overhang.

R5. The composition of any one of embodiments R1 to R4, wherein the oligonucleotide overhang comprises 1, 2, 3, 4, 5, 6, 7, 8, 9, 10, 11, 12, 13, 14, 15, 16, 17, 18, 19 or 20 nucleotides.

R6. The composition of any one of embodiments R1 to R5, wherein the oligonucleotides in the plurality of oligonucleotide species comprise oligonucleotide overhangs having different sequences for a particular overhang length.

R7. The composition of embodiment R6, wherein the oligonucleotides in the plurality of oligonucleotide species comprise all possible overhang sequence combinations for a particular overhang length.

R8. The composition of embodiment R7, wherein the oligonucleotides in the plurality of oligonucleotide species comprise all possible overhang sequence combinations for each overhang length.

R9. The composition of embodiment R6, R7 or R8, wherein the oligonucleotide overhang sequences are random.

R10. The composition of any one of embodiments R1 to R9, wherein the oligonucleotide overhang identification sequence is specific to length of the oligonucleotide overhang.

R11. The composition of any one of embodiments R1 to R10, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

R12. The composition of any one of embodiments R1 to R11, wherein an oligonucleotide species comprises no overhang and comprises an oligonucleotide overhang identification sequence specific to having no overhang.

S1. A kit comprising:
the composition of any one of embodiments R1 to R12; and
instructions for using the composition to modify nucleic acid ends.

S2. The kit of embodiment S1, further comprising an agent comprising a phosphatase activity.

S3. The kit of embodiment S1 or S2, further comprising an agent comprising a phosphoryl transfer activity.

S4. The kit of any one of embodiments S1 to S3, further comprising an agent comprising a ligase activity.

S5. The kit of any one of embodiments S1 to S4, further comprising an agent comprising an RNA ligase activity.

S6. The kit of any one of embodiments S1 to S5, further comprising a strand-displacing polymerase.

S7. The kit of any one of embodiments S1 to S6, further comprising one or more cleavage agents.

S8. The kit of embodiment S7, wherein the one or more cleavage agents comprise a ribonuclease (RNAse).

S9. The kit of embodiment S8, wherein the RNAse is an endoribonuclease.

S10. The kit of embodiment S8 or S9, wherein the RNAse is RNAse III.

T1. A method for producing a nucleic acid library, comprising:
a) combining a nucleic acid composition comprising target nucleic acids and a first pool of oligonucleotide species, wherein:
i) some or all of the target nucleic acids comprise an overhang,
ii) some or all of the oligonucleotides in the first pool of oligonucleotide species comprise an overhang capable of hybridizing to a target nucleic acid overhang, wherein each oligonucleotide species has a unique overhang sequence and length,
iii) each oligonucleotide in the first pool of oligonucleotide species comprises an oligonucleotide overhang identification sequence specific to one or more features of the oligonucleotide overhang,
iv) each oligonucleotide in the first pool of oligonucleotide species comprises a first primer binding domain, and
v) the nucleic acid composition and the first pool of oligonucleotide species are combined under conditions in which oligonucleotide overhangs hybridize to target nucleic acid overhangs having a corresponding length, thereby forming a first set of combined products;
b) cleaving the first set of combined products, thereby forming cleaved products; and
c) combining the cleaved products and a second pool of oligonucleotide species, wherein:
i) each oligonucleotide in the second pool of oligonucleotide species comprises a first end and a second end,
ii) each oligonucleotide in the second pool of oligonucleotide species comprises a second primer binding domain, wherein the first primer binding domain and the second primer binding domain are different, and
iii) the cleaved products and the second pool of oligonucleotide species are combined under conditions in which the oligonucleotides in the second pool of oligonucleotide species attach at the first end to at least one end of the cleaved products, thereby forming a second set of combined products.

T1.1 The method of embodiment T1, further comprising:
d) contacting, under amplification conditions, the second set of combined products with two or more amplification primer species, wherein a first primer species comprises a nucleotide sequence complementary to the first primer binding domain and a second primer binding domain comprises a nucleotide sequence complementary to the second primer binding domain, thereby generating amplification products.

T2. The method of embodiment T1 or T1.1, wherein the target nucleic acids comprise nucleic acid fragments larger than 500 bp.

T3. The method of embodiment T1 or T1.1, wherein the target nucleic acids comprise nucleic acid fragments larger than 1000 bp.

T4. The method of any one of embodiments T1 to T3, wherein (b) comprises contacting the first set of combined products under cleavage conditions with one or more cleavage agents capable of cleaving the combined products.

T5. The method of any one of embodiments T1 to T3, wherein (b) comprises mechanical shearing.

T6. The method of any one of embodiments T1 to T5, wherein some or all of the oligonucleotides in the first pool of oligonucleotide species comprise one or more modified nucleotides.

T7. The method of embodiment T6, wherein the one or more modified nucleotides are capable of blocking attachment to other oligonucleotides in the pool.

T8. The method of any one of embodiments T1 to T7, wherein some or all of the oligonucleotides in the second pool of oligonucleotide species comprise one or more modified nucleotides at the second end.

T9. The method of embodiment T8, wherein the one or more modified nucleotides are capable of blocking attachment of the second end of the oligonucleotide to the cleaved products.

T10. The method of any one of embodiments T1 to T9, further comprising sequencing the amplification products by a sequencing process.

T11. The method of embodiment T10, wherein the sequencing process generates short sequence reads.

T12. The method of any one of embodiments T1 to T11, wherein the first pool of oligonucleotide species comprises oligonucleotides having a 5' overhang and oligonucleotides having a 3' overhang.

T13. The method of any one of embodiments T1 to T12, wherein the first pool of oligonucleotide species comprises oligonucleotides having a 5' overhang, oligonucleotides having a 3' overhang, and oligonucleotides having no overhang.

T14. The method of embodiment T12 or T13, wherein the oligonucleotides that comprise an overhang comprise a duplex portion, and a single-stranded overhang.

T15. The method of any one of embodiments T12 to T14, wherein the oligonucleotide overhang comprises 1, 2, 3, 4, 5, 6, 7, 8, 9, 10, 11, 12, 13, 14, 15, 16, 17, 18, 19 or 20 nucleotides.

T16. The method of any one of embodiments T1 to T15, wherein the oligonucleotides in the first pool of oligonucleotide species comprise oligonucleotide overhangs having different sequences for a particular overhang length.

T17. The method of embodiment T16, wherein the oligonucleotides in the first pool of oligonucleotide species comprise all possible overhang sequence combinations for a particular overhang length.

T18. The method of embodiment T17, wherein the oligonucleotides in the first pool of oligonucleotide species comprise all possible overhang sequence combinations for each overhang length.

T19. The method of embodiment T16, T17 or T18, wherein the oligonucleotide overhang sequences are random.

T20. The method of any one of embodiments T1 to T19, wherein an end of an oligonucleotide in the first pool of oligonucleotide species is capable of being covalently linked to an end of a target nucleic acid to which the oligonucleotide is hybridized in the first set of combined products.

T21. The method of embodiment T20, wherein the 3' end of an oligonucleotide strand in the first pool of oligonucleotide species is capable of being covalently linked to the 5' end of a strand in the target nucleic acid to which the oligonucleotide is hybridized in the first set of combined products.

T22. The method of any one of embodiments T1 to T21, comprising after (b) repairing the ends of the cleaved products.

T23. The method of any one of embodiments T1 to T22, comprising after (b) adding one or more unpaired nucleotides to the ends of the cleaved products.

T24. The method of embodiment T23, wherein the oligonucleotides in the second pool of oligonucleotide species comprise one or more nucleotides at the first end that are complementary to the one or more nucleotides added to the cleaved products.

T25. The method of embodiment T24, wherein the oligonucleotides in the second pool of oligonucleotide species hybridize at the first end to at least one end of the cleaved products.

T26. The method of any one of embodiments T1 to T25, wherein an end of an oligonucleotide in the second pool of oligonucleotide species is capable of being covalently linked to an end of a cleaved product to which the oligonucleotide is attached in the second set of combined products.

T27. The method of embodiment T26, wherein the 3' end of an oligonucleotide strand in the second pool of oligonucleotide species is capable of being covalently linked to the 5' end of a strand in the cleaved product to which the oligonucleotide is attached in the second set of combined products.

T28. The method of any one of embodiments T1 to T27, wherein the oligonucleotides in the second pool of oligonucleotide species do not comprise an overhang capable of hybridizing to a native target nucleic acid overhang.

T28.1 The method of any one of embodiments T1 to T28, wherein the oligonucleotides in the second pool of oligonucleotide species do not comprise an oligonucleotide overhang identification sequence.

T29. The method of any one of embodiments T1 to T28.1, wherein the oligonucleotide overhang identification sequence on each oligonucleotide in the first pool of oligonucleotide species is specific to length of the oligonucleotide overhang.

T30. The method of any one of embodiments T1 to T29, wherein the oligonucleotide overhang identification sequence on each oligonucleotide in the first pool of oligonucleotide species is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

T31. The method of any one of embodiments T1 to T30, wherein some of the target nucleic acids comprise no overhang.

T32. The method of any one of embodiments T1 to T31, wherein an oligonucleotide species in the first pool of oligonucleotide species comprises no overhang and comprises an oligonucleotide overhang identification sequence specific to having no overhang.

T33. The method of any one of embodiments T1 to T32, wherein the target nucleic acids comprising an overhang comprise a duplex region and a single-stranded overhang.

T34. The method of any one of embodiments T1 to T33, wherein each target nucleic acid comprising an overhang comprises an overhang at one end or an overhang at both ends.

T35. The method of any one of embodiments T1 to T34, wherein an end, or both ends, of each target nucleic acid comprising an overhang independently comprises a 5' overhang or a 3' overhang.

T36. The method of any one of embodiments T1 to T35, wherein the target nucleic acids comprise deoxyribonucleic acid (DNA) fragments.

T37. The method of embodiment T36, wherein the DNA fragments are obtained from cells.

T38. The method of embodiment T36 or T37, wherein the DNA fragments comprise genomic DNA fragments.

T39. The method of any one of embodiments T1 to T35, wherein the target nucleic acids comprise ribonucleic acid (RNA) fragments.

T40. The method of embodiment T39, wherein the RNA fragments are obtained from cells.

T41. The method of any one of embodiments T1 to T40, wherein the target nucleic acids comprise cell-free nucleic acid fragments.

T42. The method of any one of embodiments T1 to T41, wherein the target nucleic acids comprise circulating cell-free nucleic acid fragments.

T43. The method of any one of embodiments T1 to T42, wherein the overhangs in target nucleic acids are native overhangs.

T44. The method of any one of embodiments T1 to T43, wherein the overhangs in target nucleic acids are unmodified overhangs.

T45. The method of any one of embodiments T1 to T44, wherein the target nucleic acids are not modified in length prior to combining with the plurality of oligonucleotide species.

T46. The method of any one of embodiments T1 to T45, comprising preparing the nucleic acid composition prior to (a), by a process consisting essentially of isolating nucleic acid from a sample, thereby generating the nucleic acid composition.

T47. The method of any one of embodiments T1 to T46, comprising exposing the first set of combined products to conditions under which an end of the target nucleic acid is joined to an end of the oligonucleotide to which it is hybridized.

T48. The method of embodiment T47, comprising contacting the first set of combined products with an agent comprising a ligase activity under conditions in which an end of a target nucleic acid is covalently linked to an end of the oligonucleotide to which the target nucleic acid is hybridized.

T49. The method of any one of embodiments T1 to T48, comprising exposing the second set of combined products to conditions under which an end of the cleaved product is joined to an end of the oligonucleotide to which it is attached.

T50. The method of embodiment T49, comprising contacting the second set of combined products with an agent comprising a ligase activity under conditions in which an end of a cleaved product is covalently linked to an end of the oligonucleotide to which the target nucleic acid is attached.

T51. The method of any one of embodiments T1 to T50, comprising prior to (a), contacting the target nucleic acid composition with an agent comprising a phosphatase activity under conditions in which target nucleic acids are dephosphorylated, thereby generating a dephosphorylated target nucleic acid composition.

T52. The method of embodiment T51, comprising prior to (a), contacting the dephosphorylated target nucleic acid composition with an agent comprising a phosphoryl transfer activity under conditions in which a 5' phosphate is added to a 5' end of target nucleic acids.

T53. The method of any one of embodiments T1 to T52, comprising prior to (a), contacting the first pool of oligonucleotide species with an agent comprising a phosphatase activity under conditions in which the oligonucleotides are dephosphorylated, thereby generating a first pool of dephosphorylated oligonucleotide species.

T54. The method of any one of embodiments T1 to T53, comprising prior to (c), contacting the second pool of oligonucleotide species with an agent comprising a phosphoryl transfer activity under conditions in which a 5' phosphate is added to a 5' end of oligonucleotide species at the first end.

T55. The method of any one of embodiments T1 to T54, wherein the target nucleic acids are obtained from a sample from a subject.

T56. The method of embodiment T55, wherein the subject is a human.

T57. The method of any one of embodiments T1 to T56, comprising prior to (a), separating the target nucleic acids according to fragment length.

T58. The method of any one of embodiments T1 to T56, wherein the target nucleic acids are not separated by length prior to (a).

U1. A composition comprising:
  a) a first pool of oligonucleotide species, wherein:
    i) some or all of the oligonucleotides in the first pool of oligonucleotide species comprise an overhang capable of hybridizing to a target nucleic acid overhang, wherein each oligonucleotide species has a unique overhang sequence and length,
    ii) each oligonucleotide in the first pool of oligonucleotide species comprises an oligonucleotide overhang identification sequence specific to one or more features of the oligonucleotide overhang, and
    iii) each oligonucleotide in the first pool of oligonucleotide species comprises a first primer binding domain; and
  b) a second pool of oligonucleotide species, wherein:
    i) each oligonucleotide in the second pool of oligonucleotide species comprises a first end and a second end, and
    ii) each oligonucleotide in the second pool of oligonucleotide species comprises a second primer binding domain, wherein the first primer binding domain and the second primer binding domain are different.

U2. The composition of embodiment U1, wherein some or all of the oligonucleotides in the first pool of oligonucleotide species comprise one or more modified nucleotides.

U3. The composition of embodiment U2, wherein the one or more modified nucleotides are capable of blocking attachment to other oligonucleotides in the pool.

U4. The composition of any one of embodiments U1 to U3, wherein some or all of the oligonucleotides in the second pool of oligonucleotide species comprise one or more modified nucleotides at the second end.

U5. The composition of embodiment U4, wherein the one or more modified nucleotides are capable of blocking attachment of the second end of the oligonucleotide to cleaved target nucleic acids.

U6. The composition of any one of embodiments U1 to U5, wherein the first pool of oligonucleotide species comprises oligonucleotides having a 5' overhang and oligonucleotides having a 3' overhang.

U7. The composition of any one of embodiments U1 to U6, wherein the first pool of oligonucleotide species comprises oligonucleotides having a 5' overhang, oligonucleotides having a 3' overhang, and oligonucleotides having no overhang.

U8. The composition of embodiment T12 or T13, wherein the oligonucleotides that comprise an overhang comprise a duplex portion, and a single-stranded overhang.

U9. The composition of any one of embodiments U6 to U8, wherein the oligonucleotide overhang comprises 1, 2, 3, 4, 5, 6, 7, 8, 9, 10, 11, 12, 13, 14, 15, 16, 17, 18, 19 or 20 nucleotides.

U10. The composition of any one of embodiments U1 to U9, wherein the oligonucleotides in the first pool of oligonucleotide species comprise oligonucleotide overhangs having different sequences for a particular overhang length.

U11. The composition of embodiment U10, wherein the oligonucleotides in the first pool of oligonucleotide species comprise all possible overhang sequence combinations for a particular overhang length.

U12. The composition of embodiment U11, wherein the oligonucleotides in the first pool of oligonucleotide species comprise all possible overhang sequence combinations for each overhang length.

U13. The composition of embodiment U10, U11, or U12, wherein the oligonucleotide overhang sequences are random.

U14. The composition of any one of embodiments U1 to U13, wherein the oligonucleotides in the second pool of oligonucleotide species comprise one or more unpaired nucleotides at the first end.

U15. The composition of any one of embodiments U1 to U14, wherein the oligonucleotides in the second pool of oligonucleotide species do not comprise an overhang capable of hybridizing to a native target nucleic acid overhang.

U15.1 The composition of any one of embodiments U1 to U15, wherein the oligonucleotides in the second pool of oligonucleotide species do not comprise an oligonucleotide overhang identification sequence.

U16. The composition of any one of embodiments U1 to U15.1, wherein the oligonucleotide overhang identification sequence on each oligonucleotide in the first pool of oligonucleotide species is specific to length of the oligonucleotide overhang.

U17. The composition of any one of embodiments U1 to U16, wherein the oligonucleotide overhang identification sequence on each oligonucleotide in the first pool of oligonucleotide species is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

U18. The composition of any one of embodiments U1 to U17, wherein an oligonucleotide species in the first pool of oligonucleotide species comprises no overhang and comprises an oligonucleotide overhang identification sequence specific to having no overhang.

V1. A kit, comprising:
the composition of any one of embodiments U1 to U18; and
instructions for using the composition to produce a nucleic acid library.

V2. The kit of embodiment V1, further comprising an agent comprising a phosphatase activity.

V3. The kit of embodiment V1 or V2, further comprising an agent comprising a phosphoryl transfer activity.

V4. The kit of any one of embodiments V1 to V3, further comprising an agent comprising a ligase activity.

V5. The kit of any one of embodiments V1 to V4, further comprising an agent comprising a cleavage activity.

V6. The kit of any one of embodiments V1 to V5, further comprising an agent comprising a polymerase activity.

V7. The kit of any one of embodiments V1 to V6, further comprising a first amplification primer species and a second amplification primer species, wherein the first primer species comprises a nucleotide sequence complementary to the first primer binding domain and the second primer species comprises a nucleotide sequence complementary to the second primer binding domain.

V8. The kit of any one of embodiments V1 to V7, further comprising one or more agents for performing nucleic acid amplification.

W1. A method for producing a nucleic acid library, comprising:
a) combining a nucleic acid composition comprising target nucleic acids and a first pool of oligonucleotide species, wherein:
  i) some or all of the target nucleic acids comprise an overhang,
  ii) some or all of the oligonucleotides in the first pool of oligonucleotide species comprise an overhang at a first end capable of hybridizing to a target nucleic acid overhang, wherein each oligonucleotide species has a unique overhang sequence and length,
  iii) each oligonucleotide in the first pool of oligonucleotide species comprises an oligonucleotide overhang identification sequence specific to one or more features of the oligonucleotide overhang,
  iv) each oligonucleotide in the first pool of oligonucleotide species comprises a first primer binding domain, and
  v) the nucleic acid composition and the first pool of oligonucleotide species are combined under conditions in which oligonucleotide overhangs hybridize to target nucleic acid overhangs having a corresponding length, thereby forming a first set of combined products;
b) cleaving the first set of combined products, thereby forming cleaved products; and
c) combining the cleaved products and a second pool of oligonucleotide species, wherein:
  i) each oligonucleotide in the second pool of oligonucleotide species comprises a first strand and a second strand, wherein the first strand is shorter than the second strand, and wherein the first strand and the second strand are complementary at a first end of the oligonucleotide and the second strand comprises a single strand at a second end of the oligonucleotide,
  ii) each oligonucleotide in the second pool of oligonucleotide species comprises an oligonucleotide identification sequence specific to the second pool of oligonucleotide species,
  iii) each oligonucleotide in the second pool of oligonucleotide species comprises a second primer binding domain on the second strand, wherein the first primer binding domain and the second primer binding domain are different, and
  iv) the cleaved products and the second pool of oligonucleotide species are combined under conditions in which oligonucleotides in the second pool of oligonucleotide species attach to at least one end of the cleaved products, thereby forming a second set of combined products.

W1.1 The method of embodiment W1, further comprising:
  d) contacting, under amplification conditions, the second set of combined products with two or more amplification primer species, wherein a first primer species comprises a nucleotide sequence complementary to the first primer binding domain and a second primer species comprises a nucleotide sequence complementary to the second primer binding domain, thereby generating amplification products.

W2. The method of embodiment W1 or W1.1, wherein the target nucleic acids comprise nucleic acid fragments larger than 500 bp.

W3. The method of embodiment W1 or W1.1, wherein the target nucleic acids comprise nucleic acid fragments larger than 1000 bp.

W4. The method of any one of embodiments W1 to W3, wherein (b) comprises contacting the first set of combined products under cleavage conditions with one or more cleavage agents capable of cleaving the combined products.

W5. The method of any one of embodiments W1 to W3, wherein (b) comprises mechanical shearing.

W6. The method of any one of embodiments W1 to W5, wherein some or all of the oligonucleotides in the first pool of oligonucleotide species comprise one or more modified nucleotides at a second end.

W7. The method of embodiment W6, wherein the one or more modified nucleotides are capable of blocking attachment of the second end of the oligonucleotide to target nucleic acids.

W8. The method of any one of embodiments W1 to W7, wherein some or all of the oligonucleotides in the second pool of oligonucleotide species comprise one or more modified nucleotides at the second end.

W9. The method of embodiment W8, wherein the one or more modified nucleotides are capable of blocking attachment of the second end of the oligonucleotide to the cleaved products.

W10. The method of any one of embodiments W1 to W9, further comprising sequencing the amplification products by a sequencing process.

W11. The method of embodiment W10, wherein the sequencing process generates short sequence reads.

W12. The method of any one of embodiments W1 to W11, wherein the first pool of oligonucleotide species comprises oligonucleotides having a 5' overhang and oligonucleotides having a 3' overhang.

W13. The method of any one of embodiments W1 to W12, wherein the first pool of oligonucleotide species comprises oligonucleotides having a 5' overhang, oligonucleotides having a 3' overhang, and oligonucleotides having no overhang.

W14. The method of embodiment W12 or W13, wherein the oligonucleotides that comprise an overhang comprise a duplex portion, and a single-stranded overhang.

W15. The method of any one of embodiments W12 to W14, wherein the oligonucleotides that comprise an overhang comprise (1) two strands and an overhang at a first end and two non-complementary strands at a second end, or (2) one strand capable of forming a hairpin structure having a single-stranded loop and an overhang.

W16. The method of any one of embodiments W12 to W15, wherein the oligonucleotide overhang comprises 1, 2, 3, 4, 5, 6, 7, 8, 9, 10, 11, 12, 13, 14, 15, 16, 17, 18, 19 or 20 nucleotides.

W17. The method of any one of embodiments W1 to W16, wherein the oligonucleotides in the first pool of oligonucleotide species comprise oligonucleotide overhangs having different sequences for a particular overhang length.

W18. The method of embodiment W17, wherein the oligonucleotides in the first pool of oligonucleotide species comprise all possible overhang sequence combinations for a particular overhang length.

W19. The method of embodiment W18, wherein the oligonucleotides in the first pool of oligonucleotide species comprise all possible overhang sequence combinations for each overhang length.

W20. The method of embodiment W17, W18 or W19, wherein the oligonucleotide overhang sequences are random.

W21. The method of any one of embodiments W1 to W20, wherein an end of an oligonucleotide in the first pool of oligonucleotide species is capable of being covalently linked to an end of a target nucleic acid to which the oligonucleotide is hybridized in the first set of combined products.

W22. The method of embodiment W21, wherein the 3' end of an oligonucleotide strand in the first pool of oligonucleotide species is capable of being covalently linked to the 5' end of a strand in the target nucleic acid to which the oligonucleotide is hybridized in the first set of combined products.

W23. The method of any one of embodiments W1 to W22, comprising after (b) repairing the ends of the cleaved products.

W24. The method of any one of embodiments W1 to W23, comprising after (b) adding one or more unpaired nucleotides to the ends of the cleaved products.

W25. The method of embodiment W24, wherein the oligonucleotides in the second pool of oligonucleotide species comprise one or more nucleotides at the first end that are complementary to the one or more nucleotides added to the cleaved products.

W26. The method of embodiment W25, wherein the oligonucleotides in the second pool of oligonucleotide species hybridize at the first end to at least one end of the cleaved products.

W27. The method of any one of embodiments W1 to W26, wherein an end of an oligonucleotide in the second pool of oligonucleotide species is capable of being covalently linked to an end of a cleaved product to which the oligonucleotide is attached in the second set of combined products.

W28. The method of embodiment W27, wherein the 3' end of an oligonucleotide strand in the second pool of oligonucleotide species is capable of being covalently linked to the 5' end of a strand in the cleaved product to which the oligonucleotide is attached in the second set of combined products.

W29. The method of any one of embodiments W1 to W28, wherein the oligonucleotides in the second pool of oligonucleotide species do not comprise an overhang capable of hybridizing to a native target nucleic acid overhang.

W29.1 The method of any one of embodiments W1 to W29, wherein the oligonucleotides in the second pool of oligonucleotide species do not comprise an oligonucleotide overhang identification sequence.

W30. The method of any one of embodiments W1 to W29.1, wherein the oligonucleotide overhang identification sequence on each oligonucleotide in the first pool of oligonucleotide species is specific to length of the oligonucleotide overhang.

W31. The method of any one of embodiments W1 to W30, wherein the oligonucleotide overhang identification sequence on each oligonucleotide in the first pool of oligonucleotide species is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

W32. The method of any one of embodiments W1 to W31, wherein some of the target nucleic acids comprise no overhang.

W33. The method of any one of embodiments W1 to W32, wherein an oligonucleotide species in the first pool of oligonucleotide species comprises no overhang and comprises an oligonucleotide overhang identification sequence specific to having no overhang.

W34. The method of any one of embodiments W1 to W33, wherein the target nucleic acids comprising an overhang comprise a duplex region and a single-stranded overhang.

W35. The method of any one of embodiments W1 to W34, wherein each target nucleic acid comprising an overhang comprises an overhang at one end or an overhang at both ends.

W36. The method of any one of embodiments W1 to W35, wherein an end, or both ends, of each target nucleic acid comprising an overhang independently comprises a 5' overhang or a 3' overhang.

W37. The method of any one of embodiments W1 to W36, wherein the target nucleic acids comprise deoxyribonucleic acid (DNA) fragments.

W38. The method of embodiment W37, wherein the DNA fragments are obtained from cells.

W39. The method of embodiment W37 or W38, wherein the DNA fragments comprise genomic DNA fragments.

W40. The method of any one of embodiments W1 to W36, wherein the target nucleic acids comprise ribonucleic acid (RNA) fragments.

W41. The method of embodiment W40, wherein the RNA fragments are obtained from cells.

W42. The method of any one of embodiments W1 to W41, wherein the target nucleic acids comprise cell-free nucleic acid fragments.

W43. The method of any one of embodiments W1 to W42, wherein the target nucleic acids comprise circulating cell-free nucleic acid fragments.

W44. The method of any one of embodiments W1 to W43, wherein the overhangs in target nucleic acids are native overhangs.

W45. The method of any one of embodiments W1 to W44, wherein the overhangs in target nucleic acids are unmodified overhangs.

W46. The method of any one of embodiments W1 to W45, wherein the target nucleic acids are not modified in length prior to combining with the plurality of oligonucleotide species.

W47. The method of any one of embodiments W1 to W46, comprising preparing the nucleic acid composition prior to (a), by a process consisting essentially of isolating nucleic acid from a sample, thereby generating the nucleic acid composition.

W48. The method of any one of embodiments W1 to W47, comprising exposing the first set of combined products to conditions under which an end of the target nucleic acid is joined to an end of the oligonucleotide to which it is hybridized.

W49. The method of embodiment W48, comprising contacting the first set of combined products with an agent comprising a ligase activity under conditions in which an end of a target nucleic acid is covalently linked to an end of the oligonucleotide to which the target nucleic acid is hybridized.

W50. The method of any one of embodiments W1 to W49, comprising exposing the second set of combined products to conditions under which an end of the cleaved product is joined to an end of the oligonucleotide to which it is attached.

W51. The method of embodiment W50, comprising contacting the second set of combined products with an agent comprising a ligase activity under conditions in which an end of a cleaved product is covalently linked to an end of the oligonucleotide to which the target nucleic acid is attached.

W52. The method of any one of embodiments W1 to W51, comprising prior to (a), contacting the target nucleic acid composition with an agent comprising a phosphatase activity under conditions in which target nucleic acids are dephosphorylated, thereby generating a dephosphorylated target nucleic acid composition.

W53. The method of embodiment W52, comprising prior to (a), contacting the dephosphorylated target nucleic acid composition with an agent comprising a phosphoryl transfer activity under conditions in which a 5' phosphate is added to a 5' end of target nucleic acids.

W54. The method of any one of embodiments W1 to W53, comprising prior to (a), contacting the first pool of oligonucleotide species with an agent comprising a phosphatase activity under conditions in which the oligonucleotides are dephosphorylated, thereby generating a first pool of dephosphorylated oligonucleotide species.

W55. The method of any one of embodiments W1 to W54, comprising prior to (c), contacting the second pool of oligonucleotide species with an agent comprising a phosphoryl transfer activity under conditions in which a 5' phosphate is added to a 5' end of the first strand.

W56. The method of any one of embodiments W1 to W55, wherein the target nucleic acids are obtained from a sample from a subject.

W57. The method of embodiment W56, wherein the subject is a human.

W58. The method of any one of embodiments W1 to W57, comprising prior to (a), separating the target nucleic acids according to fragment length.

W59. The method of any one of embodiments W1 to W57, wherein the target nucleic acids are not separated by length prior to (a).

X1. A composition comprising:
  a) a first pool of oligonucleotide species, wherein:
    i) some or all of the oligonucleotides in the first pool of oligonucleotide species comprise an overhang capable of hybridizing to a target nucleic acid overhang, wherein each oligonucleotide species has a unique overhang sequence and length,
    ii) each oligonucleotide in the first pool of oligonucleotide species comprises an oligonucleotide overhang identification sequence specific to one or more features of the oligonucleotide overhang, and
    iii) each oligonucleotide in the first pool of oligonucleotide species comprises a first primer binding domain; and
  b) a second pool of oligonucleotide species, wherein:
    i) each oligonucleotide in the second pool of oligonucleotide species comprises a first strand and a second strand, wherein the first strand is shorter than the second strand, and wherein the first strand and the second strand are complementary at a first end of the oligonucleotide and the second strand comprises a single strand at a second end of the oligonucleotide, ii) each oligonucleotide in the first pool of oligonucleotide species comprises an oligonucleotide identification sequence specific to the second pool of oligonucleotide species, and (iii) each oligonucleotide in the second pool of oligonucleotide species comprises a second primer binding domain on the second strand, wherein the first primer binding domain and the second primer binding domain are different.

X2. The composition of embodiment X1, wherein some or all of the oligonucleotides in the first pool of oligonucleotide species comprise one or more modified nucleotides at a second end.

X3. The composition of embodiment X2, wherein the one or more modified nucleotides are capable of blocking attachment of the second end of the oligonucleotide to target nucleic acids.

X4. The composition of any one of embodiments X1 to X3, wherein some or all of the oligonucleotides in the second pool of oligonucleotide species comprise one or more modified nucleotides at the second end.

X5. The composition of embodiment X4, wherein the one or more modified nucleotides are capable of blocking attachment of the second end of the oligonucleotide to cleaved target nucleic acids.

X6. The composition of any one of embodiments X1 to X5, wherein the first pool of oligonucleotide species comprises oligonucleotides having a 5' overhang and oligonucleotides having a 3' overhang.

X7. The composition of any one of embodiments X1 to X6, wherein the first pool of oligonucleotide species comprises oligonucleotides having a 5' overhang, oligonucleotides having a 3' overhang, and oligonucleotides having no overhang.

X8. The composition of embodiment X6 or X7, wherein the oligonucleotides that comprise an overhang comprise a duplex portion, and a single-stranded overhang.

X9. The composition of any one of embodiments X6 to X8, wherein the oligonucleotides that comprise an overhang comprise (1) two strands and an overhang at a first end and two non-complementary strands at a second end, or (2) one strand capable of forming a hairpin structure having a single-stranded loop and an overhang.

X10. The composition of any one of embodiments X6 to X9, wherein the oligonucleotide overhang comprises 1, 2, 3, 4, 5, 6, 7, 8, 9, 10, 11, 12, 13, 14, 15, 16, 17, 18, 19 or 20 nucleotides.

X11. The composition of any one of embodiments X1 to X10, wherein the oligonucleotides in the first pool of oligonucleotide species comprise oligonucleotide overhangs having different sequences for a particular overhang length.

X12. The composition of embodiment X11, wherein the oligonucleotides in the first pool of oligonucleotide species comprise all possible overhang sequence combinations for a particular overhang length.

X13. The composition of embodiment X12, wherein the oligonucleotides in the first pool of oligonucleotide species comprise all possible overhang sequence combinations for each overhang length.

X14. The composition of embodiment X11, X12, or X13, wherein the oligonucleotide overhang sequences are random.

X15. The composition of any one of embodiments X1 to X14, wherein the oligonucleotides in the second pool of oligonucleotide species comprise one or more unpaired nucleotides at the first end.

X16. The composition of any one of embodiments X1 to X15, wherein the oligonucleotides in the second pool of oligonucleotide species do not comprise an overhang capable of hybridizing to a native target nucleic acid overhang.

X16.1 The composition of any one of embodiments X1 to X16, wherein the oligonucleotides in the second pool of oligonucleotide species do not comprise an oligonucleotide overhang identification sequence.

X17. The composition of any one of embodiments X1 to X16.1, wherein the oligonucleotide overhang identification sequence on each oligonucleotide in the first pool of oligonucleotide species is specific to length of the oligonucleotide overhang.

X18. The composition of any one of embodiments X1 to X17, wherein the oligonucleotide overhang identification sequence on each oligonucleotide in the first pool of oligonucleotide species is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

X19. The composition of any one of embodiments X1 to X18, wherein an oligonucleotide species in the first pool of oligonucleotide species comprises no overhang and comprises an oligonucleotide overhang identification sequence specific to having no overhang.

Y1. A kit, comprising:
the composition of any one of embodiments X1 to X19; and
instructions for using the composition to produce a nucleic acid library.

Y2. The kit of embodiment Y1, further comprising an agent comprising a phosphatase activity.

Y3. The kit of embodiment Y1 or Y2, further comprising an agent comprising a phosphoryl transfer activity.

Y4. The kit of any one of embodiments Y1 to Y3, further comprising an agent comprising a ligase activity.

Y5. The kit of any one of embodiments Y1 to Y4, further comprising an agent comprising a cleavage activity.

Y6. The kit of any one of embodiments Y1 to Y5, further comprising an agent comprising a polymerase activity.

Y7. The kit of any one of embodiments Y1 to Y6, further comprising a first amplification primer species and a second amplification primer species, wherein the first primer species comprises a nucleotide sequence complementary to the first primer binding domain and the second primer species comprises a nucleotide sequence complementary to the second primer binding domain.

Y8. The kit of any one of embodiments Y1 to Y7, further comprising one or more agents for performing nucleic acid amplification.

Z1. A method for producing a nucleic acid library, comprising:
a) contacting a nucleic acid composition comprising target nucleic acids with an agent comprising a phosphatase activity under conditions in which target nucleic acids are dephosphorylated, thereby generating dephosphorylated target nucleic acids, wherein some or all of the target nucleic acids comprise an overhang; and
b) combining the dephosphorylated target nucleic acids and a plurality of oligonucleotide species, wherein:

i) some or all of the oligonucleotides in the plurality of oligonucleotide species comprise an overhang capable of hybridizing to a target nucleic acid overhang, wherein each oligonucleotide species has a unique overhang sequence and length;
ii) each oligonucleotide in the plurality of oligonucleotide species comprises an oligonucleotide overhang identification sequence specific to one or more features of the oligonucleotide overhang; and
iii) the nucleic acid composition and the plurality of oligonucleotide species is combined under conditions in which oligonucleotide overhangs hybridize to target nucleic acid overhangs having a corresponding length, thereby forming hybridization products.

Z2. The method of embodiment Z1, comprising prior to (b), contacting the dephosphorylated target nucleic acids with an agent comprising a phosphoryl transfer activity under conditions in which a 5' phosphate is added to a 5' end of target nucleic acids.

Z3. The method of embodiment Z1 or Z2, comprising prior to (b), contacting the plurality of oligonucleotide species with an agent comprising a phosphatase activity under conditions in which the oligonucleotides are dephosphorylated, thereby generating a plurality of dephosphorylated oligonucleotide species.

Z4. The method of any one of embodiments Z1 to Z3, wherein some or all of the oligonucleotides in the plurality of oligonucleotide species comprise two strands, and the overhang at a first end and two non-complementary strands at a second end.

Z5. The method of any one of embodiments Z1 to Z3, wherein some or all of the oligonucleotides in the plurality of oligonucleotide species comprise one strand capable of forming a hairpin structure having a single-stranded loop and an overhang.

Z6. The method of any one of embodiments Z1 to Z5, comprising sequencing the hybridization products, or amplification products thereof, by a sequencing process, thereby generating sequence reads, wherein the sequence reads comprise forward sequence reads and reverse sequence reads.

Z7. The method of embodiment Z6, comprising quantifying the sequence reads thereby generating a sequence read quantification, wherein the reverse sequence reads are quantified, and the forward sequence reads are excluded from the quantification.

Z8. The method of embodiment Z6, comprising analyzing overhang information associated with overhang identification sequences that indicate presence of an overhang for the reverse sequence reads, thereby generating an analysis.

Z9. The method of embodiment Z8, comprising omitting from the analysis overhang information associated with overhang identification sequences that indicate presence of an overhang for the forward sequence reads.

Z10. The method of embodiment Z8 or Z9, comprising analyzing overhang information associated with overhang identification sequences that indicate no overhang for the forward sequence reads and the reverse sequence reads.

Z11. The method of any one of embodiments Z1 to Z10, comprising one or more features of any one of embodiments A1 to A68, C1 to C68, E1 to E64, G1 to G56, I1 to I76, Q1 to Q42, T1 to T58, and W1 to W59.

A'1. A method for analyzing nucleic acid comprising:
a) combining a nucleic acid composition comprising target nucleic acids and a plurality of oligonucleotide species, wherein:
  i) some or all of the target nucleic acids comprise an overhang;
  ii) some or all of the oligonucleotides in the plurality of oligonucleotide species comprise an overhang capable of hybridizing to a target nucleic acid overhang, wherein each oligonucleotide species has a unique overhang sequence and length;
  iii) each oligonucleotide in the plurality of oligonucleotide species comprises an oligonucleotide overhang identification sequence specific to one or more features of the oligonucleotide overhang; and
  iv) the nucleic acid composition and the plurality of oligonucleotide species is combined under conditions in which oligonucleotide overhangs hybridize to target nucleic acid overhangs having a corresponding length, thereby forming hybridization products;
b) sequencing the hybridization products, or amplification products thereof, by a sequencing process, thereby generating sequence reads, wherein the sequence reads comprise forward sequence reads and reverse sequence reads; and
c) analyzing overhang information associated with overhang identification sequences that indicate presence of an overhang for the reverse sequence reads, thereby generating an analysis, and omitting from the analysis overhang information associated with overhang identification sequences that indicate presence of an overhang for the forward sequence reads.

A'2. The method of embodiment A'1, wherein (c) comprises analyzing overhang information associated with overhang identification sequences that indicate no overhang for the forward sequence reads and the reverse sequence reads.

A'3. The method of embodiment A'1 or A'2, wherein some or all of the oligonucleotides in the plurality of oligonucleotide species comprise two strands, and the overhang at a first end and two non-complementary strands at a second end.

A'4. The method of embodiment A'1 or A'2, wherein some or all of the oligonucleotides in the plurality of oligonucleotide species comprise one strand capable of forming a hairpin structure having a single-stranded loop and an overhang.

A'5. The method of any one of embodiments A'1 to A'4, comprising prior to (a), contacting the target nucleic acids with an agent comprising a phosphatase activity under conditions in which target nucleic acids are dephosphorylated, thereby generating dephosphorylated target nucleic acids.

A'6. The method of embodiment A'5, comprising contacting the dephosphorylated target nucleic acids with an agent comprising a phosphoryl transfer activity under conditions in which a 5' phosphate is added to a 5' end of target nucleic acids.

A'7. The method of any one of embodiments A'1 to A'6, comprising prior to (a), contacting the plurality of oligonucleotide species with an agent comprising a phosphatase activity under conditions in which the oligonucleotides are dephosphorylated, thereby generating a plurality of dephosphorylated oligonucleotide species.

A'8. The method of any one of embodiments A'1 to A'7, wherein (c) is performed using a microprocessor.

A'9. The method of any one of embodiments A'1 to A'8, comprising one or more features of any one of embodiments A1 to A68, C1 to C68, E1 to E64, G1 to G56, I1 to I76, Q1 to Q42, T1 to T58, and W1 to W59.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for producing a nucleic acid library, comprising:
   combining a nucleic acid composition comprising target nucleic acids and a plurality of oligonucleotide species, wherein:
   a) some or all of the target nucleic acids comprise an overhang;
   b) each oligonucleotide in the plurality of oligonucleotide species comprises two strands;
   c) each oligonucleotide in the plurality of oligonucleotide species comprises an overhang at a first end, or some of the oligonucleotides in the plurality of oligonucleotide species comprise an overhang at a first end and some of the oligonucleotides in the plurality of oligonucleotide species comprise no overhang at a first end, wherein the overhang, when present, is capable of hybridizing to a target nucleic acid overhang, wherein each oligonucleotide species having an overhang has a unique overhang sequence and length;
   d) each oligonucleotide in the plurality of oligonucleotide species comprises at a second end (i) two non-complementary strands and (ii) one or more blocked nucleotides;
   e) each oligonucleotide in the plurality of oligonucleotide species comprises an oligonucleotide overhang identification sequence specific to no overhang or specific to one or more features of the oligonucleotide overhang, wherein the one or more features comprise length of the overhang; and
   f) the nucleic acid composition and the plurality of oligonucleotide species are combined under conditions in which oligonucleotide overhangs hybridize to target nucleic acid overhangs having a corresponding length, thereby forming hybridization products.

2. The method of claim 1, wherein the plurality of oligonucleotide species comprises oligonucleotides having a 5' overhang and oligonucleotides having a 3' overhang.

3. The method of claim 1, wherein the plurality of oligonucleotide species comprises oligonucleotides having a 5' overhang, oligonucleotides having a 3' overhang, and oligonucleotides having no overhang.

4. The method of claim 1, wherein the oligonucleotides in the plurality of oligonucleotide species having overhangs comprise:
   i) oligonucleotide overhangs having different sequences for a particular overhang length;
   ii) all possible overhang sequence combinations for a particular overhang length; or
   iii) all possible overhang sequence combinations for each overhang length.

5. The method of claim 4, wherein the oligonucleotide overhang sequences are random.

6. The method of claim 1, wherein the oligonucleotide overhang identification sequence is specific to length of the oligonucleotide overhang and is specific to one or more features of the oligonucleotide overhang chosen from (i) a 5' overhang, (ii) a 3' overhang, (iii) a particular sequence, (iv) a combination of (i) and (iii), or (v) a combination of (ii) and (iii).

7. The method of claim 1, wherein:
i) some of the target nucleic acids comprise no overhang; and
ii) an oligonucleotide species comprises no overhang and comprises an oligonucleotide overhang identification sequence specific to having no overhang.

8. The method of claim 1, wherein:
i) the target nucleic acids comprising an overhang comprise a duplex region and a single-stranded overhang; and
ii) each target nucleic acid comprising an overhang comprises an overhang at one end or an overhang at both ends.

9. The method of claim 1, wherein an end, or both ends, of each target nucleic acid comprising an overhang independently comprises a 5' overhang or a 3' overhang.

10. The method of claim 1, wherein the target nucleic acids comprise cell-free nucleic acid fragments.

11. The method of claim 1, wherein the overhangs in target nucleic acids are native overhangs and/or are unmodified overhangs.

12. The method of claim 1, wherein the target nucleic acids are not modified in length prior to combining with the plurality of oligonucleotide species.

13. The method of claim 1, comprising:
i) contacting the hybridization products with an agent comprising a ligase activity under conditions in which the 5' end of a target nucleic acid is covalently linked to the 3' end of the oligonucleotide to which the target nucleic acid is hybridized, thereby forming ligation products; and
ii) contacting the ligation products with an agent comprising a nick-sealing ligase activity under conditions in which the 3' end of a target nucleic acid is covalently linked to the 5' end of the oligonucleotide to which the target nucleic acid is hybridized, thereby forming nick-sealed ligation products; or
iii) contacting the ligation products with a strand-displacing polymerase, thereby forming blunt-ended nucleic acid fragments.

14. The method of claim 1, comprising prior to the combining of a nucleic acid composition comprising target nucleic acids and a plurality of oligonucleotide species, contacting the target nucleic acids with an agent comprising a phosphatase activity under conditions in which target nucleic acids are dephosphorylated, thereby generating dephosphorylated target nucleic acids.

15. The method of claim 14, comprising contacting the dephosphorylated target nucleic acids with an agent comprising a phosphoryl transfer activity under conditions in which a 5' phosphate is added to a 5' end of target nucleic acids.

16. The method of claim 1, comprising prior to the combining of a nucleic acid composition comprising target nucleic acids and a plurality of oligonucleotide species, contacting the plurality of oligonucleotide species with an agent comprising a phosphatase activity under conditions in which the oligonucleotides are dephosphorylated, thereby generating a plurality of dephosphorylated oligonucleotide species.

17. The method of claim 1, wherein each of the two non-complementary strands at the second end of the oligonucleotide species comprises a primer binding domain, wherein one of the non-complementary strands comprises a first primer binding domain, and the other non-complementary strand comprises a second primer binding domain, wherein the first primer binding domain and second primer binding domain are different.

18. The method of claim 1, comprising sequencing the hybridization products, or amplification products thereof, by a sequencing process, thereby generating sequence reads, wherein the sequence reads comprise forward sequence reads and reverse sequence reads.

19. The method of claim 18, comprising analyzing overhang information associated with overhang identification sequences that indicate presence of an overhang for the reverse sequence reads, thereby generating an analysis, and omitting from the analysis overhang information associated with overhang identification sequences that indicate presence of an overhang for the forward sequence reads.

20. A method for producing a nucleic acid library, comprising:
a) combining a nucleic acid composition comprising target nucleic acids and a first pool of oligonucleotide species, wherein:
i) some or all of the target nucleic acids comprise an overhang,
ii) each oligonucleotide in the first pool of oligonucleotide species comprises an overhang at a first end capable of hybridizing to a target nucleic acid overhang, or some of the oligonucleotides in the first pool of oligonucleotide species comprise an overhang at a first end capable of hybridizing to a target nucleic acid overhang and some of the oligonucleotides in the first pool of oligonucleotide species comprise no overhang at a first end, wherein each oligonucleotide species having an overhang has a unique overhang sequence and length,
iii) each oligonucleotide in the first pool of oligonucleotide species comprises an oligonucleotide overhang identification sequence specific to no overhang or specific to one or more features of the oligonucleotide overhang, wherein the one or more features comprise length of the overhang,
iv) each oligonucleotide in the first pool of oligonucleotide species comprises a first primer binding domain, and
v) the nucleic acid composition and the first pool of oligonucleotide species are combined under conditions in which oligonucleotide overhangs hybridize to target nucleic acid overhangs having a corresponding length, thereby forming a first set of combined products;
b) contacting the first set of combined products with a cleavage agent that cleaves the target nucleic acids, thereby forming cleaved products wherein an oligonucleotide from the first pool of oligonucleotides is hybridized at a first end of the cleaved product and no oligonucleotide is hybridized at a second end of the cleaved product; and
c) combining the cleaved products and a second pool of oligonucleotide species, wherein:
i) each oligonucleotide in the second pool of oligonucleotide species comprises a first strand and a second strand, wherein the first strand is shorter than the second strand, and wherein the first strand and the second strand are complementary at a first end of the oligonucleotide and the second strand comprises a single strand at a second end of the oligonucleotide,
ii) each oligonucleotide in the second pool of oligonucleotide species comprises an oligonucleotide identification sequence specific to the second pool of oligonucleotide species,
iii) each oligonucleotide in the second pool of oligonucleotide species comprises a second primer binding domain on the second strand, wherein the first primer binding domain and the second primer binding domain are different, and
iv) the cleaved products and the second pool of oligonucleotide species are combined under conditions in which oligonucleotides in the second pool of oligonucleotide species attach to the second end of the cleaved products, thereby forming a second set of combined products.

21. The method of claim 1, wherein each oligonucleotide overhang identification sequence comprises a nucleic acid sequence that is unique for each oligonucleotide comprising an overhang of a particular length or no overhang.

22. The method of claim 1, wherein each oligonucleotide overhang identification sequence comprises a nucleic acid sequence that is unique for each oligonucleotide comprising an overhang of a particular length or no overhang and a particular 5' or 3' overhang directionality, when an overhang is present.

23. The method of claim 20, wherein the first pool of oligonucleotide species comprises oligonucleotides having a 5' overhang and oligonucleotides having a 3' overhang.

24. The method of claim 20, wherein the first pool of oligonucleotide species comprises oligonucleotides having a 5' overhang and oligonucleotides having a 3' overhang, and oligonucleotides having no overhang.

25. The method of claim 20, wherein the oligonucleotides in the first pool of oligonucleotide species having overhangs comprise:
i) oligonucleotide overhangs having different sequences for a particular overhang length;
ii) all possible overhang sequence combinations for a particular overhang length; or
iii) all possible overhang sequence combinations for each overhang length.

26. The method of claim 25, where the oligonucleotide overhang sequences are random.

27. The method of claim 20, wherein the oligonucleotide overhang identification sequence on each oligonucleotide in the first pool of oligonucleotide species is specific to length of the oligonucleotide overhang and is specific to one or more features of the oligonucleotide overhang chose from (i) a 5' overhang, (ii) a 3' overhang, (iii) a particular sequence, (iv) a combination of (i) and (iii), or (v) a combination of (ii) and (iii).

28. The method of claim 20, wherein:
i) some of the target nucleic acids comprise no overhang; and
ii) an oligonucleotide species in the first pool of oligonucleotide species comprises no overhang and comprises an oligonucleotide overhang identification sequence specific to having no overhang.

29. The method of claim 20, where:
i) the target nucleic acids comprising an overhang comprise a duplex region and a single-stranded overhang; and
ii) each target nucleic acid comprising an overhang comprises an overhang at one end or an overhang at both ends.

30. The method of claim 20, wherein an end, or both ends, of each target nucleic acid comprising an overhang independently comprises a 5' overhang or a 3' overhang.

31. The method of claim 20, wherein the target nucleic acids comprise cell-free nucleic acid fragments.

32. The method of claim 20, wherein the overhangs in target nucleic acids are native overhangs and/or are unmodified overhangs.

33. The method of claim 20, wherein the target nucleic acids are not modified in length prior to combining with the first pool of oligonucleotide species.

34. The method of claim 20, comprising prior to (a), contacting the target nucleic acids with an agent comprising a phosphatase activity under conditions in which target nucleic acids are dephosphorylated, thereby generating dephosphorylated target nucleic acids.

35. The method of claim 34, comprising contacting the dephosphorylated target nucleic acids with an agent comprising a phosphoryl transfer activity under conditions in which a 5' phosphate is added to a 5' end of target nucleic acids.

36. The method of claim 20, comprising prior to (a), contacting the first pool of oligonucleotide species with an agent comprising a phosphate activity under conditions in which the oligonucleotides are dephosphorylated, thereby generating a plurality of dephosphorylated oligonucleotide species.

37. The method of claim 20, where each oligonucleotide overhang identification sequence comprises a nucleic acid sequence that is unique for each oligonucleotide comprising an overhang of a particular length or no overhang.

38. The method of claim 20, wherein each oligonucleotide overhang identification sequence comprises a nucleic acid sequence that is unique for each oligonucleotide comprising an overhang of a particular length or no overhang and a particular 5' or 3' overhang directionality, when an overhang is present.

* * * * *

UNITED STATES PATENT AND TRADEMARK OFFICE
CERTIFICATE OF CORRECTION

PATENT NO. : 11,584,929 B2  
APPLICATION NO. : 16/961113  
DATED : February 21, 2023  
INVENTOR(S) : Harkins Kincaid et al.

Page 1 of 1

It is certified that error appears in the above-identified patent and that said Letters Patent is hereby corrected as shown below:

In the Claims

In Column 188, Line 11, delete "where" and insert -- wherein --, therefor.

In Column 188, Line 44, delete "where" and insert -- wherein --, therefor.

Signed and Sealed this  
Fifteenth Day of August, 2023

Katherine Kelly Vidal  
*Director of the United States Patent and Trademark Office*